US012788696B2

(12) United States Patent
Gianneschi et al.

(10) Patent No.: US 12,788,696 B2
(45) Date of Patent: Nov. 10, 2026

(54) HYDROPHOBIC SYNTHETIC MELANIN NANOPARTICLES

(71) Applicant: Northwestern University, Evanston, IL (US)

(72) Inventors: Nathan C. Gianneschi, Wilmette, IL (US); Xuhao Zhou, Evanston, IL (US); Navjit Kaur Paul, Evanston, IL (US); Kurt Q. Lu, Chicago, IL (US); Ummiye Venus Onay, Skokie, IL (US); Dauren Biyashev, Chicago, IL (US); Spencer Evans, Evanston, IL (US); Michael Demczuk, Chicago, IL (US)

(73) Assignee: Northwestern University, Evanston, IL (US)

( * ) Notice: Subject to any disclaimer, the term of this patent is extended or adjusted under 35 U.S.C. 154(b) by 200 days.

(21) Appl. No.: 18/601,746

(22) Filed: Mar. 11, 2024

(65) Prior Publication Data

US 2024/0366486 A1 Nov. 7, 2024

Related U.S. Application Data

(63) Continuation of application No. PCT/US2023/035593, filed on Oct. 20, 2023.

(60) Provisional application No. 63/418,257, filed on Oct. 21, 2022.

(51) Int. Cl.

| | |
|---|---|
| ***A61K 8/49*** | (2006.01) |
| ***A61Q 19/04*** | (2006.01) |

(52) U.S. Cl.

CPC ............ *A61K 8/4926* (2013.01); *A61Q 19/04* (2013.01)

(58) Field of Classification Search

CPC ............................ A61K 47/54; A61K 47/6929

See application file for complete search history.

(56) References Cited

U.S. PATENT DOCUMENTS

| | | | |
|---|---|---|---|
| 4,861,760 | A | 8/1989 | Mazuel et al. |
| 4,911,920 | A | 3/1990 | Jani et al. |
| 5,212,162 | A | 5/1993 | Missel et al. |
| 5,403,841 | A | 4/1995 | Lang et al. |
| 2022/0332670 | A1 | 10/2022 | Zhou et al. |

FOREIGN PATENT DOCUMENTS

| | | |
|---|---|---|
| KR | 2021/124898 | 10/2021 |
| WO | WO 2018/013609 | 1/2018 |
| WO | WO 2021/021350 | 2/2021 |
| WO | WO 2021/087076 | 5/2021 |
| WO | WO 2021/096692 | 5/2021 |
| WO | WO 2022/140532 | 6/2022 |
| WO | WO 2022/232356 | 11/2022 |
| WO | WO 2023/150205 | 8/2023 |

OTHER PUBLICATIONS

Abdullahi et al. (2014) “Animal models in burn research,” Cellular and Molecular Life Sciences. 71(17):3241-3255.

Al-Muhammed et al. (1996) “In-vivo studies on dexamethasone sodium phosphate liposomes,” J Microencapsul 13(3):293-306. doi: 10.3109/02652049609026017. PMID: 8860685.

Ansell et al. (2012) “Animal models of wound repair: Are they cutting it?” Experimental Dermatology 21(8):581-585.

Au et al. (2015) “Suppression of Hyperactive Immune Responses Protects Against Nitrogen Mustard Injury,” J Invest Dermatol. 135, 2971-2981.

Banerjee (2013) “Overcoming the stratum corneum barrier: a nano approach,” Drug Delivery and Translational Research. 3(3):205-208.

Barillo et al. (2020) “Safety evaluation of silver-ion dressings in a porcine model of deep dermal wounds: A GLP study,” Toxicol Lett. 319:111-118.

Baspinar et al. (2012) “Penetration and release studies of positively and negatively charged nanoemulsions—is there a benefit of the positive charge?” Int J Pharm. 430(1-2):247-252.

Battistella et al. (2020) “Mimicking Natural Human Hair Pigmentation with Synthetic Melanin,” ACS Cent. Sci. 6, 1179-1188.

Biyashev et al. (2020) “A novel treatment for skin repair using a combination of spironolactone and vitamin D3,” Ann N Y Acad Sci.

Borak et al. (1992) “Agents of chemical warfare: sulfur mustard,” Ann Emerg Med. 21(3):303-308.

Brenner et al. (2008) “The Protective Role of Melanin Against UV Damage in Human Skin,” Photochem Photobiol. 84(3):539-549.

Cao et al. (2020) “Radical-Enriched Artificial Melanin,” Chemistry of Materials. 32(13):5759-5767.

Cao et al. (Feb. 2021) “Unraveling the Structure and Function of Melanin through Synthesis,” J Am Chem Soc. 143(7):2622-2637.

Cao et al. (Feb. 2023) “Biomimetic pheomelanin to unravel the electronic, molecular and supramolecular structure of the natural product,” Chem Sci. 14(15):4183-4192.PMC10094096.

Cao et al. (Jul. 2020) “Selenomelanin: An Abiotic Selenium Analogue of Pheomelanin,” J Am Chem Soc. 142(29):12802-12810.

Carmignani et al. (Jan. 2022) “In Vitro and Ex Vivo Investigation of the Effects of Polydopamine Nanoparticle Size on Their Antioxidant and Photothermal Properties: Implications for Biomedical Applications,” ACS Appl. Nano Mater. 5, 1702-1713.

Casillas et al. (2000) “Therapeutic approaches to dermatotoxicity by sulfur mustard. I. Modulaton of sulfur mustard-induced cutaneous injury in the mouse ear vesicant model,” J Appl Toxicol. 20 Suppl 1:S145-151.

Cecchini et al. (2017) “Modeling Fungal Melanin Buildup: Biomimetic Polymerization of 1,8-Dihydroxynaphthalene Mapped by Mass Spectrometry,” Chem. Eur. J. 23, 8092-8098.

(Continued)

*Primary Examiner* — Genevieve S Alley

(74) *Attorney, Agent, or Firm* — Leydig, Voit & Mayer, Ltd.

(57) ABSTRACT

Aspects disclosed herein include a material and formulations having the material, the material comprising functionalized artificial melanin nanoparticles, wherein: each functionalized artificial melanin nanoparticle comprises a surface functionalized with a modifier agent via a linker group; wherein the modifier agent comprises the linker group and a functional group attached to the linker group; and wherein the linker group is an amine group. Aspects also include a method of healing skin damage using the disclosed formulations.

36 Claims, 74 Drawing Sheets

(56) References Cited

OTHER PUBLICATIONS

Chang et al. (2018) "Expression of cytokines and chemokines in mouse skin treated with sulfur mustard," Toxicol Appl Pharmacol. 355:52-59.PMC6438172.
Chen et al. (2011) "1,25-Dihydroxyvitamin D(3) suppresses inflammation-induced expression of plasminogen activator inhibitor-1 by blocking nuclear factor-kappaB activation," Arch Biochem Biophys. 507(2):241-247.PMC3049452.
Cho et al. (2001) "Hydrogen Peroxide Stimulates Macrophage Vascular Endothelial Growth Factor Release," Am J Physiol Heart Circ Physiol. 280:H2357-H2363.
Chonn et al. (1995) "Recent advances in liposomal drug-delivery systems," Curr. Opin. Biotechnol. 6:698-708.
Cohen-Lahav et al. (2006) "Vitamin D decreases NFkappaB activity by increasing IkappaBalpha levels," Nephrol Dial Transplant. 21(4): 889-897.
Comino-Sanz et al. (Aug. 2021) "The Role of Antioxidants on Wound Healing: A Review of the Current Evidence," J Clin Med. 10(16):3558.
Cui et al. (2020) "Activation of JUN in fibroblasts promotes pro-fibrotic programme and modulates protective immunity," Nat Commun. 11(1):2795.PMC7270081.
Dai et al. (2015) "Monodispersed Nb205 Microspheres: Facile Synthesis, Air/Water Interfacial Self-Assembly, Nb2O5-Based Composite Films, and Their Selective No. 2 Sensing," Adv. Mater. Interfaces 2, 1500167.
D'Alba et al. (2019) "Melanosomes: Biogenesis, Properties, and Evolution of an Ancient Organelle," Physiol. Rev. 99, 1-19.
Darchini-Maragheh et al. (2018) "Delayed Complications and Long-term Management of Sulfur Mustard Poisoning: Recent Advances by Iranian Researchers (Part I of II)," Iran J Med Sci. 43(2):103-124.PMC5936843.
Das et al. (2016) "Early indicators of survival following exposure to mustard gas: Protective role of 25(OH)D," Toxicol Lett. 248:9-15.PMC5588853.
Das et al. (2016) "The physics of stratum corneum lipid membranes," Philos Trans A Math Phys Eng Sci. 374(2072). PMC4920276.
Das et al. (2018) "Defining the timing of 25(OH)D rescue following nitrogen mustard exposure," Cutan Ocul Toxicol. 37(2):127-132. PMC6025804.
Deng et al. (2019) "M1 Macrophage Mediated Increased Reactive Oxygen Species (ROS) Influence Wound Healing via the MAPK Signaling in vitro and in vivo," Toxicol Appl Pharmacol. 366:83-95.
Devita et al. (2008) "A history of cancer chemotherapy," Cancer Res. 68(21):8643-8653.
D'Ischia et al. (2020) "Melanin Biopolymers: Tailoring Chemical Complexity for Materials Design," Angew. Chem. Int. Ed. 59, 11196-11205.
Eisenman et al. (2012) "Synthesis and assembly of fungal melanin," Appl. Microbiol. Biotechnol. 93, 931-940.
Ernst et al. (Jan. 2023) "Vitamin D3 and deconvoluting a rash," JCI Insight. 8(2).PMC9977299.
Eyles et al. (1997) "Oral Delivery and Fate of Poly(lactic acid) Microsphere-encapsulated Interferon in Rats," J Pharm. Pharmacol. 49:669-674.
Ezquerra et al. (2009) "Porcine myelomonocytic markers and cell populations," Developmental & Comparative Immunology. 33(3):284-298.
Fitzgerald (2008) "Chemical warfare and medical response during World War I," Am J Public Health. 98(4):611-625.PMC2376985.
Frew et al. (2020) "The erythema Q-score, an imaging biomarker for redness in skin inflammation," Experimental Dermatology 30 (3), 377-383.
Friedman et al. (Jun. 2021) "Physical properties of gold nanoparticles affect skin penetration via hair follicles," Nanomedicine. 36:102414.
Gao et al. (1995) "Controlled Release of a Contraceptive Steroid from Biodegradable and Injectable Gel Formulations: In Vitro Evaluation," Pharm. Res. 12:857-863.
Grether-Beck et al. (Nov. 2021) "Air Pollution-Induced Tanning of Human Skin," Br J Dermatol. 185(5): 1026-1034.
Griffin et al. (Sep. 2021) "JUN promotes hypertrophic skin scarring via CD36 in preclinical in vitro and in vivo models," Sci Transl Med. 13(609):eabb3312.PMC8988368.
Guo et al. (2008) "Solution-Based Doping of Manganese into Colloidal ZnO Nanorods," The Journal of Physical Chemistry C. 112(24):8832-8838.
Guzik et al. (2003) "Nitric oxide and superoxide in inflammation and immune regulation," J Physiol Pharmacol. 54(4):469-487.
Holstege et al. (1997) "Chemical warfare. Nerve agent poisoning," Crit Care Clin. 13(4):923-942.
Hong et al. (2016) "Sprayable Ultrafast Polydopamine Surface Modifications," Adv. Mater. Interfaces 3, 1500857.
Hu et al. (2020) "Structurally Colored Inks from Synthetic Melanin-Based Crosslinked Supraparticles," ACS Materials Letters. 3(1):50-55.
Hu et al. (Aug. 2021) "Non-Iridescent Structural Color Control via Inkjet Printing of Self-Assembled Synthetic Melanin Nanoparticles," Chem. Mater. 33, 6433-6442.
Huang et al. (2017) "Mimicking Melanosomes: Polydopamine Nanoparticles as Artificial Microparasols," ACS Cent Sci. 3(6):564-569.PMC5492417.
International Search Report and Written Opinion, dated Jun. 28, 2024, corresponding to International Application No. PCT/US2023/035593, (from which the present application claims priority,) 16 pp.
Jain et al. (2011) "Sulfur mustard analog, 2-chloroethyl ethyl sulfide-induced skin injury involves DNA damage and induction of inflammatory mediators, in part via oxidative stress, in SKH-1 hairless mouse skin," Toxicol Lett. 205(3):293-301.PMC3207490.
Jain et al. (2014) "Myeloperoxidase deficiency attenuates nitrogen mustard-induced skin injuries," Toxicology. 320:25-33. PMC4019690.
Jia et al. (Jan. 2021) "Strategic Advances in Spatiotemporal Control of Bioinspired Phenolic Chemistries in Materials Science," Adv. Funct. Mater. 31, 2008821.
Joseph et al. (2011) "Structural changes in the skin of hairless mice following exposure to sulfur mustard correlate with inflammation and DNA damage," Exp Mol Pathol. 91(2):515-527.PMC3630073.
Joseph et al. (2016) "Tissue injury and repair following cutaneous exposure of mice to sulfur mustard," Ann N Y Acad Sci. 1378(1): 118-123.PMC5063676.
Joseph et al. (2018) "Sulfur mustard induced mast cell degranulation in mouse skin is inhibited by a novel anti-inflammatory and anticholinergic bifunctional prodrug," Toxicol Lett. 293:77-81. PMC5938161.
Ju et al. (2011) "Bioinspired Polymerization of Dopamine to Generate Melanin-Like Nanoparticles Having an Excellent Free-Radical-Scavenging Property," Biomacromolecules 12 (3), 625-632.
Jung et al. (2006) "Preparation and Characterization of Eugenol-Grafted Chitosan Hydrogels and their Antioxidant Activities," J App Polym Sci. 99(6):3500-3506.
Kan et al. (2003) "Sulfur mustard-induced apoptosis in hairless guinea pig skin," Toxicol Pathol. 31(2): 185-190.
Kehe et al. (2009) "Molecular toxicology of sulfur mustard-induced cutaneous inflammation and blistering," Toxicology. 263(1):12-19.
Kim et al. (2012) "Biological importance and applications of squalene and squalane," Adv Food Nutr Res. 65:223-233.
Kumar et al. (2015) "Nitrogen mustard exposure of murine skin induces DNA damage, oxidative stress and activation of MAPK/Akt-AP1 pathway leading to induction of inflammatory and proteolytic mediators," Toxicol Lett. 235(3): 161-171.PMC4430414.
Lagishetty et al. (2011) "Vitamin D metabolism and innate immunity," Mol Cell Endocrinol. 347(1-2):97-105.PMC3200473.
Langenberg et al. (1998) "Toxicokinetics of sulfur mustard and its DNA-adducts in the hairless guinea pig," Drug Chem Toxicol. 21 Suppl 1:131-147.
Laskin et al. (2010) "Oxidants and Antioxidants in Sulfur Mustard-Induced Injury," Ann N Y Acad Sci. 1203(1):92-100.
Laskin et al. (2011) "Macrophages and tissue injury: agents of defense or destruction?" Annu Rev Pharmacol Toxicol. 51:267-288.
Lee et al. (2007) "Mussel-Inspired Surface Chemistry for Multifunctional Coatings," Science 318, 426-430.

(56) References Cited

OTHER PUBLICATIONS

Li et al. (2007) "Pathophysiology of Acute Wound Healing," Clin Dermatol. 25(1):9-18.
Li et al. (Jan. 2022) "Tension gradient-driven rapid self-assembly method of large-area colloidal crystal film and its application in multifunctional structural color displays," Chem. Eng. J. 427, 130658.
Lin et al. (2007) "Melanocyte Biology and Skin Pigmentation," Nature. 445(7130):843-850.
Lindsay et al. (1996) "Assessment of the biochemical effects of percutaneous exposure of sulphur mustard in an in vitro human skin system," Hum Exp Toxicol. 15(3):237-244.
Liu et al. (2016) "Synthesis of hollow carbon nanostructures using a ZnO template method," New Carbon Materials. 31(1):87-91.
Liu et al. (2017) "Capillary Gradient-Induced Self-Assembly of Periodic Au Spherical Nanoparticle Arrays on an Ultralarge Scale via a Bisolvent System at Air/Water Interface," Adv. Mater. Interfaces 4, 1600976.
Liu et al. (2020) "Melanin-Like Nanomaterials for Advanced Biomedical Applications: A Versatile Platform with Extraordinary Promise," Adv. Sci. 7, 1903129.
Liu et al. (2020) "pH-Triggered Assembly of Natural Melanin Nanoparticles for Enhanced PET Imaging," Frontiers in Chemistry, 8, 755, pp. 1-9.
Loo et al. (2011) "Mechanism of Hydrogen Peroxide-Induced Keratinocyte Migration in a Scratch-Wound Model," Free Radic Biol Med. 51(4):884-892.
Maia et al. (2019) "pavo 2: New tools for the spectral and spatial analysis of colour in r," Methods in Ecology and Evolution 10, 1097-1107.
Manini et al. (2018) "Characterization and Fate of Hydrogen-Bonded Free-Radical Intermediates and Their Coupling Products from the Hydrogen Atom Transfer Agent 1,8-Naphthalenediol," ACS Omega 3, 3918-3927.
Manini et al. (2019) "A Robust Fungal Allomelanin Mimic: An Antioxidant and Potent π-Electron Donor with Free-Radical Properties that can be Tuned by Ionic Liquids," ChemPlusChem 84, 1331-1337.
Manini et al. (2020) ""Blackness" is an index of redox complexity in melanin polymers," Polym. Chem. 11, 5005-5010.
Manini et al. (Apr. 2020) "Synthetic mycomelanin thin films as emergent bio-inspired interfaces controlling the fate of embryonic stem cells," J. Mater. Chem. B 8, 4412-4418.
Mattes et al. (1986) "DNA sequence selectivity of guanine-N7 alkylation by nitrogen mustards," Nucleic Acids Res. 14(7):2971-2987.PMC339715.
Mavridi-Printezi et al. (2020) "Bio-Applications of Multifunctional Melanin Nanoparticles: From Nanomedicine to Nanocosmetics," Nanomaterials 10.
Mavridi-Printezi et al. (Sep. 2021) "The Photophysics and Photochemistry of Melanin-Like Nanomaterials Depend on Morphology and Structure," Chem. Eur. J. 27, 16309-16319.
Mccallum et al. (Mar. 2021) "Allomelanin: A Biopolymer of Intrinsic Microporosity," J Am Chem Soc. 143(10):4005-4016.
Montagna et al. (1964) "The Skin of the Domestic Pig," J Invest Dermatol. 42:11-21.
Naghii (2002) "Sulfur mustard intoxication, oxidative stress, and antioxidants," Mil Med. 167(7):573-575.
"NanoComposix's Guide to Dynamic Light Scattering Measurement and Analysis" [dated Feb. 2015 (version 1.4), published by nanoComposix of San Diego, CA, and available at nanoComposix_Guidelines_for_DLS_Measurements_and_Analysis (last accessed Jun. 26, 2019).
Neil et al. (2020) "Human Skin Explant Model for the Investigation of Topical Therapeutics," Sci Rep 10(1).
Nguyen et al. (2013) "Characteristics of Curcumin-Loaded Poly (Lactic Acid) Nanofibers for Wound Healing," J Mater Sci. 48(20):7125-7133.
Nyska et al. (2001) "Effects of iodine on inducible nitric oxide synthase and cyclooxygenase-2 expression in sulfur mustard-induced skin injury in guinea pigs," Arch Toxicol. 74(12):768-774.
Ostro et al. (1989) "Use of liposomes as injectable-drug delivery systems," Am. J. Hosp. Pharm. 46, 1576-1587.
Paromov et al. (2007) "Sulfur mustard toxicity following dermal exposure: role of oxidative stress, and antioxidant therapy," J Burns Wounds. 7:e7.PMC2064967.
Radi (2018) "Oxygen radicals, nitric oxide, and peroxynitrite: Redox pathways in molecular medicine," Proc Natl Acad Sci U S A. 115(23):5839-5848.PMC6003358.
Rao (1995) "Recent developments of collagen-based materials for medical applications and drug delivery systems," J Biomater Sci. Polym. Ed. 7:623-645.
Requena et al. (1988) "Chemical warfare. Cutaneous lesions from mustard gas," J Am Acad Dermatol. 19(3):529-536.
Ries et al. (2009) "Matrix metalloproteinase-9 expression and release from skin fibroblasts interacting with keratinocytes: Upregulation in response to sulphur mustard," Toxicology. 263(1):26-31.
Robertson et al. (2012) "Adaptation of the Black Yeast Wangiella dermatitidis to Ionizing Radiation: Molecular and Cellular Mechanisms," PLoS ONE 7, e48674.
Rogalla et al. (2019) "Hot wings: thermal impacts of wing coloration on surface temperature during bird flight," J. R. Soc. Interface 16, 20190032.
Rogalla et al. (Jul. 2021) "The evolution of darker wings in seabirds in relation to temperature-dependent flight efficiency," J. R. Soc. Interface 18, 20210236.
Roy et al. (2006) "Dermal Wound Healing Is Subject to Redox Control," Mol Ther. 13(1):211-220.
Sanchez-Quesada et al. (2018) "Squalene Stimulates a Key Innate Immune Cell to Foster Wound Healing and Tissue Repair," Evid Based Complement Alternat Med. 2018:9473094.PMC6186384.
Sawyer et al. (2000) "Effects of selected arginine analogues on sulphur mustard toxicity in human and hairless guinea pig skin keratinocytes," Toxicol Appl Pharmacol. 163(1):75-85.
Shakarjian et al. (2006) "Preferential Expression of Matrix Metalloproteinase-9 in Mouse Skin After Sulfur Mustard Exposure," J Appl Toxicol. 26(3):239-246.
Shakarjian et al. (2010) "Mechanisms mediating the vesicant actions of sulfur mustard after cutaneous exposure," Toxicol Sci. 114(1):5-19.PMC2819970.
Sharma et al. (2010) "Nitrogen and sulphur mustard induced histopathological observations in mouse visceral organs," J Environ Biol. 31(6):891-905.
Sharma et al. (May 2010) "Comparative toxic effect of nitrogen mustards (HN-1, HN-2, and HN-3) and sulfur mustard on hematological and biochemical variables and their protection by DRDE-07 and its analogues," Int J Toxicol. 29(4):391-401.
Shen et al. (2020) "Natural Polyphenol Inspired Polycatechols for Efficient siRNA Delivery," CCS Chemistry 2, 146-157.
Shi et al. (1996) "Regulation of Macrophage Inflammatory Protein-160 mRNA by Oxidative Stress," J Biol Chem. 271(10):5878-5883.
SIES (2015) "Oxidative Stress: A Concept in Redox Biology and Medicine," Redox Biol. 4:180-183.PMC4309861.
Simon et al. (2010) "The Red and the Black," Acc Chem Res. 43(11):1452-1460.
Siwicka et al. (Feb. 2021) "Synthetic Porous Melanin," JACS. 143(8):3094-3103.
Steinritz et al. (2009) "Sulphur mustard induces time- and concentration-dependent regulation of NO-synthesizing enzymes," Toxicol Lett. 188(3):263-269.
Summerfield et al. (2015) "The immunology of the porcine skin and its value as a model for human skin," Molecular Immunology. 66(1):14-21.
Sunil et al. (2012) "Role of reactive nitrogen species generated via inducible nitric oxide synthase in vesicant-induced lung injury, inflammation and altered lung functioning," Toxicol Appl Pharmacol. 261(1):22-30.
Sunoqrot et al. (2020) "Tuning the Surface Chemistry of Melanin-Mimetic Polydopamine Nanoparticles Drastically Enhances their Accumulcation into Excised Human Skin," ACS Biomaterials Science & Engineering, 6, 4424-4435.

(56) References Cited

OTHER PUBLICATIONS

Suzuki et al. (Jul. 2022) "Whole picture of human stratum corneum ceramides, including the chain-length diversity of long-chain bases," J Lipid Res. 63(7): 100235.PMC9240646.
Thomas et al. (2003) "Panther: A Library of Protein Families and Subfamilies Indexed by Function," Genome Res. 2003;13(9):2129-2141.
Tripathi (2007) "The role of nitric oxide in inflammatory reactions," FEMS Immunol Med Microbiol. 51(3):443-452.
Vallet et al. (2012) "Acute and long-term transcriptional responses in sulfur mustard-exposed SKH-1 hairless mouse skin," Cutan Ocul Toxicol. 31(1):38-47.
Vogel et al. (2011) "Wafer-Scale Fabrication of Ordered Binary Colloidal Monolayers with Adjustable Stoichiometries," Adv. Funct. Mater. 21, 3064-3073.
Wahler et al. (2020) "Antioxidant/stress response in mouse epidermis following exposure to nitrogen mustard," Exp Mol Pathol. 114:104410.PMC7237310.
Wang et al. (2018) "Superoxide Dismutases: Dual Roles in Controlling ROS Damage and Regulating ROS Signaling," J Cell Biol. 217(6):1915-1928.
Wang et al. (2020) "Metal-Containing Polydopamine Nanomaterials: Catalysis, Energy, and Theranostics, " Small, 16, e1907042.
Wu et al. (Feb. 2021) "Phenolic-enabled nanotechnology: versatile particle engineering for biomedicine," Chem. Soc. Rev. 50, 4432-4483.
Xiao et al. (2015) "Bio-Inspired Structural Colors Produced via Self-Assembly of Synthetic Melanin Nanoparticles," ACS Nano 9, 5454-5460.
Xiao et al. (2017) "Bioinspired Bright Noniridescent Photonic Melanin Supraballs," Sci. Adv. 3, e1701151.
Xiao et al. (2019) "Experimental and theoretical evidence for molecular forces driving surface segregation in photonic colloidal assemblies," Sci. Adv. 5, eaax1254.
Xiao et al. (2020) "Bioinspired Melanin-Based Optically Active Materials," Advanced Optical Materials 8, 19, 2000932.
Xiao et al. (Jan. 2017) "A Cooperative Copper Metal-Organic Framework-Hydrogel System Improves Wound Healing in Diabetes," Adv Funct Mater. 27(1):1604872.
Xie et al. (Mar. 2021) "Peroxidase-Like Reactivity at Iron-Chelation Sites in a Mesoporous Synthetic Melanin," CCS Chemistry 3, 1483-1490.
Yang et al. (2014) "Jack of all trades: versatile catechol crosslinking mechanisms," Chem. Soc. Rev. 43, 8271-8298.
Yang et al. (2019) "Recent developments in polydopamine fluorescent nanomaterials," Mater. Horiz. 7, 746-761.
Yang et al. (2020) "Structural and Functional Tailoring of Melanin-Like Polydopamine Radical Scavengers," CCS Chemistry 2, 128-138.
Yang et al. (Jun. 2021) "Stimuli-responsive polydopamine-based smart materials," Chem. Soc. Rev. 50, 8319-8343.
Yaren et al. (2007) "Lung toxicity of nitrogen mustard may be mediated by nitric oxide and peroxynitrite in rats," Res Vet Sci. 83(1):116-122.
Yilmaz et al. (2006) "Effect of lipid-containing, positively charged nanoemulsions on skin hydration, elasticity and erythema—an in vivo study," Int J Pharm. 307(2):232-238.
Zhou et al. (2019) "Artificial Allomelanin Nanoparticles," ACS Nano. 13(10):10980-10990.
Zhou et al. (Apr. 2021) "Anisotropic Synthetic Allomelanin Materials via Solid-State Polymerization of Self-Assembled 1,8-Dihydroxynaphthalene Dimers," Angew Chem Int Ed Engl. 60(32):17464-17471.
Zhou et al. (Nov. 2022) "Hydrophobic Melanin via Post-Synthetic Modification for Controlled Self-Assembly," ACS Nano. 16(11):19087-19095.
Zou et al. (2020) "Regulating the absorption spectrum of polydopamine," Sci. Adv. 6, eabb4696.

4 mg/mL in $H_2O$

S-AMNP-$NMe_2$
C 66.12%
H 4.858%
N 5.31%

$C_4N_2$ 1,8-DHN: $C_{10}$

C 9.10%
N 5.31%
C 57.02%

Each DHN unit contains
(9.10/4)/(57.02/10)= 0.40

1: $H_2O$ + $CH_2Cl_2$

2: $H_2O$ + $CHCl_3$

3: $H_2O$ + Toluene

4: $H_2O$ + Ethyl Acetate

5: $H_2O$ + Hexane

6: $H_2O$ + Cyclohexane

W-AMNP-$C_{18}$

H-AMNP-$C_{18}$

L-AMNP-$C_{18}$

| | L1 (nm) | L2 (nm) | L3 (nm) | L4 (nm) |
|---|---|---|---|---|
| Solid | 181 ± 5 | 364 ± 10 | 550 ± 16 | 770 ± 23 |
| Walnut | 174 ± 10 | 277 ± 9 | 442 ± 19 | 546 ± 15 |
| Hollow | 164 ± 6 | 309 ± 14 | 454 ± 14 | 577 ± 20 |
| Lacey | 163 ± 11 | 272 ± 6 | 425 ± 11 | 539 ± 20 |

Demographic information
| Ethnicity (self-described) | Number of participants |
|---|---|
| African American | 2 |
| Caucasian | 5 |
| Hispanic, Latino or Spanish origin | 2 |
| Unspecified/Declined | 1 |
FIG. 37D
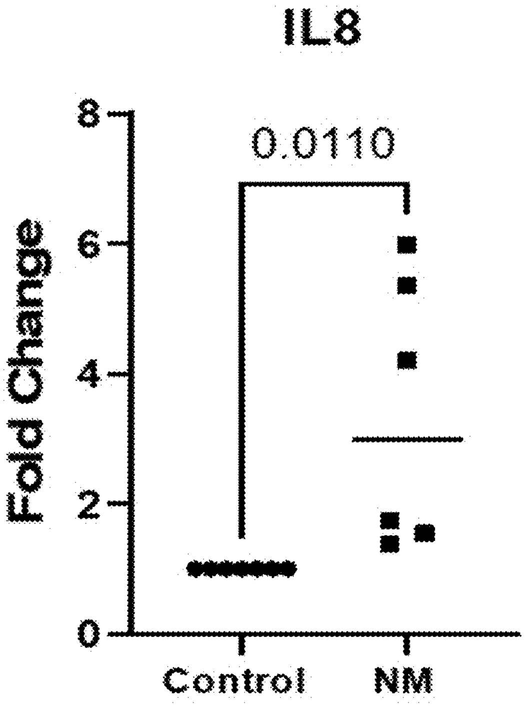
FIG. 38A
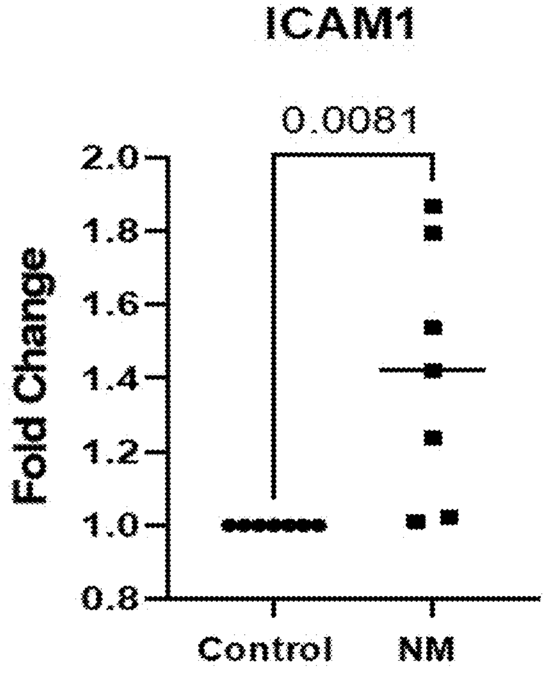
FIG. 38B

TEST

| VEHICLE FORMULATION | NM | NM + SMP1 | NM + SMP2 |
|---|---|---|---|
| Aquaphor | 1, 2, 4, 5, 7, 8 | 1, 2, 4, 5, 7, 8 | 1, 2, 4, 5, 7, 8 |
| Cerave | 1, 3, 4, 6, 7, 9 | 1, 3, 4, 6, 7, 9 | 1, 3, 4, 6, 7, 9 |
| Hydrogel | 2, 3, 5, 6, 8, 9 | 2, 3, 5, 6, 8, 9 | 2, 3, 5, 6, 8, 9 |

[a] Diameter of particles determined via TEM & DLS
[b] DPPH Assay
[c] Contact angle measurements
[d] FT-IR Spectroscopy, XPS, ssNMR, Mass Spectrometry

HYDROPHOBIC SYNTHETIC MELANIN NANOPARTICLES

CROSS REFERENCE TO RELATED APPLICATIONS

This application is a continuation of and claims the benefit of priority to PCT International Application No. PCT/US2023/035593, filed Oct. 20, 2023, which claims the benefit of priority to U.S. Provisional Patent Application No. 63/418,257, filed Oct. 21, 2022, each of which is hereby incorporated by reference in its entirety.

STATEMENT REGARDING FEDERALLY SPONSORED RESEARCH OR DEVELOPMENT

This application was made with government support under grant number AR079795 awarded by the National Institutes of Health and grant number FA9550-18-1-0142 awarded by the Air Force Office of Scientific Research. The government has certain rights in the invention.

BACKGROUND OF INVENTION

Melanin is a natural pigment found in skin and hair that serves a primary role in UV radiation protection by absorption of incident radiation and by radical scavenging activity. Synthetic or artificial melanin materials successfully recapitulate these properties, obtained via oxidative polymerization of inexpensive monomers, bypassing issues of yield and purity that arise from natural extraction. The resulting materials are typically hydrophilic, which limits the application of these materials beyond aqueous systems.

SUMMARY OF THE INVENTION

The materials and methods disclosed herein provide surface-modified or functionalized artificial melanin materials, such as artificial melanin nanoparticles, optionally hydrophobic artificial melanin nanoparticles, methods for making these, formulations of these materials, and method for treating subjects, such as to facilitate skin healing, using these materials and formulations. Methods, disclosed herein, for functionalizing artificial melanin nanoparticles provide a scheme for a wide range of functionalization or property modifications of artificial melanin materials, including but not limited to increasing hydrophobicity thereof.

Aspects disclosed herein include a functionalized artificial melanin material comprising: a surface functionalized with a modifier agent via a linker group; wherein the modifier agent comprises the linker group and a functional group attached to the linker group; and wherein the linker group is a nucleophilic group.

Aspects disclosed herein include a melanin-containing formulation comprising: one or more solvents (optionally one or more hydrophobic solvents); and a functionalized artificial melanin material dispersed in the one or more solvents; wherein: the functionalized artificial melanin material comprises a surface functionalized with a modifier agent via a linker group; the modifier agent comprises the linker group and a functional group attached to the linker group; and the linker group is a nucleophilic group.

Aspects disclosed herein include a method for treatment of a subject, the method comprising: topically administering a melanin formulation to damaged skin of the subject; wherein the functionalized artificial melanin material comprises a surface functionalized with a modifier agent via a linker group; wherein the modifier agent comprises the linker group and a functional group attached to the linker group; wherein the linker group is a nucleophilic group; wherein the melanin formulation comprises one or more solvents (optionally one or more hydrophobic solvents) and the functionalized artificial melanin material dispersed in the one or more solvents (optionally one or more hydrophobic solvents); wherein the administered functionalized artificial melanin material comprises an extracellular functionalized artificial melanin material at the damaged skin; and facilitating skin healing at the damaged skin via at least the extracellular functionalized artificial melanin material; wherein the step of facilitating skin healing comprises at least a portion of the extracellular artificial melanin material performing a therapeutic extracellular activity.

Aspects disclosed herein include a method for making a functionalized artificial melanin material, the method comprising: providing unfunctionalized artificial melanin nanoparticles; and exposing, for a finite time, the unfunctionalized artificial melanin nanoparticles to a precursor of the modifier agent; wherein the step of exposing comprises: conjugating the unfunctionalized artificial melanin nanoparticles with the precursor thereby forming functionalized artificial melanin nanoparticles having a modifier agent; wherein the functionalized artificial melanin nanoparticles comprises a surface functionalized with the modifier agent via a linker group; wherein the modifier agent comprises the linker group and a functional group attached to the linker group; and wherein the linker group is a nucleophilic group.

Aspects disclosed herein include a functionalized artificial melanin material comprising: a surface functionalized with a modifier agent via a linker group; wherein the modifier agent comprises the linker group and a functional group attached to the linker group; and wherein the linker group is an amine group. Optionally, the material comprises functionalized artificial melanin nanoparticles, wherein each functionalized artificial melanin nanoparticle independently comprises a surface functionalized with the modifier agent via the linker group.

Aspects disclosed herein include a material comprising functionalized artificial melanin nanoparticles, wherein: each functionalized artificial melanin nanoparticle comprises a surface or portion functionalized with a modifier agent via a linker group; wherein the modifier agent comprises the linker group and a functional group attached to the linker group; and wherein the linker group is an amine group. Optionally, the linker group is attached to a respective particle via a single bond or a double bond. Optionally, the linker group is a primary amine group. Optionally, the linker group is characterized by formula FX1A or FX1B:

(FX1A)

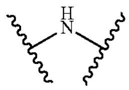

or (FX1A)

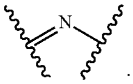

.

Optionally, the modifier agent is characterized by formula FX2A or FX2B:

(FX2A)

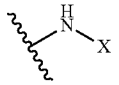

or (FX2B)

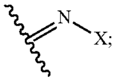

wherein X is the functional group. Optionally, each linker group is independently attached to a phenyl group or a quinone of a respective artificial melanin nanoparticle. Optionally, the modifier agent attached to the respective functionalized artificial melanin nanoparticle is a product of a Michael Addition or via a Schiff Base reaction. Optionally, the functionalized surface is at least partially an outer surface of each artificial melanin nanoparticle and/or at least partially an inner pore surface of each artificial melanin nanoparticle. Optionally, the artificial melanin nanoparticles are characterized as polydopamine and/or allomelanin.

Aspects disclosed herein further include dispersions comprising: one or more solvents; and the material (or functionalized artificial melanin nanoparticles thereof), according to any embodiment(s) disclosed herein, in the one or more solvents. Optionally, the dispersion (or material thereof) is characterized by a contact angle of at least 90°, optionally at least 110°, optionally at least 120°. As used herein, contact angles greater than 90 degrees is defined as hydrophobic. In embodiments, sessile drop measurements using water as the solvent is an adequate measure of hydrophobicity. Optionally, the dispersion (or material thereof) is characterized by a pH selected from the range of 3 to 11.

Aspects disclosed herein further include thin films of the material (or functionalized artificial melanin nanoparticles thereof), according to any embodiment(s) disclosed herein. Optionally, the thin film has or exhibits structural color. Optionally, the thin film has one or more monolayers of the functionalized artificial melanin nanoparticles. Optionally, the thin film has one, two, three, or four monolayers of the functionalized artificial melanin nanoparticles.

Aspects disclosed herein further include methods for making the material (or functionalized artificial melanin nanoparticles thereof), according to any embodiment(s) disclosed herein, the methods comprising: providing unfunctionalized artificial melanin nanoparticles; and exposing, for a finite time, the unfunctionalized artificial melanin nanoparticles to a precursor of the modifier agent; wherein the step of exposing comprises: conjugating the unfunctionalized artificial melanin nanoparticles with the precursor thereby forming the functionalized artificial melanin nanoparticles having the modifier agent. In embodiments, unfunctionalized artificial melanin nanoparticles are free of the modifier agent, according to embodiments thereof disclosed herein, or are pre-functionalization/pre-modification by addition/conjugation of the modifier agent (or precursor thereof) to artificial melanin nanoparticles. Optionally, the unfunctionalized artificial melanin nanoparticles are hydrophilic and are dispersed in an aqueous solution. Optionally, the step of conjugating comprises making the functionalized artificial melanin nanoparticles more hydrophobic (e.g., higher contact angle) than the provided unfunctionalized artificial melanin nanoparticles. Optionally, the method comprises aging or oxidizing the unfunctionalized artificial melanin nanoparticles, optionally to form or increase content of quinones in the unfunctionalized artificial melanin nanoparticles.

Without wishing to be bound by any particular theory, there may be discussion herein of beliefs or understandings of underlying principles relating to the devices and methods disclosed herein. It is recognized that regardless of the ultimate correctness of any mechanistic explanation or hypothesis, an embodiment of the invention can nonetheless be operative and useful.

BRIEF DESCRIPTION OF THE DRAWINGS

FIG. 1A: Schematic synthesis of fresh AMNP, aged AMNP, and modified AMNP. FIG. 1B: TEM images of solid AMNP (S-AMNP), walnut AMNP (W-AMNP), hollow AMNP (H-AMNP), and lacey AMNP (L-AMNP), scale bars 200 nm.

FIG. 2A: Post-synthetic modification on AMNP using DMEN, and TEM image of resulting S-AMNP-$NMe_2$, scale bar 200 nm.

FIG. 2B: XPS (i) survey spectra, (ii) $N_{1s}$ spectra of S-AMNP; (iii) Survey spectra, (iv) $N_{1s}$ spectra of S-AMNP-$NMe_2$. FIG. 2C: (i) Hydrodynamic diameter and (ii) Zeta potentials of S-AMNP and S-AMNP-$NMe_2$ in Mili-Q water at different pH. FIG. 2D: STEM-EDX mapping analysis of S-AMNP-$NMe_2$, scale bars 200 nm.

FIG. 3A: Post-synthetic modification on AMNP using $C_6$—$NH_2$ and $C_{18}$—$NH_2$, and TEM image of resulting S-AMNP-$C_{18}$, scale bar 200 nm. FIG. 3B: XPS survey spectra and $N_{1s}$ spectra of S-AMNP-$C_6$ and S-AMNP-$C_{18}$. FIG. 3C: (i) Hydrodynamic diameter of S-AMNP, S-AMNP-$C_6$, and S-AMNP-$C_{18}$ in EtOH; (ii) FTIR spectra of S-AMNP, S-AMNP-$C_6$, and S-AMNP-$C_{18}$. FIG. 3D: Distribution of S-AMNP, S-AMNP-$C_{18}$, and S-AMNP-$C_6$ in water and different solvents ($CH_2Cl_2$, $CHCl_3$, and ethyl acetate). FIG. 3E: Static water contact angle data of drop-casted S-AMNP, S-AMNP-$C_{18}$, and S-AMNP-$C_6$ films.

FIG. 4A: General procedure of air/water interfacial self-assembly. FIG. 4B: Top-view SEM images of S-AMNP-$C_{18}$ monolayer, scale bars (i) 1 μm, (ii) 500 nm, and (iii) corresponding FFT image. FIG. 4C: Reflectance spectra of S-AMNP-$C_{18}$ with different number of layers (L1, L2, L3, L4). The experimental reflectance curves are averaged over 5 locations on the film and the shaded region represents error bars as standard deviation. FIG. 4D: Cross-sectional SEM images and corresponding optical microscopy images of (i) L1, (ii) L2, (iii) L3, and (iv) L4 of S-AMNP-$C_{18}$. FIG. 4E: Cross-sectional SEM images and corresponding optical microscopy images of (i) L1, (ii) L2, (iii) L3, and (iv) L4 of W-AMNP-$C_{18}$. FIG. 4F: Cross-sectional SEM images and corresponding optical microscopy images of (i) L1, (ii) L2, (iii) L3, and (iv) L4 of H-AMNP-$C_{18}$. FIG. 4G: Cross-sectional SEM images and corresponding optical microscopy images of (i) L1, (ii) L2, (iii) L3, and (iv) L4 of L-AMNP-$C_{18}$, scale bars 500 nm.

(FIG. 12B) H-AMNP (206.8 nm, PDI=0.195) and H-AMNP-$NMe_2$ (307.5 nm, PDI=0.324); (FIG. 12C) L-AMNP (200.7 nm, PDI=0.205) and L-AMNP-$NMe_2$ (254.1 nm, PDI=0.202). FIG. 12D: Zeta potentials of AMNP and AMNP-NMez in Mili-Q water.

FIG. 18A: Survey and $N_{1s}$ spectra of AMNP-$C_5$—OH modified by 5-amino-1-pentanol; (FIG. 18B) Survey and $N_{1s}$ spectra of AMNP-tBu modified by tert-butylamine; (FIG. 18C) Survey and $N_{1s}$ spectra of AMNP-$C_{10}$—OH modified by 10-amino-1-decanol; (FIG. 18D) Survey and $N_{1s}$ spectra of AMNP-$C_6$—$NH_2$ modified by 1,6-hexanediamine; (FIG. 18E) Survey, $N_{1s}$, and $F_{1s}$ spectra of AMNP-F modified by 2,2,3,3,4,4,5,5,6,6,7,7,8,8,9,9,9-heptadecafluorononylamine.

FIG. 23A: AMNP-$C_{18}$. FIG. 23B: PDA-$C_{18}$.

FIG. 24A: Compared AMNP and hydrophobic AMNPs. There is an emergence of new peaks that correspond to 2920 $cm^{-1}$ and 2850 $cm^{-1}$ that correspond to alkane C—H bond stretch, indicating attachment of the alkylamine to the surface of the particle. FIG. 24B: FTIR spectra of PDA and PDA-$C_{18}$, showing peaks at 2920 $cm^{-1}$ and 2850 $cm^{-1}$ that correspond to alkane C—H bond stretches.

FIG. 34A: Generalized scheme for polydopamine (PDA) preparation and modification. FIG. 34B: Core=active SMP component. Shell=covalent surface modification. FIG. 34C: TEM images and zeta (z) potential of the 5 PDA-based SMPs. FIG. 34D: Generalized scheme for allomelanin (ANP) preparation and further modification. FIG. 34E: TEM images and zeta potential of the 5 ANP-based SMPs.

FIGS. 37A-37D: Degree of subepidermal blisters and necrotic (dyskeratotic) keratinocytes on H&E (black arrows). Severity scored by blinded dermatopathologist. Human explants exposed to NM followed by intervention with vehicle or PDA (n=10). NTC=no NM treatment control. Scale bar=100 μm. Demographic information. 10 participants were all females, age range 25-51 years, median age ±s.d. 36±6.4 years.

FIGS. 38A-38D: Biomarker validation in human skin explants correlate with clinical trial study of NM exposure in vivo, upregulation of numerous inflammatory pathways. FIGS. 38A-38B: IL-8 and ICAM1 protein confirmed and quantitative protein Ab array (T-test, n=6-7). FIGS. 38C-38D: ccl20 and osm gene expression confirmed by qRT-PCR (T-test, n=7).

FIG. 41A: PDA intervention significantly reduces early wound area reduction on days 2 and 3 (n=16) (FIG. 41B) resulting in smaller wounds at day 14. FIG. 41C: NM causes deep injury in the skin. PDA intervention limits the depth of injury. FIG. 41D: Immunophenotyping of wounds and corresponding splenic populations show increase in reparative immune cells.

FIG. 43A: Rate of eschar detachment plotted (n=10). FIG. 43B: Wound histology at day 16. FIG. 43C: PDA intervention shows significantly reduced phospho-JNK activation with (p<0.05, n=3). FIG. 43D: Smaller focal scars measured by Masson's trichome staining.

FIG. 44B: UV+PDA in water has superficial damage. FIG. 44C: UV+PDA in Aquaphor® has relatively mild epidermal damage. FIG. 44D: UV+PDA-C18 in Aquaphor® has superficial epidermal damage w/no sub-epidermal blister. FIG. 44E: Skin redness measurements using chromameter on day 2 after initiation of sunburn (p=0.02, n=5). Solubility of modified PDA SMPs (FIG. 44F) enables compounding into a low concentration for in different skin vehicles (FIG. 44G).

FIG. 50A is an illustration showing the modifier agents attached to a melanin nanoparticle. FIG. 50B shows a chemical linking scheme between several monomer units of the PDA particle and the modifier agents.

STATEMENTS REGARDING CHEMICAL COMPOUNDS AND NOMENCLATURE

Figure 1A:
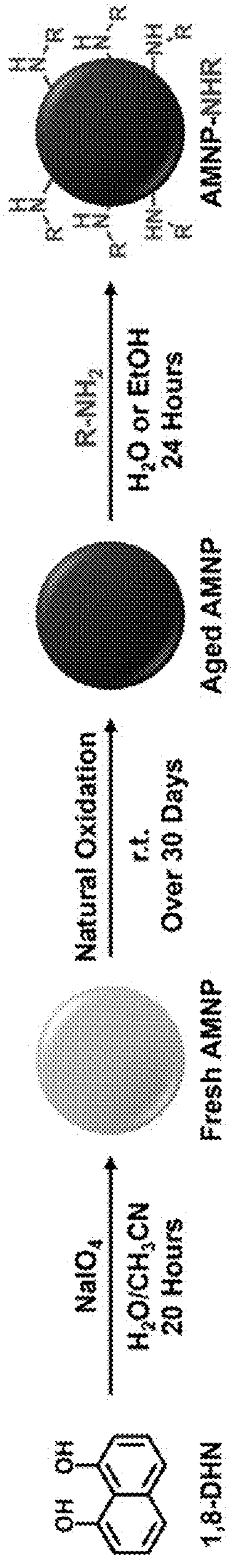
FIGS. 1A-1B: Synthesis and post-synthetic modification of AMNPs.

In general, the terms and phrases used herein have their art-recognized meaning, which can be found by reference to standard texts, journal references and contexts known to those skilled in the art. The following definitions are provided to clarify their specific use in the context of the invention.

The term "damaged skin" refers to a region of skin of a living subject, the region comprising damaged skin tissue. The damaged skin may optionally comprise free radical species, including extracellular free radical species. The damaged skin may optionally comprise inflammation. The damaged skin may optionally be a closed wound. The damaged skin may optionally include a stratum corneum. The damaged skin may optionally include one or more visible blisters, microscopic vesicles, and separation of the epidermis from the dermis. The damaged skin thereof may optionally include thermally-induced damage, chemically-induced damage, UV-induced damage, mechanical-friction damage, infection cellulitis-induced damage, and/or radiation-induced damage.

The term "closed wound" is intended to be consistent with the term of art, particularly in the fields of biomedical sciences, generally referring to a wound where there remnants of superficial skin attached. Generally, a closed wound may optionally, but not necessarily, comprise one or more small openings and/or compromised focal areas while having remnants of superficial skin attached. For example, generally, a lesion formed by excision biopsy of skin may be characterized as an open wound rather than a closed wound. For example, an open ulcer bed may be characterized as an open wound rather than a closed wound.

Scarring of skin or scarred skin refers to the same terms as understand by one of skill in dermatology. In particular, in aspects, this refers to skin having altered, abnormally appearing skin, raised skin, palpable nodules underneath the visible surface, altered skin color not resembling adjacent normal unaffected skin, altered shiny appearing skin, altered skin w/o visible hair, and/or altered skin the is less mobile and flexible compared to unaffected skin.

The term "therapeutic extracellular activity" refers to a therapeutic activity or therapeutic function that occurs extracellularly and/or involves at least one extracellular species directly performing or directly participating in the activity. The term "therapeutic extracellular activity" is intended to be understood by one of skill in art of biomedical sciences. For example, a therapeutic extracellular activity may refer to an extracellular melanin material performing or participating in a therapeutic activity. For example, a therapeutic extracellular activity may refer to an extracellular species being acted upon to therapeutic effect. For example, a therapeutic extracellular activity may refer to an extracellular melanin material performing or participating in a therapeutic activity upon or with an extracellular species, such as but not limited to extracellular free radical species, extracellular inflammatory factor(s), and/or extracellular enzymatic factor(s). A therapeutic activity or function is an activity or function that has a therapeutic or pharmaceutical effect or benefit, such as for treatment or amelioration of an injury, wound, tissue damage, disease, pathology, or condition. A therapeutic activity or function may comprise one or more chemical and/or physical processes, such as one or more chemical reactions or transformations, one or more physical transformations, covalent or non-covalent association or interaction between species, adsorption, etc. therapeutic activity may include, for example, processes such as, but not limited to, quenching or scavenging, adsorption, regulation such as downregulation of gene expression, inhibition of activity or function of one or more species such as but not limited to proteins, enzymes, or gene expression factors, and any combination thereof. The term "therapeutic intracellular activity" refers to a therapeutic activity or therapeutic function that occurs intracellular and/or involves at least one intracellular species directly performing or directly participating in the activity. A therapeutic activity or function may optionally be both a therapeutic extracellular activity and a therapeutic intracellular activity if both extracellular and intracellular species are involved or participating, for example.

The term "inflammatory factor" refers to a factor, as the term is recognized in the art, particularly biomedical sciences, associated with inflammation. An inflammatory factor may include, but is not limited to, proteins, genes, enzymes, and/or other factors associated with inflammation. The term "enzymatic factor" refers to a factor, as the term is recognized in the art, particularly biomedical sciences, associated with enzyme activity, optionally including enzymes associated with inflammation. Inflammatory factors and/or enzymatic factors may include, but are not limited to, TNFα, iNOS, MMP9, ERK1/2, p38, JNK, one or more factors associated with downregulation of pro-inflammatory signaling, one or more factors regulating expression of one or more genes associated with inflammation, one or more factors regulating expression of one or more genes associated with apoptosis, one or more factors regulating expression of MMP9, one or more proteins associated with the MAPK/ERK pathway, one or more enzymes associated with the MAPK/ERK pathway, or any combination of these. The term "apoptosis factor" refers to a factor, as the term is recognized in the art, particularly biomedical sciences, associated with cellular apoptosis.

The term "wound" refers to a region of a living subject having damaged tissue. The wound may optionally comprise free radical species, including extracellular free radical species. The wound may optionally comprise inflammation. The wound optionally is a wound of skin tissue or optionally includes damaged skin tissue. The wound may optionally include a stratum corneum. The wound may optionally include one or more blisters. The wound or the damaged tissue thereof may optionally include thermally-induced damage, chemically-induced damage, UV-induced damage, mechanical-friction damage, infection cellulitis-induced damage, and/or radiation-induced damage.

The term "free radical species" is intended to be consistent with the term as recognized by one of skill in the art of chemistry or biochemistry. A free radical species is generally a molecular species capable of independent existence and which comprise one or more unpaired electrons. Free radical species may include those that are mutagenic, carcinogenic, cause production of DNA strand breaks, and/or create DNA-protein crosslinks. Exemplary free radical species, include but are not limited to, reactive oxygenated species such as reactive oxygen species (ROS).

The terms "quenching" and "scavenging" are used interchangeably herein and refer to a process of quenching or scavenging free radical species consistent with the art of chemistry or biochemistry. Generally, quenching refers to a process or reaction with or involving a free radical species that results in a conversion/transformation of the free radical species to one or more products that are not free radical species or otherwise the cessation of the existence of the free radical species as a result of the reaction.

The term "non-melanin therapeutic agent" refers to a therapeutic agent that is not and does not itself comprise a melanin material. A therapeutic agent may be, for example, a species such as a compound, molecule, or a moiety that is therapeutically or pharmaceutically active when exposed to a living subject or is capable of treating or managing a condition, such as a disease, in a living subject. For example, a therapeutic agent may be or comprise a small molecule drug, a polymer, a peptide, an amino acid, DNA, or RNA. Optionally, for example, a therapeutic agent is one or more therapeutic agents (one or more compounds, molecules, or moieties, etc.) capable of facilitating skin healing.

The term "extracellular" when describing a species or process is intended to be consistent with the art of pharmacology or biochemistry and refers to the described species or process being found or occurring outside of a cell (i.e., not intracellular).

The term "subject" or "patient" refers to a living organism suffering from or having a wound, disease, or condition that can be treated or remediated, at least in part, by administration of a formulation or melanin material as provided herein. Non-limiting examples include humans, other mammals, bovines, rats, mice, dogs, monkeys, goat, sheep, cows, deer, and other non-mammalian animals. In some embodiments, such as some of Aspects 1-61, a subject is human. In some embodiments, such as some of Aspects 1-61, a subject is a mammal. In some embodiments, such as some of Aspects 1-61, a subject is a mouse. In some embodiments, such as some of Aspects 1-61, a subject is an experimental animal. In some embodiments, such as some of Aspects 1-61, a subject is a rat. In some embodiments, such as some of Aspects 1-61, a subject is a test animal.

The terms "reactive oxygen species" and "ROS" as used interchangeably herein refer, in the usual and customary sense, to transient species, typically formed during exposure to radiation (e.g., UV irradiation) capable of inducing oxidative decomposition.

The terms "cell" and "biological cell" are used interchangeably are refer to a cell carrying out metabolic or other function sufficient to preserve or replicate its genomic DNA. A cell can be identified by well-known methods in the art including, for example, presence of an intact membrane, staining by a particular dye, ability to produce progeny or, in the case of a gamete, ability to combine with a second gamete to produce a viable offspring. Cells may include prokaryotic and eukaryotic cells. Prokaryotic cells include but are not limited to bacteria. Eukaryotic cells include but are not limited to yeast cells and cells derived from plants and animals, for example mammalian, insect (e.g., spodoptera) and human cells. A "viable cell" is a living biological cell.

The term "formulation" refers to a melanin (e.g., a melanin derivative) composition, which comprises melanin or a derivative thereof, melanin precursors (e.g., materials utilized in the synthesis of melanin), or additional additives such as solvents (e.g., carriers), lubricants, dispersants, oils, fragrances, natural ingredients, pharmaceutically acceptable excipients, etc.

The term "melanin" generally refers to one or more compounds or materials that function as a pigment, such as when internalized or taken up by a biological cell, for example. It is also noted that melanin is not necessarily taken up by cells. Melanin can be incorporated in or on cell walls in fungi, for example, such as to provide rigidity, defense mechanisms, and more. In another illustrative example, melanin is used by birds, such as where melanin is organized in a matrix of keratin or similar type of biological material, where it can be organized into monolayers or multilayers to provide structural color, warmth, and more. A melanin compound or material may be, but is not limited to, a melanin monomer, a melanin oligomer, a melanin polymer, a melanin nanoparticle, a melanin layer (e.g., a melanin thin film or coating), or other melanin material, for example. For example, melanin nanoparticles internalized by a biological cell function as a pigment in the cell.

The terms "artificial melanin" and "synthetic melanin" are used interchangeably herein and refer to one or more melanin compounds, molecules, or materials, such as melanin monomers, melanin oligomers, or melanin nanoparticles, that are synthesized and are at least partially, or preferably entirely, not derived from or not extracted from a natural source, such as a biological source, a living organism, or a once living organism. The terms "synthetic" and "artificial" are used interchangeably herein when referring to a melanin or a material comprising a melanin. The terms "synthetic melanin nanoparticles" and "artificial melanin nanoparticles" are used interchangeably herein, and are intended to have the same meaning throughout the present disclosure, and refer to nanoparticles formed of artificial melanin, such as artificial melanin monomers and/or artificial melanin oligomers. The terms "synthetic melanin thin film" and "artificial melanin thin film" are used interchangeably herein, and are intended to have the same meaning throughout the present disclosure, and refer to a thin film formed of artificial melanin, such as artificial melanin monomers and/or artificial melanin oligomers. The terms "synthetic melanin layer" and "artificial melanin layer" are used interchangeably herein, and are intended to have the same meaning throughout the present disclosure, and refer to a layer formed of artificial melanin, such as artificial melanin monomers and/or artificial melanin oligomers. An artificial melanin nanoparticle, artificial melanin thin film, artificial melanin layer, and any compound, material, or formulation comprising any of these, comprises artificial melanin monomers, artificial melanin oligomers, and/or artificial melanin polymers. Optionally, an artificial melanin nanoparticle, artificial melanin thin film, artificial melanin layer, and any compound, material, or formulation comprising any of these, consists of or consists essentially of artificial melanin, such as artificial melanin monomers, artificial melanin oligomers, and/or artificial melanin polymers. Optionally, an artificial melanin nanoparticle, artificial melanin thin film, artificial melanin layer, and any compound, material, or formulation comprising any of these, is free (or substantially free) of artificial melanin monomers and comprises artificial melanin oligomers and/or artificial melanin polymers. Preferably, each artificial melanin monomer, artificial melanin oligomer, and artificial melanin polymer of an artificial melanin nanoparticle, artificial melanin thin film, artificial melanin layer, and any compound, material, or formulation comprising any of these, is not bound to, conjugated to, attached to, coated by, encompassed by or chemically otherwise associated with a natural or biological proteinaceous lipid. A natural or biological proteinaceous lipid refers to a naturally or biologically derived lipid or a lipid extracted from a natural or biological source, such as a once living organism, said lipid comprising one or more proteins such as the lipid (plasma) membrane of a melanocyte or melanosome). Optionally, each artificial melanin monomer, artificial melanin oligomer, and artificial melanin polymer of an artificial melanin nanoparticle, artificial melanin thin film, artificial melanin layer, and any compound, material, or formulation comprising any of these, is not bound to, conjugated to, attached to, coated by, encompassed by or otherwise chemically associated with a natural or biological lipid (e.g. a lipid bilayer, lipid membrane or phospholipid compound). A natural or biological lipid refers to a naturally or biologically derived lipid or a lipid extracted from a natural or biological source, such as a once living organism. Optionally, any artificial melanin monomer, artificial melanin oligomer, and artificial melanin polymer of an artificial melanin nanoparticle, artificial melanin thin film, artificial melanin layer, and any compound, material, or formulation comprising any of these, is bound to, conjugated to, attached to, coated by, encompassed by, and/or otherwise associated with a synthetic or artificial lipid or with a synthetic or artificial phospholipid. A synthetic or artificial lipid refers to a synthesized lipid that is not derived from or is not extracted from a natural or biological source, such as a once living organism.

As used herein, modification and functionalization may be used interchangeably to refer to modifying or functionalizing artificial melanin nanoparticles with a modifier agent to change one or more characteristics, such as increase hydrophobicity, of the artificial melanin nanoparticles.

The term "artificial melanin precursor" refers to a compound or material that can form an artificial melanin material after a chemical reaction, such as after a chemical reaction with an oxidation agent. An artificial melanin precursor can be, but is not necessarily, itself a melanin. For example, an artificial melanin precursor can be, but is not necessarily, a melanin monomer. For example, contacting artificial melanin precursors such as melanin monomers with an oxidizing agent can result in oxidative oligomerization (or, polymerization) among the artificial melanin precursors thereby forming artificial melanin material(s).

The term "selenomelanin" refers to melanin comprising selenium. For example, a selenomelanin material comprises selenium. Preferably, a chemical formula of a selenomelanin material comprises selenium (e.g., at least one selenium atom).

In certain embodiments, the term "pheomelanin" refers to a melanin whose chemical formula comprises at least one substituted or unsubstituted benzothiazine, at least one substituted or unsubstituted benzothiazole, at least one substituted or unsubstituted benzoselenazole, at least one substituted or unsubstituted benzoselenazine, at least one derivative of any of these, or any combination of these. In certain embodiments, the term pheomelanin refers to a melanin made from L-DOPA and cysteine, whose chemical formula comprises at least one substituted or unsubstituted benzothiazine, at least one substituted or unsubstituted benzothiazole, at least one substituted or unsubstituted benzoselenazole, at least one substituted or unsubstituted benzoselenazine, at least one derivative of any of these, or any combination of these. In certain embodiments, a selenium pheomelanin refers to a melanin whose chemical formula comprises at least one substituted or unsubstituted benzoselenazole, at least one substituted or unsubstituted benzoselenazine, at least one derivative of any of these, or any combination of these.

In certain embodiments, the term eumelanin refers to a melanin whose chemical formula comprises at least one dihydoxyindole (DHI) (e.g., 5,6-dihydroxyindole), at least one dihydroxyindole-2-carboxylic acid (DHICA) (e.g., 5,6-dihydroxyindole-2-carboxylic acid), or a combination of these.

The term "nanoparticle" as used herein, refers to a physical particle having at least one size characteristic or physical dimension less than less than 1 μm. Preferably, term "nanoparticle" as used herein, refers to a physical particle whose longest size characteristic or physical dimension is less than 1 μm.

The term "size characteristic" refers to a property, or set of properties, of a particle that directly or indirectly relates to a size attribute. According to some embodiments, a size characteristic corresponds to an empirically-derived size characteristic of a particle(s) being detected, such as a size characteristic based on, determined by, or corresponding to data from any technique or instrument that may be used to determine a particle size, such as electron microscope (e.g., SEM and TEM) or a light scattering technique (e.g., DLS). For example, a size characteristic can correspond to a spherical particle exhibiting similar or substantially same properties, such as aerodynamic, hydrodynamic, optical, and/or electrical properties, as the particle(s) being detected). According to some embodiments, a size characteristic corresponds to a physical dimension, such as a cross-sectional size (e.g., length, width, thickness, or diameter).

The term "particles" refers to small solid objects that may be dispersed and/or suspended in a fluid (e.g., liquid). For example, a slurry, a dispersion, and a suspension each include particles in a fluid. The terms "particle" and "particulate" may be used interchangeably. An exemplary particle is an artificial melanin nanoparticle. A plurality of particles may be associated together to form an agglomerate of particles. Generally, the term "particle", such as "nanoparticle" or "melanin nanoparticle", refers to an individual particle rather than to an agglomerate of such individual particles.

The term "dispersed" refers to species, such as particles, in a fluid forming a dispersion. As used herein, the term "dispersion" broadly refers to a mixture of one or more chemical species, such as particles, in a fluid, such as the art-recognized meaning of solution, dispersion, and/or suspension. The chemical species, such as particles, dispersed in a dispersion can be referred as a dispersed species. Preferably, a dispersion is a mixture of particles, such as artificial melanin particles, in a liquid, such as a solvent. Preferably, but not necessarily, a dispersion is a homogeneous mixture. In the context of a dispersion, the term "homogeneous" refers to a liquid mixture that appears uniform to the naked eye. In contrast, a heterogeneous liquid mixture includes particles that are precipitated from or suspended in the liquid mixture and are large enough to be distinctly identifiable by the naked eye in the liquid mixture. A heterogeneous liquid mixture includes, for example, sedimented and/or sedimenting particles. Preferably, but not necessarily, the term "dispersion" is broadly intended to include solutions and dispersions, such as colloids, which are not heterogenous liquid mixtures. Preferably, but not necessarily, a dispersion is a microscopically homogenous, or uniform, mixture of particles in a liquid, such as a solvent. Preferably, but not necessarily, a dispersion is thermodynamically favored remain stably dispersed or is thermodynamically favored to segregate by sedimentation but wherein sedimentation is kinetically slowed or prevented. Particles, of a dispersion, that are characterized as stably dispersed remain dispersed in the dispersion and do not sediment or precipitate out of the liquid, of the dispersion, for at least 5 hours, preferably at least 12 hours, preferably at least 24 hours, and more preferably at least 1 week, under normal temperature and pressure (NTP) and exposure to air. In embodiments, particles that are not or cannot be dispersed in a fluid refer to particles that form precipitates or sediments upon being mixed in the fluid.

When referring to a material, such as a polymer, being aqueous, the term "aqueous" refers to said material being dispersed, dissolved, or otherwise solvated by water. An "aqueous solution" refers to a solution that comprises water as solvent and one or more solute species dispersed, dissolved, or otherwise solvated by the water. An aqueous process, such as a polymerization, is a process taking place in an aqueous solution. Optionally, but not necessarily, an aqueous solution or an aqueous solvent includes 20 vol. % or less, optionally 15 vol. % or less, optionally 10 vol. % or less, preferably 5 vol. % or less, of a non-water or organic species. Optionally, but not necessarily, an aqueous solution or an aqueous solvent includes 20 vol. % or less, optionally 15 vol. % or less, optionally 10 vol. % or less, preferably 5 vol. % or less, of a non-water liquid.

The term "aging", when used in reference to artificial melanin nanoparticles herein, refers to a process by which synthesized and isolated artificial melanin nanoparticles oxidize, and optionally further darker, over time during exposure to oxygen, such due to exposure to air. Isolated artificial melanin nanoparticles can be artificial melanin nanoparticles that are purified, such as by centrifugation, and re-dispersed in water, such as ultrapure water, or optionally another solvent or solvent solution. For example, artificial melanin nanoparticles may age if the particles are dispersed in water and are stored in a vial with the vial's top on (closed) and with the top not being opened for some extended period of time, because there is residual oxygen in the container. The aging process can alter certain properties or characteristics of artificial melanin nanoparticles, such as increasing solubility in organic solvent or decreasing toxicity to certain living biological cells. For example, without wishing to be bound by any particular theory, in some embodiments, freshly synthesized artificial melanin nanoparticles can be dynamic and shed monomers or oligomers into a cell when internalized by the cell. For example, without wishing to be bound by any particular theory, in some embodiments, freshly synthesized artificial melanin nanoparticles can be dynamic and have surface chemistry oxidation state that is not optimal for living cells when internalized by cells. For example, without wishing to be bound by any particular theory, in some embodiments, the aging process can lead to more crosslinking or otherwise chemical association between melanin compounds (monomers, oligomers) in the artificial melanin nanoparticles, potentially leading to reduced cytotoxicity, such as due to reduced shedding of melanin compounds into the cell and/or altering or stabilizing of the particles' surface chemistry.

The term "peak size" size refers to the statistical mode, or peak frequency, of a particle size distribution, or the particle size most commonly found in the particle size distribution. A particle size distribution can be measured using dynamic light scattering, for example.

The term "substantially" refers to a property, condition, or value that is within 20%, 10%, within 5%, within 1%, optionally within 0.1%, or is equivalent to a reference property, condition, or value. The term "substantially equal", "substantially equivalent", or "substantially unchanged", when used in conjunction with a reference value describing a property or condition, refers to a value that is within 20%, within 10%, optionally within 5%, optionally within 1%, optionally within 0.1%, or optionally is equivalent to the provided reference value. For example, a diameter is substantially equal to 100 nm (or, "is substantially 100 nm") if the value of the diameter is within 20%, optionally within 10%, optionally within 5%, optionally within 1%, within 0.1%, or optionally equal to 100 nm. The term "substantially greater", when used in conjunction with a reference value describing a property or condition, refers to a value that is at least 1%, optionally at least 5%, optionally at least 10%, or optionally at least 20% greater than the provided reference value. The term "substantially less", when used in conjunction with a reference value describing a property or condition, refers to a value that is at least 1%, optionally at least 5%, optionally at least 10%, or optionally at least 20% less than the provided reference value.

As used herein, the term "about" means a range of values including the specified value, which a person of ordinary skill in the art would consider reasonably similar to the specified value. In embodiments, about means within a standard deviation using measurements generally acceptable in the art. In embodiments, about means a range extending to +/−10% of the specified value. In embodiments, about means the specified value.

The term "administering" as used herein, refers to oral administration, administration as an inhaled aerosol or as an inhaled dry powder, suppository, topical contact, intravenous, parenteral, intraperitoneal, intramuscular, intralesional, intrathecal, intranasal or subcutaneous administration, or the implantation of a slow-release device, e.g., a mini-osmotic pump, to a subject. Administration is by any route, including parenteral and transmucosal (e.g., buccal, sublingual, palatal, gingival, nasal, vaginal, rectal, or transdermal). Parenteral administration includes, e.g., intravenous, intramuscular, intra-arteriole, intradermal, subcutaneous, intraperitoneal, intraventricular, and intracranial. Other modes of delivery include, but are not limited to, the use of liposomal formulations, intravenous infusion, transdermal patches, etc. By "co-administer" it is meant that a composition described herein is administered at the same time, just prior to, or just after the administration of one or more additional therapies, for example cancer therapies such as chemotherapy, hormonal therapy, radiotherapy, or immunotherapy. The compound of the invention can be administered alone or can be co-administered to the patient. Co-administration is meant to include simultaneous or sequential administration of the compound individually or in combination (more than one compound or agent). The compositions of the present invention can be delivered transdermally, by a topical route, formulated as applicator sticks, solutions, suspensions, emulsions, gels, creams, ointments, pastes, jellies, paints, powders, and aerosols. Oral preparations include tablets, pills, powder, dragees, capsules, liquids, lozenges, cachets, gels, syrups, slurries, suspensions, etc., suitable for ingestion by the patient. Solid form preparations include powders, tablets, pills, capsules, cachets, suppositories, and dispersible granules. Liquid form preparations include solutions, suspensions, and emulsions, for example, water or water/propylene glycol solutions. The compositions of the present invention may additionally include components to provide sustained release and/or comfort. Such components include high molecular weight, anionic mucomimetic polymers, gelling polysaccharides and finely-divided drug carrier substrates. These components are discussed in greater detail in U.S. Pat. Nos. 4,911,920; 5,403,841; 5,212,162; and 4,861,760. The entire contents of these patents are incorporated herein by reference in their entirety for all purposes. The compositions of the present invention can also be delivered as microspheres for slow release in the body. For example, microspheres can be administered via intradermal injection of drug-containing microspheres, which slowly release subcutaneously (see Rao, J Biomater Sci. Polym. Ed. 7:623-645, 1995; as biodegradable and injectable gel formulations (see, e.g., Gao Pharm. Res. 12:857-863, 1995); or, as microspheres for oral administration (see, e.g., Eyles, J Pharm. Pharmacol. 49:669-674, 1997). In another embodiment, the formulations of the compositions of the present invention can be delivered by the use of liposomes which fuse with the cellular membrane or are endocytosed, i.e., by employing receptor ligands attached to the liposome, that bind to surface membrane protein receptors of the cell resulting in endocytosis. By using liposomes, particularly where the liposome surface carries receptor ligands specific for target cells, or are otherwise preferentially directed to a specific organ, one can focus the delivery of the compositions of the present invention into the target cells in vivo. (See, e.g., Al-Muhammed, J. Microencapsul. 13:293306, 1996; Chonn, Curr. Opin. Biotechnol. 6:698-708, 1995; Qstio, Am. J Hasp. Pharm. 46:1576-1587, 1989).

The term "contacting" may include allowing two species to react, interact, or physically touch, wherein the two species may be, for example, a pharmaceutical composition as provided herein and a cell. In embodiments contacting includes, for example, allowing a pharmaceutical composition as described herein to interact with a cell or a patient.

The terms "analog" and "analogue" are used interchangeably and are used in accordance with their plain ordinary meaning within Chemistry and Biology and refers to a chemical compound that is structurally similar to another compound (i.e., a so-called "reference" compound) but differs in composition, e.g., in the replacement of one atom by an atom of a different element, or in the presence of a particular functional group, or the replacement of one functional group by another functional group, or the absolute stereochemistry of one or more chiral centers of the reference compound, including isomers thereof. Accordingly, an analog is a compound that is similar or comparable in function and appearance but not in structure or origin to a reference compound.

Except where otherwise specified, the term "molecular weight" refers to an average molecular weight. Except where otherwise specified, the term "average molecular weight," refers to number-average molecular weight. Number average molecular weight is defined as the total weight of a sample volume divided by the number of molecules within the sample. As is customary and well known in the art, peak average molecular weight and weight average molecular weight may also be used to characterize the molecular weight of the distribution of polymers within a sample.

The term "weight-average molecular weight" ($M_w$) refers to the average molecular weight defined as the sum of the products of the molecular weight of each polymer molecule ($M_i$) multiplied by its weight fraction ($w_i$): $M_w = \Sigma w_i M_i$. As is customary and well known in the art, peak average molecular weight and number average molecular weight may also be used to characterize the molecular weight of the distribution of polymers within a sample.

The term "wt. %" or "wt %" refers to a weight percent, or a mass fraction represented as a percentage by mass. The term "at. %" or "at %" refers to an atomic percent, or an atomic ratio represented as a percentage of a type of atom with respect to total atoms in a given matter, such as a molecule, compound, material, nanoparticle, polymer, dispersion, etc.

The term "oligomerization" refers to a chemical process of converting a monomer or a mixture of monomers into an oligomer. The term "oxidative oligomerization" refers to a chemical process of oligomerization that includes chemical oxidation of one or more monomers to form an oligomer. An oligomerization is a polymerization process, wherein an oligomer is formed as a result of the polymerization.

As used herein, the term "polymer" refers to a molecule composed of repeating structural units connected by covalent chemical bonds often characterized by a number of repeating units, also referred to as base units (e.g., greater than or equal to 2 base units). As used herein, a term "polymer" is inclusive of an "oligomer" (i.e., an oligomer is a polymer; i.e., a polymer is optionally an oligomer). An "oligomer" refers to a molecule composed of repeating structural units, also referred to as base units, connected by covalent chemical bonds often characterized by a number of repeating units less such that the oligomer is a low molecular weight polymer. Preferably, but not necessarily, for example, an oligomer has equal to or less than 100 repeating units. Preferably, but not necessarily, for example, an oligomer has a lower molecular weight less than or equal to 10,000 Da. Oligomers may be the polymerization product of one or more monomer precursors. Polymerization of one or more monomers, or monomer precursors, resulting in formation of an oligomer may be referred to as oligomerization. An oligomer optionally includes 100 or less, 50 or less, 15 or less, 12 or less, 10 or less, or 5 or less repeating units (or, "base units"). An oligomer may be characterized has having a molecular weight of 10,000 Da or less, 5,000 Da or less, 1,000 Da or less, 500 Da or less, or 200 Da or less. A dimer, a trimer, a tetramer, or a pentamer is an oligomer having two, three, four, or five, respectively, repeating units, or base units. Polymers can have, for example, greater than 100 repeating units. Polymers can have, for example, a high molecular weight, such as greater than 10,000 Da, in some embodiments greater than or equal to 50,000 Da or greater than or equal to 100,000 Da. The term polymer includes homopolymers, or polymers consisting essentially of a single repeating monomer subunit. The term polymer also includes copolymers which are formed when two or more different types of monomers are linked in the same polymer. Copolymers may comprise two or more monomer subunits, and include random, block, brush, brush block, alternating, segmented, grafted, tapered and other architectures. Useful polymers include organic polymers or inorganic polymers that may be in amorphous, semi-amorphous, crystalline or semi-crystalline states. Polymer side chains capable of cross linking polymers (e.g., physical cross linking) may be useful for some applications.

An "oligomer" refers to a molecule composed of repeating structural units, also referred to as base units, connected by covalent chemical bonds often characterized by a number of repeating units less than that of a polymer (e.g., equal to or less than 100 repeating units) and a lower molecular weights (e.g. less than or equal to 10,000 Da) than polymers. Oligomers may be the polymerization product of one or more monomer precursors. Polymerization of one or more monomers, or monomer precursors, resulting in formation of an oligomer may be referred to as oligomerization. An oligomer optionally includes 100 or less, 50 or less, 15 or less, 12 or less, 10 or less, or 5 or less repeating units (or, "base units"). An oligomer may be characterized has having a molecular weight of 10,000 Da or less, 5,000 Da or less, 1,000 Da or less, 500 Da or less, or 200 Da or less. A dimer, a trimer, a tetramer, or a pentamer is an oligomer having two, three, four, or five, respectively, repeating units, or base units.

As used herein, the term "group" may refer to a functional group of a chemical compound. Groups of the present compounds refer to an atom or a collection of atoms that are a part of the compound. Groups of the present invention may be attached to other atoms of the compound via one or more covalent bonds. Groups may also be characterized with respect to their valence state. The present invention includes groups characterized as monovalent, divalent, trivalent, etc. valence states.

The term "moiety" refers to a group, such as a functional group, of a chemical compound or molecule. A moiety is a collection of atoms that are part of the chemical compound or molecule. The present invention includes moieties characterized as monovalent, divalent, trivalent, etc. valence states. Generally, but not necessarily, a moiety comprises more than one functional group.

As used herein, the term "substituted" refers to a compound wherein one or more hydrogens is replaced by another functional group, provided that the designated atom's normal valence is not exceeded. An exemplary substituent includes, but is not limited to: a halogen or halide, an alkyl, a cycloalkyl, an aryl, a heteroaryl, an acyl, an alkoxy, an alkenyl, an alkynyl, an alkylaryl, an arylene, a heteroarylene, an alkenylene, a cycloalkenylene, an alkynylene, a hydroxyl (—OH), a carbonyl (RCOR'), a sulfide (e.g., RSR'), a phosphate ($ROP(=O)(OH)_2$), an azo (RNNR'), a cyanate (ROCN), an amine (e.g., primary, secondary, or tertiary), an imine (RC(=NH)R'), a nitrile (RCN), a pyridinyl (or pyridyl), a diamine, a triamine, an azide, a diimine, a triimine, an amide, a diimide, or an ether (ROR'); where each of R and R' is independently a hydrogen or a substituted or unsubstituted alkyl group, aryl group, alkenyl group, or a combination of these. Optional substituent functional groups are also described below. Optionally in any of Aspects 1-148 or optionally in any preceding Aspect, the term substituted refers to a compound wherein each of more than one hydrogen is replaced by another functional group, such as a halogen group. For example, when the substituent is oxo (i.e., =O), then two hydrogens on the atom are replaced. The substituent group can be any substituent group described herein. For example, substituent groups can include one or more of a hydroxyl, an amino (e.g., primary, secondary, or tertiary), an aldehyde, a carboxylic acid, an ester, an amide, a ketone, nitro, an urea, a guanidine, cyano, fluoroalkyl (e.g., trifluoromethane), halo (e.g., fluoro), aryl (e.g., phenyl), heterocyclyl or heterocyclic group (i.e., cyclic group, e.g., aromatic (e.g., heteroaryl) or non-aromatic where the cyclic group has one or more heteroatoms), oxo, or combinations thereof. Combinations of substituents and/or variables are permissible provided that the substitutions do not significantly adversely affect synthesis or use of the compound.

As used herein, the term "derivative" refers to a compound wherein an atom or functional group is replaced by another atom or functional group (e.g., a substituent function group as also described below), including, but not limited to: a hydrogen, a halogen or halide, an alkyl, a cycloalkyl, an aryl, a heteroaryl, an acyl, an alkoxy, an alkenyl, an alkynyl, an alkylaryl, an arylene, a heteroarylene, an alkenylene, a cycloalkenylene, an alkynylene, a hydroxyl (—OH), a carbonyl (RCOR'), a sulfide (e.g., RSR'), a phosphate ($ROP(=O)(OH)_2$), an azo (RNNR'), a cyanate (ROCN), an amine (e.g., primary, secondary, or tertiary), an imine (RC(=NH)R'), a nitrile (RCN), a pyridinyl (or pyridyl), a diamine, a triamine, an azide, a diimine, a triimine, an amide, a diimide, or an ether (ROR'); where each of R and R' is independently a hydrogen or a substituted or unsubstituted alkyl group, aryl group, alkenyl group, or a combination of these. Optional substituent functional groups are also described below. Preferably, the term "derivative" refers to a compound wherein one or two atoms or functional groups are independently replaced by another atom or functional group. Optionally, the term derivative does not refer to or include replacement of a chalcogen atom (S, Se) that is a member of a heterocyclic group. Optionally, and unless otherwise stated, the term derivative does not refer to or include replacement of a chalcogen atom (S, Se) nor a N (nitrogen) where the chalcogen atom and the N are members same heterocyclic group. Optionally, but not necessarily, the term derivative does not include breaking a ring structure, replacement of a ring member, or removal of a ring member.

As is customary and well known in the art, hydrogen atoms in formula, are not always explicitly shown, for example, hydrogen atoms bonded to the carbon atoms of aromatic, heteroaromatic, and alicyclic rings are not always explicitly shown. The structures provided herein, for example in the context of the description of formula and schematics and structures in the drawings, are intended to convey to one of reasonable skill in the art the chemical composition of compounds of the methods and compositions of the invention, and as will be understood by one of skill in the art, the structures provided do not indicate the specific positions and/or orientations of atoms and the corresponding bond angles between atoms of these compounds.

The term "hydrocarbyl group" refers to any univalent radical or group, derived from a hydrocarbon, or in other words a univalent group formed by removing a hydrogen atom from a hydrocarbon. Examples of hydrocarbyl groups include but are not limited to a methyl group, an ethyl group, a phenyl group, etc. A hydrocarbyl group can be substituted, such as a hydrogen replaced with a halogen (see also definition of substituted groups above), or unsubstituted. A hydrocarbyl group can saturated or unsaturated.

As used herein, the terms "alkylene" and "alkylene group" are used synonymously and refer to a divalent group derived from an alkyl group as defined herein. The invention includes compounds having one or more alkylene groups. Alkylene groups in some compounds function as linking and/or spacer groups. Compounds of the invention may have substituted and/or unsubstituted $C_1$-$C_{20}$ alkylene, $C_1$-$C_{10}$ alkylene and $C_1$-$C_5$ alkylene groups, for example, as one or more linking groups (e.g. $L^1$-$L^6$).

As used herein, the terms "cycloalkylene" and "cycloalkylene group" are used synonymously and refer to a divalent group derived from a cycloalkyl group as defined herein. The invention includes compounds having one or more cycloalkylene groups. Cycloalkyl groups in some compounds function as linking and/or spacer groups. Compounds of the invention may have substituted and/or unsubstituted $C_3$-$C_{20}$ cycloalkylene, $C_3$-$C_{10}$ cycloalkylene and $C_8$-$C_5$ cycloalkylene groups, for example, as one or more linking groups (e.g. $L^1$-$L^6$).

As used herein, the terms "arylene" and "arylene group" are used synonymously and refer to a divalent group derived from an aryl group as defined herein. The invention includes compounds having one or more arylene groups. Optionally in any of Aspects 1-148 or optionally in any preceding Aspect, an arylene is a divalent group derived from an aryl group by removal of hydrogen atoms from two intra-ring carbon atoms of an aromatic ring of the aryl group. Arylene groups in some compounds function as linking and/or spacer groups. Arylene groups in some compounds function as chromophore, fluorophore, aromatic antenna, dye and/or imaging groups. Compounds of the invention include substituted and/or unsubstituted $C_3$-$C_{30}$ arylene, $C_3$-$C_{20}$ arylene, $C_3$-$C_{10}$ arylene and $C_1$-$C_5$ arylene groups, for example, as one or more linking groups (e.g. $L^1$-$L^6$).

As used herein, the terms "heteroarylene" and "heteroarylene group" are used synonymously and refer to a divalent group derived from a heteroaryl group as defined herein. The invention includes compounds having one or more heteroarylene groups. In an embodiment, a heteroarylene is a divalent group derived from a heteroaryl group by removal of hydrogen atoms from two intra-ring carbon atoms or intra-ring nitrogen atoms of a heteroaromatic or aromatic ring of the heteroaryl group. Heteroarylene groups in some compounds function as linking and/or spacer groups. Heteroarylene groups in some compounds function as chromophore, aromatic antenna, fluorophore, dye and/or imaging groups. Compounds of the invention include substituted and/or unsubstituted $C_3$-$C_{30}$ heteroarylene, $C_3$-$C_{20}$ heteroarylene, $C_1$-$C_{10}$ heteroarylene and $C_3$-$C_5$ heteroarylene groups, for example, as one or more linking groups (e.g. $L^1$-$L^6$).

As used herein, the terms "alkenylene" and "alkenylene group" are used synonymously and refer to a divalent group derived from an alkenyl group as defined herein. The invention includes compounds having one or more alkenylene groups. Alkenylene groups in some compounds function as linking and/or spacer groups. Compounds of the invention include substituted and/or unsubstituted $C_2$-$C_{20}$ alkenylene, $C_2$-$C_{10}$ alkenylene and $C_2$-$C_5$ alkenylene groups, for example, as one or more linking groups (e.g. $L^1$-$L^6$).

As used herein, the terms "cylcoalkenylene" and "cylcoalkenylene group" are used synonymously and refer to a divalent group derived from a cylcoalkenyl group as defined herein. The invention includes compounds having one or more cylcoalkenylene groups. Cycloalkenylene groups in some compounds function as linking and/or spacer groups. Compounds of the invention include substituted and/or unsubstituted $C_3$-$C_{20}$ cylcoalkenylene, $C_3$-$C_{10}$ cylcoalkenylene and $C_3$-$C_5$ cylcoalkenylene groups, for example, as one or more linking groups (e.g. $L^1$-$L^6$).

As used herein, the terms "alkynylene" and "alkynylene group" are used synonymously and refer to a divalent group derived from an alkynyl group as defined herein. The invention includes compounds having one or more alkynylene groups. Alkynylene groups in some compounds function as linking and/or spacer groups. Compounds of the invention include substituted and/or unsubstituted $C_2$-$C_{20}$ alkynylene, $C_2$-$C_{10}$ alkynylene and $C_2$-$C_5$ alkynylene groups, for example, as one or more linking groups (e.g. $L^1$-$L^6$).

As used herein, the term "halo" refers to a halogen group such as a fluoro (—F), chloro (—CI), bromo (—Br), iodo (—I) or astato (—At).

The term "heterocyclic" refers to ring structures containing at least one other kind of atom, in addition to carbon, in the ring. Examples of such heteroatoms include nitrogen, oxygen and sulfur. Heterocyclic rings include heterocyclic alicyclic rings and heterocyclic aromatic rings. Examples of heterocyclic rings include, but are not limited to, pyrrolidinyl, piperidyl, imidazolidinyl, tetrahydrofuryl, tetrahydrothienyl, furyl, thienyl, pyridyl, quinolyl, isoquinolyl, pyridazinyl, pyrazinyl, indolyl, imidazolyl, oxazolyl, thiazolyl, pyrazolyl, pyridinyl, benzoxadiazolyl, benzothiadiazolyl, triazolyl and tetrazolyl groups. Atoms of heterocyclic rings can be bonded to a wide range of other atoms and functional groups, for example, provided as substituents.

The term "carbocyclic" refers to ring structures containing only carbon atoms in the ring. Carbon atoms of carbocyclic rings can be bonded to a wide range of other atoms and functional groups, for example, provided as substituents.

The term "alicyclic ring" refers to a ring, or plurality of fused rings, that is not an aromatic ring. Alicyclic rings include both carbocyclic and heterocyclic rings.

The term "aromatic ring" refers to a ring, or a plurality of fused rings, that includes at least one aromatic ring group. The term aromatic ring includes aromatic rings comprising carbon, hydrogen and heteroatoms. Aromatic ring includes carbocyclic and heterocyclic aromatic rings. Aromatic rings are components of aryl groups.

The term "fused ring" or "fused ring structure" refers to a plurality of alicyclic and/or aromatic rings provided in a fused ring configuration, such as fused rings that share at least two intra ring carbon atoms and/or heteroatoms.

As used herein, the term "alkoxyalkyl" refers to a substituent of the formula alkyl-O-alkyl.

As used herein, the term "polyhydroxyalkyl" refers to a substituent having from 2 to 12 carbon atoms and from 2 to 5 hydroxyl groups, such as the 2,3-dihydroxypropyl, 2,3,4-trihydroxybutyl or 2,3,4,5-tetrahydroxypentyl residue.

As used herein, the term "polyalkoxyalkyl" refers to a substituent of the formula alkyl-(alkoxy)$_n$-alkoxy wherein n is an integer from 1 to 10, preferably 1 to 4, and more preferably for some embodiments 1 to 3.

Amino acids include glycine, alanine, valine, leucine, isoleucine, methionine, proline, phenylalanine, tryptophan, asparagine, glutamine, glycine, serine, threonine, serine, threonine, asparagine, glutamine, tyrosine, cysteine, lysine, arginine, histidine, aspartic acid and glutamic acid. As used herein, reference to "a side chain residue of a natural α-amino acid" specifically includes the side chains of the above-referenced amino acids. Peptides and peptide moieties, as used and described herein, comprise two or more amino acid groups connected via peptide bonds.

Amino acids and amino acid groups refer to naturally-occurring amino acids, unnatural (non-naturally occurring) amino acids, and/or combinations of these. Naturally-occurring amino acids are those encoded by the genetic code, as well as those amino acids that are later modified, e.g., hydroxyproline, γ-carboxyglutamate, and O-phosphoserine. Naturally-occurring α-amino acids include, without limitation, alanine (Ala), cysteine (Cys), aspartic acid (Asp), glutamic acid (Glu), phenylalanine (Phe), glycine (Gly), histidine (His), isoleucine (Ile), arginine (Arg), lysine (Lys), leucine (Leu), methionine (Met), asparagine (Asn), proline (Pro), glutamine (Gln), serine (Ser), threonine (Thr), valine (Val), tryptophan (Trp), tyrosine (Tyr), and combinations thereof. Stereoisomers of a naturally-occurring α-amino acids include, without limitation, D-alanine (D-Ala), D-cysteine (D-Cys), D-aspartic acid (D-Asp), D-glutamic acid (D-Glu), D-phenylalanine (D-Phe), D-histidine (D-His), D-isoleucine (D-Ile), D-arginine (D-Arg), D-lysine (D-Lys), D-leucine (D-Leu), D-methionine (D-Met), D-asparagine (D-Asn), D-proline (D-Pro), D-glutamine (D-Gln), D-serine (D-Ser), D-threonine (D-Thr), D-valine (D-Val), D-tryptophan (D-Trp), D-tyrosine (D-Tyr), and combinations thereof.

Unnatural (non-naturally occurring) amino acids include, without limitation, amino acid analogs, amino acid mimetics, synthetic amino acids, N-substituted glycines, and N-methyl amino acids in either the L- or D-configuration that function in a manner similar to the naturally-occurring amino acids. For example, "amino acid analogs" can be unnatural amino acids that have the same basic chemical structure as naturally-occurring amino acids (i.e., a carbon that is bonded to a hydrogen, a carboxyl group, an amino group) but have modified side-chain groups or modified peptide backbones, e.g., homoserine, norleucine, methionine sulfoxide, methionine methyl sulfonium. "Amino acid mimetics" refer to chemical compounds that have a structure that is different from the general chemical structure of an amino acid, but that functions in a manner similar to a naturally-occurring amino acid. Amino acids may be referred to herein by either the commonly known three letter symbols or by the one-letter symbols recommended by the IUPAC-IUB Biochemical Nomenclature Commission.

The terms "monomer unit," "repeating monomer unit," "repeating unit," and "polymerized monomer" can be used interchangeably and refer to a monomeric portion of a polymer described herein which is derived from or is a product of polymerization of one individual "monomer" or "polymerizable monomer." Each individual monomer unit of a polymer is derived from or is a product of polymerization of one polymerizable monomer. Each individual "monomer unit" or "repeating unit" of a polymer comprises one (polymerized) polymer backbone group. For example, in a polymer that comprises monomer units X and Y arranged as X-Y-X-Y-X-Y-X-Y (where each X is identical to each other X and each Y is identical to each other Y), each X and each Y is independently can be referred to as a repeating unit or monomer unit.

Alkyl groups include straight-chain, branched and cyclic alkyl groups. Alkyl groups include those having from 1 to 30 carbon atoms. Alkyl groups include small alkyl groups having 1 to 3 carbon atoms. Alkyl groups include medium length alkyl groups having from 4-10 carbon atoms. Alkyl groups include long alkyl groups having more than 10 carbon atoms, particularly those having 10-30 carbon atoms. The term cycloalkyl specifically refers to an alky group having a ring structure such as ring structure comprising 3-30 carbon atoms, optionally 3-20 carbon atoms and optionally 2-10 carbon atoms, including an alkyl group having one or more rings. Cycloalkyl groups include those having a 3-, 4-, 5-, 6-, 7-, 8-, 9- or 10-member carbon ring(s) and particularly those having a 3-, 4-, 5-, 6-, 7-, or 8-member ring(s). The carbon rings in cycloalkyl groups can also carry alkyl groups. Cycloalkyl groups can include bicyclic and tricycloalkyl groups. Alkyl groups are optionally substituted. Substituted alkyl groups include among others those which are substituted with aryl groups, which in turn can be optionally substituted. Specific alkyl groups include methyl, ethyl, n-propyl, iso-propyl, cyclopropyl, n-butyl, s-butyl, t-butyl, cyclobutyl, n-pentyl, branched-pentyl, cyclopentyl, n-hexyl, branched hexyl, and cyclohexyl groups, all of which are optionally substituted. Substituted alkyl groups include fully halogenated or semihalogenated alkyl groups, such as alkyl groups having one or more hydrogens replaced with one or more fluorine atoms, chlorine atoms, bromine atoms and/or iodine atoms. Substituted alkyl groups include fully fluorinated or semifluorinated alkyl groups, such as alkyl groups having one or more hydrogens replaced with one or more fluorine atoms. An alkoxy group is an alkyl group that has been modified by linkage to oxygen and can be represented by the formula R—O and can also be referred to as an alkyl ether group. Examples of alkoxy groups include, but are not limited to, methoxy, ethoxy, propoxy, butoxy and heptoxy. Alkoxy groups include substituted alkoxy groups wherein the alky portion of the groups is substituted as provided herein in connection with the description of alkyl groups. As used herein MeO-refers to $CH_3O$—. Compositions of some embodiments of the invention comprise alkyl groups as terminating groups, such as polymer backbone terminating groups and/or polymer side chain terminating groups. Substituted alkyl groups may include substitution to incorporate one or more silyl groups, for example wherein one or more carbons are replaced by Si.

Alkenyl groups include straight-chain, branched and cyclic alkenyl groups. Alkenyl groups include those having 1, 2 or more double bonds and those in which two or more of the double bonds are conjugated double bonds. Alkenyl groups include those having from 2 to 20 carbon atoms. Alkenyl groups include small alkenyl groups having 2 to 3 carbon atoms. Alkenyl groups include medium length alkenyl groups having from 4-10 carbon atoms. Alkenyl groups include long alkenyl groups having more than 10 carbon atoms, particularly those having 10-20 carbon atoms.

Cycloalkenyl groups include those in which a double bond is in the ring or in an alkenyl group attached to a ring. The term cycloalkenyl specifically refers to an alkenyl group having a ring structure, including an alkenyl group having a 3-, 4-, 5-, 6-, 7-, 8-, 9- or 10-member carbon ring(s) and particularly those having a 3-, 4-, 5-, 6- or 7-member ring(s). The carbon rings in cycloalkenyl groups can also carry alkyl groups. Cycloalkenyl groups can include bicyclic and tricyclic alkenyl groups. Alkenyl groups are optionally substituted. Substituted alkenyl groups include among others those which are substituted with alkyl or aryl groups, which groups in turn can be optionally substituted. Specific alkenyl groups include ethenyl, prop-1-enyl, prop-2-enyl, cycloprop-1-enyl, but-1-enyl, but-2-enyl, cyclobut-1-enyl, cyclobut-2-enyl, pent-1-enyl, pent-2-enyl, branched pentenyl, cyclopent-1-enyl, hex-1-enyl, branched hexenyl, cyclohexenyl, all of which are optionally substituted. Substituted alkenyl groups include fully halogenated or semihalogenated alkenyl groups, such as alkenyl groups having one or more hydrogens replaced with one or more fluorine atoms, chlorine atoms, bromine atoms and/or iodine atoms. Substituted alkenyl groups include fully fluorinated or semifluorinated alkenyl groups, such as alkenyl groups having one or more hydrogen atoms replaced with one or more fluorine atoms. Compositions of some embodiments of the invention comprise alkenyl groups as terminating groups, such as polymer backbone terminating groups and/or polymer side chain terminating groups.

Aryl groups include groups having one or more 5-, 6-7-, or 8-member aromatic rings, including heterocyclic aromatic rings. The term heteroaryl specifically refers to aryl groups having at least one 5-, 6-7-, or 8-member heterocyclic aromatic rings. Aryl groups can contain one or more fused aromatic rings, including one or more fused heteroaromatic rings, and/or a combination of one or more aromatic rings and one or more nonaromatic rings that may be fused or linked via covalent bonds. Heterocyclic aromatic rings can include one or more N, O, or S atoms in the ring. Heterocyclic aromatic rings can include those with one, two or three N atoms, those with one or two O atoms, and those with one or two S atoms, or combinations of one or two or three N, O or S atoms. Aryl groups are optionally substituted. Substituted aryl groups include among others those that are substituted with alkyl or alkenyl groups, which groups in turn can be optionally substituted. Specific aryl groups include phenyl, biphenyl groups, pyrrolidinyl, imidazolidinyl, tetrahydrofuryl, tetrahydrothienyl, furyl, thienyl, pyridyl, quinolyl, isoquinolyl, pyridazinyl, pyrazinyl, indolyl, imidazolyl, oxazolyl, thiazolyl, pyrazolyl, pyridinyl, benzoxadiazolyl, benzothiadiazolyl, and naphthyl groups, all of which are optionally substituted. Substituted aryl groups include fully halogenated or semihalogenated aryl groups, such as aryl groups having one or more hydrogens replaced with one or more fluorine atoms, chlorine atoms, bromine atoms and/or iodine atoms. Substituted aryl groups include fully fluorinated or semifluorinated aryl groups, such as aryl groups having one or more hydrogens replaced with one or more fluorine atoms. Aryl groups include, but are not limited to, aromatic group-containing or heterocylic aromatic group-containing groups corresponding to any one of the following: benzene, naphthalene, naphthoquinone, diphenylmethane, fluorene, anthracene, anthraquinone, phenanthrene, tetracene, tetracenedione, pyridine, quinoline, isoquinoline, indoles, isoindole, pyrrole, imidazole, oxazole, thiazole, pyrazole, pyrazine, pyrimidine, purine, benzimidazole, furans, benzofuran, dibenzofuran, carbazole, acridine, acridone, phenanthridine, thiophene, benzothiophene, dibenzothiophene, xanthene, xanthone, flavone, coumarin, azulene or anthracycline. As used herein, a group corresponding to the groups listed above expressly includes an aromatic or heterocyclic aromatic group, including monovalent, divalent and polyvalent groups, of the aromatic and heterocyclic aromatic groups listed herein are provided in a covalently bonded configuration in the compounds of the invention at any suitable point of attachment. In embodiments, aryl groups contain between 5 and 30 carbon atoms. In embodiments, aryl groups contain one aromatic or heteroaromatic six-member ring and one or more additional five- or six-member aromatic or heteroaromatic ring. In embodiments, aryl groups contain between five and eighteen carbon atoms in the rings. Aryl groups optionally have one or more aromatic rings or heterocyclic aromatic rings having one or more electron donating groups, electron withdrawing groups and/or targeting ligands provided as substituents. Compositions of some embodiments of the invention comprise aryl groups as terminating groups, such as polymer backbone terminating groups and/or polymer side chain terminating groups.

Arylalkyl groups are alkyl groups substituted with one or more aryl groups wherein the alkyl groups optionally carry additional substituents and the aryl groups are optionally substituted. Specific alkylaryl groups are phenyl-substituted alkyl groups, e.g., phenylmethyl groups. Alkylaryl groups are alternatively described as aryl groups substituted with one or more alkyl groups wherein the alkyl groups optionally carry additional substituents and the aryl groups are optionally substituted. Specific alkylaryl groups are alkyl-substituted phenyl groups such as methylphenyl. Substituted arylalkyl groups include fully halogenated or semihalogenated arylalkyl groups, such as arylalkyl groups having one or more alkyl and/or aryl groups having one or more hydrogens replaced with one or more fluorine atoms, chlorine atoms, bromine atoms and/or iodine atoms. Compositions of some embodiments of the invention comprise arylalkyl groups as terminating groups, such as polymer backbone terminating groups and/or polymer side chain terminating groups.

As to any of the groups described herein which contain one or more substituents, it is understood that such groups do not contain any substitution or substitution patterns which are sterically impractical and/or synthetically non-feasible. In addition, the compounds of this invention include all stereochemical isomers arising from the substitution of these compounds. Optional substitution of alkyl groups includes substitution with one or more alkenyl groups, aryl groups or both, wherein the alkenyl groups or aryl groups are optionally substituted. Optional substitution of alkenyl groups includes substitution with one or more alkyl groups, aryl groups, or both, wherein the alkyl groups or aryl groups are optionally substituted. Optional substitution of aryl groups includes substitution of the aryl ring with one or more alkyl groups, alkenyl groups, or both, wherein the alkyl groups or alkenyl groups are optionally substituted.

Optional substituents for any alkyl, alkenyl and aryl group includes substitution with one or more of the following substituents, among others:

halogen, including fluorine, chlorine, bromine or iodine;

pseudohalides, including —CN;

—COOR where R is a hydrogen or an alkyl group or an aryl group and more specifically where R is a methyl, ethyl, propyl, butyl, or phenyl group all of which groups are optionally substituted;

—COR where R is a hydrogen or an alkyl group or an aryl group and more specifically where R is a methyl, ethyl, propyl, butyl, or phenyl group all of which groups are optionally substituted;

—$CON(R)_2$ where each R, independently of each other R, is a hydrogen or an alkyl group or an aryl group and more specifically where R is a methyl, ethyl, propyl, butyl, or phenyl group all of which groups are optionally substituted; and where R and R can form a ring which can contain one or more double bonds and can contain one or more additional carbon atoms;

—$OCON(R)_2$ where each R, independently of each other R, is a hydrogen or an alkyl group or an aryl group and more specifically where R is a methyl, ethyl, propyl, butyl, or phenyl group all of which groups are optionally substituted; and where R and R can form a ring which can contain one or more double bonds and can contain one or more additional carbon atoms;

—$N(R)_2$ where each R, independently of each other R, is a hydrogen, or an alkyl group, or an acyl group or an aryl group and more specifically where R is a methyl, ethyl, propyl, butyl, phenyl or acetyl group, all of which are optionally substituted; and where R and R can form a ring which can contain one or more double bonds and can contain one or more additional carbon atoms;

—SR, where R is hydrogen or an alkyl group or an aryl group and more specifically where R is hydrogen, methyl, ethyl, propyl, butyl, or a phenyl group, which are optionally substituted;

—$SO_2R$, or —SOR where R is an alkyl group or an aryl group and more specifically where R is a methyl, ethyl, propyl, butyl, or phenyl group, all of which are optionally substituted;

—OCOOR where R is an alkyl group or an aryl group;

—$SO_2N(R)_2$ where each R, independently of each other R, is a hydrogen, or an alkyl group, or an aryl group all of which are optionally substituted and wherein R and R can form a ring which can contain one or more double bonds and can contain one or more additional carbon atoms; and OR where R is H, an alkyl group, an aryl group, or an acyl group all of which are optionally substituted. In a particular example R can be an acyl yielding-OCOR" where R" is a hydrogen or an alkyl group or an aryl group and more specifically where R" is methyl, ethyl, propyl, butyl, or phenyl groups all of which groups are optionally substituted.

Specific substituted alkyl groups include haloalkyl groups, particularly trihalomethyl groups and specifically trifluoromethyl groups. Specific substituted aryl groups include mono-, di-, tri, tetra- and pentahalo-substituted phenyl groups; mono-, di-, tri-, tetra-, penta-, hexa-, and hepta-halo-substituted naphthalene groups; 3- or 4-halo-substituted phenyl groups, 3- or 4-alkyl-substituted phenyl groups, 3- or 4-alkoxy-substituted phenyl groups, 3- or 4-RCO-substituted phenyl, 5- or 6-halo-substituted naphthalene groups. More specifically, substituted aryl groups include acetylphenyl groups, particularly 4-acetylphenyl groups; fluorophenyl groups, particularly 3-fluorophenyl and 4-fluorophenyl groups; chlorophenyl groups, particularly 3-chlorophenyl and 4-chlorophenyl groups; methylphenyl groups, particularly 4-methylphenyl groups; and methoxyphenyl groups, particularly 4-methoxyphenyl groups.

As to any of the above groups which contain one or more substituents, it is understood that such groups do not contain any substitution or substitution patterns which are sterically impractical and/or synthetically non-feasible.

Many of the molecules disclosed herein contain one or more ionizable groups. Ionizable groups include groups from which a proton can be removed (e.g., —COOH) or added (e.g., amines) and groups that can be quaternized (e.g., amines). All possible ionic forms of such molecules and salts thereof are intended to be included individually in the disclosure herein. With regard to salts of the compounds herein, one of ordinary skill in the art can select from among a wide variety of available counterions that are appropriate for preparation of salts of this invention for a given application. In specific applications, the selection of a given anion or cation for preparation of a salt can result in increased or decreased solubility of that salt.

The compounds of this invention can contain one or more chiral centers. Accordingly, this invention is intended to include racemic mixtures, diastereomers, enantiomers, tautomers and mixtures enriched in one or more stereoisomer. The scope of the invention as described and claimed encompasses the racemic forms of the compounds as well as the individual enantiomers and non-racemic mixtures thereof.

As used herein, the term "isomers" refers to compounds having the same number and kind of atoms, and hence the same molecular weight, but differing in respect to the structural arrangement or configuration of the atoms.

The term "tautomer," as used herein, refers to one of two or more structural isomers which exist in equilibrium and which are readily converted from one isomeric form to another. It will be apparent to one skilled in the art that certain compounds of this invention may exist in tautomeric forms, all such tautomeric forms of the compounds being within the scope of the invention.

Unless otherwise stated, structures depicted herein are also meant to include all stereochemical forms of the structure; i.e., the R and S configurations for each asymmetric center. Therefore, single stereochemical isomers as well as enantiomeric and diastereomeric mixtures of the present compounds are within the scope of the invention.

Unless otherwise stated, structures depicted herein are also meant to include compounds which differ only in the presence of one or more isotopically enriched atoms. For example, compounds having the present structures except for the replacement of a hydrogen by a deuterium or tritium, or the replacement of a carbon by $^{13}C$- or $^{14}C$-enriched carbon are within the scope of this invention.

The compounds of the present invention may also contain unnatural proportions of atomic isotopes at one or more of the atoms that constitute such compounds. For example, the compounds may be radiolabeled with radioactive isotopes, such as for example tritium ($^3H$), iodine-125 ($^{125}I$), or carbon-14 ($^{14}C$). All isotopic variations of the compounds of the present invention, whether radioactive or not, are encompassed within the scope of the present invention.

The symbol  denotes the point of attachment of one or more chemical moieties, one or more functional groups, one or more atoms, one or more ions, an unpaired electron, or one or more other chemical species to the represented molecule, compound, or chemical formula. For example, in the formula

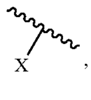

,

"X" represents a molecule or compound, the symbol  denotes a point of attachment of one or more chemical moieties, one or more functional groups, one or more atoms, one or more ions, an unpaired electron, or one or more other chemical species to X (where X corresponds to the represented molecule, compound, or chemical formula) via covalent bonding, wherein the covalent bonding can be any feasible covalent bond, including, but not limited to, a single bond, a double bond, or a triple bond. As an illustrative example, in the moiety

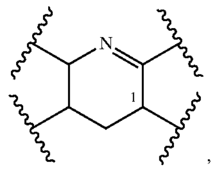 [SMILES: *C1=NC(*)C(*)CC1*]
, the carbon labeled "1" has point of attachment which can be a double bond to another species, such a double bond to an oxygen, or two single bonds to two independent species, such as two distinct single bonds each to a hydrogen. As another illustrative example, when two points of attachment are shown on a single atom of a molecule, such as in the moiety

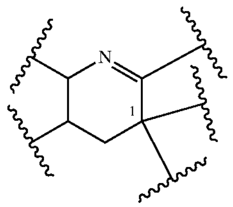 [SMILES: *C1=NC(*)C(*)CC1(*)*]

where the carbon labeled "1" has two points of attachment shown, the shown points of attachment on the same single atom (e.g., carbon 1), can be interpreted as representing either a preferable embodiment of two distinct bonds to that same single atom (e.g., two hydrogens bonded to carbon 1) or an optional embodiment of a single point of attachment to said same single atom (e.g., the two points of attachment on carbon 1 can optionally be consolidated as representing one double to carbon 1, such as a double bond to oxygen). As used herein, the various functional groups represented will be understood to have a point of attachment at the functional group having the hyphen or dash (-) or a dash used in combination with an asterisk (*). In other words, in the case of $—CH_2CH_2CH_3$ or $—CH_2CH_2CH_3$, it will be understood that the point of attachment is the $CH_2$ group at the far left. If a group is recited without an asterisk or a dash, then the attachment point is indicated by the plain and ordinary meaning of the recited group.

Where substituent groups are specified by their conventional chemical formulae, written from left to right, they equally encompass the chemically identical substituents that would result from writing the structure from right to left, e.g., $—CH_2O—$ is equivalent to $—OCH_2—$.

The term "±" refers to an inclusive range of values, such that "X±Y," wherein each of X and Y is independently a number, refers to an inclusive range of values selected from the range of X−Y to X+Y. In the cases of "X±Y" wherein Y is a percentage (e.g., 1.0±20%), the inclusive range of values is selected from the range of X−Z to X+Z, wherein Z is equal to X. (Y/100). For example, 1.0±20% refers to the inclusive range of values selected from the range of 0.8 to 1.2.

The term "and/or" is used herein, in the description and in the claims, to refer to a single element alone and any combination of elements from the list in which the term "and/or" appears. A listing of two or more elements having the term "and/or" is a listing of embodiments including embodiments having any of the individual elements alone as well as embodiments having any combination of the listed elements. For example, the phrase "element A and/or element B" is a listing of embodiments intended to include embodiments having element A alone, having element B alone, as well as embodiments having both elements A and B taken together. In other words, for example, the phrase "element A and/or element B" is equivalent to the phrase "element A, element B, or both element A and element B". Likewise, therefore, for example, the phrase "element A, element B, and/or element C" is a listing of embodiments intended to include embodiments having element A alone, having element B alone, having element C alone, having elements A and B taken together, having elements A and C taken together, having elements B and C taken together, as well as embodiments having elements A, B, and C taken together.

The term "melanin purity" can be used to characterize a collection or plurality of melanin materials (e.g., a plurality of artificial melanin nanoparticles, optionally in a dispersion or formulation) and refers to a relative measure of purity or content of a melanin type (e.g., pheomelanin) corresponding to a given melanin material with respect to all types (e.g., eumelanin, neuromelanin, pyomelanin, allomelanin and pheomelanin) of melanin materials in the collection or plurality of melanin materials. The term "pheomelanin purity" refers the relative purity or content of artificial melanin molecules and artificial melanin materials, or artificial melanin polymers or artificial melanin base units thereof, that are or comprise pheomelanin (in a collection or plurality of melanin or melanin-containing molecules or materials) with respect to all artificial melanin molecules and materials, or artificial melanin polymers or base units thereof, in said collection or plurality. Melanin purity is a quantitative value selected from the range of 0 to 1.

The term "polydispersity" or "dispersity" refers to a measure of heterogeneity of sizes particles. For example, polydispersity can be used to characterize a width of a particle size distribution (e.g., particle size vs. count or frequency), such as a particle size distribution of artificial melanin nanoparticles. For example, polydispersity may characterize heterogeneity of sizes of artificial melanin nanoparticles, such as artificial melanin nanoparticles in a solvent or artificial melanin nanoparticles in a dry state, such as those forming a film or layer. A "polydispersity index" is a measure of polydispersity. A polydispersity index can be measured using Dynamic Light Scattering (DLS), for example. Particles characterized by a polydispersity index of less than 0.1 are typically referred to as "monodisperse". For example, a polydispersity index (PDI) can be calculated as the square of the standard deviation of the particle size distribution divided by its mean:

$$=\left(\frac{\sigma}{d}\right)^2,$$

where σ is standard deviation of the particle size distribution and d is the mean diameter of the particle size distribution.

Polydispersity and polydispersity index, as well as techniques for determining these, are further described in "NanoComposix's Guide to Dynamic Light Scattering Measurement and Analysis" [dated February 2015 (version 1.4), published by nanoComposix of San Diego, CA, and available at nanoComposix_Guidelines_for_DLS_Measurements_and_Analysis (last accessed Jun. 26, 2019)], which is incorporated herein by reference. The polydispersity index can also be calculated from electron microscope (SEM and/or TEM) images where the diameter is measured using software such as ImageJ, followed by calculating a mean size of the distribution, and then using the aforementioned equation to calculate the polydispersity index.

The term "size stable" refers to stability of particles in a dispersion with respect to a size characteristic of said particles. Preferably, particles in a dispersion characterized as size stable are characterized by a size characteristic being within 50%, within 40%, within 30%, preferably within 20%, more preferably within 15%, still more preferably within 10%, further more preferably within 5%, or equivalent to a reference or initial size characteristic, under given conditions and optionally for a given time. For example, nanoparticles of a dispersion characterized as size-stable in the dispersion having a pH of at least 11, with respect to an average size of the nanoparticle in the dispersion having a pH of 7, have an average size in the pH 11 dispersion that is within 50%, within 40%, within 30%, preferably within 20%, more preferably within 15%, still more preferably within 10%, further more preferably within 5%, or equivalent to an average size of the otherwise equivalent nanoparticles in the otherwise equivalent dispersion having a pH of 7. Preferably, but not necessarily, nanoparticles characterized as size stable as so size stable for time that is at least 1 hour to 5 hours, preferably at least 5 hours to 12 hours, more preferably at least 12 hours to 1 week, still more preferably at least 1 week.

The term "self-assembly" refers to a process in which individual elements assemble into a network or organized structure without external direction. In an embodiment, self-assembly leads to a decrease in entropy of a system. In an embodiment, self-assembly may be induced, or initiated, via contacting or reacting the individual elements, optionally at a certain critical concentration, and/or via temperature and/or via pressure. A "self-assembled structure" is a structure or network formed by self-assembly. In an embodiment, self-assembly is a polymer crystallization process. The Gibbs free energy of the self-assembled structure is lower than of the sum of the individual components in their non-organized arrangement prior to self-assembly under otherwise identical conditions (e.g., temperature and pressure). In an embodiment, entropy of a self-assembled structure is lower than that of the sum of the individual components in their non-organized arrangement prior to self-assembly under otherwise identical conditions (e.g., temperature and pressure). For example, artificial melanin nanoparticles of this disclosure can form by self-assembly of a plurality of oligomers and/or melanin monomers. For example, structures or layers (e.g., films) for artificial melanin nanoparticles may form by self-assembly, such as structures or layers formed of artificial melanin nanoparticles and exhibiting structural color.

As used herein, the terms "AMNP" and "ANP" are equivalent and interchangeable and refer to artificial allomelanin nanoparticles.

As used herein, the terms "artificial" and "synthetic" in reference to melanin (e.g., "artificial melanin" and "synthetic melanin", respectively) are equivalent and interchangeable.

As used herein, unless otherwise stated explicitly, the term "NM" refers to nitrogen mustard, an exemplary chemical that induces damage to skin.

As used herein, the term "SMP" refers to synthetic (or artificial) melanin particle. In some aspects and examples, an SMP is a synthetic/artificial polydopamine (PDA) particle. In some aspects and examples, an SMP is a synthetic/artificial allomelanin (ANMP or ANP) particle.

In an embodiment, a composition or compound of the invention, such as an alloy or precursor to an alloy, is isolated or substantially purified. In an embodiment, an isolated or purified compound is at least partially isolated or substantially purified as would be understood in the art. In an embodiment, a substantially purified composition, compound or formulation of the invention has a chemical purity of 95%, optionally for some applications 99%, optionally for some applications 99.9%, optionally for some applications 99.99%, and optionally for some applications 99.999% pure.

DETAILED DESCRIPTION OF THE INVENTION

In the following description, numerous specific details of the devices, device components and methods of the present invention are set forth in order to provide a thorough explanation of the precise nature of the invention. It will be apparent, however, to those of skill in the art that the invention can be practiced without these specific details.

Certain Exemplary Aspects and Embodiments

Various aspects are contemplated and disclosed herein, several of which are set forth in the paragraphs below. It is explicitly contemplated and disclosed that any aspect or portion thereof can be combined to form an aspect. In addition, it is explicitly contemplated and disclosed that: any reference to Aspect 1 includes reference to Aspects 1a, 1b, 1c, 1d, and any combination thereof (i.e., any reference to an aspect includes reference to that aspect's lettered versions). Moreover, the terms "any preceding aspect" and "any one of the preceding aspects" means any aspect that appears prior to the aspect that contains such phrase (for example, the sentence "Aspect 15: The material, dispersion, formulation, or method of any preceding Aspect . . . " means that any Aspect prior to Aspect 15 is referenced, including letter versions). For example, it is contemplated and disclosed that, optionally, any composition, method, or formulation of any the below aspects may be useful with or combined with any other aspect provided below. Further, for example, it is contemplated and disclosed that any embodiment or aspect described above may, optionally, be combined with any of the below listed aspects or any portion(s) thereof.

Aspect 1a: A functionalized artificial melanin material comprising:

a surface functionalized with a modifier agent via a linker group;

wherein the modifier agent comprises the linker group and a functional group attached to the linker group; and wherein the linker group is a nucleophilic group.

Aspect 1b: A melanin-containing formulation comprising:

one or more solvents (optionally one or more hydrophobic solvents); and a functionalized artificial melanin material dispersed in the one or more solvents;

wherein:

the functionalized artificial melanin material comprises a surface functionalized with a modifier agent via a linker group;

the modifier agent comprises the linker group and a functional group attached to the linker group; and the linker group is a nucleophilic group.

Aspect 1c: A method for treatment of a subject, the method comprising:

topically administering a melanin formulation to damaged skin of the subject;

wherein the functionalized artificial melanin material comprises a surface functionalized with a modifier agent via a linker group;

wherein the modifier agent comprises the linker group and a functional group attached to the linker group;

wherein the linker group is a nucleophilic group;

wherein the melanin formulation comprises one or more solvents (optionally one or more hydrophobic solvents) and the functionalized artificial melanin material dispersed in the one or more solvents (optionally one or more hydrophobic solvents);

wherein the administered functionalized artificial melanin material comprises an extracellular functionalized artificial melanin material at the damaged skin; and facilitating skin healing at the damaged skin via at least the extracellular functionalized artificial melanin material;

wherein the step of facilitating skin healing comprises at least a portion of the extracellular artificial melanin material performing a therapeutic extracellular activity.

Aspect 1d: A method for making a functionalized artificial melanin material, the method comprising:

providing unfunctionalized artificial melanin nanoparticles; and exposing, for a finite time, the unfunctionalized artificial melanin nanoparticles to a precursor of the modifier agent;

wherein the step of exposing comprises:

conjugating the unfunctionalized artificial melanin nanoparticles with the precursor thereby forming functionalized artificial melanin nanoparticles having a modifier agent;

wherein the functionalized artificial melanin nanoparticles comprises a surface functionalized with the modifier agent via a linker group;

wherein the modifier agent comprises the linker group and a functional group attached to the linker group; and wherein the linker group is a nucleophilic group.

Aspect 1e: The formulation of Aspect 1b or the method of Aspect 1c, wherein the formulation is non-aqueous, hydrophobic, or intermediate. Aspect 1f: The formulation of Aspect 1b or the method of Aspect 1c, wherein the formulation is non-aqueous and hydrophobic. Aspect 1g: The formulation of Aspect 1b or the method of Aspect 1c, wherein the formulation comprises both an aqueous solvent or phase and a non-aqueous or hydrophobic solvent or phase. Aspect 1h: The formulation of Aspect 1b or the method of Aspect 1c, wherein the formulation comprises both a hydrophilic solvent or phase and a hydrophobic solvent or phase. Aspect 1i: The formulation of Aspect 1b or the method of Aspect 1c, wherein the artificial melanin material (optionally being artificial melanin nanoparticles) is dispersed by both a hydrophilic phase and a hydrophobic phase of the formulation. Aspect 1j: The formulation of Aspect 1b or the method of Aspect 1c, wherein the artificial melanin material (optionally being artificial melanin nanoparticles) is dispersed by a hydrophilic solvent or phase, a hydrophobic solvent or phase, or both a hydrophilic solvent or phase and a hydrophobic solvent or phase of the formulation. Aspect 1k: The formulation of Aspect 1b or the method of Aspect 1c, wherein the artificial melanin material (optionally being artificial melanin nanoparticles) is dispersed by both one or more hydrophilic solvents and by one or more hydrophobic solvents in the formulation. Aspect 1l: The formulation of Aspect 1b or the method of Aspect 1c, wherein the formulation comprises one or more hydrophilic solvents, such as but not necessarily limited to water. Aspect 1m: The formulation of Aspect 1b or the method of Aspect 1c, wherein the formulation is characterized as intermediate between hydrophilic and hydrophobic. Aspect 1n: The formulation of Aspect 1b or the method of Aspect 1c, wherein the artificial melanin material (optionally being artificial melanin nanoparticles) is intermediate between hydrophilic and hydrophobic such that it is and/or can be associated with or present in both hydrophilic or water phase(s) and in hydrophobic phase(s). Aspect 1o: The material, formulation, or method of any preceding Aspect, wherein the artificial melanin material (optionally being artificial melanin nanoparticles) is characterized as intermediate between hydrophilic and hydrophobic such that it can be associated with, present in, or dispersed in both hydrophilic or water phase(s) and in hydrophobic phase(s). Aspect 1p: The material, formulation, or method of any preceding Aspect, wherein the artificial melanin material (optionally being artificial melanin nanoparticles) is associated with, present in, or dispersed in the one or more hydrophobic solvents of the formulation. Aspect 1q: The material, formulation, or method of any preceding Aspect, wherein the artificial melanin material (optionally being artificial melanin nanoparticles) is associated with, present in, or dispersed in the one or more hydrophobic solvents of the formulation. Aspect 1r: The material, formulation, or method of any preceding Aspect, wherein the artificial melanin material (optionally being artificial melanin nanoparticles) is associated with, present in, or dispersed in one or more hydrophilic solvents of the formulation.

Aspect 2a: The material, dispersion, formulation, or method of any preceding Aspect, comprising functionalized artificial melanin nanoparticles, wherein each functionalized artificial melanin nanoparticle independently comprises a surface functionalized with the modifier agent via the linker group. Aspect 2b: The material, dispersion, formulation, or method of any preceding Aspect, being functionalized artificial melanin nanoparticles, wherein each functionalized artificial melanin nanoparticle independently comprises a surface functionalized with the modifier agent via the linker group.

Aspect 3: The material, dispersion, formulation, or method of any preceding Aspect, wherein the linker group is an amine group, a thiol group, or any combination thereof.

Aspect 4: The material, dispersion, formulation, or method of any preceding Aspect, wherein the linker group is an amine group.

Aspect 5: The material, dispersion, formulation, or method of any preceding Aspect, wherein the linker group is a primary amine group.

Aspect 6: The material, dispersion, formulation, or method of any preceding Aspect, wherein the linker group is characterized by formula FX1A or FX1B:

(FX1A)

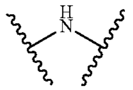

or (FX1A)

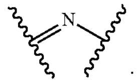

.

Aspect 7a: The material, dispersion, formulation, or method of any preceding Aspect, wherein the functional group is hydrophobic or lends at least partial hydrophobicity to the functionalized artificial melanin material or to functionalized artificial melanin nanoparticles thereof.

Aspect 8a: The material, dispersion, formulation, or method of any preceding Aspect, wherein the functionalized artificial melanin material is hydrophobic and/or the functionalized artificial melanin material forms a stable colloid in a non-aqueous hydrophobic solvent at a concentration of said material selected from the range of approximately 0.5 mg/mL to approximately 100 mg/mL, and wherein any range and value therebetween inclusively is explicitly contemplated and disclosed herein, such as optionally selected from the range of approximately 1.0 mg/mL to approximately 100 mg/mL, optionally selected from the range of approximately 1.5 mg/mL to approximately 100 mg/mL, optionally selected from the range of approximately 2.0 mg/mL to approximately 100 mg/mL, optionally selected from the range of approximately 2.5 mg/mL to approximately 100 mg/mL, optionally selected from the range of approximately 1.0 mg/mL to approximately 75 mg/mL, optionally selected from the range of approximately 1.0 mg/mL to approximately 50 mg/mL, optionally selected from the range of approximately 1.0 mg/mL to approximately 40 mg/mL, optionally selected from the range of approximately 1.0 mg/mL to approximately 30 mg/mL, optionally selected from the range of approximately 1.0 mg/mL to approximately 20 mg/mL, optionally selected from the range of approximately 1.0 mg/mL to approximately 10 mg/mL, optionally selected from the range of approximately 1.0 mg/mL to approximately 5 mg/mL. Aspect 8b: The material, dispersion, formulation, or method of any preceding Aspect, wherein the functionalized artificial melanin material is characterized as intermediate between hydrophilic and hydrophobic such that it is configured to be associated with, present in, or dispersed in both hydrophilic or water phase(s) and in hydrophobic phase(s) hydrophobic such that the functionalized artificial melanin material is configured to form a stable colloid a solution or formulation having hydrophilic or water phase(s), hydrophobic phase(s), or both, optionally when a concentration of said material in said solution or formulation is selected from the range of approximately 0.5 mg/mL to approximately 100 mg/mL, and wherein any range and value therebetween inclusively is explicitly contemplated and disclosed herein, such as optionally selected from the range of approximately 1.0 mg/mL to approximately 100 mg/mL, optionally selected from the range of approximately 1.5 mg/mL to approximately 100 mg/mL, optionally selected from the range of approximately 2.0 mg/mL to approximately 100 mg/mL, optionally selected from the range of approximately 2.5 mg/mL to approximately 100 mg/mL, optionally selected from the range of approximately 1.0 mg/mL to approximately 75 mg/mL, optionally selected from the range of approximately 1.0 mg/mL to approximately 50 mg/mL, optionally selected from the range of approximately 1.0 mg/mL to approximately 40 mg/mL, optionally selected from the range of approximately 1.0 mg/mL to approximately 30 mg/mL, optionally selected from the range of approximately 1.0 mg/mL to approximately 20 mg/mL, optionally selected from the range of approximately 1.0 mg/mL to approximately 10 mg/mL, optionally selected from the range of approximately 1.0 mg/mL to approximately 5 mg/mL.

Aspect 9: The material, dispersion, formulation, or method of any preceding Aspect, wherein a dispersion or formulation having said functionalized artificial melanin material or the functionalized artificial melanin nanoparticles thereof at a concentration selected from the range of 0.5 mg/mL to 100 mg/mL is characterized by a contact angle of at least approximately 90°, optionally at least approximately 100°, optionally at least approximately 105°, optionally at least approximately 110°, optionally at least approximately 115°, optionally at least approximately 120°, optionally at least approximately 125°, optionally at least approximately 130°, optionally at least approximately 135°, optionally at least approximately 140°, optionally at least approximately 145°, optionally at least approximately 150°, optionally at least approximately 155°, optionally at least approximately 160°.

Aspect 10: The material, dispersion, formulation, or method of any preceding Aspect, wherein a dispersion or formulation having said functionalized artificial melanin material or the functionalized artificial melanin nanoparticles thereof at a concentration selected from the range of 0.5 mg/mL to 100 mg/mL is characterized by a contact angle selected from the range of approximately 115° to approximately 180°, optionally selected from the range of approximately 120° to approximately 180°, optionally selected from the range of approximately 125° to approximately 180°, optionally selected from the range of approximately 130° to approximately 180°, optionally selected from the range of approximately 135° to approximately 180°, optionally selected from the range of approximately 140° to approximately 180°, optionally selected from the range of approximately 145° to approximately 180°, optionally selected from the range of approximately 150° to approximately 180°, optionally selected from the range of approximately 155° to approximately 180°, optionally selected from the range of approximately 115° to approximately 160°, optionally selected from the range of approximately 120° to approximately 160°, optionally selected from the range of approximately 125° to approximately 160°, optionally selected from the range of approximately 130° to approximately 160°, optionally selected from the range of approximately 135° to approximately 160°, optionally selected from the range of approximately 140° to approximately 160°, optionally selected from the range of approximately 145° to approximately 180°.

Aspect 11: The material, dispersion, formulation, or method of any preceding Aspect, wherein said functionalized artificial melanin material or the functionalized artificial melanin nanoparticles thereof have a zeta potential greater than or equal to −40 mV (optionally greater than or equal to approximately −35 mV, optionally greater than or equal to approximately −30 mV, optionally greater than or equal to approximately −25 mV, optionally greater than or equal to approximately −20 mV, optionally greater than or equal to approximately −15 mV, optionally greater than or equal to approximately −10 mV, optionally greater than or equal to approximately −5 mV, optionally greater than or equal to approximately 5 mV, optionally greater than or equal to approximately 10 mV, optionally greater than or equal to approximately 15 mV, optionally greater than or equal to approximately 20 mV) when dispersed in water and/or in a non-aqueous hydrophobic solvent at a concentration selected from the range of 0.5 mg/mL to 100 mg/mL.

Aspect 12: The material, dispersion, formulation, or method of any preceding Aspect, wherein the modifier agent is characterized by formula FX2A or FX2B:

(FX2A)

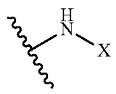

or (FX2B)

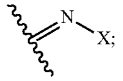

wherein X is the functional group.

Aspect 13: The material, dispersion, formulation, or method of any preceding Aspect, wherein each linker group is independently attached to a phenyl group or a quinone of the artificial melanin material or of a respective artificial melanin nanoparticle.

Aspect 14: The material, dispersion, formulation, or method of any preceding Aspect, wherein the modifier agent attached to the artificial melanin material or to the respective functionalized artificial melanin nanoparticle is a product of a Michael Addition or via a Schiff Base reaction.

Aspect 15: The material, dispersion, formulation, or method of any preceding Aspect, wherein the linker group of the modifier agent is attached at an outer surface of the functionalized artificial melanin material or of functionalized artificial melanin nanoparticle thereof, is attached at an inner pore surface of the functionalized artificial melanin material or of functionalized artificial melanin nanoparticle thereof, or both.

Aspect 16: The material, dispersion, formulation, or method of any preceding Aspect, wherein the functionalized artificial melanin material or at least a portion of functionalized artificial melanin nanoparticles thereof comprise at least two different modifier agents.

Aspect 17a: The material, dispersion, formulation, or method of any preceding Aspect, wherein the material comprises at least 5% by mass of the modifier agent. Aspect 17b: The material, dispersion, formulation, or method of any preceding Aspect, wherein the material comprises at least 5% by mass and less than 75% by mass of the modifier agent.

Aspect 18: The material, dispersion, formulation, or method of any preceding Aspect, wherein the functional group faces a solution or environment to which the functionalized artificial melanin material, or functionalized artificial melanin nanoparticle thereof, is exposed.

Aspect 19a: The material, dispersion, formulation, or method of any preceding Aspect, wherein the functional group is selected from the group consisting of a substituted or unsubstituted $C_4$-$C_{30}$ hydrocarbyl group, a substituted or unsubstituted $C_4$-$C_{30}$ alkyl group, a substituted or unsubstituted $C_4$-$C_{30}$ cycloalkyl group, a substituted or unsubstituted $C_4$-$C_{30}$ aryl group, a substituted or unsubstituted $C_4$-$C_{30}$ heteroaryl group, a substituted or unsubstituted $C_4$-$C_{30}$ acyl group, a substituted or unsubstituted $C_4$-$C_{30}$ alkoxy group, a substituted or unsubstituted $C_4$-$C_{30}$ alkenyl group, a substituted or unsubstituted $C_4$-$C_{30}$ alkynyl group, a substituted or unsubstituted $C_4$-$C_{30}$ alkylaryl group, and any combination thereof. Aspect 19b: The material, dispersion, formulation, or method of any preceding Aspect, wherein the functional group comprises a substituted or unsubstituted $C_4$-$C_{30}$ hydrocarbyl group, a substituted or unsubstituted $C_4$-$C_{30}$ alkyl group, a substituted or unsubstituted $C_4$-$C_{30}$ cycloalkyl group, a substituted or unsubstituted $C_4$-$C_{30}$ aryl group, a substituted or unsubstituted $C_4$-$C_{30}$ heteroaryl group, a substituted or unsubstituted $C_4$-$C_{30}$ acyl group, a substituted or unsubstituted $C_4$-$C_{30}$ alkoxy group, a substituted or unsubstituted $C_4$-$C_{30}$ alkenyl group, a substituted or unsubstituted $C_4$-$C_{30}$ alkynyl group, a substituted or unsubstituted $C_4$-$C_{30}$ alkylaryl group, or any combination thereof.

Aspect 20a: The material, dispersion, formulation, or method of any preceding Aspect, wherein the functional group is selected from the group consisting of a $C_4$-$C_{30}$ alkyl group, a $C_4$-$C_{30}$ alkenyl group, a $C_4$-$C_{30}$ alkynyl group, and any combination thereof. Aspect 20b: The material, dispersion, formulation, or method of any preceding Aspect, wherein the functional group is selected from the group consisting of a $C_4$-$C_{30}$ alkyl group, a $C_4$-$C_{30}$ alkenyl group, a $C_4$-$C_{30}$ alkynyl group, or any combination thereof.

Aspect 21a: The material, dispersion, formulation, or method of any preceding Aspect, wherein the functional group is a substituted or unsubstituted $C_6$-$C_{30}$ hydrocarbyl group. Aspect 21b: The material, dispersion, formulation, or method of any preceding Aspect, wherein the functional group is a substituted or unsubstituted $C_6$-$C_{24}$ hydrocarbyl group. Aspect 21c: The material, dispersion, formulation, or method of any preceding Aspect, wherein the functional group is a substituted or unsubstituted $C_6$-$C_{20}$ hydrocarbyl group. Aspect 21d: The material, dispersion, formulation, or method of any preceding Aspect, wherein the functional group is a substituted or unsubstituted $C_6$-$C_{18}$ hydrocarbyl group. Aspect 21e: The material, dispersion, formulation, or method of any preceding Aspect, wherein the functional group is a substituted or unsubstituted $C_8$-$C_{30}$ hydrocarbyl group. Aspect 21f: The material, dispersion, formulation, or method of any preceding Aspect, wherein the functional group is a substituted or unsubstituted $C_8$-$C_{24}$ hydrocarbyl group. Aspect 21g: The material, dispersion, formulation, or method of any preceding Aspect, wherein the functional group is a substituted or unsubstituted $C_{12}$-$C_{30}$ hydrocarbyl group. Aspect 21h: The material, dispersion, formulation, or method of any preceding Aspect, wherein the functional group is a substituted or unsubstituted $C_{12}$-$C_{24}$ hydrocarbyl group. Aspect 21i: The material, dispersion, formulation, or method of any preceding Aspect, wherein the functional group is a substituted or unsubstituted $C_{12}$-$C_{20}$ hydrocarbyl group.

Aspect 22a: The material, dispersion, formulation, or method of any preceding Aspect, wherein the functional group is a substituted or unsubstituted $C_6$-$C_{30}$ alkyl group. Aspect 22b: The material, dispersion, formulation, or method of any preceding Aspect, wherein the functional group is a substituted or unsubstituted $C_6$-$C_{24}$ alkyl group. Aspect 22c: The material, dispersion, formulation, or method of any preceding Aspect, wherein the functional group is a substituted or unsubstituted $C_6$-$C_{20}$ alkyl group. Aspect 22d: The material, dispersion, formulation, or method of any preceding Aspect, wherein the functional group is a substituted or unsubstituted $C_6$-$C_{18}$ alkyl group. Aspect 22e: The material, dispersion, formulation, or method of any preceding Aspect, wherein the functional group is a substituted or unsubstituted $C_8$-$C_{30}$ alkyl group. Aspect 22f: The material, dispersion, formulation, or method of any preceding Aspect, wherein the functional group is a substituted or unsubstituted $C_8$-$C_{24}$ alkyl group. Aspect 22g: The material, dispersion, formulation, or method of any preceding Aspect, wherein the functional group is a substituted or unsubstituted $C_{12}$-$C_{30}$ alkyl group. Aspect 22h: The material, dispersion, formulation, or method of any preceding Aspect, wherein the functional group is a substituted or unsubstituted $C_{12}$-$C_{24}$ alkyl group. Aspect 22i: The material, dispersion, formulation, or method of any preceding Aspect, wherein the functional group is a substituted or unsubstituted $C_{12}$-$C_{20}$ alkyl group.

Aspect 23: The material, dispersion, formulation, or method of any preceding Aspect, wherein the functional group is a substituted or unsubstituted $C_8$-$C_{24}$ alkyl group.

Aspect 24a: The material, dispersion, formulation, or method of any preceding Aspect, wherein the functional group is selected from the group consisting of a substituted or unsubstituted $C_4$-$C_{30}$ hydrocarbyl group, a substituted or unsubstituted $C_4$-$C_{30}$ alkyl group, a substituted or unsubstituted $C_4$-$C_{30}$ cycloalkyl group, a substituted or unsubstituted $C_4$-$C_{30}$ aryl group, a substituted or unsubstituted $C_4$-$C_{30}$ heteroaryl group, a substituted or unsubstituted $C_4$-$C_{30}$ acyl group, a substituted or unsubstituted $C_4$-$C_{30}$ alkoxy group, a substituted or unsubstituted $C_4$-$C_{30}$ alkenyl group, a substituted or unsubstituted $C_4$-$C_{30}$ alkynyl group, a substituted or unsubstituted $C_4$-$C_{30}$ alkylaryl group, a substituted or unsubstituted hydroxyl group, a substituted or unsubstituted carbonyl group, a substituted or unsubstituted sulfide group, a substituted or unsubstituted thiol group, a substituted or unsubstituted phosphate group, a substituted or unsubstituted azo group, a substituted or unsubstituted cyanate group, a substituted or unsubstituted primary amine group, a substituted or unsubstituted secondary amine group, a substituted or unsubstituted tertiary group, a substituted or unsubstituted imine group, a substituted or unsubstituted nitrile group, a substituted or unsubstituted pyridinyl group, a substituted or unsubstituted diamine group, a substituted or unsubstituted triamine group, a substituted or unsubstituted azide group, a substituted or unsubstituted diimine group, a substituted or unsubstituted triimine group, a substituted or unsubstituted amide group, a substituted or unsubstituted diimide group, a substituted or unsubstituted ether group, and any combination thereof. Aspect 24b: The material, dispersion, formulation, or method of any preceding Aspect, wherein the functional group comprises a substituted or unsubstituted $C_4$-$C_{30}$ hydrocarbyl group, a substituted or unsubstituted $C_4$-$C_{30}$ alkyl group, a substituted or unsubstituted $C_4$-$C_{30}$ cycloalkyl group, a substituted or unsubstituted $C_4$-$C_{30}$ aryl group, a substituted or unsubstituted $C_4$-$C_{30}$ heteroaryl group, a substituted or unsubstituted $C_4$-$C_{30}$ acyl group, a substituted or unsubstituted $C_4$-$C_{30}$ alkoxy group, a substituted or unsubstituted $C_4$-$C_{30}$ alkenyl group, a substituted or unsubstituted $C_4$-$C_{30}$ alkynyl group, a substituted or unsubstituted $C_4$-$C_{30}$ alkylaryl group, a substituted or unsubstituted hydroxyl group, a substituted or unsubstituted carbonyl group, a substituted or unsubstituted sulfide group, a substituted or unsubstituted thiol group, a substituted or unsubstituted phosphate group, a substituted or unsubstituted azo group, a substituted or unsubstituted cyanate group, a substituted or unsubstituted primary amine group, a substituted or unsubstituted secondary amine group, a substituted or unsubstituted tertiary group, a substituted or unsubstituted imine group, a substituted or unsubstituted nitrile group, a substituted or unsubstituted pyridinyl group, a substituted or unsubstituted diamine group, a substituted or unsubstituted triamine group, a substituted or unsubstituted azide group, a substituted or unsubstituted diimine group, a substituted or unsubstituted triimine group, a substituted or unsubstituted amide group, a substituted or unsubstituted diimide group, a substituted or unsubstituted ether group, or any combination thereof.

Aspect 25a: The material, dispersion, formulation, or method of any preceding Aspect, wherein the functional group is selected from the group consisting of a substituted or unsubstituted $C_4$-$C_{30}$ hydrocarbyl group, a substituted or unsubstituted $C_4$-$C_{30}$ alkyl group, a substituted or unsubstituted $C_4$-$C_{30}$ cycloalkyl group, a substituted or unsubstituted $C_4$-$C_{30}$ aryl group, a substituted or unsubstituted $C_4$-$C_{30}$ heteroaryl group, a substituted or unsubstituted $C_4$-$C_{30}$ acyl group, a substituted or unsubstituted $C_4$-$C_{30}$ alkoxy group, a substituted or unsubstituted $C_4$-$C_{30}$ alkenyl group, a substituted or unsubstituted $C_4$-$C_{30}$ alkynyl group, a substituted or unsubstituted $C_4$-$C_{30}$ alkylaryl group, a substituted or unsubstituted primary amine group, a substituted or unsubstituted secondary amine group, a substituted or unsubstituted tertiary amine group, and any combination thereof. Aspect 25b: The material, dispersion, formulation, or method of any preceding Aspect, wherein the functional group comprises a substituted or unsubstituted $C_4$-$C_{30}$ hydrocarbyl group, a substituted or unsubstituted $C_4$-$C_{30}$ alkyl group, a substituted or unsubstituted $C_4$-$C_{30}$ cycloalkyl group, a substituted or unsubstituted $C_4$-$C_{30}$ aryl group, a substituted or unsubstituted $C_4$-$C_{30}$ heteroaryl group, a substituted or unsubstituted $C_4$-$C_{30}$ acyl group, a substituted or unsubstituted $C_4$-$C_{30}$ alkoxy group, a substituted or unsubstituted $C_4$-$C_{30}$ alkenyl group, a substituted or unsubstituted $C_4$-$C_{30}$ alkynyl group, a substituted or unsubstituted $C_4$-$C_{30}$ alkylaryl group, a substituted or unsubstituted primary amine group, a substituted or unsubstituted secondary amine group, a substituted or unsubstituted tertiary amine group, or any combination thereof.

Aspect 26: The material, dispersion, formulation, or method of any preceding Aspect, wherein each modifier agent is independently selected from the group consisting of 1-hexylamine, 3,3-dimethylbutylamine, octadecylamine, 5-amino-1-pentanol, t-butylamine, 10-amino-1-decanol, 1,6-hexanediamine, and 2,2,3,3,4,4,5,5,6,6,7,7,8,8,9,9,9-heptadecafluorononylamine.

Aspect 27: The material, dispersion, formulation, or method of any preceding Aspect, wherein the functionalized artificial melanin material comprises amorphous functionalized artificial melanin material.

Aspect 28: The material, dispersion, formulation, or method of any preceding Aspect, wherein the functionalized artificial melanin material or each of the functionalized artificial melanin nanoparticles thereof is not bound to, conjugated to, attached to, coated by, encompassed by, or otherwise chemically associated with a natural or biological proteinaceous matrix, component, or lipid.

Aspect 29: The material, dispersion, formulation, or method of any preceding Aspect, wherein the functionalized artificial melanin material or each of the functionalized artificial melanin nanoparticles thereof is characterized as eumelanin, pheomelanin, allomelanin, or a combination of these.

Aspect 30: The material, dispersion, formulation, or method of any preceding Aspect, wherein the functionalized artificial melanin material comprises artificial allomelanin nanoparticles, artificial polydopamine nanoparticles, or any combination thereof.

Aspect 31: The material, dispersion, formulation, or method of any preceding Aspect, wherein the functionalized artificial melanin material or the functionalized artificial melanin nanoparticles thereof are porous and have a Brunauer-Emmett-Teller (BET) area selected from the range of 70 $m^2/g$ to 800 $m^2/g$, and wherein any range and value therebetween is explicitly contemplated and disclosed herein.

Aspect 32: The material, dispersion, formulation, or method of any preceding Aspect, wherein the functionalized artificial melanin material or the functionalized artificial melanin nanoparticles thereof are non-porous or have a Brunauer-Emmett-Teller (BET) area less than 20 $m^2/g$, and wherein any range and value less than 20 $m^2/g$ is explicitly contemplated and disclosed herein.

Aspect 33: The material, dispersion, formulation, or method of any preceding Aspect, wherein the functionalized artificial melanin material comprises functionalized artificial melanin particles having a cross-sectional size on average selected from the range of 10 nm to 1000 nm, wherein any range and value therebetween is explicitly contemplated and disclosed herein, as measured by transmission electron microscopy and/or dynamic light scattering.

Aspect 34: The material, dispersion, formulation, or method of any preceding Aspect, wherein the functionalized artificial melanin material comprises functionalized artificial melanin particles having a cross-sectional size on average selected from the range of 10 nm to 100 nm, 100 nm to 500 nm, or a combination thereof, as measured by transmission electron microscopy and/or dynamic light scattering.

Aspect 35: The material, dispersion, formulation, or method of any preceding Aspect being characterized by a DPPH radical scavenging activity of at least 30% with 50 μg of the functionalized artificial melanin material.

Aspect 36: The material of any one of the preceding Aspects being a thin film.

Aspect 37: The material of any one of the preceding Aspects being a thin film, wherein the thin film exhibits structural color.

Aspect 38: The material of any one of the preceding Aspects being a thin film, wherein the thin film comprises one or more monolayers of the functionalized artificial melanin nanoparticles.

Aspect 39: The material of any one of the preceding Aspects being a thin film, wherein the thin film comprises one, two, three, or four monolayers of the functionalized artificial melanin nanoparticles.

Aspect 40: The material of any one of the preceding Aspects being a thin film, wherein the thin film is at a liquid-liquid interface, at a liquid-gas interface, or on a substrate.

Aspect 41: The material of any one of the preceding Aspects being a thin film, wherein the thin film has an area selected from the range of 0.25 $cm^2$ to 9 $cm^2$.

Aspect 42: The material of any one of the preceding Aspects being a thin film, wherein the thin film is on a skin.

Aspect 43: A melanin-containing formulation comprising:

one or more solvents (optionally one or more hydrophobic solvents); and the functionalized artificial melanin material of any one of the preceding Aspects dispersed in the one or more solvents.

Aspect 44a: A melanin-containing formulation comprising:

one or more solvents (optionally one or more hydrophobic solvents); and a functionalized artificial melanin material dispersed in the one or more solvents;

wherein:

the functionalized artificial melanin material comprises a surface functionalized with a modifier agent via a linker group;

the modifier agent comprises the linker group and a functional group attached to the linker group; and the linker group is a nucleophilic group.

Aspect 44b: The formulation of any preceding Aspect, wherein the formulation is non-aqueous, hydrophobic, or intermediate. Aspect 44c: The formulation of any preceding Aspect, wherein the formulation is non-aqueous and hydrophobic. Aspect 44d: The formulation of any preceding Aspect, wherein the formulation comprises both an aqueous solvent or phase and a non-aqueous or hydrophobic solvent or phase. Aspect 44e: The formulation of any preceding Aspect, wherein the formulation comprises both a hydrophilic solvent or phase and a hydrophobic solvent or phase.

Aspect 44f: The formulation of any preceding Aspect, wherein the artificial melanin material (optionally being artificial melanin nanoparticles) is dispersed by both a hydrophilic phase and a hydrophobic phase of the formulation. Aspect 44g: The formulation of any preceding Aspect, wherein the artificial melanin material (optionally being artificial melanin nanoparticles) is dispersed by a hydrophilic solvent or phase, a hydrophobic solvent or phase, or both a hydrophilic solvent or phase and a hydrophobic solvent or phase of the formulation. Aspect 44h: The formulation of any preceding Aspect, wherein the artificial melanin material (optionally being artificial melanin nanoparticles) is dispersed by both one or more hydrophilic solvents and by one or more hydrophobic solvents in the formulation. Aspect 44i: The formulation of any preceding Aspect, wherein the formulation comprises one or more hydrophilic solvents, such as but not necessarily limited to water. Aspect 44j: The formulation of any preceding Aspect, wherein the formulation is characterized as intermediate between hydrophilic and hydrophobic. Aspect 44k: The formulation of any preceding Aspect, wherein the artificial melanin material (optionally being artificial melanin nanoparticles) is intermediate between hydrophilic and hydrophobic such that it is and/or can be associated with or present in both hydrophilic or water phase(s) and in hydrophobic phase(s). Aspect 44l: The formulation of any preceding Aspect, wherein the artificial melanin material (optionally being artificial melanin nanoparticles) is characterized as intermediate between hydrophilic and hydrophobic such that it can be associated with, present in, or dispersed in both hydrophilic or water phase(s) and in hydrophobic phase(s). Aspect 44m: The formulation of any preceding Aspect, wherein the artificial melanin material (optionally being artificial melanin nanoparticles) is associated with, present in, or dispersed in the one or more hydrophobic solvents of the formulation. Aspect 44n: The formulation of any preceding Aspect, wherein the artificial melanin material (optionally being artificial melanin nanoparticles) is associated with, present in, or dispersed in the one or more hydrophobic solvents of the formulation. Aspect 440: The formulation of any preceding Aspect, wherein the artificial melanin material (optionally being artificial melanin nanoparticles) is associated with, present in, or dispersed in one or more hydrophilic solvents of the formulation.

Aspect 45: The formulation of any preceding Aspect, wherein the functionalized artificial melanin material comprises functionalized artificial melanin nanoparticles, each functionalized artificial melanin nanoparticle independently comprising a surface functionalized with the modifier agent via the linker group.

Aspect 46: The formulation of any preceding Aspect, wherein a concentration of the artificial melanin material in the melanin formulation is selected from the range of approximately 0.5 mg/mL to approximately 100 mg/mL, and wherein any value and range therebetween is explicitly contemplated and disclosed herein, such as optionally selected from the range of approximately 1.0 mg/mL to approximately 100 mg/mL, optionally selected from the range of approximately 1.5 mg/mL to approximately 100 mg/mL, optionally selected from the range of approximately 2.0 mg/mL to approximately 100 mg/mL, optionally selected from the range of approximately 2.5 mg/mL to approximately 100 mg/mL, optionally selected from the range of approximately 1.0 mg/mL to approximately 75 mg/mL, optionally selected from the range of approximately 1.0 mg/mL to approximately 50 mg/mL, optionally selected from the range of approximately 1.0 mg/mL to approximately 40 mg/mL, optionally selected from the range of approximately 1.0 mg/mL to approximately 30 mg/mL, optionally selected from the range of approximately 1.0 mg/mL to approximately 20 mg/mL, optionally selected from the range of approximately 1.0 mg/mL to approximately 10 mg/mL, optionally selected from the range of approximately 1.0 mg/mL to approximately 5 mg/mL.

Aspect 47: The formulation of any preceding Aspect, wherein a concentration of the functionalized artificial melanin nanoparticles is selected from the range of approximately 0.5 mg/mL to approximately 100 mg/mL, and wherein any value and range therebetween is explicitly contemplated and disclosed herein.

Aspect 48: The formulation of any preceding Aspect being characterized by a contact angle of at least approximately 90°, optionally at least 100°, optionally at least 105°, optionally at least 110°, optionally at least 115°, optionally at least 120°, optionally at least 125°, optionally at least 130°, optionally at least 135°, optionally at least 140°, optionally at least 145°, optionally at least 150°, optionally at least 155°, optionally at least approximately 160°.

Aspect 49: The formulation of any preceding Aspect being characterized by a contact angle selected from the range of approximately 115° to approximately 180°, optionally selected from the range of approximately 120° to approximately 180°, optionally selected from the range of 125° to 180°, optionally selected from the range of 130° to 180°, optionally selected from the range of 135° to 180°, optionally selected from the range of 140° to 180°, optionally selected from the range of 145° to 180°, optionally selected from the range of 150° to 180°, optionally selected from the range of 155° to 180°, optionally selected from the range of 115° to 160°, optionally selected from the range of 120° to 160°, optionally selected from the range of 125° to 160°, optionally selected from the range of 130° to 160°, optionally selected from the range of 135° to 160°, optionally selected from the range of 140° to 160°, optionally selected from the range of 145° to 180°.

Aspect 50: The formulation of any preceding Aspect, wherein the dispersed functionalized artificial melanin nanoparticles are characterized by a zeta potential magnitude of greater than approximately 20.

Aspect 51: The formulation of any preceding Aspect, wherein the dispersed functionalized artificial melanin nanoparticles are characterized by a zeta potential greater than or equal to approximately −40 mV, optionally greater than or equal to approximately −35 mV, optionally greater than or equal to approximately −30 mV, optionally greater than or equal to approximately −25 mV, optionally greater than or equal to approximately −20 mV, optionally greater than or equal to approximately −15 mV, optionally greater than or equal to approximately −10 mV, optionally greater than or equal to approximately −5 mV, optionally greater than or equal to approximately 5 mV, optionally greater than or equal to approximately 10 mV, optionally greater than or equal to approximately 15 mV, optionally greater than or equal to approximately 20 mV.

Aspect 52: The formulation of any preceding Aspect, wherein the dispersed functionalized artificial melanin nanoparticles are characterized by a positive zeta potential.

Aspect 53: The formulation of any preceding Aspect being characterized as a stable colloid.

Aspect 54: The formulation of any preceding Aspect being an ointment, a cream, a gel, a paste, or any combination thereof.

Aspect 55: The formulation of any preceding Aspect, wherein the one or more hydrophobic solvents are organic solvents.

Aspect 56: The formulation of any preceding Aspect, wherein the one or more hydrophobic solvents form at least approximately 60%, optionally at least 65%, optionally at least 70%, optionally at least 75%, optionally at least 80%, optionally at least 85%, optionally at least 95%, optionally at least 95%, of a total solvent concentration in formulation.

Aspect 57: The formulation of any preceding Aspect, wherein the one or more hydrophobic solvents are at least approximately 60%, optionally at least 65%, optionally at least 70%, optionally at least 75%, optionally at least 80%, optionally at least 85%, optionally at least 95%, optionally at least 95%, of the formulation.

Aspect 58: The formulation of any preceding Aspect having less than or equal to approximately 40 vol. % of water, optionally less than or equal to approximately 35 vol. % of water, optionally less than or equal to approximately 30 vol. % of water, optionally less than or equal to approximately 25 vol. % of water, optionally less than or equal to approximately 20 vol. % of water, optionally less than or equal to approximately 15 vol. % of water, optionally less than or equal to approximately 10 vol. % of water, optionally less than or equal to approximately 5 vol. % of water, optionally less than or equal to approximately 1 vol. % of water.

Aspect 59: The formulation of any preceding Aspect, wherein the one or more hydrophobic solvents comprise dichloromethane, chloroform, tetrahydrofuran, toluene, ethyl acetate, hexane, cyclohexane, squalene, squalene, a petrolatum, a petrolatum-containing solvent or solvent mixture, a petrolatum ointment, a petrolatum jelly-based ointment, or any combination thereof.

Aspect 60: The formulation of any preceding Aspect, wherein the one or more hydrophobic solvents comprise a petrolatum or petroleum jelly.

Aspect 61: The formulation of any preceding Aspect comprising an organogel.

Aspect 62: The formulation of any preceding Aspect, wherein the one or more hydrophobic solvents are a solvent formulation suitable as carrier for wound healing.

Aspect 63a: The formulation of any preceding Aspect being a sunscreen or sunblock product for application to skin; wherein the functionalized artificial melanin material is provided in the formulation to facilitate skin healing in the event of UV-induced skin damage. Aspect 63b: The formulation of any preceding Aspect being an additive in a sunscreen or sunblock product for application to skin; wherein the functionalized artificial melanin material is provided in the formulation to facilitate skin healing in the event of UV-induced skin damage.

Aspect 64: The formulation of any preceding Aspect having a viscosity selected from the range of approximately 12 cP to approximately 64000 cP at 25° C. as measured using a viscometer and/or rheometer.

Aspect 65: The formulation of any preceding Aspect being therapeutically effective for facilitating skin healing when administered to damaged skin.

Aspect 66: A method for treatment of a subject, the method comprising:

topically administering a melanin formulation, according to the formulation of any one of the preceding Aspects, to damaged skin of the subject;

wherein the melanin formulation comprises the functionalized artificial melanin material according to any one of the preceding Aspects;

wherein the administered functionalized artificial melanin material comprises an extracellular functionalized artificial melanin material at the damaged skin; and facilitating skin healing at the damaged skin via at least the extracellular functionalized artificial melanin material;

wherein the step of facilitating skin healing comprises at least a portion of the extracellular artificial melanin material performing a therapeutic extracellular activity.

Aspect 67a: A method for treatment of a subject, the method comprising:

topically administering a melanin formulation to damaged skin of the subject;

wherein the functionalized artificial melanin material comprises a surface functionalized with a modifier agent via a linker group;

wherein the modifier agent comprises the linker group and a functional group attached to the linker group;

wherein the linker group is a nucleophilic group;

wherein the melanin formulation comprises one or more solvents (optionally one or more hydrophobic solvents) and the functionalized artificial melanin material dispersed in the one or more hydrophobic solvents; and wherein the administered functionalized artificial melanin material comprises an extracellular functionalized artificial melanin material at the damaged skin; and facilitating skin healing at the damaged skin via at least the extracellular functionalized artificial melanin material;

wherein the step of facilitating skin healing comprises at least a portion of the extracellular artificial melanin material performing a therapeutic extracellular activity.

Aspect 67b: The formulation of any preceding Aspect, wherein the formulation is non-aqueous, hydrophobic, or intermediate. Aspect 67c: The formulation of any preceding Aspect, wherein the formulation is non-aqueous and hydrophobic. Aspect 67d: The formulation of any preceding Aspect, wherein the formulation comprises both an aqueous solvent or phase and a non-aqueous or hydrophobic solvent or phase. Aspect 67e: The formulation of any preceding Aspect, wherein the formulation comprises both a hydrophilic solvent or phase and a hydrophobic solvent or phase. Aspect 67f: The formulation of any preceding Aspect, wherein the artificial melanin material (optionally being artificial melanin nanoparticles) is dispersed by both a hydrophilic phase and a hydrophobic phase of the formulation. Aspect 67g: The formulation of any preceding Aspect, wherein the artificial melanin material (optionally being artificial melanin nanoparticles) is dispersed by a hydrophilic solvent or phase, a hydrophobic solvent or phase, or both a hydrophilic solvent or phase and a hydrophobic solvent or phase of the formulation. Aspect 67h: The formulation of any preceding Aspect, wherein the artificial melanin material (optionally being artificial melanin nanoparticles) is dispersed by both one or more hydrophilic solvents and by one or more hydrophobic solvents in the formulation. Aspect 67i: The formulation of any preceding Aspect, wherein the formulation comprises one or more hydrophilic solvents, such as but not necessarily limited to water. Aspect 67j: The formulation of any preceding Aspect, wherein the formulation is characterized as intermediate between hydrophilic and hydrophobic. Aspect 67k: The formulation of any preceding Aspect, wherein the artificial melanin material (optionally being artificial melanin nanoparticles) is intermediate between hydrophilic and hydrophobic such that it is and/or can be associated with or present in both hydrophilic or water phase(s) and in hydrophobic phase(s). Aspect 67l: The formulation of any preceding Aspect, wherein the artificial melanin material (optionally being artificial melanin nanoparticles) is characterized as intermediate between hydrophilic and hydrophobic such that it can be associated with, present in, or dispersed in both hydrophilic or water phase(s) and in hydrophobic phase(s). Aspect 67m: The formulation of any preceding Aspect, wherein the artificial melanin material (optionally being artificial melanin nanoparticles) is associated with, present in, or dispersed in the one or more hydrophobic solvents of the formulation. Aspect 67n: The formulation of any preceding Aspect, wherein the artificial melanin material (optionally being artificial melanin nanoparticles) is associated with, present in, or dispersed in the one or more hydrophobic solvents of the formulation. Aspect 67o: The formulation of any preceding Aspect, wherein the artificial melanin material (optionally being artificial melanin nanoparticles) is associated with, present in, or dispersed in one or more hydrophilic solvents of the formulation.

Aspect 68: The method for treatment of any preceding Aspect, wherein the functionalized artificial melanin material comprises functionalized artificial melanin nanoparticles, each functionalized artificial melanin nanoparticle independently comprising a surface functionalized with the modifier agent via the linker group.

Aspect 69: The method for treatment of any preceding Aspect, wherein the damaged skin is a closed wound, an eroded wound, or both.

Aspect 70: The method for treatment of any preceding Aspect, wherein the damaged skin is associated with thermally-induced damage, chemically-induced damage, radiation-induced damage, mechanical-friction damage, and/or infection cellulitis-induced damage.

Aspect 71: The method for treatment of any preceding Aspect, wherein the radiation-induced damage is UV-induced damage and the chemically-induced damage is mustard-induced (optionally nitrogen mustard-induced) damage.

Aspect 75: The method for treatment of any preceding Aspect, wherein the damaged skin comprises one or more of blisters, vesicles, and denuded skin.

Aspect 73: The method for treatment of any preceding Aspect, wherein at least a portion of the extracellular melanin material is in the stratum corneum at the damaged skin.

Aspect 74: The method for treatment of any preceding Aspect, wherein the damaged skin comprises extracellular free radical species; and wherein the therapeutic extracellular activity comprises the at least a portion of the extracellular artificial melanin material quenching at least the extracellular free radical species.

Aspect 75: The method for treatment of any preceding Aspect, wherein the extracellular free radical species comprise reactive oxygenated species.

Aspect 76: The method for treatment of any preceding Aspect, wherein at least a portion of the quenched extracellular free radical species are in a stratum corneum.

Aspect 77: The method for treatment of any preceding Aspect, wherein the damaged skin comprises inflammation; and wherein the step of facilitating skin healing comprises at least a portion of the administered artificial melanin material directly and/or indirectly reducing the inflammation.

Aspect 78: The method for treatment of any preceding Aspect, wherein the therapeutic extracellular activity comprises the at least a portion of the extracellular artificial melanin material directly and/or indirectly reducing the inflammation.

Aspect 79: The method for treatment of any preceding Aspect, wherein directly and/or indirectly reducing the inflammation comprises at least a portion of the administered artificial melanin adsorbing one or more inflammatory factors, one or more factors, one or more scarring and/or fibrotic factors, or any combination thereof.

Aspect 80: The method for treatment of any preceding Aspect, wherein directly and/or indirectly reducing the inflammation comprises at least a portion of the extracellular artificial melanin adsorbing one or more extracellular inflammatory factors one or more extracellular enzymatic factors, one or more extracellular scarring and/or fibrotic factors, or any combination thereof.

Aspect 81: The method for treatment of any preceding Aspect, wherein the one or more inflammatory factors and/or one or more enzymatic factors comprise TNFα, iNOS, MMP9, MMP3, MMP9, CXCL1, one or more proteins associated with the MAPK/ERK pathway, and/or one or more enzymes associated with the MAPK/ERK pathway.

Aspect 82: The method for treatment of any preceding Aspect, wherein at least a portion of the adsorbed inflammatory factors and/or adsorbed extracellular enzymatic factors are in a stratum corneum.

Aspect 83: The method for treatment of any preceding Aspect, wherein the step of facilitating comprises at least a portion of the administered artificial melanin directly and/or indirectly downregulating inflammation-related genes and/or apoptosis-related genes and/or collagen degrading enzymes and/or fibroblast scarring and fibrotic genes compared to when the artificial melanin materials is absent.

Aspect 84: The method for treatment of any preceding Aspect, wherein the step of facilitating comprises at least a portion of the administered artificial melanin directly and/or indirectly inhibiting apoptosis compared to when the artificial melanin materials is absent.

Aspect 85: The method for treatment of any preceding Aspect, wherein at least 50% of the administered artificial melanin material is the extracellular artificial melanin material.

Aspect 86: The method for treatment of any preceding Aspect, wherein the extracellular artificial melanin material is present extracellularly as long as being present at the damaged skin.

Aspect 87: The method for treatment of any preceding Aspect, wherein the step of facilitating skin healing further comprises at least a portion of the administered artificial melanin material performing a therapeutic intracellular activity.

Aspect 88: The method for treatment of any preceding Aspect, wherein the therapeutic intracellular activity comprises:

quenching intracellular free radical species; and/or adsorbing one or more intracellular inflammatory factors and/or one or more intracellular enzymatic factors.

Aspect 89: The method for treatment of any preceding Aspect, wherein the skin healing comprises:

a reduction in a wound area comprising the damaged tissue;

a reduction of the inflammation at the damaged skin;

an increase in superoxide dismutase activity at the damaged skin;

a reduction in bi-fold skin thickness at the damaged skin;

a reduction in skin edema at the damaged skin;

a reduction in time to eschar detachment at the damaged skin;

a reduction in a depth of injury at the damaged skin;

a stabilization of an epithelial layer at the damaged skin;

a reduction in skin scar collagen formation at the damaged skin; or any combination thereof.

Aspect 90: The method for treatment of any preceding Aspect, wherein the skin healing is characterized by one or more of the following healing characteristics being less than the same one or more healing characteristics in absence of the artificial melanin material during the skin healing:

a total time to reduce of an amount or concentration of a damaged tissue to 30% of that immediately prior to administering the melanin formulation;

a total time to reduce inflammation at the damaged skin to 40% of that immediately prior to administering the melanin formulation;

a total time to reduce bi-fold skin thickness at the damaged skin to 25% of that immediately prior to administering the melanin formulation;

a total time to reduce skin edema at the damaged skin to 25% of that immediately prior to administering the melanin formulation;

a total time to reduce a depth of injury at the damaged skin to 30% of that immediately prior to administering the melanin formulation;

a total time to eschar detachment in the region;

any combination thereof.

Aspect 91: The method for treatment of any preceding Aspect, wherein the skin healing is characterized by one or more of the following healing characteristics being greater than the same one or more healing characteristics in absence of the artificial melanin material during the skin healing:

a rate of reduction in a wound area comprising the damaged skin;

a rate of reduction of inflammation at the damaged skin;

a rate of reduction of bi-fold skin thickness at the damaged skin;

a rate of reduction of skin edema at the damaged skin;

a rate of reduction of a depth of injury at the damaged skin;

a rate of stabilization of an epithelial layer at the damaged skin;

an activity of superoxide dismutase at the damaged skin;

a reduction in skin scar collagen formation at the damaged skin; or any combination thereof.

Aspect 92: The method for treatment of any preceding Aspect, wherein the skin healing comprises a reduction, at the damaged skin, of one or more inflammatory factors and/or of one or more enzymatic factors by 20% to 50% at 72 hours (in presence of the functionalized artificial melanin material; at 72 hours of treatment with the formulation).

Aspect 93: The method for treatment of any preceding Aspect, wherein the skin healing comprises:

a reduction, at the damaged skin, of CXCL1 by 30-50% at 72 hours (in presence of the functionalized artificial melanin material; at 72 hours of treatment with the formulation);

a reduction, at the damaged skin, of MMP3 by 20-30% at 72 hours (in presence of the functionalized artificial melanin material; at 72 hours of treatment with the formulation);

a reduction, at the damaged skin, of MMP9 by 40% at 72 hours (in presence of the functionalized artificial melanin material; at 72 hours of treatment with the formulation);

a reduction, at the damaged skin, of Col3a1 by 30-40% at 72 hours (in presence of the functionalized artificial melanin material; at 72 hours of treatment with the formulation);

a reduction, at the damaged skin, of one or more proteins associated with the MAPK/ERK pathway by at 72 hours (in presence of the functionalized artificial melanin material; at 72 hours of treatment with the formulation);

an increase, at the damaged skin, of one or more proteins including CD31 associated with angiogenesis (blood vessel formation) by at 72 hours (in presence of the functionalized artificial melanin material; at 72 hours of treatment with the formulation);

a reduction, at the damaged skin, of osm, IL-8, ccl20, and/or ICAM1 by 20-30 at 72 hours (in presence of the functionalized artificial melanin material; at 72 hours of treatment with the formulation);

or any combination thereof.

Aspect 94: The method for treatment of any preceding Aspect, wherein the melanin formulation comprises one or more additives.

Aspect 95: The method for treatment of any preceding Aspect, wherein the melanin formulation is free of artificial melanin material loaded or functionalized with a non-melanin therapeutic agent.

Aspect 96: The method for treatment of any preceding Aspect, wherein the melanin formulation is free of hollow and/or semi-hollow melanin particles carrying a non-melanin therapeutic agent.

Aspect 97: The method for treatment of any preceding Aspect, wherein the melanin formulation is free of a non-melanin therapeutic agent.

Aspect 98: The method for treatment of any preceding Aspect, wherein the melanin formulation is such that the step of administering comprises forming a layer of the artificial melanin material over at least a portion of the damaged skin.

Aspect 99: The method for treatment of any preceding Aspect, wherein the step of administering occurs after a skin damage event has occurred in the region of the subject.

Aspect 100: The method for treatment of any preceding Aspect comprising damaging skin to form the damaged skin prior to the step of administering.

Aspect 101: The method for treatment of any preceding Aspect, comprising repeating the step of administering.

Aspect 102: The method for treatment of any preceding Aspect, wherein the subject is a mammal and/or the healed skin is mammalian skin.

Aspect 103: The method for treatment of any preceding Aspect, wherein the melanin formulation is characterized as an ointment, a cream, a gel, a paste, or any combination thereof.

Aspect 104: The method for treatment of any preceding Aspect, wherein the one or more hydrophobic solvents form at least approximately 60%, optionally at least 65%, optionally at least 70%, optionally at least 75%, optionally at least 80%, optionally at least 85%, optionally at least 95%, optionally at least 95%, of a total solvent concentration in formulation.

Aspect 105: The method for treatment of any preceding Aspect, wherein the one or more hydrophobic solvents comprise dichloromethane, chloroform, tetrahydrofuran, toluene, ethyl acetate, hexane, cyclohexane, squalene, squalene, a petrolatum, a petrolatum-containing solvent or solvent mixture, a petrolatum ointment, a petrolatum jelly-based ointment, or any combination thereof.

Aspect 106: The method for treatment of any preceding Aspect, wherein the one or more hydrophobic solvents comprise a petrolatum or petroleum jelly.

Aspect 107: The method for treatment of any preceding Aspect, wherein the melanin formulation is a sunscreen or sunblock product for application to skin; wherein the functionalized artificial melanin material is provided in the formulation to facilitate skin healing in the event of UV-induced skin damage.

Aspect 108a: The method for treatment of any preceding Aspect, wherein a concentration of the functionalized artificial melanin material in the melanin formulation is selected from the range of 0.5 mg/mL to 100 mg/mL, and wherein any range and value therebetween inclusively is explicitly contemplated and disclosed herein. Aspect 108b: The method for treatment of any preceding Aspect, wherein a concentration of the functionalized artificial melanin material in the melanin formulation is selected from the range of approximately 0.5 mg/mL to approximately 100 mg/mL, optionally selected from the range of approximately 1.0 mg/mL to approximately 100 mg/mL, optionally selected from the range of approximately 1.5 mg/mL to approximately 100 mg/mL, optionally selected from the range of approximately 2.0 mg/mL to approximately 100 mg/mL, optionally selected from the range of approximately 2.5 mg/mL to approximately 100 mg/mL, optionally selected from the range of approximately 1.0 mg/ml to approximately 75 mg/mL, optionally selected from the range of approximately 1.0 mg/mL to approximately 50 mg/mL, optionally selected from the range of approximately 1.0 mg/mL to approximately 40 mg/mL, optionally selected from the range of approximately 1.0 mg/mL to approximately 30 mg/mL, optionally selected from the range of approximately 1.0 mg/mL to approximately 20 mg/mL, optionally selected from the range of approximately 1.0 mg/mL to approximately 10 mg/mL, optionally selected from the range of approximately 1.0 mg/mL to approximately 5 mg/mL.

Aspect 109a: The method for treatment of any preceding Aspect, wherein the melanin formulation is characterized by a contact angle of at least approximately 90°, optionally at least approximately 100°, optionally at least approximately 105°, optionally at least approximately 110°, optionally at least approximately 115°, optionally at least approximately 120°, optionally at least approximately 125°, optionally at least approximately 130°, optionally at least approximately 135°, optionally at least approximately 140°, optionally at least approximately 145°, optionally at least approximately 150°, optionally at least approximately 155°, optionally at least approximately 160°. Aspect 109b: The method for treatment of any preceding Aspect, wherein the melanin formulation is characterized by a contact angle selected from the range of approximately 115° to approximately 180°, optionally selected from the range of approximately 120° to approximately 180°, optionally selected from the range of approximately 125° to approximately 180°, optionally selected from the range of approximately 130° to approximately 180°, optionally selected from the range of approximately 135° to approximately 180°, optionally selected from the range of approximately 140° to approximately 180°, optionally selected from the range of approximately 145° to approximately 180°, optionally selected from the range of approximately 150° to approximately 180°, optionally selected from the range of approximately 155° to approximately 180°, optionally selected from the range of approximately 115° to approximately 160°, optionally selected from the range of approximately 120° to approximately 160°, optionally selected from the range of approximately 125° to approximately 160°, optionally selected from the range of approximately 130° to approximately 160°, optionally selected from the range of approximately 135° to approximately 160°, optionally selected from the range of approximately 140° to approximately 160°, optionally selected from the range of approximately 145° to approximately 180°.

Aspect 110: The method for treatment of any preceding Aspect, wherein the dispersed functionalized artificial melanin nanoparticles in the melanin formulation are characterized by a zeta potential greater than or equal to approximately −40 mV, optionally greater than or equal to approximately −35 mV, optionally greater than or equal to approximately −30 mV, optionally greater than or equal to approximately −25 mV, optionally greater than or equal to approximately −20 mV, optionally greater than or equal to approximately −15 mV, optionally greater than or equal to approximately −10 mV, optionally greater than or equal to approximately −5 mV, optionally greater than or equal to approximately 5 mV, optionally greater than or equal to approximately 10 mV, optionally greater than or equal to approximately 15 mV, optionally greater than or equal to approximately 20 mV.

Aspect 111: The method for treatment of any preceding Aspect, wherein the melanin formulation is characterized as a stable colloid.

Aspect 112: A method for making the functionalized artificial melanin material of any one of the preceding Aspects, the method comprising:

providing unfunctionalized artificial melanin nanoparticles; and exposing, for a finite time, the unfunctionalized artificial melanin nanoparticles to a precursor of the modifier agent;

wherein the step of exposing comprises:

conjugating the unfunctionalized artificial melanin nanoparticles with the precursor thereby forming the functionalized artificial melanin nanoparticles having the modifier agent.

Aspect 113: A method for making a functionalized artificial melanin material, the method comprising:

providing unfunctionalized artificial melanin nanoparticles; and exposing, for a finite time, the unfunctionalized artificial melanin nanoparticles to a precursor of the modifier agent;

wherein the step of exposing comprises:

conjugating the unfunctionalized artificial melanin nanoparticles with the precursor thereby forming functionalized artificial melanin nanoparticles having a modifier agent;

wherein the functionalized artificial melanin nanoparticles comprises a surface functionalized with the modifier agent via a linker group;

wherein the modifier agent comprises the linker group and a functional group attached to the linker group; and wherein the linker group is a nucleophilic group.

Aspect 114: The method for making a functionalized artificial melanin material according to any preceding Aspect thereof, wherein the linker group is an amine group, a thiol group, or any combination thereof.

Aspect 115: The method for making a functionalized artificial melanin material according to any preceding Aspect thereof, wherein the linker group is an amine group.

Aspect 116: The method for making a functionalized artificial melanin material according to any preceding Aspect thereof, wherein the unfunctionalized artificial melanin nanoparticles are hydrophilic and are dispersed in an aqueous solution.

Aspect 117: The method for making a functionalized artificial melanin material according to any preceding Aspect thereof, wherein the step of exposing comprises adding an amount of the precursor to the aqueous solution having the unfunctionalized artificial melanin nanoparticles.

Aspect 118: The method for making a functionalized artificial melanin material according to any preceding Aspect thereof, wherein the step of conjugating comprises making the functionalized artificial melanin nanoparticles more hydrophobic than the provided unfunctionalized artificial melanin nanoparticles.

Aspect 119: The method for making a functionalized artificial melanin material according to any preceding Aspect thereof, comprising extracting the material or the functionalized artificial melanin nanoparticles thereof.

Aspect 120: The method for making a functionalized artificial melanin material according to any preceding Aspect thereof comprising aging or oxidizing the unfunctionalized artificial melanin nanoparticles to form or increase content of quinones in the unfunctionalized artificial melanin nanoparticles.

Aspect 121: The method for making a functionalized artificial melanin material according to any preceding Aspect thereof, wherein the step of providing comprises making the unfunctionalized artificial melanin nanoparticles.

Aspect 122: The method for making a functionalized artificial melanin material according to any preceding Aspect thereof, wherein the step of conjugating occurs via a Michael Addition or via a Schiff Base reaction.

Aspect 123: The material, dispersion, formulation, or method of any preceding Aspect, wherein the functionalized artificial melanin material or each of the functionalized artificial melanin nanoparticles thereof is not bound to, conjugated to, attached to, coated by, encompassed by, or otherwise chemically associated with a natural or biological proteinaceous matrix, component, or lipid.

Aspect 124: The material, dispersion, formulation, or method of any preceding Aspect, wherein the functionalized artificial melanin material or each of the functionalized artificial melanin nanoparticles thereof is characterized as eumelanin, pheomelanin, allomelanin, or a combination of these.

Aspect 125: The material, dispersion, formulation, or method of any preceding Aspect, wherein the functionalized artificial melanin material comprises artificial allomelanin nanoparticles, artificial polydopamine nanoparticles, or any combination thereof.

Aspect 126: The material, dispersion, formulation, or method of any preceding Aspect, wherein the functionalized artificial melanin material or each of the functionalized artificial melanin nanoparticles thereof comprises a plurality of melanin oligomers and/or polymers; and wherein each melanin oligomer and/or polymer comprises a plurality of covalently-bonded melanin base units.

Aspect 127: The material, dispersion, formulation, or method of any preceding Aspect, wherein said melanin base units comprise one or more substituted or unsubstituted catechol-based monomer units, substituted or unsubstituted polyol-based monomer units, substituted or unsubstituted phenol-based monomer units, substituted or unsubstituted indole-based monomer units, substituted or unsubstituted benzothiazine-based monomer units, substituted or unsubstituted benzothiazole-based monomer units, substituted or unsubstituted dopamine-based monomer units, or any combination of these.

Aspect 128: The material, dispersion, formulation, or method of any preceding Aspect, wherein the functionalized artificial melanin material comprises artificial allomelanin nanoparticles.

Aspect 129: The material, dispersion, formulation, or method of any preceding Aspect, wherein the functionalized artificial melanin material comprises solid or nonporous artificial allomelanin nanoparticles, walnut artificial allomelanin nanoparticles, hollow artificial allomelanin nanoparticles, lacey artificial allomelanin nanoparticles, or a combination thereof.

Aspect 130: The material, dispersion, formulation, or method of any preceding Aspect, wherein at least a portion of said melanin base units each independently comprises substituted or unsubstituted naphthalene.

Aspect 131: The material, dispersion, formulation, or method of any preceding Aspect, wherein at least a portion of said melanin base units each independently comprises dihydroxynaphthalene.

Aspect 132: The material, dispersion, formulation, or method of any preceding Aspect, wherein at least a portion of the artificial melanin material comprises melanin oligomers free of nitrogen.

Aspect 133: The material, dispersion, formulation, or method of any preceding Aspect, wherein at least a portion of the artificial melanin material comprises polydopamine.

Aspect 134: The material, dispersion, formulation, or method of any preceding Aspect, wherein at least a portion of said melanin base units each independently comprises a substituted or unsubstituted dopamine monomer.

Aspect 135: The material, dispersion, formulation, or method of any preceding Aspect, wherein at least a portion of said melanin base units each independently is selected from the group consisting of substituted or unsubstituted dihydroxydopamine monomer units, substituted or unsubstituted dioxydopamine monomer units, substituted or unsubstituted dihydroxynaphthalene monomer units, substituted or unsubstituted dihydroxyphenylalanine monomer units, substituted or unsubstituted dioxydopamine monomer units, substituted or unsubstituted tyrosine monomer units, substituted or unsubstituted tyramine monomer units, any derivative of these, and any combination of these.

Aspect 136: The material, dispersion, formulation, or method of any preceding Aspect, wherein at least a portion of said melanin base units each independently is selected from the group consisting of 3,4-dihydroxydopamine monomer units, 3,4-dioxydopamine monomer units, 3,4-dihydroxynaphthalene monomer units, 1,8-dihydroxynapthalene, I-3,4-dihydroxyphenylalanine monomer units, and any combination of these.

Aspect 137: The material, dispersion, formulation, or method of any preceding Aspect, wherein at least 50% of the plurality of melanin oligomers are selected from the group consisting of monomer units, dimers, trimers, tetramers, pentamers, and any combination thereof.

Aspect 138: The material, dispersion, formulation, or method of any preceding Aspect, wherein each melanin oligomer is non-covalently associated with at least one other melanin oligomer or a melanin monomer via at least one of hydrogen bonding and TT-TT stacking of naphthalene rings; wherein the melanin monomer comprises the melanin base unit.

Aspect 139: The material, dispersion, formulation, or method of any preceding Aspect, wherein the artificial melanin material comprises a porous artificial melanin material; and wherein the melanin oligomers and/or polymers of the porous artificial melanin material are arranged to form an internal structure having a plurality of pores; wherein the porous artificial melanin material is characterized by a pore volume per mass of material greater than or equal to 0.1 $cm^3/g$ and wherein at least a portion of said pores have at least one size dimension greater than or equal to 0.5 nm.

Aspect 140: The material, dispersion, formulation, or method of any preceding Aspect, wherein the artificial melanin material comprises artificial melanin particles; and wherein at least a portion of the artificial melanin particles are solid particles, hollow particles, lacey particles, or any combinations of these.

Aspect 141: The material, dispersion, formulation, or method of any preceding Aspect, wherein at least a portion of the artificial melanin material comprises one or more selenomelanin polymers; wherein the one or more selenomelanin polymers comprise a plurality of covalently bonded selenomelanin base units; and wherein a chemical formula of each of the one or more selenomelanin base units comprises at least one selenium atom.

Aspect 142: The material, dispersion, formulation, or method of any preceding Aspect, wherein each selenomelanin polymer is a pheomelanin.

Aspect 143: The material, dispersion, formulation, or method of any preceding Aspect, wherein the chemical formula of each of the one or more selenomelanin base units comprises at least one covalent bond with each of the at least one selenium atom.

Aspect 144: The material, dispersion, formulation, or method of any preceding Aspect, wherein the chemical formula of each of the one or more selenomelanin base units comprises a substituted or unsubstituted benzoselenazine or a derivative thereof, a substituted or unsubstituted benzoselenazole or a derivative thereof, a substituted or unsubstituted 7,10-dihydro-2H-[1,4]selenazino [3,2-h]isoquinolin-3(4H)-one or a derivative thereof, a substituted or unsubstituted benzoselenazinone or a derivative thereof, or any combination of these.

Aspect 145: The material, formulation, dispersion, thin film, or method of any preceding Aspect, wherein the functionalized artificial melanin material of any preceding Aspects is a functionalized form, according to Aspect(s) herein, of an artificial melanin material according to any Aspect described below or henceforth.

Aspect 146: The material, formulation, dispersion, thin film, or method of any preceding Aspect, wherein the functionalized artificial melanin material of any preceding Aspects is a functionalized form, according to Aspect(s) herein, of an artificial melanin material according to any described in International Patent App. No. PCT/US2017/041596 (published as International Pat. Pub. No. WO2018013609A2), International Patent App. No. PCT/US2020/039769 (published as International Pat. Pub. No. WO2021021350A3), International Patent App. No. PCT/US2020/057902 (published as International Pat. Pub. No. WO2021087076A1), in International Patent App. No. PCT/US2020/057939 (published as International Pat. Pub. No. WO2021096692A1), International Patent App. No. PCT/US2023/012182 (published as International Pat. Pub. No. WO2023150205A1), International Patent App. No. PCT/US2022/026669 (published as International Pat. Pub. No. WO2022232356A1), and/or in International Patent App. No. PCT/US2021/064842 (published as International Pat. Pub. No. WO2022140532A2).

Aspect 147: The material, formulation, dispersion, thin film, or method of any preceding Aspect, wherein the functionalized artificial melanin material of any preceding Aspects is an artificial melanin material according to any Aspect described below or henceforth which is functionalized according to any Aspect(s) described herein.

Aspect 148: The material, formulation, dispersion, thin film, or method of any preceding Aspect, wherein the functionalized artificial melanin material of any preceding Aspects is an artificial melanin material according to any described in International Patent App. No. PCT/US2017/041596 (published as International Pat. Pub. No. WO2018013609A2), International Patent App. No. PCT/US2020/039769 (published as International Pat. Pub. No. WO2021021350A3), International Patent App. No. PCT/US2020/057902 (published as International Pat. Pub. No. WO2021087076A1), in International Patent App. No. PCT/US2020/057939 (published as International Pat. Pub. No. WO2021096692A1), International Patent App. No. PCT/US2023/012182 (published as International Pat. Pub. No. WO2023150205A1), International Patent App. No. PCT/US2022/026669 (published as International Pat. Pub. No. WO2022232356A1), and/or in International Patent App. No. PCT/US2021/064842 (published as International Pat. Pub. No. WO2022140532A2), which is functionalized according to any Aspect(s) described herein.

Various potentially useful and optional descriptions, background information, applications or uses of embodiments and aspects herein, terminology (to the extent not inconsistent with the terms as defined herein), mechanisms, compositions (such as artificial melanin nanoparticles and compositions and characteristics thereof), methods, techniques, measurements, calculations, definitions, and other embodiments and aspects are found in: International Patent App. No. PCT/US2017/041596 (published as International Pat. Pub. No. WO2018013609A2), International Patent App. No. PCT/US2020/039769 (published as International Pat. Pub. No. WO2021021350A3), International Patent App. No. PCT/US2020/057902 (published as International Pat. Pub. No. WO2021087076A1), International Patent App. No. PCT/US2020/057939 (published as International Pat. Pub. No. WO2021096692A1), International Patent App. No. PCT/US2023/012182 (published as International Pat. Pub. No. WO2023150205A1), International Patent App. No. PCT/US2022/026669 (published as International Pat. Pub. No. WO2022232356A1), and International Patent App. No. PCT/US2021/064842 (published as International Pat. Pub. No. WO2022140532A2), each of which is incorporated herein by reference in its entirety, to the extent not inconsistent herewith.

Optionally in any of Aspects 1-148 or optionally in any preceding Aspect, the artificial melanin material comprises synthetic melanin particles, also referred to herein as artificial melanin particles, also referred to interchangeably herein as artificial melanin-like particles or synthetic melanin-like particles, prepared by spontaneous oxidation of melanin monomers in an aqueous solution under alkaline conditions, to produce biocompatible, synthetic analogues of naturally occurring melanosomes.

Optionally in any of Aspects 1-148 or optionally in any preceding Aspect, the artificial melanin material comprises synthetic melanin particles comprising non-natural particles composed of (e.g. comprising, consisting of, or consisting essentially of) melanin that is not bound to, conjugated to, attached to, coated by, encompassed by or otherwise associated with a lipid (i.e. a lipid comprising one or more proteins such as the lipid (plasma) membrane of a melanocyte or melanosome). Optionally in any of Aspects 1-148 or optionally in any preceding Aspect, the artificial melanin material comprises synthetic melanin particles comprising non-natural particles composed of (e.g. consisting of or consisting essentially of) melanin that is not bound to, conjugated to, attached to, coated by, encompassed by or otherwise associated with a proteinaceous lipid (i.e. a lipid comprising one or more proteins such as the lipid (plasma) membrane of a melanocyte or melanosome).

Optionally in any of Aspects 1-148 or optionally in any preceding Aspect, the artificial melanin material comprises synthetic melanin particles comprising melanin polymer being a fused ring melanin polymer which includes (e.g. consists of or consists essentially of) monomers of fused ring heteroaryl monomer and/or fused ring heterocycloalkyl monomers. Optionally in any of Aspects 1-148 or optionally in any preceding Aspect, the artificial melanin material comprises synthetic melanin particles comprising melanin polymer being a fused ring metal-binding melanin polymer comprising a melanin polymer bound to a plurality of transitions metals including but not limited to iron. Optionally in any of Aspects 1-148 or optionally in any preceding Aspect, the artificial melanin material comprises synthetic melanin particles comprising a fused ring melanin polymer being a dopamine monomer, including but not limited to dihydoxydopamine, 3,4-dihydoxydopamine, dioxydpoamine and/or 3,4-dioxydopamine. Optionally in any of Aspects 1-148 or optionally in any preceding Aspect, each of a fused ring heteroaryl monomer and/or fused ring heterocycloalkyl monomer may be substituted with one or more substituents selected from hydroxyl, carboxyl and/or oxy. Optionally in any of Aspects 1-148 or optionally in any preceding Aspect, each of the fused ring heteroaryl monomer is a 6,6-fused ring heteroaryl monomer, a 5,6-fused ring heteroaryl monomer or 6,5-fused ring heteroaryl monomer and each of the fused ring heterocycloalkyl moieties is a 6,6-fused ring heterocycloalkyl monomer, a 5,6-fused ring heterocycloalkyl 1 monomer or 6,5-fused ring heterocycloalkyl monomer. Optionally in any of Aspects 1-148 or optionally in any preceding Aspect, the fused ring heteroaryl monomers and/or fused ring heterocycloalkyl monomers (in the monovalent or bivalent form) are selected from indole (such as dihydroxyindole, 5,6-dihydroxyindole (DHI), 5,6-dihydroxyindole-2-carboxylic acid, dioxyindole, 5,6-dioxyindole, 5,6-droxyindole-2-carboxylic acid), benzothiazine, benzothiazole. Optionally in any of Aspects 1-148 or optionally in any preceding Aspect, the fused ring monomeric units of the fused ring melanin polymer are dihydroxy fused ring units (e.g. dihydroxy fused ring heteroaryl monomers and/or dihydroxy fused ring heterocycloalkyl monomers) wherein the hydroxy substituents are attached to adjacent carbons of a 6 membered ring (e.g. 6 membered carbon ring) of a fused ring monomer (also referred to herein as a "catechol fused ring monomer"). Optionally in any of Aspects 1-148 or optionally in any preceding Aspect, the fused ring melanin polymer may also contained oxidized versions of the dihydroxy fused ring units wherein one or both of the hydroxyl substituents are oxy substituents. Optionally in any of Aspects 1-148 or optionally in any preceding Aspect, the synthetic melanin particles can be in the form of a sphere, hollow sphere, nanorod, worm-like configuration, cylindrical configuration, and the like, with at least one dimensional axis thereof of from about 1 nm to about 1000 nm, from about 1 nm to about 1000 nm, from about 50 nm to about 500 nm, or from about 100 nm to about 300 nm, preferably with a high aspect ratio. Optionally in any of Aspects 1-148 or optionally in any preceding Aspect, synthetic melanin particles is in the form of a sphere of from about 50 nm to about 500 nm, from about 100 nm to about 300 nm, from about 150 nm to about 250 nm, or about 250 nm in average diameter. Optionally in any of Aspects 1-148 or optionally in any preceding Aspect, the synthetic melanin particles are in the form of a hollow sphere, optionally filled with silica. Optionally in any of Aspects 1-148 or optionally in any preceding Aspect, the synthetic melanin particles are capable of functioning as a pigment. Optionally in any of Aspects 1-148 or optionally in any preceding Aspect, the synthetic melanin particles are synthetic melanin nanoparticles.

Optionally in any of Aspects 1-148 or optionally in any preceding Aspect, an artificial melanin material disclosed herein comprises artificial melanin nanoparticles, wherein: each melanin nanoparticle of the plurality of artificial melanin nanoparticles comprises a plurality of melanin oligomers; each melanin oligomer comprises a plurality of covalently-bonded melanin base units; and each melanin base unit comprises substituted or unsubstituted naphthalene.

Optionally in any of Aspects 1-148 or optionally in any preceding Aspect, an artificial melanin material disclosed herein comprises artificial melanin nanoparticles, wherein: each melanin nanoparticle of the plurality of artificial melanin nanoparticles comprises a plurality of melanin oligomers; each melanin oligomer comprises a plurality of covalently-bonded melanin base units; and the plurality of artificial melanin nanoparticles are characterized by a peak size selected from the range of 100 nm to 300 nm and a polydispersity index selected to be less than or equal to 0.10, and optionally for some embodiments a polydispersity index selected to be less than or equal to 0.3 and optionally for some embodiments a polydispersity index selected to be less than or equal to 0.2. Optionally, the plurality of artificial melanin nanoparticles are characterized by a peak size selected from the range of 100 nm to 200 nm and a polydispersity index selected to be less than or equal to 0.10.

Optionally in any of Aspects 1-148 or optionally in any preceding Aspect, an artificial melanin material disclosed herein comprises artificial melanin nanoparticles, wherein: each melanin nanoparticle of the plurality of artificial melanin nanoparticles comprises a plurality of melanin oligomers; each melanin oligomer comprises a plurality of covalently-bonded melanin base units; and the plurality of artificial melanin nanoparticles exhibits structural color. Optionally, the plurality of artificial melanin nanoparticles exhibits structural color when the plurality of artificial melanin nanoparticles are in the form of a layer or film, such as a monolayer or thicker, or in the form of a pellet, such as a free-standing pellet, for example. Optionally, the plurality of artificial melanin nanoparticles exhibits structural color when the plurality of artificial melanin nanoparticles are in the form of a packed and/or ordered structure. Optionally, the plurality of artificial melanin nanoparticles exhibits structural color when the plurality of artificial melanin nanoparticles are dried or otherwise deposited onto a substrate.

Optionally in any of Aspects 1-148 or optionally in any preceding Aspect, an artificial melanin material disclosed herein comprises artificial melanin nanoparticles wherein: each melanin nanoparticle of the plurality of artificial melanin nanoparticles comprises a plurality of melanin oligomers; each melanin oligomer comprises a plurality of covalently-bonded melanin base units; and at least 50% of the plurality of melanin oligomers are selected from the group consisting of monomers, dimers, trimers, tetramers, pentamers, and any combination thereof. The monomers, dimers, trimers, tetramers, and pentamers have one, two, three, four, and five melanin base units, respectively. Optionally, at least 30%, optionally at least 40%, optionally at least 50%, optionally at least 60%, optionally at least 80%, of the plurality of melanin oligomers are selected from the group consisting of dimers, trimers, tetramers, pentamers, and any combination thereof, and the artificial melanin nanoparticles further comprise monomers. Optionally, at least 50% of the plurality of melanin oligomers are selected from the group consisting of dimers, trimers, tetramers, pentamers, and any combination thereof, and the artificial melanin nanoparticles further comprise monomers. Optionally, at least 30%, optionally at least 40%, optionally at least 50%, optionally at least 60%, optionally at least 80%, of the plurality of melanin oligomers are selected from the group consisting of dimers, trimers, tetramers, and any combination thereof, and the artificial melanin nanoparticles further comprise monomers. Optionally, at least 50% of the plurality of melanin oligomers are selected from the group consisting of dimers, trimers, tetramers, and any combination thereof, and the artificial melanin nanoparticles further comprise monomers. Optionally, at least 30% by mass, optionally at least 40% by mass, optionally at least 50% by mass, optionally at least 60% by mass, optionally at least 80% by mass, of each or of each of at least 80% of the plurality of artificial melanin nanoparticles is the monomers (each monomer having only one melanin base unit) and/or the melanin oligomers selected from the group consisting of dimers, trimers, tetramers, pentamers and any combination thereof. Optionally, at least 30% by mass, optionally at least 40% by mass, optionally at least 50% by mass, optionally at least 60% by mass, optionally at least 80% by mass, of each or of each of at least 80% of the plurality of artificial melanin nanoparticles is the monomers (each monomer having only one melanin base unit) and the melanin oligomers selected from the group consisting of dimers, trimers, tetramers, pentamers and any combination thereof. Optionally, at least 30% by mass, optionally at least 40% by mass, optionally at least 50% by mass, optionally at least 60% by mass, optionally at least 80% by mass, of each or of each of at least 80% of the plurality of artificial melanin nanoparticles is the monomers (each monomer having only one melanin base unit) and/or the melanin oligomers selected from the group consisting of dimers, trimers, tetramers, and any combination thereof. Optionally, at least 30% by mass, optionally at least 40% by mass, optionally at least 50% by mass, optionally at least 60% by mass, optionally at least 80% by mass, of each or of each of at least 80% of the plurality of artificial melanin nanoparticles is the monomers (each monomer having only one melanin base unit) and the melanin oligomers selected from the group consisting of dimers, trimers, tetramers, and any combination thereof.

Optionally in any of Aspects 1-148 or optionally in any preceding Aspect, an artificial melanin material disclosed herein comprises artificial melanin nanoparticles, wherein: each melanin nanoparticle of the plurality of artificial melanin nanoparticles comprises a plurality of melanin oligomers; each melanin oligomer comprises a plurality of covalently-bonded melanin base units; and each nanoparticle has a sphericity of less than 0.90 and has a shape characterized as at least one of: walnut-like, a collapsed sphere or collapsed ellipsoid, and a sphere or ellipsoid having a plurality of indentations.

Optionally in any of Aspects 1-148 or optionally in any preceding Aspect, an artificial melanin material disclosed herein comprises artificial melanin nanoparticles, wherein: each melanin nanoparticle of the plurality of artificial melanin nanoparticles comprises a plurality of melanin oligomers; each melanin oligomer comprises a plurality of covalently-bonded melanin base units; and the plurality of artificial melanin nanoparticles are characterized by a radical scavenging activity greater than that of polydopamine nanoparticles having the same diameter as the plurality of artificial melanin nanoparticles under otherwise identical condition. Optionally, the plurality of artificial melanin nanoparticles are characterized by a radical scavenging activity at least 5%, optionally at least 10%, optionally at least 15%, optionally at least 20%, greater than that of polydopamine nanoparticles having the same diameter as the plurality of artificial melanin nanoparticles under otherwise identical condition.

Optionally in any of Aspects 1-148 or optionally in any preceding Aspect, an artificial melanin material disclosed herein comprises artificial melanin nanoparticles, wherein: each melanin base unit comprises substituted or unsubstituted naphthalene. Optionally in any of Aspects 1-148 or optionally in any preceding Aspect, an artificial melanin material disclosed herein comprises artificial melanin nanoparticles, wherein: each melanin base unit comprises dihydroxynaphthalene. Optionally in any of Aspects 1-148 or optionally in any preceding Aspect, an artificial melanin material disclosed herein comprises artificial melanin nanoparticles, wherein: each melanin base unit comprises 1,8-dihydroxynaphthalene. According to certain embodiments, each melanin base unit comprises a structure having the formula FX100:

(FX100)

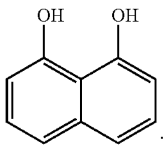

Optionally in any of Aspects 1-148 or optionally in any preceding Aspect, an artificial melanin material disclosed herein comprises artificial melanin nanoparticles, wherein: each melanin oligomer is free of nitrogen. According to certain embodiments, at least 20%, optionally at least 40%, optionally at least 50%, optionally at least 80% of the plurality of melanin oligomers are dimers having two covalently-bonded melanin base units. Optionally in any of Aspects 1-148 or optionally in any preceding Aspect, an artificial melanin material disclosed herein comprises artificial melanin nanoparticles, wherein: 20% to 80% of the plurality of melanin oligomers are dimers having two covalently-bonded melanin base units. Optionally in any of Aspects 1-148 or optionally in any preceding Aspect, an artificial melanin material disclosed herein comprises artificial melanin nanoparticles, wherein: at least 50% of the plurality of melanin oligomers are selected from the group consisting of monomers, dimers, trimers, tetramers, pentamers, and any combination thereof. The monomers, dimers, trimers, tetramers, and pentamers have one, two, three, four, and five melanin base units, respectively. Optionally, at least 30%, optionally at least 40%, optionally at least 50%, optionally at least 60%, optionally at least 80%, of the plurality of melanin oligomers are selected from the group consisting of dimers, trimers, tetramers, pentamers, and any combination thereof, and the artificial melanin nanoparticles further comprise monomers. Optionally in any of Aspects 1-148 or optionally in any preceding Aspect, an artificial melanin material disclosed herein comprises artificial melanin nanoparticles, wherein: at least 40% of the plurality of melanin oligomers are selected from the group consisting of monomers, dimers, trimers, tetramers, pentamers, and any combination thereof. Optionally in any of Aspects 1-148 or optionally in any preceding Aspect, an artificial melanin material disclosed herein comprises artificial melanin nanoparticles, wherein: at least 20%, optionally at least 40%, optionally at least 80%, of the plurality of melanin oligomers are selected from the group consisting of monomers, dimers, and trimers, and any combination thereof. Optionally in any of Aspects 1-148 or optionally in any preceding Aspect, an artificial melanin material disclosed herein comprises artificial melanin nanoparticles, wherein: at least 50% of the plurality of melanin oligomers are selected from the group consisting of monomers, dimers, and trimers, and any combination thereof. Optionally in any of Aspects 1-148 or optionally in any preceding Aspect, an artificial melanin material disclosed herein comprises artificial melanin nanoparticles, wherein: at least 30% by mass, optionally at least 40% by mass, optionally at least 50% by mass, optionally at least 60% by mass, optionally at least 80% by mass, of each or of each of at least 80% of the plurality of artificial melanin nanoparticles is the monomers (each monomer having only one melanin base unit) and/or the melanin oligomers selected from the group consisting of dimers, trimers, tetramers, pentamers and any combination thereof. Optionally in any of Aspects 1-148 or optionally in any preceding Aspect, an artificial melanin material disclosed herein comprises artificial melanin nanoparticles, wherein: at least 30% by mass, optionally at least 40% by mass, optionally at least 50% by mass, optionally at least 60% by mass, optionally at least 80% by mass, of each or of each of at least 80% of the plurality of artificial melanin nanoparticles is the monomers (each monomer having only one melanin base unit) and the melanin oligomers selected from the group consisting of dimers, trimers, tetramers, pentamers and any combination thereof. Optionally in any of Aspects 1-148 or optionally in any preceding Aspect, an artificial melanin material disclosed herein comprises artificial melanin nanoparticles, wherein: at least 30% by mass, optionally at least 40% by mass, optionally at least 50% by mass, optionally at least 60% by mass, optionally at least 80% by mass, of each or of each of at least 80% of the plurality of artificial melanin nanoparticles is the monomers (each monomer having only one melanin base unit) and/or the melanin oligomers selected from the group consisting of dimers, trimers, tetramers, and any combination thereof. Optionally in any of Aspects 1-148 or optionally in any preceding Aspect, an artificial melanin material disclosed herein comprises artificial melanin nanoparticles, wherein: at least 30% by mass, optionally at least 40% by mass, optionally at least 50% by mass, optionally at least 60% by mass, optionally at least 80% by mass, of each or of each of at least 80% of the plurality of artificial melanin nanoparticles is the monomers (each monomer having only one melanin base unit) and the melanin oligomers selected from the group consisting of dimers, trimers, tetramers, and any combination thereof. Optionally in any of Aspects 1-148 or optionally in any preceding Aspect, an artificial melanin material disclosed herein comprises artificial melanin nanoparticles, wherein: each melanin oligomer is non-covalently associated with at least one other melanin oligomer via at least one of hydrogen bonding and IT-TT stacking of naphthalene rings. Optionally in any of Aspects 1-148 or optionally in any preceding Aspect, an artificial melanin material disclosed herein comprises artificial melanin nanoparticles, wherein: each melanin oligomer is non-covalently associated with at least one other melanin oligomer or melanin monomer via at least one of hydrogen bonding and IT-IT stacking of naphthalene rings. Optionally in any of Aspects 1-148 or optionally in any preceding Aspect, an artificial melanin material disclosed herein comprises artificial melanin nanoparticles, wherein: a melanin monomer comprises the melanin base unit.

Optionally in any of Aspects 1-148 or optionally in any preceding Aspect, an artificial melanin material disclosed herein comprises artificial melanin nanoparticles, wherein: at least 50%, optionally at least 75%, optionally at least 90%, optionally at least 95%, of the plurality of nanoparticles is characterized by a sphericity of greater than 0.90. Optionally in any of Aspects 1-148 or optionally in any preceding Aspect, an artificial melanin material disclosed herein comprises artificial melanin nanoparticles, wherein: the plurality nanoparticles is characterized by a polydispersity index less than or equal to 0.10. Optionally in any of Aspects 1-148 or optionally in any preceding Aspect, an artificial melanin material disclosed herein comprises artificial melanin nanoparticles, wherein: each nanoparticle has a size characteristics, such as diameter, selected from the range of 10 nm to less than or equal to 1000 nm, optionally 100±50 nm to 300±50 nm. Optionally in any of Aspects 1-148 or optionally in any preceding Aspect, an artificial melanin material disclosed herein comprises artificial melanin nanoparticles, wherein: an average size characteristics, such as average diameter, of the artificial melanin nanoparticles is selected from the range of 10 nm to less than or equal to 1000 nm, optionally 20 nm to 500 nm, optionally 100 nm to 900 nm, optionally 200 nm to 900 nm, optionally 100 nm to 800 nm, optionally greater than 250 nm and less than 1000 nm. Optionally in any of Aspects 1-148 or optionally in any preceding Aspect, an artificial melanin material disclosed herein comprises artificial melanin nanoparticles, wherein: each of at least 55% (optionally at least 75%, optionally at least 80%, optionally at least 85%) of the nanoparticles has a size characteristic, such as diameter, selected from the range of greater than 200 nm, optionally greater than 250 nm, to less than 1000 nm. Optionally in any of Aspects 1-148 or optionally in any preceding Aspect, an artificial melanin material disclosed herein comprises artificial melanin nanoparticles, wherein: each nanoparticle has a size characteristics, such as diameter, selected from the range of 10 nm to less than or equal to 1000 nm, optionally 100 nm to 300 nm. Optionally in any of Aspects 1-148 or optionally in any preceding Aspect, an artificial melanin material disclosed herein comprises artificial melanin nanoparticles, wherein: each nanoparticle has a size characteristics, such as diameter, selected from the range of 20 nm to 300±50 nm. Optionally in any of Aspects 1-148 or optionally in any preceding Aspect, an artificial melanin material disclosed herein comprises artificial melanin nanoparticles, wherein: the plurality of artificial melanin nanoparticles are characterized by a peak size selected from the range of 10 nm to less than or equal to 1000 nm, optionally 100 nm to 300 nm. Optionally in any of Aspects 1-148 or optionally in any preceding Aspect, an artificial melanin material disclosed herein comprises artificial melanin nanoparticles, wherein: the plurality of artificial melanin nanoparticles are characterized by a peak size selected from the range of 10 nm to less than or equal to 1000 nm, optionally 100 nm to 200 nm. Optionally in any of Aspects 1-148 or optionally in any preceding Aspect, an artificial melanin material disclosed herein comprises artificial melanin nanoparticles, wherein: the plurality of artificial melanin nanoparticles are characterized by a peak size selected from the range of 50 nm to 300 nm, optionally 50 nm to 200 nm.

Optionally in any of Aspects 1-148 or optionally in any preceding Aspect, an artificial melanin material in the melanin formulation disclosed herein comprises artificial melanin nanoparticles, wherein the melanin formulation comprises a solvent or solvent mixture being at least 50% water, optionally at least 75% water, optionally at least 90% water, optionally at least 95%, by volume. According to certain embodiments, the solvent or solvent mixture comprises an organic solvent. According to certain embodiments, the solvent or solvent mixture comprises a buffer. According to certain embodiments, the organic solvent comprises methanol, ethanol, acetonitrile, acetone dichloromethane, dimethylformamide, ethyl acetate, acetone, or any combination thereof. Optionally in any of Aspects 1-148 or optionally in any preceding Aspect, artificial melanin nanoparticles are allowed to further age or further oxidize after synthesis. Optionally in any of Aspects 1-148 or optionally in any preceding Aspect, aging or further oxidation of the nanoparticles affects the solubility or dispersibility (in the melanin formulation), such as increasing stability in the presence of organic solvents. According to certain embodiments, the nanoparticles in the melanin formulation are characterized by a zeta potential or an average zeta potential selected from the range of −50 mV to −10 mV, optionally −40 to −20 mV, optionally in a solvent or solvent solution that is at least 95% water by volume. According to certain embodiments, the nanoparticles in the melanin formulation are stably dispersed without forming precipitates after at least 5 hours at a concentration selected from the range of 0.01 mg/mL to 5 mg/mL, optionally 0.01 mg/mL to 1 mg/mL, optionally within 20% of 0.1 mg/mL. According to certain embodiments, the nanoparticles in the melanin formulation are stably dispersed without forming precipitates after at least 12 hours at a concentration selected from the range of 0.01 mg/mL to 5 mg/mL, optionally 0.01 mg/ml to 1 mg/mL, optionally within 20% of 0.1 mg/mL.

Optionally in any of Aspects 1-148 or optionally in any preceding Aspect, an artificial melanin material disclosed herein comprises melanin monomers each melanin monomer having substituted or unsubstituted naphthalene. Optionally in any of Aspects 1-148 or optionally in any preceding Aspect, an artificial melanin material disclosed herein comprises melanin monomers each melanin monomer having dihydroxynaphthalene. Optionally in any of Aspects 1-148 or optionally in any preceding Aspect, an artificial melanin material disclosed herein comprises melanin monomers each melanin monomer having 1,8-dihydroxynaphthalene. Optionally in any of Aspects 1-148 or optionally in any preceding Aspect, an artificial melanin material disclosed herein comprises melanin monomers each melanin monomer being free of nitrogen. According to certain embodiments, the artificial melanin material is not derived or extracted from a biological source or a living organism.

Optionally in any of Aspects 1-148 or optionally in any preceding Aspect, an artificial melanin material disclosed herein or plurality of artificial melanin nanoparticles thereof is characterized by a radical scavenging activity greater than that of polydopamine nanoparticles having the same diameter as the plurality of artificial melanin nanoparticles under otherwise identical condition. Optionally in any of Aspects 1-148 or optionally in any preceding Aspect, an artificial melanin material disclosed herein or plurality of artificial melanin nanoparticles thereof is characterized by a radical scavenging activity at least 10%, optionally at least 15%, optionally at least 50%, greater than that of polydopamine nanoparticles having the same diameter as the plurality of artificial melanin nanoparticles under otherwise identical condition. Optionally in any of Aspects 1-148 or optionally in any preceding Aspect, an artificial melanin material disclosed herein or plurality of artificial melanin nanoparticles thereof is characterized by a radical scavenging activity of at least 0.012 mol/g using an assay of 2,2-diphenyl-1-(2,4,6-trinitrophenyl) hydrazyl (DPPH).

Optionally in any of Aspects 1-148 or optionally in any preceding Aspect, an artificial melanin material disclosed herein comprises one or more porous artificial melanin materials. Optionally in any of Aspects 1-148 or optionally in any preceding Aspect, an artificial melanin material disclosed herein comprises an porous artificial melanin material comprising: (i) one or more melanin oligomers, polymers or a combination thereof; wherein the one or more melanin oligomers and/or polymers comprise a plurality of covalently-bonded melanin base units; wherein the melanin oligomers and/or polymers are arranged to form an internal structure having a plurality of pores. Optionally in any of Aspects 1-148 or optionally in any preceding Aspect, an artificial melanin material disclosed herein comprises an porous artificial melanin material comprising: (i) one or more melanin oligomers, polymers or a combination thereof; wherein the one or more melanin oligomers and/or polymers comprise a plurality of covalently-bonded melanin base units; wherein the melanin oligomers and/or polymers are arranged to form an internal structure having a plurality of pores; wherein the porous artificial melanin material is characterized by a pore volume per mass of material greater than or equal to 0.1 $cm^3/g$, optionally greater than or equal to 0.3 $cm^3/g$, and wherein at least a portion of the pores have at least one size dimension, such as cross section dimension or longitudinal dimension, greater than or equal to 0.5 nm. Optionally in any of Aspects 1-148 or optionally in any preceding Aspect, an artificial melanin material disclosed herein comprises a porous artificial melanin material characterized by an average pore volume per mass of material selected from the range of 0.1 $cm^3/g$ to 0.6 $cm^3/g$, and optionally 0.1 to 1 $cm^3/g$ and optionally 0.3 $cm^3/g$ to 0.6 $cm^3/g$. Optionally in any of Aspects 1-148 or optionally in any preceding Aspect, an artificial melanin material disclosed herein comprises a porous artificial melanin material being a microporous material or a mesoporous material. Optionally in any of Aspects 1-148 or optionally in any preceding Aspect, an artificial melanin material disclosed herein comprises a porous artificial melanin material wherein the pores of the porous artificial melanin material include micropores each having at least one average size dimension, such as a cross sectional dimension and/or longitudinal dimension, selected from the range of 0.5 nm to 2.5 nm, and optionally 0.5 nm to 1.3 nm. Optionally in any of Aspects 1-148 or optionally in any preceding Aspect, an artificial melanin material disclosed herein comprises a porous artificial melanin material wherein the pores of the porous artificial melanin material include mesopores each having at least one average size dimension, such as a cross sectional dimension and/or longitudinal dimension, selected from the range of 2 nm to 50 nm, and optionally 2 nm to 25 nm. Optionally in any of Aspects 1-148 or optionally in any preceding Aspect, an artificial melanin material disclosed herein comprises a porous artificial melanin material wherein the pores are characterized by a distribution of pore sizes over the range of 0.5 nm to 50 nm. Optionally in any of Aspects 1-148 or optionally in any preceding Aspect, an artificial melanin material disclosed herein comprises a porous artificial melanin material wherein the pores of the internal structure are formed by organization of the melanin oligomers and/or polymers of the porous artificial melanin material. Optionally in any of Aspects 1-148 or optionally in any preceding Aspect, an artificial melanin material disclosed herein comprises a porous artificial melanin material wherein the pores of the internal structure are formed by close packing and/or self-assembly of the melanin oligomers and/or polymers of the porous artificial melanin material. Optionally in any of Aspects 1-148 or optionally in any preceding Aspect, an artificial melanin material disclosed herein comprises a porous artificial melanin material wherein the pores of the internal structure are formed by templating of the melanin oligomers and/or polymers of the porous artificial melanin material. Optionally in any of Aspects 1-148 or optionally in any preceding Aspect, an artificial melanin material disclosed herein comprises a porous artificial melanin material wherein the pores are not uniformly distributed throughout the porous melanin materials, for example, because the material is non-crystalline and/or amorphous. Optionally in any of Aspects 1-148 or optionally in any preceding Aspect, an artificial melanin material disclosed herein comprises a porous artificial melanin material wherein the porous artificial melanin material is an at least partially non-crystalline material and/or an amorphous material. Optionally in any of Aspects 1-148 or optionally in any preceding Aspect, an artificial melanin material disclosed herein comprises a porous artificial melanin material wherein the pores of the internal structure are randomly distributed. Optionally in any of Aspects 1-148 or optionally in any preceding Aspect, an artificial melanin material disclosed herein comprises a porous artificial melanin material wherein the pores of the internal structure are provided in repeating structures the amorphous porous artificial melanin material provided in an at least partial non-crystalline or amorphous state. Optionally in any of Aspects 1-148 or optionally in any preceding Aspect, an artificial melanin material disclosed herein comprises a porous artificial melanin material wherein the pores of porous artificial melanin material include one or more pore types selected from the group of cylindrical pores, channel-like pores, slit-shape pores, ink-bottle pores and any combination of these.

Optionally in any of Aspects 1-148 or optionally in any preceding Aspect, an artificial melanin material disclosed herein comprises a porous artificial melanin material having porous melanin particles, such as nanoparticles. Optionally in any of Aspects 1-148 or optionally in any preceding Aspect, an artificial melanin material disclosed herein comprises a porous artificial melanin material having porous melanin particles characterized by an average size selected from the range of 20 nm to 500 nm in diameter. Optionally in any of Aspects 1-148 or optionally in any preceding Aspect, an artificial melanin material disclosed herein comprises a porous artificial melanin material having porous melanin particles being one or more of solid particles, hollow particles, lacey particles, and any combinations of these. Optionally in any of Aspects 1-148 or optionally in any preceding Aspect, an artificial melanin material disclosed herein comprises a porous artificial melanin material having solid porous artificial melanin particles, for example, with pores distributed throughout the particle, for example uniformly distributed or randomly distributed, and without a hollow configuration. Optionally in any of Aspects 1-148 or optionally in any preceding Aspect, an artificial melanin material disclosed herein comprises a porous artificial melanin material having lacey porous artificial melanin particles, for example, with pores distributed throughout the particle, for example uniformly distributed or randomly distributed, and without a hollow configuration. Optionally in any of Aspects 1-148 or optionally in any preceding Aspect, an artificial melanin material disclosed herein comprises a porous artificial melanin material having hollow porous artificial melanin particles.

Optionally in any of Aspects 1-148 or optionally in any preceding Aspect, an artificial melanin material disclosed herein comprises a porous artificial melanin material having porous melanin particles that are purified or isolated.

Optionally in any of Aspects 1-148 or optionally in any preceding Aspect, an artificial melanin material disclosed herein comprises a porous artificial melanin material having melanin base units that are one or more substituted or unsubstituted catechol-based monomers, substituted or unsubstituted polyol-based monomers, substituted or unsubstituted phenol-based monomers, substituted or unsubstituted indole-based monomers, substituted or unsubstituted benzothiazine-based monomers, substituted or unsubstituted benzothiazole-based monomers, substituted or unsubstituted dopamine-based monomers or any combination of these.

Optionally in any of Aspects 1-148 or optionally in any preceding Aspect, an artificial melanin material disclosed herein comprises a porous artificial melanin material having or being allomelanin. Optionally in any of Aspects 1-148 or optionally in any preceding Aspect, for example, at least a portion of, and optionally all of, the melanin base units each independently comprises substituted or unsubstituted naphthalene. Optionally in any of Aspects 1-148 or optionally in any preceding Aspect, for example, at least a portion of, and optionally all of, the melanin base units each independently comprises dihydroxynaphthalene. Optionally in any of Aspects 1-148 or optionally in any preceding Aspect, for example, at least a portion of, and optionally all of, the melanin base units each independently comprises 1,8-dihydroxynaphthalene. Optionally in any of Aspects 1-148 or optionally in any preceding Aspect, for example, at least a portion of, and optionally all of, the melanin base units each independently comprises a structure having the formula FX100:

(FX100)

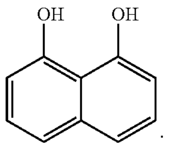

Optionally in any of Aspects 1-148 or optionally in any preceding Aspect, for example, each melanin oligomer is free of nitrogen.

Optionally in any of Aspects 1-148 or optionally in any preceding Aspect, an artificial melanin material disclosed herein comprises a porous artificial melanin material having polydopamine. Optionally in any of Aspects 1-148 or optionally in any preceding Aspect, for example, at least a portion of, and optionally all of, the melanin base units each independently comprises a substituted or unsubstituted dopamine monomer. Optionally in any of Aspects 1-148 or optionally in any preceding Aspect, for example, at least a portion of, and optionally all of, the melanin base units each independently are selected from the group consisting of substituted or unsubstituted dihydroxydopamine monomers, substituted or unsubstituted dioxydopamine monomers, substituted or unsubstituted dihydroxynaphthalene monomers, substituted or unsubstituted dioxydopamine monomers and any combination of these. Optionally in any of Aspects 1-148 or optionally in any preceding Aspect, for example, at least a portion of, and optionally all of, the melanin base units each independently are selected from the group consisting of 3,4-dihydroxydopamine monomers, 3,4-dioxydopamine monomers, 3,4-dihydroxynaphthalene monomers, and any combination of these.

Optionally in any of Aspects 1-148 or optionally in any preceding Aspect, an artificial melanin material disclosed herein comprises a porous artificial melanin material having allomelanin.

Optionally in any of Aspects 1-148 or optionally in any preceding Aspect, an artificial melanin material disclosed herein comprises substituted or unsubstituted catechol-based or polyol-based compounds. Optionally in any of Aspects 1-148 or optionally in any preceding Aspect, an artificial melanin material disclosed herein comprises substituted or unsubstituted dopamine monomers. Optionally in any of Aspects 1-148 or optionally in any preceding Aspect, an artificial melanin material disclosed herein comprises substituted or unsubstituted: dopamine monomers, 1,8-Dihydroxynaphthalene or its derivative, tyrosine monomers, tyramine monomers, amino acids, phenolamines, catecholamines, or any combination of these. Optionally in any of Aspects 1-148 or optionally in any preceding Aspect, an artificial melanin material disclosed herein comprises substituted or unsubstituted: dopamine monomers, tyrosine monomers, tyramine monomers, or a combination of these. Optionally in any of Aspects 1-148 or optionally in any preceding Aspect, an artificial melanin material disclosed herein is free of phenol derivatives, resorcinol, and/or para-phenylenediamine. Optionally, the dopamine monomers are selected from the group consisting of substituted or unsubstituted: dihydoxydopamine monomers, dihydoxydopamine dimers, dihydoxydopamine oligomers, dioxydopamine monomers, dioxydopamine dimers, dioxydopamine oligomers, dihydroxynapthalene monomers, dihydroxynapthalene dimers, dihydroxynapthalene oligomers, dioxydopamine monomers, dioxydopamine dimers, dioxydopamine oligomers, and any combination of these. Optionally, the dopamine monomers are selected from the group consisting of tyrosine and derivatives, phenol and derivatives, resorcinol and derivatives, and any combinations thereof. Optionally, the dopamine monomers are selected from the group consisting of phenol, resorcinol, L-DOPA, tyrosine and any combinations thereof. Optionally, the dopamine monomers are selected from the group consisting of cysteine derivatives, chalcogenides derivatives, selenocysteine, and any combinations thereof. Optionally in any of Aspects 1-148 or optionally in any preceding Aspect, an artificial melanin material disclosed herein comprises one or more monomers selected from the group consisting of:

(FX102)

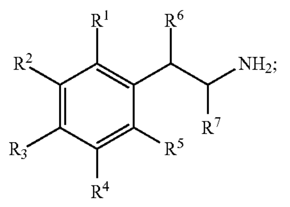

any combinations thereof, and any derivatives thereof. Optionally in any of Aspects 1-148 or optionally in any preceding Aspect, an artificial melanin material disclosed herein comprises one or more monomers having the formula (FX102):

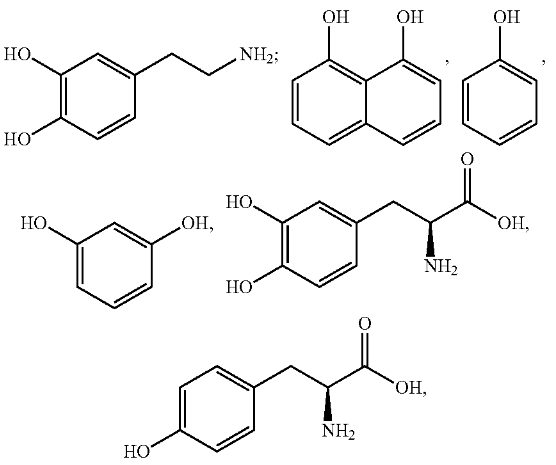

wherein one or more (optionally one, optionally two) of $R^1$-$R^7$ is-OH and wherein each of the other of $R^1$-$R^7$ is a functional group. Optionally, the each of the other of $R^1$-$R^7$ is selected from the group consisting of hydrogen, $C_1$-$C_{10}$ alkyl, $C_5$-$C_{10}$ cycloalkyl, $C_5$-$C_{10}$ aryl, $C_5$-$C_{10}$ heteroaryl, $C_1$-$C_{10}$ acyl, $C_1$-$C_{10}$ hydroxyl, $C_1$-$C_{10}$ alkoxy, $C_2$-$C_{10}$ alkenyl, $C_2$-$C_{10}$ alkynyl, $C_5$-$C_{10}$ alkylaryl, —$CO_2R^{30}$, —$CONR^{31}R^{32}$, —$COR^{33}$, —$NR^{39}R^{40}$, —$NR^{41}COR^{42}$, $C_1$-$C_{10}$ alkyl halide, acrylate, or catechol; wherein each of $R^{30}$-$R^{42}$ is independently hydrogen, $C_1$-$C_{10}$ alkyl or $C_5$-$C_{10}$ aryl. Optionally, for any method disclosed herein, the artificial melanin precursors are one or more monomers having the formula (FX103):

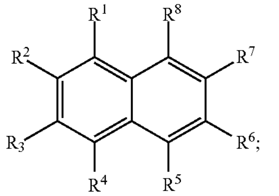

wherein one or more (optionally one, optionally two) of $R^1$-$R^8$ is-OH and wherein each of the other of $R^1$-$R^8$ is a functional group. Optionally, the each of the other of $R^1$-$R^7$ is selected from the group consisting of hydrogen, $C_1$-$C_{10}$ alkyl, $C_3$-$C_{10}$ cycloalkyl, $C_5$-$C_{10}$ aryl, $C_5$-$C_{10}$ heteroaryl, $C_1$-$C_{10}$ acyl, $C_1$-$C_{10}$ hydroxyl, $C_1$-$C_{10}$ alkoxy, $C_2$-$C_{10}$ alkenyl, $C_2$-$C_{10}$ alkynyl, $C_5$-$C_{10}$ alkylaryl, —$CO_2R^{30}$, —$CONR^{31}R^{32}$, —$COR^{33}$, —$NR^{39}R^{40}$, —$NR^{41}COR^{42}$, $C_1$-$C_{10}$ alkyl halide, acrylate, or catechol; wherein each of $R^{30}$-$R^{42}$ is independently hydrogen, $C_1$-$C_{10}$ alkyl or $C_5$-$C_{10}$ aryl. Optionally in any of Aspects 1-148 or optionally in any preceding Aspect, an artificial melanin material disclosed herein comprises one or more thiol-reactive moieties. Optionally, the thiol-reactive moieties are one or more groups selected from the group consisting of a thiol, maleimide, pyridyl disulfide-based compound, alkene, alkyl halide and any combinations thereof. Optionally in any of Aspects 1-148 or optionally in any preceding Aspect, an artificial melanin material disclosed herein comprises one or more monomers having the formula (FX102) or (FX103), wherein one or more of $R^1$-$R^8$ is a thiol-reactive moiety, such as a thiol, maleimide, pyridyl disulfide-based compound, alkene, alkyl halide and any combinations thereof.

Optionally in any of Aspects 1-148 or optionally in any preceding Aspect, an artificial melanin material disclosed herein comprises one or more artificial selenomelanin materials having: one or more selenomelanin polymers; wherein the one or more selenomelanin polymers comprise a plurality of covalently bonded selenomelanin base units; and wherein a chemical formula of each of the one or more selenomelanin base units comprises at least one selenium atom. Optionally, each selenomelanin polymer is a pheomelanin. Optionally, each of the selenomelanin monomers is an amino acid. Optionally, the chemical formula of each of the one or more selenomelanin base units comprises at least one covalent bond with each of the at least one selenium atom. Optionally, each of the one or more selenomelanin polymers is not bound to, conjugated to, attached to, coated by, encompassed by, or otherwise chemically associated with a natural or biological proteinaceous matrix, component, or lipid. Optionally, each of the plurality of selenomelanin base units is not bound to, conjugated to, attached to, coated by, encompassed by, or otherwise chemically associated with a natural or biological proteinaceous matrix, component, or lipid. Optionally, the chemical formula of each of the one or more selenomelanin base units comprises one selenium atom and two covalent bonds with the selenium atom.

Optionally, the chemical formula of each of the one or more selenomelanin base units comprises a substituted or unsubstituted benzoselenazine or a derivative thereof, a substituted or unsubstituted benzoselenazole or a derivative thereof, a substituted or unsubstituted 7,10-dihydro-2H-[1,4]selenazino [3,2-h]isoquinolin-3 (4H)-one or a derivative thereof, a substituted or unsubstituted benzoselenazinone or a derivative thereof, or any combination of these. Optionally, each of the one or more selenomelanin base units comprises a moiety characterized by formula FX111, FX112, FX113A, FX113B, FX114, a combination of any of these, or a derivative of any of these:

(FX111)

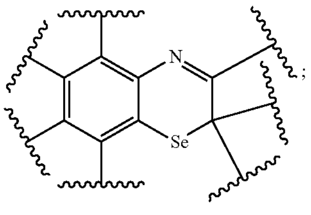

-continued (FX112)

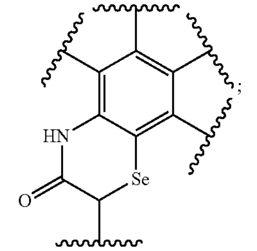

(FX113A)

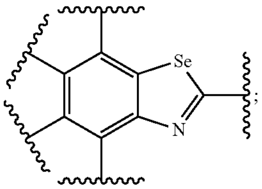

(FX113B)

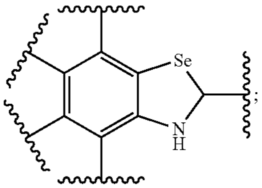

(FX114)

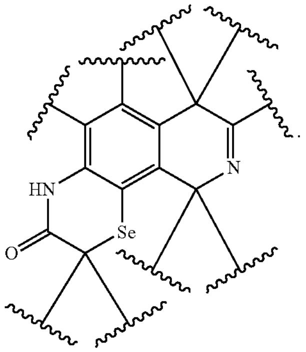

Optionally, each of the one or more selenomelanin base units comprises a moiety characterized by formula FX111, FX112, FX113A, FX113B, FX114, or a combination of any of these. Optionally, each of the one or more selenomelanin base units comprises a moiety characterized by formula FX111, FX112, FX113A, FX113B, FX114, or a combination of any of these. Optionally, each of the one or more selenomelanin base units comprises a moiety characterized by formula FX111, FX112, FX113A, FX113B, or FX114. Optionally, each of the one or more selenomelanin base units comprises a moiety characterized by formula FX111. Optionally, an artificial selenomelanin material is one or a plurality of artificial selenomelanin nanoparticles, artificial selenomelanin layers, or artificial selenomelanin thin films. Optionally, an artificial selenomelanin material is one or a plurality of artificial selenomelanin nanoparticles. Optionally, each of the one or more selenomelanin base units comprises a heterocyclic moiety comprising a Se as a member of its ring structure. Optionally, each of the one or more selenomelanin base units comprises a heterocyclic moiety comprising a Se and a N as members of its ring structure. Optionally, each of the one or more selenomelanin base units comprises a moiety characterized by formula FX123, FX124, FX125, FX126, FX127, a derivative of any one of these, or a combination of any of these:

(FX123)

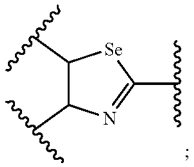

(FX124)

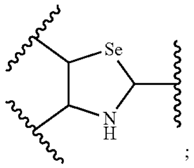

(FX125)

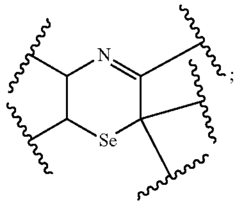

(FX126)

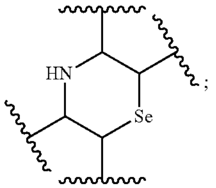

(FX127)

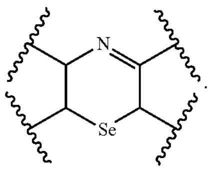

Optionally, each of the one or more selenomelanin base units comprises a moiety characterized by formula FX123, FX124, FX125, FX126, FX127, or a combination of any of these. Optionally, each of the one or more selenomelanin base units comprises a moiety characterized by formula FX123, FX124, FX125, FX126, or FX127. Optionally, each of the selenomelanin monomers is characterized by formula FX115, FX116, FX117, FX118, FX119, FX120, or FX121:

(FX115)

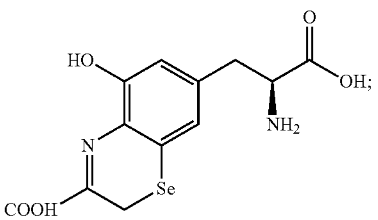

(FX116)

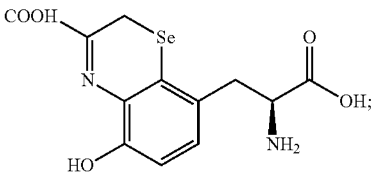

-continued (FX117)

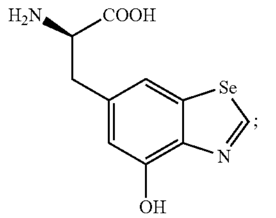

(FX118)

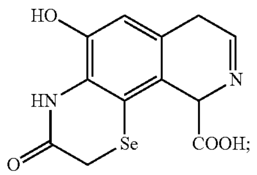

(FX119)

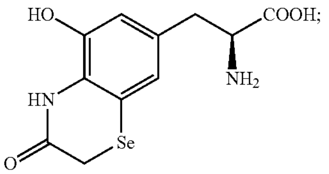

(FX120)

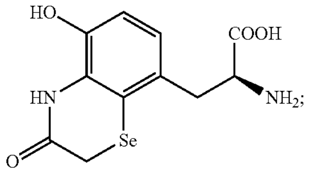

(FX121)

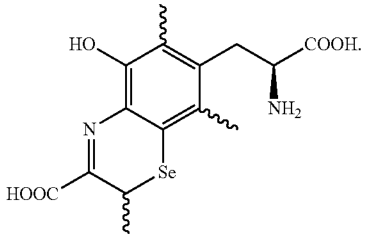

Optionally in any of Aspects 1-148 or optionally in any preceding Aspect, an artificial melanin material disclosed herein comprises one or more artificial selenomelanin materials wherein each of the one or more selenomelanin polymers is not bound to, conjugated to, attached to, coated by, encompassed by, or otherwise chemically associated with a natural or biological proteinaceous matrix, component, or lipid.

Optionally in any of Aspects 1-148 or optionally in any preceding Aspect, an artificial melanin material disclosed herein comprises one or more artificial selenomelanin materials wherein the chemical formula of each of the one or more selenomelanin base units comprises benzoselenazine and wherein the material comprises benzoselenazine at a concentration selected from the range of 10 wt. % to 100 wt. %. Optionally in any of Aspects 1-148 or optionally in any preceding Aspect, an artificial melanin material disclosed herein comprises one or more artificial selenomelanin materials having benzoselenazine at a concentration selected from the range of 50 wt. % to 60 wt. %. For example, the chemical formula of each of the one or more selenomelanin base units comprises benzoselenazine and the material can comprise benzoselenazine at a concentration of 55 wt. %. Optionally in any of Aspects 1-148 or optionally in any preceding Aspect, an artificial melanin material disclosed herein comprises one or more artificial selenomelanin materials characterized a concentration of selenium selected from the range of 2 wt. % to 23 wt. %. For example, the artificial selenomelanin material can be characterized a concentration of selenium of 12 wt. %.

Optionally in any of Aspects 1-148 or optionally in any preceding Aspect, an artificial melanin material in a melanin formulation disclosed herein comprises one or more artificial selenomelanin materials wherein the solvent or solvent mixture is at least 50% water. Optionally in any of Aspects 1-148 or optionally in any preceding Aspect, an artificial melanin material in a melanin formulation disclosed herein comprises one or more artificial selenomelanin materials having artificial selenomelanin nanoparticles characterized by an absolute value of a Zeta potential selected from the range of 15 mV to 50 mV, preferably 20 mV to 50 mV, optionally 15 mV to 40 mV, optionally 20 mV to 40 mV, optionally 15 mV to 30 mV, optionally 20 mV to 30 mV, optionally 17 mV to 34 mV. (The absolute value, or modulus, of a real number is the non-negative value of the real number without regard to its sign.) Optionally, the sign of the Zeta potential corresponding to the artificial selenomelanin nanoparticles in the artificial selenomelanin nanoparticle dispersion is negative. Optionally in any of Aspects 1-148 or optionally in any preceding Aspect, an artificial melanin material in a melanin formulation disclosed herein comprises one or more artificial selenomelanin materials having artificial selenomelanin nanoparticles being size-stable at nanoparticle concentrations selected from the range of 0.1 mg/mL to 10-4 mg/mL with respect to an average size of the nanoparticle at a concentration of 0.1 mg/mL. Optionally in any of Aspects 1-148 or optionally in any preceding Aspect, an artificial melanin material in a melanin formulation disclosed herein comprises one or more artificial selenomelanin materials having artificial selenomelanin nanoparticles being size-stable in the dispersion having a pH of 11, preferably at least 11, with respect to an average size of the nanoparticle in the dispersion having a pH of 7. Optionally in any of Aspects 1-148 or optionally in any preceding Aspect, an artificial melanin material in a melanin formulation disclosed herein comprises one or more artificial selenomelanin materials having artificial selenomelanin nanoparticles being size-stable when exposed to a concentration of NaCl selected from the range of 50 mM to 250 mM, preferably a concentration of NaCl being 250 mM, in the dispersion, with respect to an average size of the nanoparticles in an equivalent dispersion free of NaCl. Optionally in any of Aspects 1-148 or optionally in any preceding Aspect, an artificial melanin material in a melanin formulation disclosed herein comprises one or more artificial selenomelanin materials having artificial selenomelanin nanoparticles being stably dispersed in the dispersion for at least 7 days, preferably at least 14 days, preferably at least 60 days under ambient conditions.

Optionally in any of Aspects 1-148 or optionally in any preceding Aspect, an artificial melanin material in a melanin formulation disclosed herein comprises one or more artificial selenomelanin materials having artificial selenomelanin nanoparticles being characterized by a melanin purity of at least 20%, optionally at least 25%, optionally at least 30%, preferably at least 50%, more preferably at least 70%, further more preferably at least 80%, yet further more preferably at least 90%, more preferably for some applications at least 95%, still more preferably for some applications at least 99%, still further more preferably for some application at least 99.9%. Optionally in any of Aspects 1-148 or optionally in any preceding Aspect, an artificial melanin material in a melanin formulation disclosed herein comprises one or more artificial selenomelanin materials having artificial selenomelanin nanoparticles wherein each of at least 50%, optionally at least 75%, preferably at least 90%, more preferably at least 95%, further more preferably at least 99%, of the plurality of artificial melanin nanoparticles comprises a selenomelanin polymer having selenomelanin base units comprising a moiety characterized by formula FX111, FX112, FX113A, FX113B, FX114, or a combination of any of these:

(FX111)

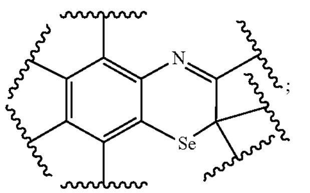

(FX112)

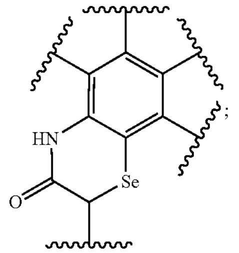

(FX113A)

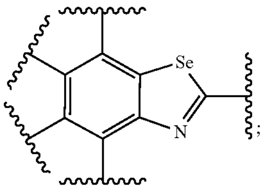

(FX113B)

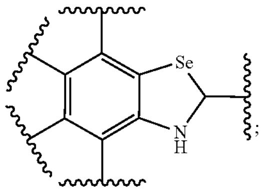

(FX114)

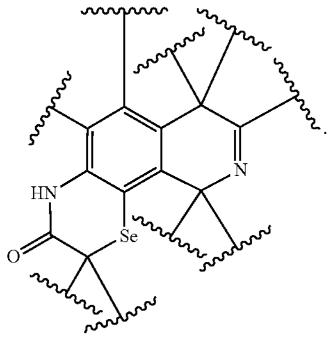

Optionally in any of Aspects 1-148 or optionally in any preceding Aspect, an artificial melanin material in a melanin formulation disclosed herein comprises one or more artificial selenomelanin materials having artificial selenomelanin nanoparticles wherein each of at least 50%, optionally at least 75%, preferably at least 90%, more preferably at least 95%, further more preferably at least 99%, of the plurality of artificial melanin nanoparticles comprises a selenomelanin polymer having selenomelanin base units comprises a heterocyclic moiety comprising a Se as a member of its ring structure. Optionally in any of Aspects 1-148 or optionally in any preceding Aspect, an artificial melanin material in a melanin formulation disclosed herein comprises one or more artificial selenomelanin materials having artificial selenomelanin nanoparticles wherein each of at least 50%, optionally at least 75%, preferably at least 90%, more preferably at least 95%, further more preferably at least 99%, of the plurality of artificial melanin nanoparticles comprises a selenomelanin polymer having selenomelanin base units comprises a heterocyclic moiety comprising a Se and a N as members of its ring structure. Optionally in any of Aspects 1-148 or optionally in any preceding Aspect, an artificial melanin material in a melanin formulation disclosed herein comprises one or more artificial selenomelanin materials having artificial selenomelanin nanoparticles wherein each of at least 50%, optionally at least 75%, preferably at least 90%, more preferably at least 95%, further more preferably at least 99%, of the plurality of artificial melanin nanoparticles comprises a selenomelanin polymer having selenomelanin base units comprises a moiety characterized by formula FX123, FX124, FX125, FX126, FX127, a derivative of any one of these, or a combination of any of these. Optionally in any of Aspects 1-148 or optionally in any preceding Aspect, an artificial melanin material in a melanin formulation disclosed herein comprises one or more artificial selenomelanin materials having artificial selenomelanin nanoparticles wherein each of at least 50%, optionally at least 75%, preferably at least 90%, more preferably at least 95%, further more preferably at least 99%, of the plurality of artificial melanin nanoparticles comprises a selenomelanin polymer having selenomelanin base units comprises a moiety characterized by formula FX123, FX124, FX125, FX126, FX127, or a combination of any of these. Optionally in any of Aspects 1-148 or optionally in any preceding Aspect, an artificial melanin material in a melanin formulation disclosed herein comprises one or more artificial selenomelanin materials having artificial selenomelanin nanoparticles wherein each of at least 50%, optionally at least 75%, preferably at least 90%, more preferably at least 95%, further more preferably at least 99%, of the plurality of artificial melanin nanoparticles comprises a selenomelanin polymer having selenomelanin base units comprises a moiety characterized by formula FX123, FX124, FX125, FX126, or FX127. Optionally in any of Aspects 1-148 or optionally in any preceding Aspect, an artificial melanin material in a melanin formulation disclosed herein comprises one or more artificial selenomelanin materials having artificial selenomelanin nanoparticles wherein each of the one or more selenomelanin nanoparticles is not bound to, conjugated to, attached to, coated by, encompassed by, or otherwise chemically associated with a natural or biological proteinaceous matrix, component, or lipid. Optionally in any of Aspects 1-148 or optionally in any preceding Aspect, an artificial melanin material in a melanin formulation disclosed herein comprises one or more artificial selenomelanin materials having artificial selenomelanin nanoparticles wherein each of at least 50%, optionally at least 75%, preferably at least 80%, preferably at least 90%, more preferably at least 95%, further more preferably at least 99%, of the artificial selenomelanin nanoparticles is free of artificial melanin monomers. Optionally in any of Aspects 1-148 or optionally in any preceding Aspect, an artificial melanin material in a melanin formulation disclosed herein comprises one or more artificial selenomelanin materials having artificial selenomelanin nanoparticles wherein each of the artificial selenomelanin nanoparticles is free of artificial melanin monomers. For example, artificial selenomelanin materials, such as nanoparticles, are extensively washed with HCl solution (e.g., once) and pure water (e.g., 3 times), as a result of which the artificial selenomelanin materials, or dispersion or formulations thereof, can be free of artificial selenomelanin monomers, as characterized by solid-state NMR, UV-Vis spectra, etc. Optionally, a melanin formulation disclosed herein comprises a concentration of melanin monomers being less than IC50 of the monomers, respectively. Optionally in any of Aspects 1-148 or optionally in any preceding Aspect, an artificial melanin material in a melanin formulation disclosed herein comprises one or more artificial selenomelanin materials having artificial selenomelanin nanoparticles wherein each of the artificial selenomelanin nanoparticles is external (extracellular) of a biological cell.

The invention can be further understood by the following non-limiting examples.

Example 1: Hydrophobic Synthetic Melanin Nanoparticles

Melanin is a natural pigment found in skin and hair that serves a primary role in UV radiation protection by absorption of incident radiation and by radical scavenging activity. Synthetic melanins successfully recapitulate these properties, obtained via oxidative polymerization of inexpensive monomers, bypassing issues of yield and purity that arise from natural extraction. The resulting materials are hydrophilic, which limits the application of these materials beyond aqueous systems. Here, we disclose a simple post-synthetic modification (or, functionalization) strategy to change the hydrophobicity of the particles via reaction with a primary alkyl amine. The resulting particles exhibit good long term stability in organic solvents, and expand applications into self-assembly and additional biological applications.

Figure 23A:
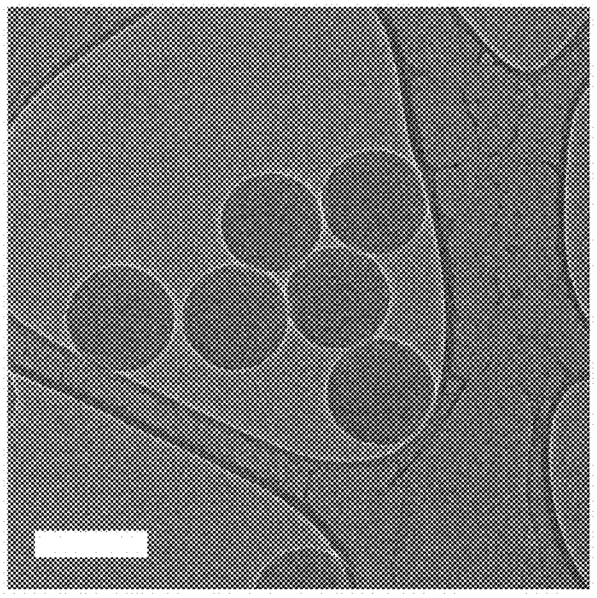
FIGS. 23A-23B: TEM Micrograph verifying spherical morphology of hydrophobic melanin nanoparticles.
Figure 23B:
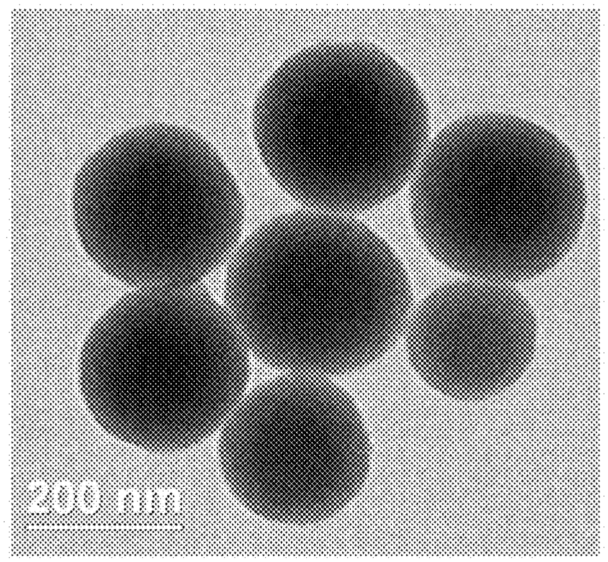

Synthetic melanin particles are obtained from the oxidative polymerization of 1,8-dihydroxynapthalene for allomelanin (AMNP) and dopamine for polydopamine (PDA) respectively. Once the particles are harvested, they are dispersed in ethanol and reacted with the primary alkyl amine overnight under constant stirring. The resulting hydrophobic particles (hAMNP and hPDA) are washed in ethanol and their morphology is confirmed by Transmission Electron Microscopy (TEM) (FIGS. 23A-23B).

Figure 24A:
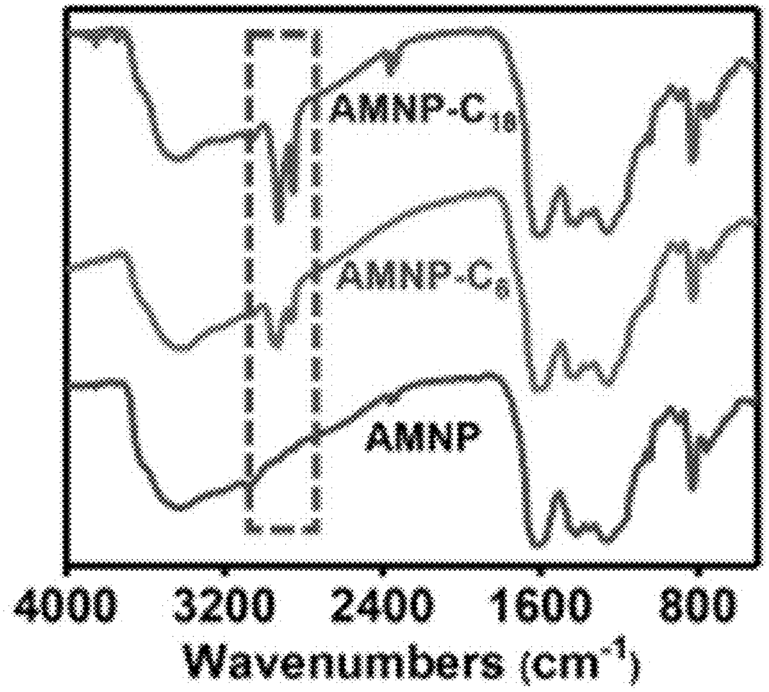
FIGS. 24A-24B: FTIR Spectra of AMNP and PDA.
Figure 24B:
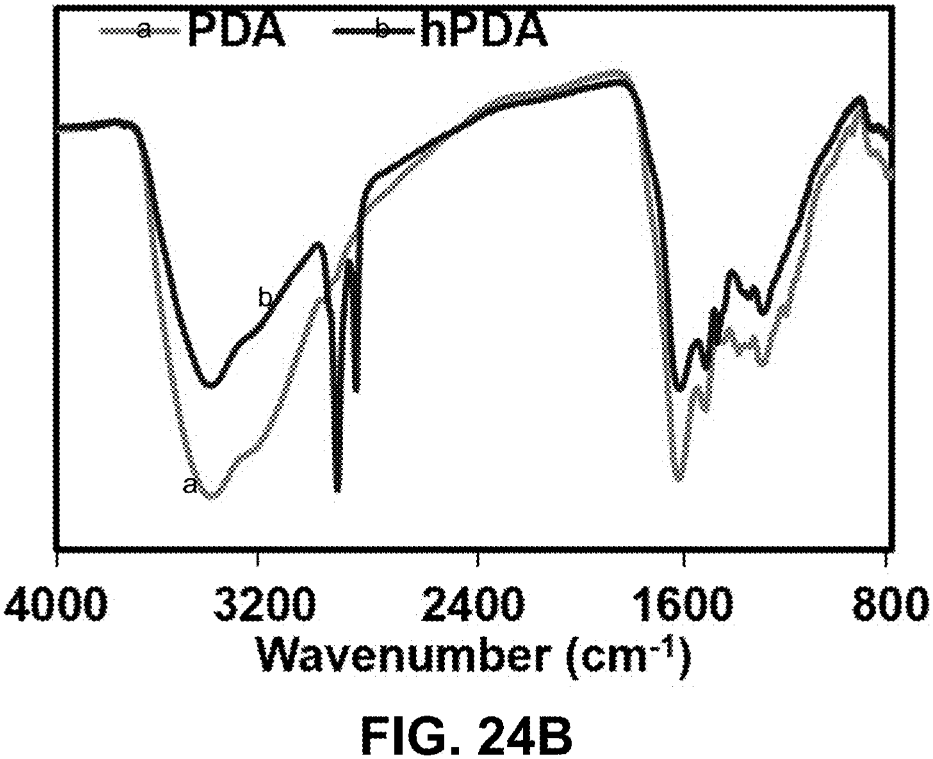

Analysis of the particles reveals an increase in particle diameter post-modification and maintains a negative zeta potential post-modification, indicating good colloidal stability in ethanol (Table 3). The Fourier Transform Infrared (FTIR) spectra of all particles pre and most modification were measured as a KBr pellet (FIGS. 24A-24B). When compared to original particles, the spectrum for synthetically modified synthetic melanin particles contains two additional peaks at 2920 $cm^{-1}$ and 2850 $cm^{-1}$. These correspond to alkane C—H bond stretch, indicating attachment of the alkylamine to the surface of the particle.

Figure 3A:
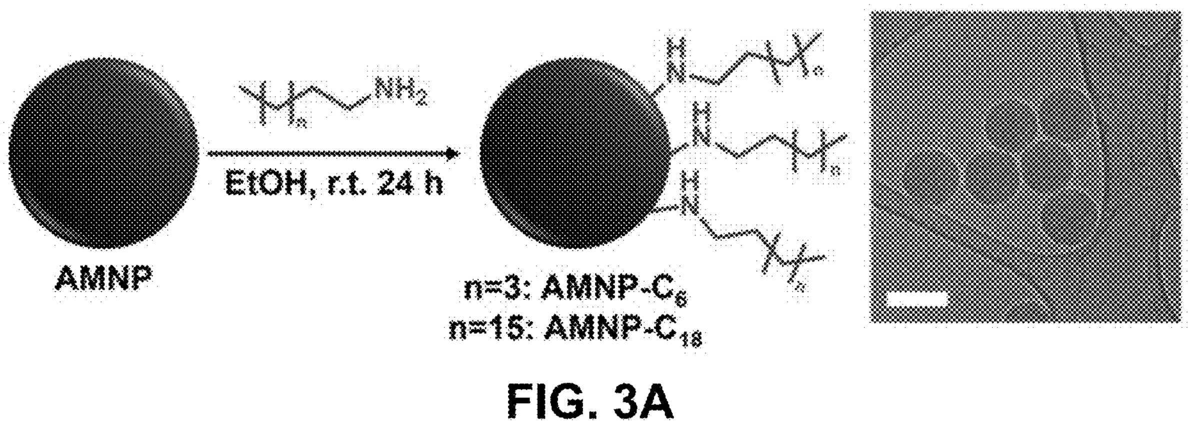
FIGS. 3A-3E: Synthesis of hydrophobic allomelanins.
Figure 3B:
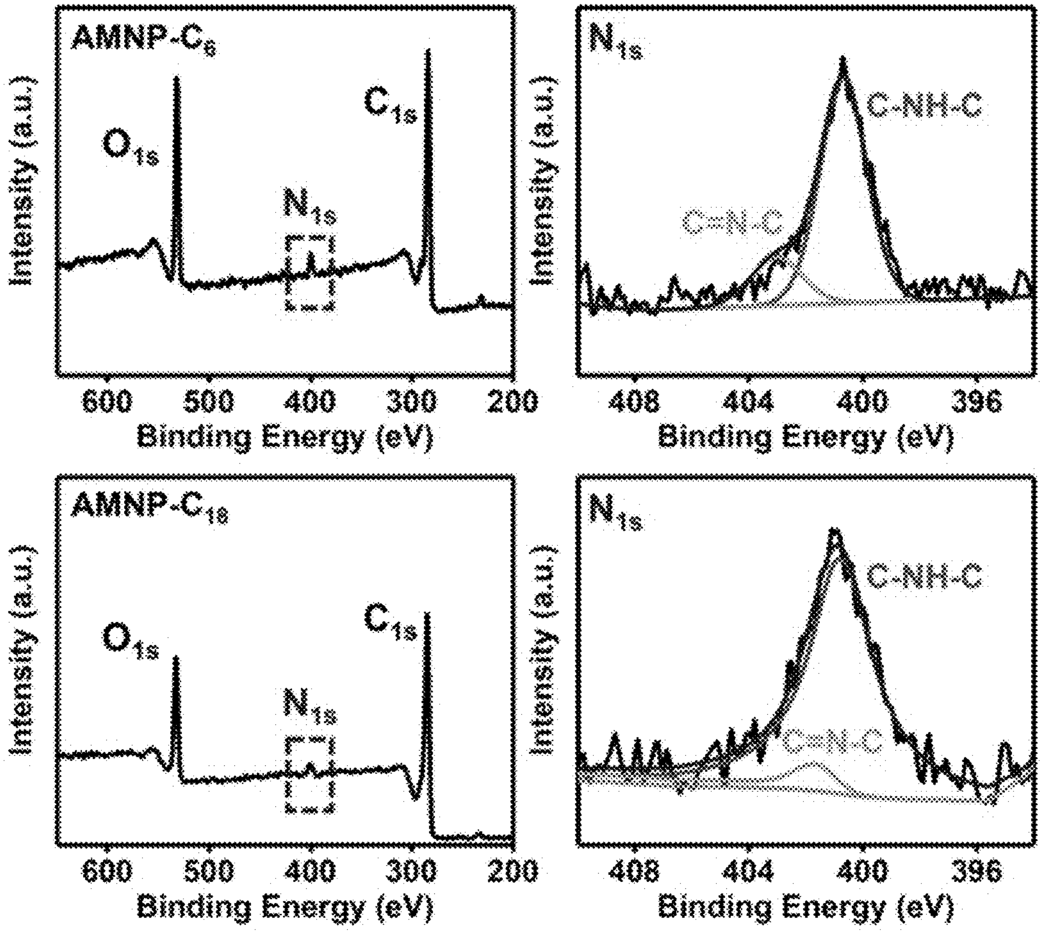
Figure 15:
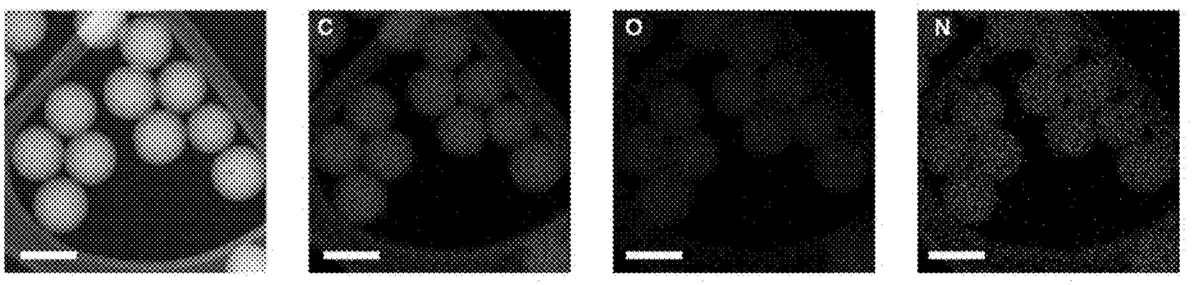
FIG. 15: STEM-EDX mapping analysis of S-AMNP-$C_{18}$, scale bars 200 nm.

Pristine AMNPs are nitrogen-free, allowing the use of X-ray Photoelectron Spectroscopy (XPS) to further confirm surface modification (FIG. 3B). Pristine AMNP particles have no nitrogen signal, but upon surface modification, a significant N signal is obtained. Additional analysis by Scanning Transmission Electron Microscopy-Energy Dispersive X-ray (STEM-EDX) further indicates even distribution of the alkyl amine across the particles. (FIG. 15).

To confirm hydrophobicity, contact angles of the particles was obtained. Films of synthetic melanin were prepared drop-casting solutions on silica chips. The water contact angle was then obtained. The pristine particles have a hydrophilic water contact angle of 41.9±0.2° and 46.35±0.06° for AMNP and PDA respectively. Upon surface functionalization, the water contact angle increases to 130.0±0.8° and 135±4° for AMNP-C18 and PDA-C18 respectively (Table 4).

Figure 25A:
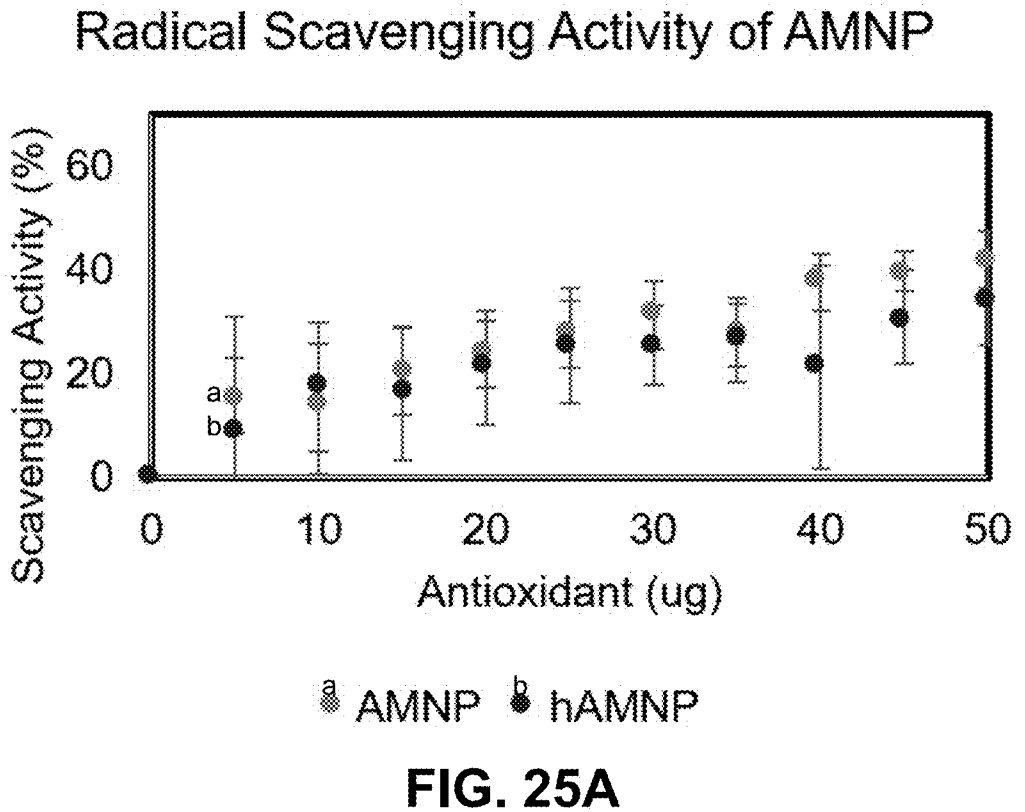
FIGS. 25A-25B: DPPH radical scavenging assay for (FIG. 25A) AMNP and (FIG. 25B) PDA.
Figure 25B:
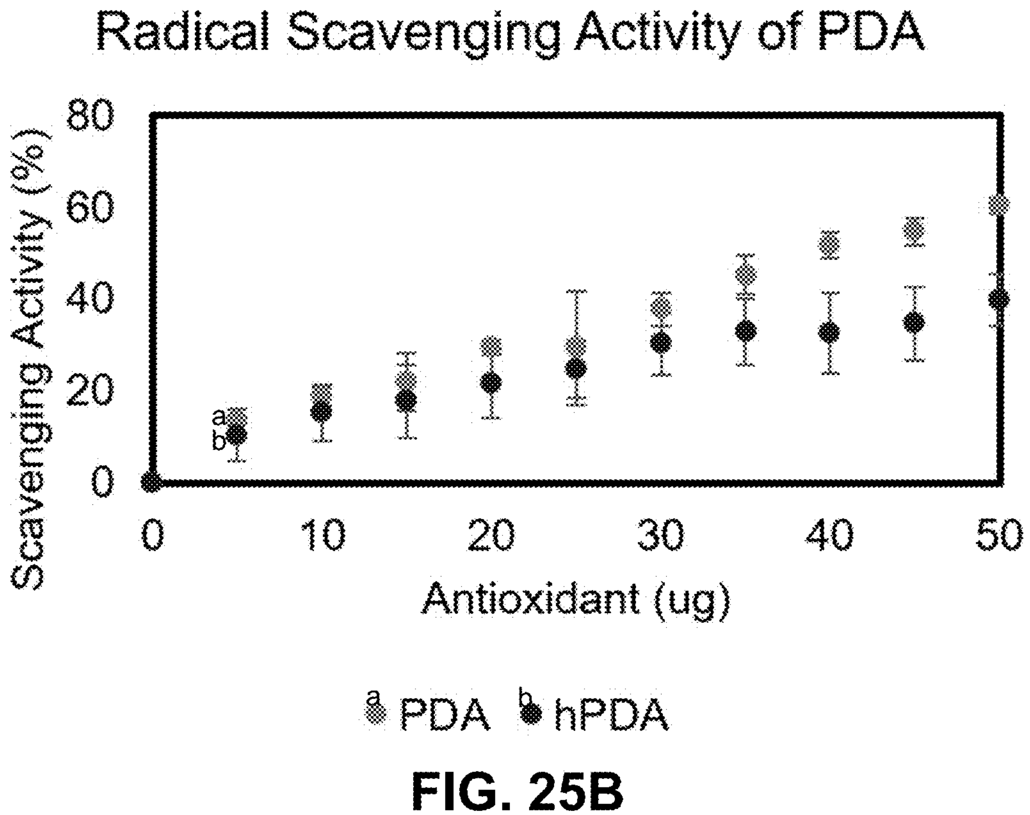

Chemical modification of the surface can impact scavenging activity of synthetic melanins, so was assayed in vitro by the 2,2-diphenyl-1-picrylhydrazyl (DPPH) assay. DPPH is a shelf-stable radical that is purple in solution and turns yellow as the radical is quenched, which is monitored at 516 nm. At 50 μg of AMNP, 60% of the radical is scavenged, while at the same amount of hAMNP, 40% of the free radical is scavenged (FIG. 25A). Similarly, at 50 μg of PDA, 60% of the radical is scavenged, while at the same amount of PDA-C18, 50% of the free radical is scavenged (FIG. 25B). While this is a decrease compared to pristine particles, radical scavenging activity is still maintained.

To explore the expanded applications of hydrophobic melanins, AMNPs have successfully been assembled into different films. The silicon substrate was prepared by submerging the silicon at the bottom of a bath of Milli-Q water. AMNP-C18 were dispersed in 1-butanol and added the colloidal suspension dropwise on the water surface, resulting in the formation of a continuous, close-packed monolayer film. The silicon substrate was then lifted out of the solution, resulting in a thin film. This process was repeated to add one layer at a time to make the bilayer and trilayer films (FIGS. 4A-4G). This protocol was applied to other AMNPs that have differing morphologies and were also able to assemble into thin films.

Figure 26:
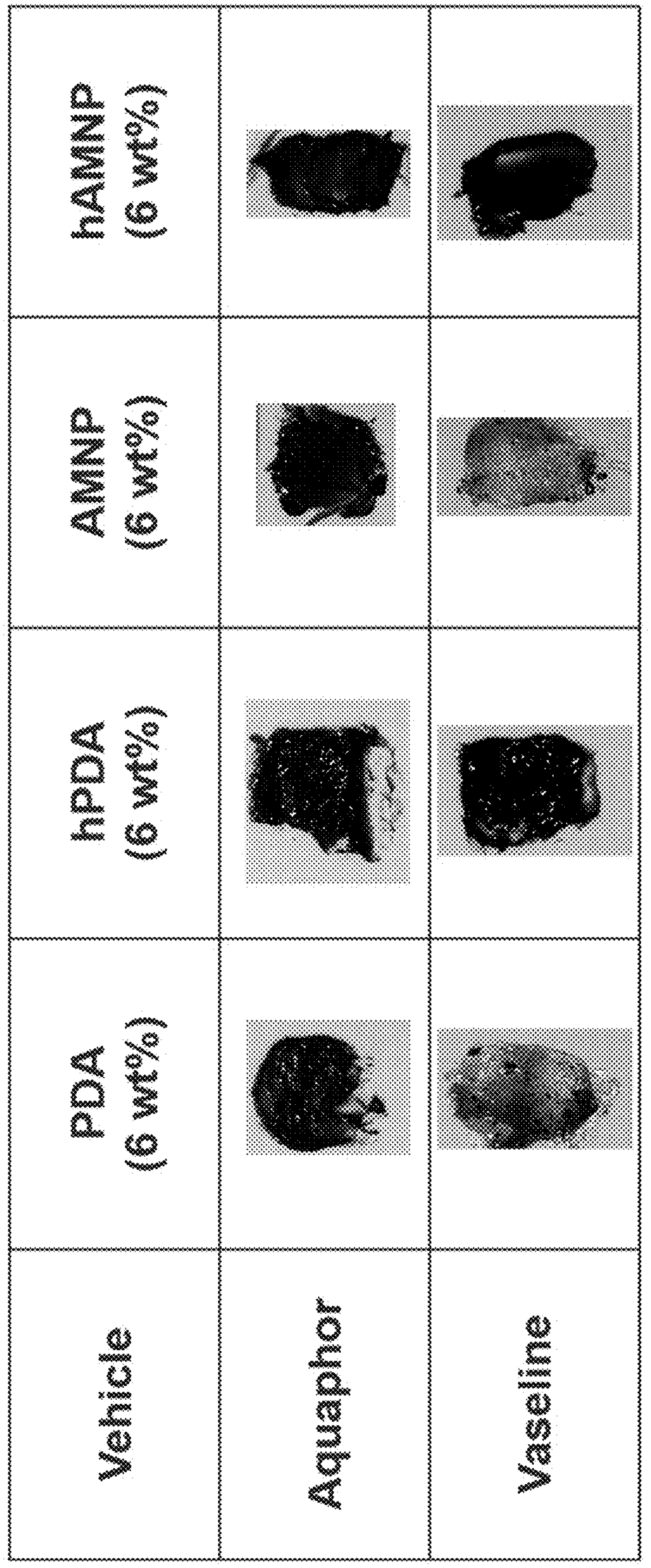
FIG. 26: Qualitative evaluation of synthetic melanin nanoparticle solubility in Aquaphor and Vaseline.
Figure 27A:
FIG. 27A: Solubility of PDA in squalane and squalene and (FIG. 27B) solubility of PDA-$C_{18}$ in squalane and squalene.
Figure 27B:
Figure 28A:
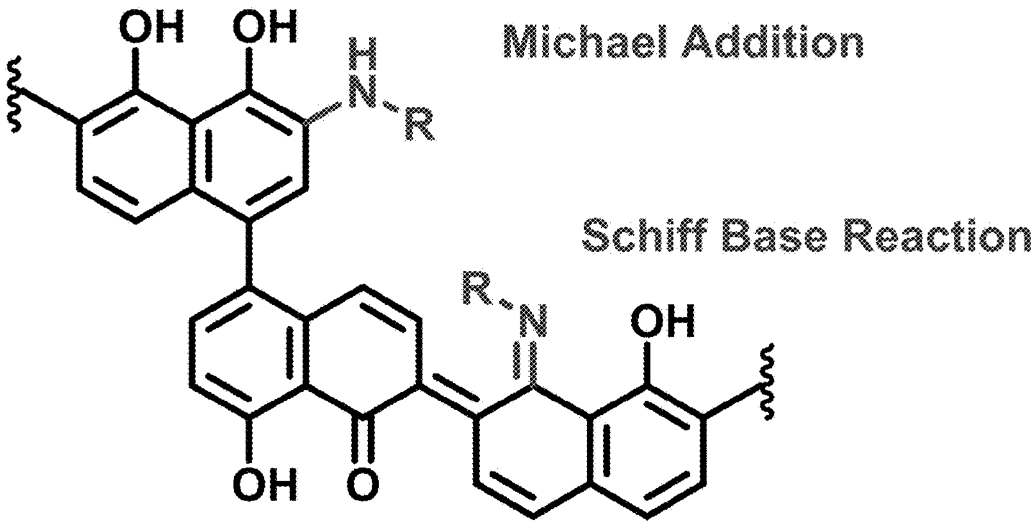
FIGS. 28A-28B: Chemical schematics of functionalization of artificial melanin nanoparticles, showing that conjugation (or, functionalization) of the modifier agent to the melanin nanoparticles, according to embodiments herein, may occur by Michael Addition and/or Schiff Base Reaction, according to embodiments herein, such that the linker group, such as an amine group, may be attached to the nanoparticle, or a naphthalene or an aromatic group thereof, via a single bond or a double bond, for example.
Figure 28B:
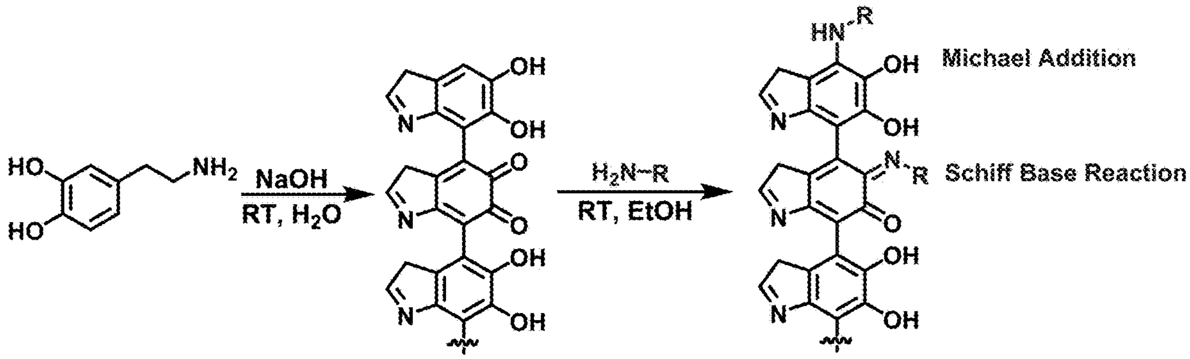

Solubility of the hydrophobic particles was qualitatively assayed in commercially available vehicles: Vaseline, Aquaphor, squalene, and squalane. Vaseline and Aquaphor are petrolatum jelly-based ointments and have been used in the clinic for skin applications in the case of wound healing. These vehicles were selected for their clinical and biological relevance. Solubility of the synthetic melanin particles were assayed in these compounds by vigorously mixing. Both hydrophobic particles, AMNP-C18 and PDA-C18, exhibit better qualitatively solubility in the various excipients compared to pristine particle by observation of fewer particulates in the suspension and even distribution of the hydrophobic particles by color (FIG. 26). Pristine particle solubility in Aquaphor can be attributed to the addition of hydrophilic glycerin in the petroleum jelly, making Aquaphor overall less hydrophobic compared to the other vehicles. In petroleum jelly, AMNP and PDA do not incorporate into the ointment, as seen by the dark particulates surrounded by clear ointment. In the case of squalene and squalane, PDA-C18 is found to better incorporate per the more uniform brown color of the solution and fewer particulates, while squalane and squalene have PDA particles settled on the bottom of the glass substrate (FIGS. 27A-27B).

Potential applications of the technology include surface assembly of synthetic melanin films, topical dermal applications, skin tanning, and enhancement of wound healing by reducing inflammation.

Advantages of this technology over other solutions include that it is scalable, the size of nanoparticles is tunable, the starting materials are inexpensive, particle character is maintained, biocompatibility, long term stability in ethanol, and it's translational across different types of synthetic melanins.

Synthetic melanin materials exhibit attractive properties such as radical scavenging and biocompatibility, however, their applications beyond aqueous substrates are limited due to poor solubility. By changing the surface chemistry from hydrophilic to hydrophobic, we have expanded the range of applications that were previously not possible with the pristine particles, such as surface assembly and dermal applications.

Example 2A: Hydrophobic Melanin Via Post-Synthetic Modification for Controlled Self-Assembly Allomelanin is a class of nitrogen-free melanin mostly found in fungi and, like all naturally occurring melanins, is hydrophilic. Herein, we develop a facile method to modify synthetic hydrophilic allomelanin to yield hydrophobic derivatives through post-synthetic modifications. Amine functionalized molecules of various kinds can be efficiently conjugated to allomelanin nanoparticles under mild conditions with high loading efficiencies. Hydrophobicity is conferred by introducing amine-terminated alkyl groups with different chain lengths. We demonstrate that the resulting hydrophobic allomelanin nanoparticles undergo air/water interfacial self-assembly in a controlled fashion enabling the generation of large scale and uniform structural colors. This work provides an efficient and tunable surface chemistry modification strategy broadening the scope of synthetic melanin structure and function beyond the known diversity found in nature.

Melanin is a group of natural pigments found in most organisms.[1] In nature, it exhibits broad functionality such as structural coloration,[2] radiation protection,[3-5] thermoregulation,[6-9] and metal chelation.[10] Synthetic mimics have been developed to unravel the structure and function of natural melanins, and to further explore a range of new functions and applications.[11-13] Over the past two decades, polydopamine, used to mimic natural eumelanin, has been the most common synthetic analogue. Synthetic mimics of other melanins have received far less attention.[14-19] Allomelanin, the focus of this work, is a nitrogen-free class of melanin often derived from the precursor 1,8-dihydroxynaphthalene (1,8-DHN) and found predominantly in fungi.[20-25] Natural allomelanins serve as protective agents in fungi, allowing them to withstand radiation.[26] Recently, synthetic allomelanin materials have been developed using chemical synthetic routes to polymerize monomeric 1,8-DHN and related dimers.[27] The resulting allomelanin nanoparticles (AMNPs) have a well-defined nanostructure, diverse morphology, radical scavenging activity, and high intrinsic microporosity originating from voids generated within the naphthalene-based polymer network, making them excellent candidate materials for radiation protection and toxin adsorption.[28,29] Indeed, we have described them as the first known biopolymers of intrinsic microporosity (BioPIMs) based on these synthetic studies, and comparison to naturally occurring materials.[28]

Figure 1B:
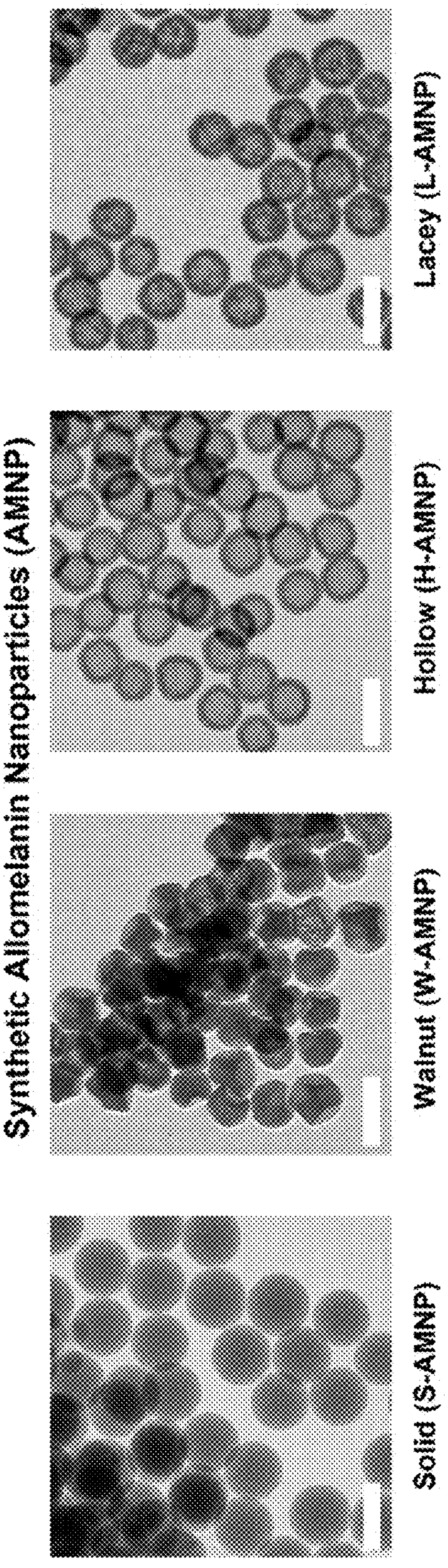

Although these synthetic allomelanins possess multiple desirable properties, a chemical approach to tune and modify their surface chemistries has not been described. Such an approach, we reasoned, would allow for dispersion in diverse solvents for processing, controlled assembly, and access to uniform properties including structural coloration. Here, we describe a facile post-synthetic modification (PSM) to expand the scope and versatility of functional groups that can be incorporated into synthetic allomelanins (FIGS. 1A-1B).

Figure 6:
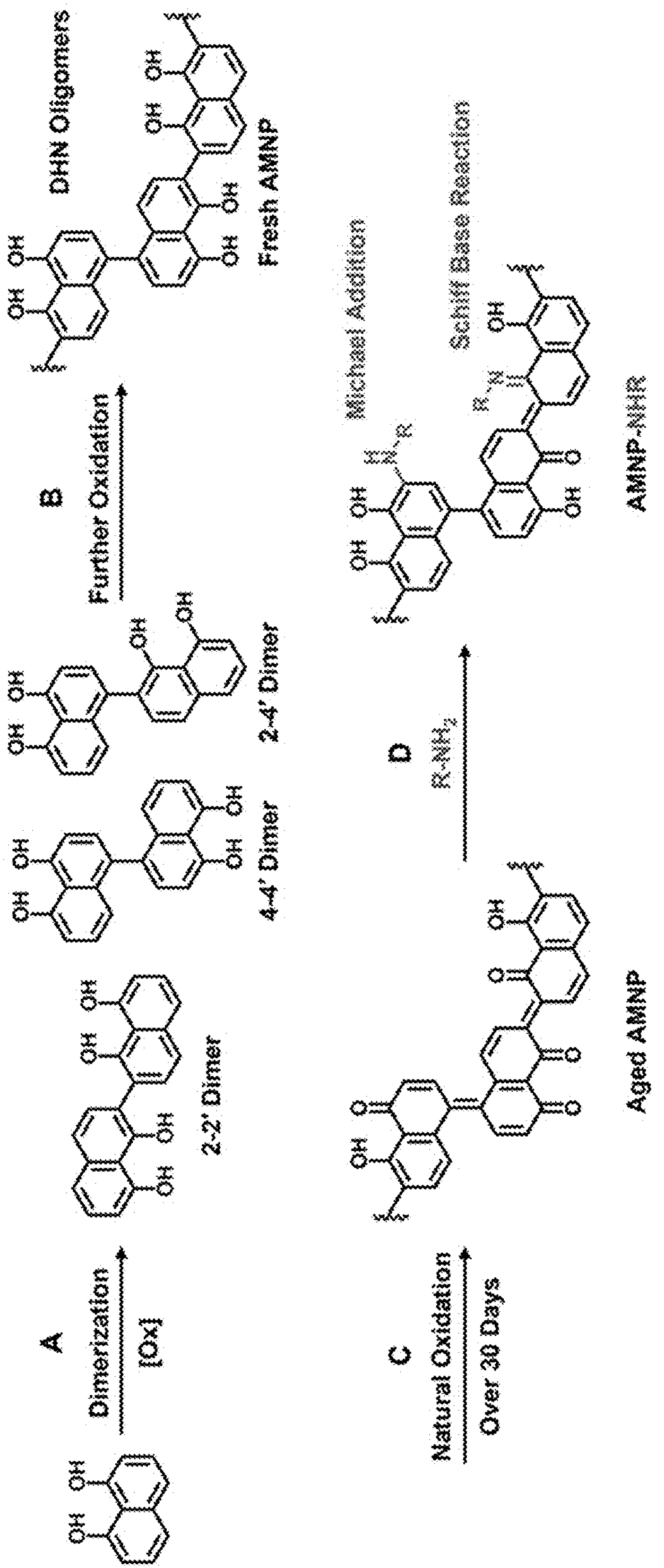
FIG. 6: Synthesis of AMNP and post-synthetic modification. (A) Upon adding the oxidizing agent, the dimerization of 1,8-DHN leads to the formation of three types of DHN dimers: 2-2' dimer, 4-4' dimer, and 2-4' dimer; (B) Further oxidation results in DHN oligomers, which self-assemble to form fresh AMNP; (C) Natural oxidation of fresh AMNP generates aged AMNP, which contains DHN oligomers with a higher degree of polymerization, more cross-linked structures, and more quinone moieties; (D) Post-synthetic modification results in AMNP-NHR, where amine molecules are conjugated to the particles through either Michael addition or Schiff base reaction.
Figure 7A:
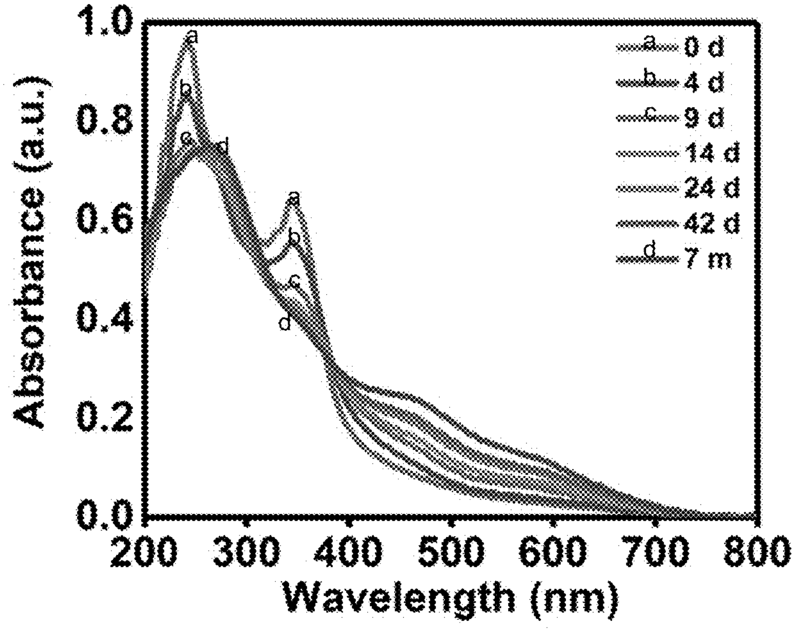
FIG. 7A: UV-Vis of S-AMNP over time. Time course following the absorbance S-AMNP at 0 day, 4 days, 9 days, 14 days, 24 days, 42 days and 7 months post-synthesis.
Figure 7B:
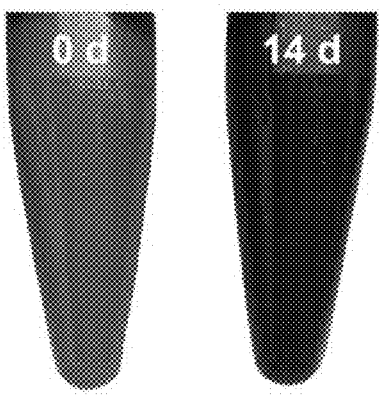
FIG. 7B: Photographs of S-AMNP in Milli-Q water at the concentration of 4 mg/mL, at 0 day and 14 days after the initial reaction.

AMNP was synthesized through the oxidative polymerization of 1,8-DHN (FIG. 1A).[27] The initial, resulting material exists as a uniform dispersion of nanoparticles referred to here as fresh AMNP, composed largely of DHN oligomers (FIG. 6).[27] As in our prior work, we observed a visible darkening of the particles in aqueous solution, from gray to black, with a broadening of peaks in UV-Vis absorbance spectra (FIGS. 7A-7B).[28] This process occurs in ambient conditions via a natural oxidation process in air. Indeed, this aging process is common for phenolic materials.[30] Aged AMNP comprise DHN monomers incorporated at higher degrees of polymerization, resulting in a more highly cross-linked structure with more quinone moieties.[30] In turn, these quinone groups in aged AMNP present potential reactive sites for further chemical modification. Nucleophilic functional groups, like amines, can then undergo either Michael addition or Schiff-base reaction on quinones to covalently modify the particles (FIG. 1A, FIG. 6).[31,32] We demonstrated that these PSMs are simple yet efficient strategies that may be generally applied to a wide range of amine-functionalized molecules. Specifically, we have successfully prepared hydrophobic allomelanins using alkyl amines with long carbon chains. The resulting hydrophobic AMNPs can be used to generate large-scale homogeneous structural colors through air/water interfacial self-assembly.

Synthesis and Characterization of Modified Synthetic Allomelanin

Figure 2A:
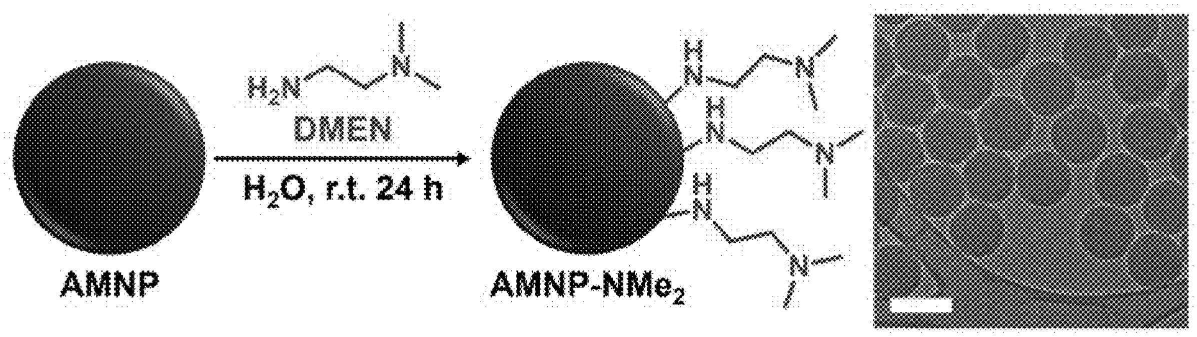
FIGS. 2A-2D: Synthesis of AMNP-$NMe_2$.
Figure 2B:
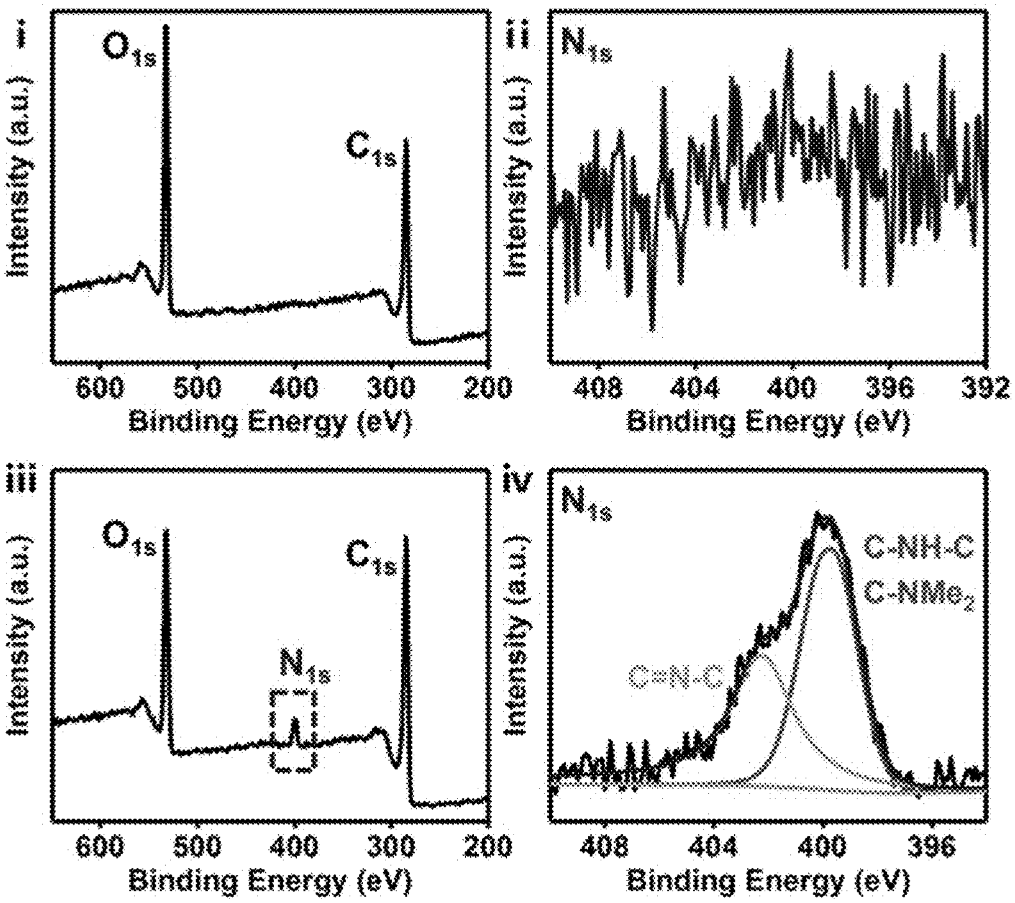
Figure 2C:
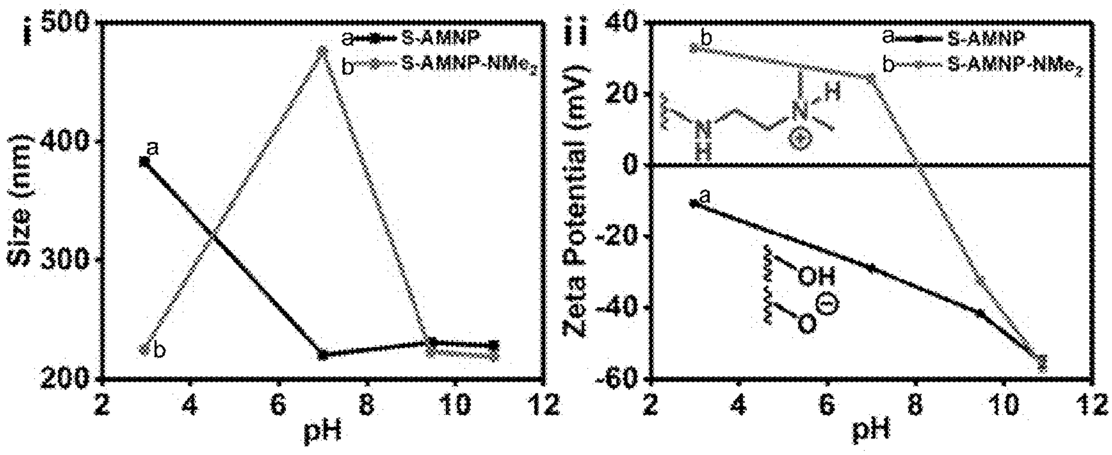
Figure 8:
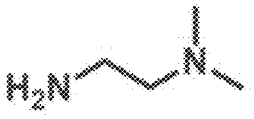
FIG. 8: Calculation to the ratio of DMEN to DHN structural unit.
Figure 8:
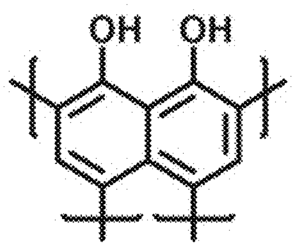
Figure 8:
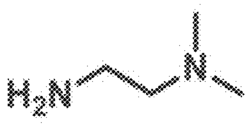

Nanoparticles: In this Example, AMNPs with different morphologies were prepared as substrates for further surface modification. Morphologies included solid AMNP (S-AMNP), walnut AMNP (W-AMNP), hollow AMNP (H-AMNP), and lacey AMNP (L-AMNP) (FIG. 1B). Syntheses were based on previous studies (see Example 2B for preparative methods).[27,28] To ensure the enrichment of quinone groups, after the synthesis of fresh AMNPs, the particles were aged under ambient conditions over 30 days for further oxidation. Transmission electron microscopy (TEM) revealed uniform, well-defined nanostructures for all four kinds of AMNP (FIG. 1B, Table 1). To test the PSM process, N, N-dimethylethylenediamine (DMEN) was first chosen as a standard amine to functionalize S-AMNP (FIGS. 2A-2D). DMEN served as a convenient marker for the modification since it contains a relatively high amount of nitrogen for analysis. Briefly, S-AMNP was dispersed in water, followed by addition of DMEN under vigorous stirring at room temperature. The final concentration of AMNP was 1.0 mg/mL. After 24 hours the particles were centrifuged and washed with water to yield S-AMNP-$NMe_2$. S-AMNP-$NMe_2$ remain well-defined spherical nanoparticles with a diameter (184±3 nm) similar to that of S-AMNP (178±4 nm) (FIG. 2A, Table 1). X-ray photoelectron spectroscopy (XPS) confirmed modification with the nitrogen containing DMEN, since the original AMNP is nitrogen-free (FIGS. 2B i and 2B ii). Specifically, in the $N_{1s}$ spectrum, C—NH—C and C-NMez at 399.7 eV, C═N—C at 402.0 eV were observed, demonstrating successful covalent conjugation between S-AMNP and DMEN (FIGS. 2B iii and 2B iv). Dynamic light scattering (DLS) indicated some aggregation post modification, with an increased hydrodynamic diameter from 220.3 nm to 475.7 nm at neutral pH and a subsequent pH dependence consistent with the amine functionalized surface (FIG. 2C i). We reasoned that this was consistent with the introduction of colloidal instability as the surface chemistry is altered. To probe this phenomenon further, zeta potential measurements were made upon modification and compared to the original AMNPs (FIG. 2C ii). Specifically, AMNPs have a negative zeta potential sufficient for maintaining a stable suspension (−28.8 mV). In turn, the dimethyl amino group on DMEN incorporated to yield S-AMNP-$NMe_2$, results in a positive surface charge (23.7 mV). The decrease in magnitude at neutral pH manifests as a more aggregated solution and confirms the installation of the functional group. Further, both DLS and zeta potential measurements exhibited pH-dependence for both S-AMNP and S-AMNP-$NMe_2$. When the pH was increased, zeta potentials decreased to −55 mV for both particles at pH 11 (FIG. 2C ii). Conversely for S-AMNP-$NMe_2$ at low pH, zeta potentials reach +35 mV and colloidal stability is restored to the now protonated particles with cationic tertiary amines. Elemental analysis was then applied to quantitatively determine the loading efficiency (Carbon, Hydrogen, Nitrogen, Sulfur). These data revealed that the nitrogen percentage increased from zero (S-AMNP) to 5.31% (S-AMNP-$NMe_2$) post modification (Table 2). The molar ratio of DMEN to DHN structural unit was calculated to be 0.40 (FIG. 8).

TABLE 1

Diameters obtained from TEM, hydrodynamic diameters, and Zeta potentials of AMNPs.

| | Diameter (nm) | Hydrodynamic Diameter (nm) | PDI | Zeta Potential (mV) |
|---|---|---|---|---|
| S-AMNP | 178 ± 4 | 220.3 | 0.086 | −28.8 |
| W-AMNP | 142 ± 11 | 179.4 | 0.054 | −31.0 |
| H-AMNP | 142 ± 9 | 206.8 | 0.195 | −30.8 |
| L-AMNP | 141 ± 5 | 200.7 | 0.205 | −29.1 |

TABLE 2

CHNS analysis of S-AMNP and S-AMNP-$NMe_2$.

| | % N | % C | % H | % S |
|---|---|---|---|---|
| Theoretical Sulfanilamide | 16.25 | 41.81 | 4.65 | 18.62 |
| Sample Sulfanilamide readback | 16.20 | 41.83 | 4.681 | 18.71 |
| S-AMNP | 0.10 | 69.84 | 3.524 | 0.007 |
| S-AMNP | 0.08 | 69.78 | 3.518 | 0.008 |
| S-AMNP | 0.07 | 69.75 | 3.509 | 0.007 |
| S-AMNP-$NMe_2$ | 5.34 | 66.08 | 4.847 | 0 |
| S-AMNP-$NMe_2$ | 5.32 | 66.22 | 4.873 | 0 |
| S-AMNP-$NMe_2$ | 5.27 | 66.06 | 4.855 | 0 |
| Sample Sulfanilamide readback | 16.29 | 41.89 | 4.738 | 18.527 |

Figure 2D:
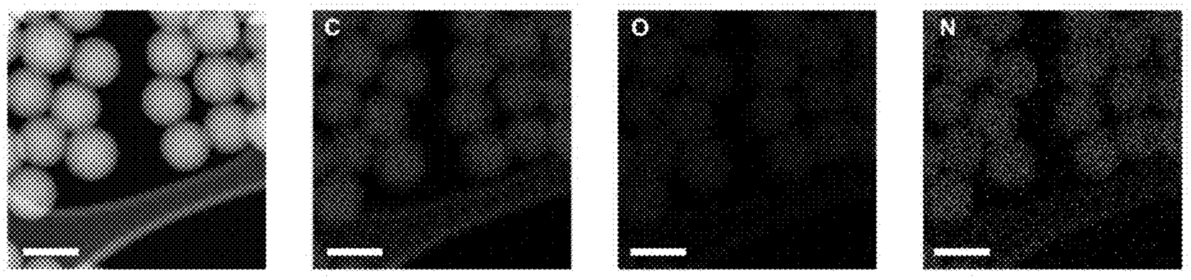
Figure 9A:
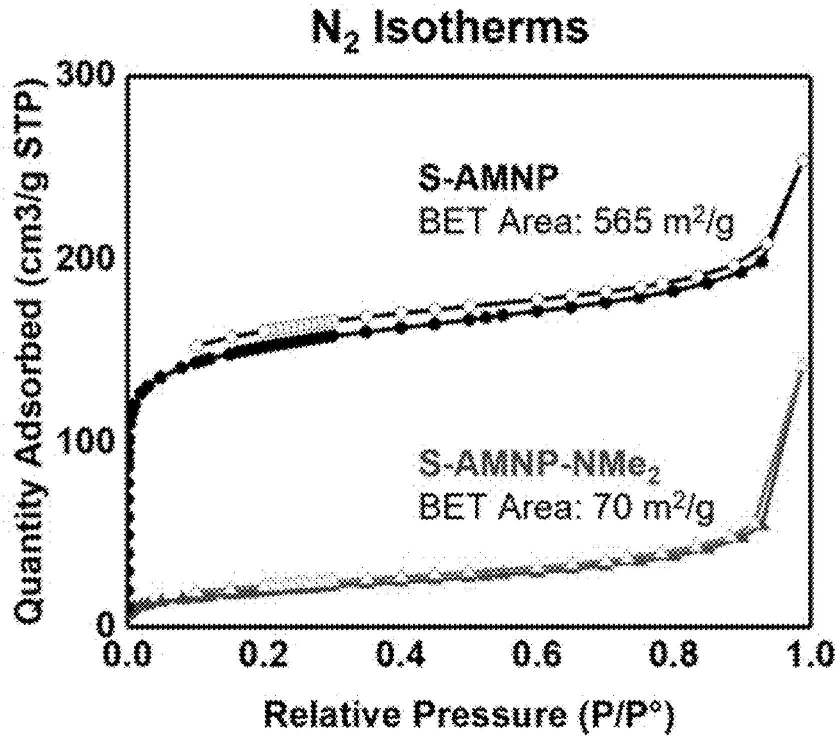
FIG. 9A: Nitrogen isotherms at 77 K and (FIG. 9B) pore size distributions of S-AMNP and S-AMNP-$NMe_2$.
Figure 9B:
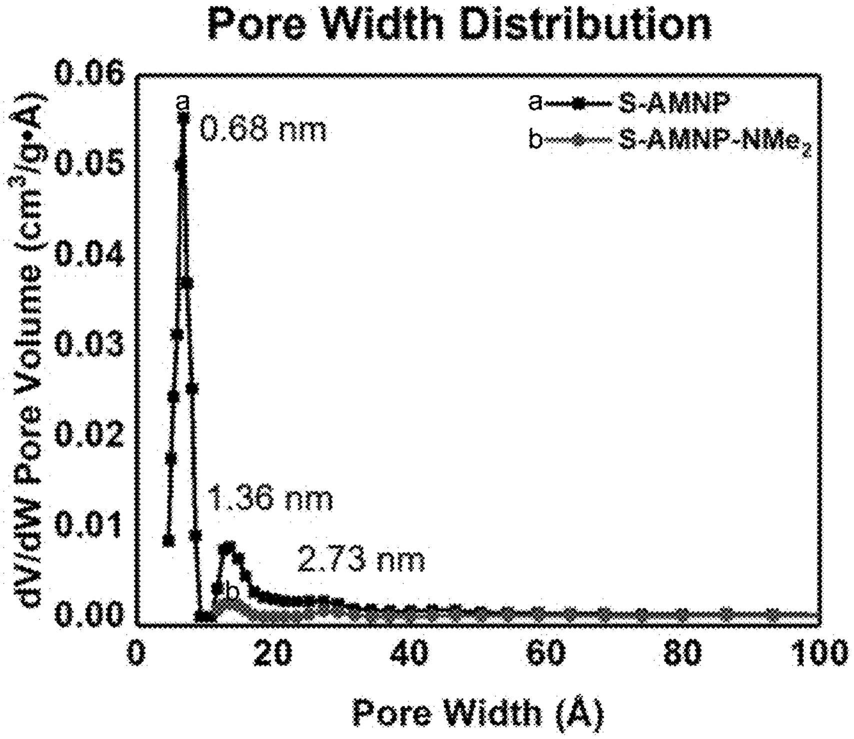
Figure 10:
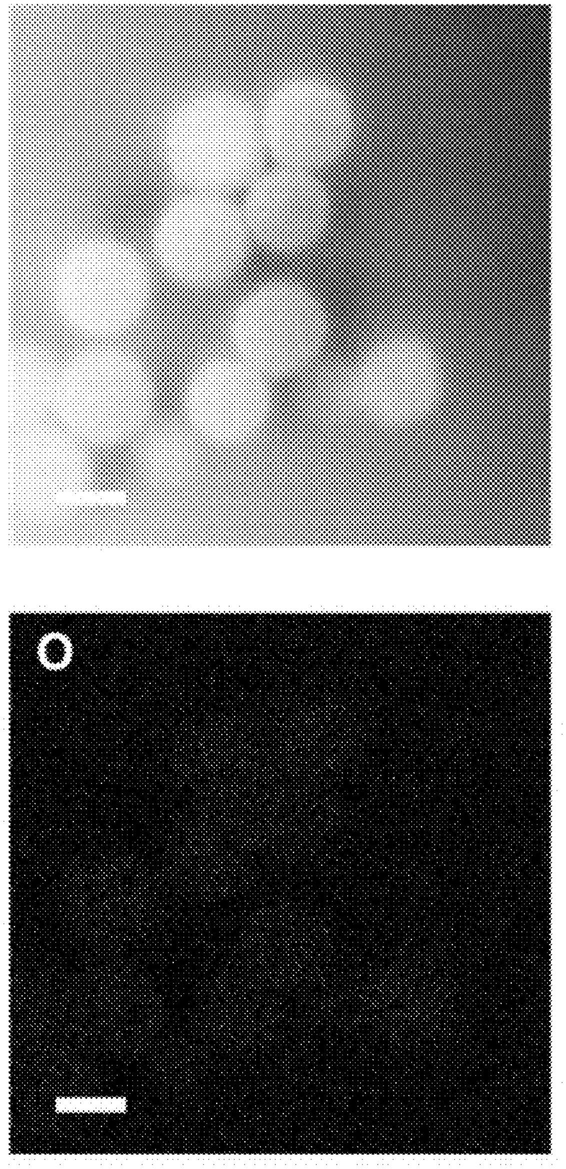
FIG. 10: STEM-EDX mapping analysis of S-AMNP-$NMe_2$, resin-embedded and sectioned to 50 nm thickness. Scale bars 100 nm.
Figure 11A:
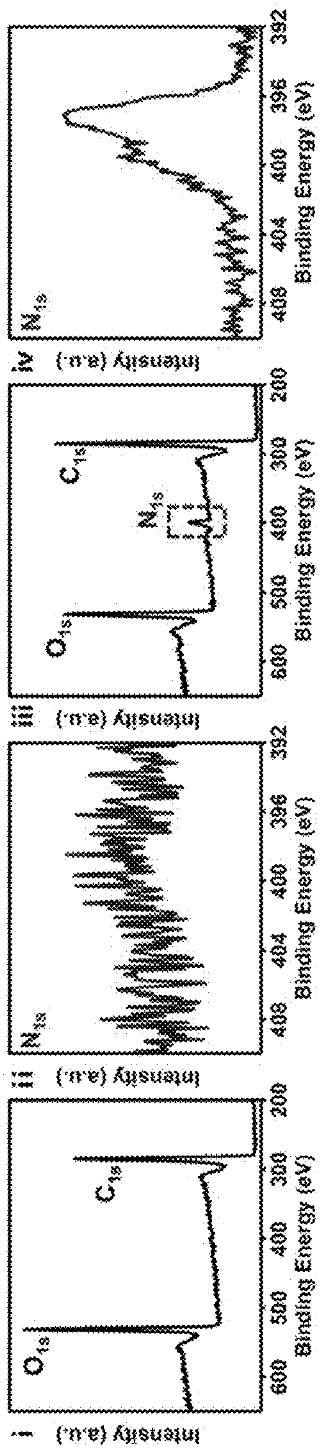
FIG. 11A: XPS (i) survey spectra, (ii) $N_{1s}$ spectra of W-AMNP; (iii) Survey spectra, (iv) $N_{1s}$ spectra of W-AMNP-$NMe_2$.
Figure 11B:
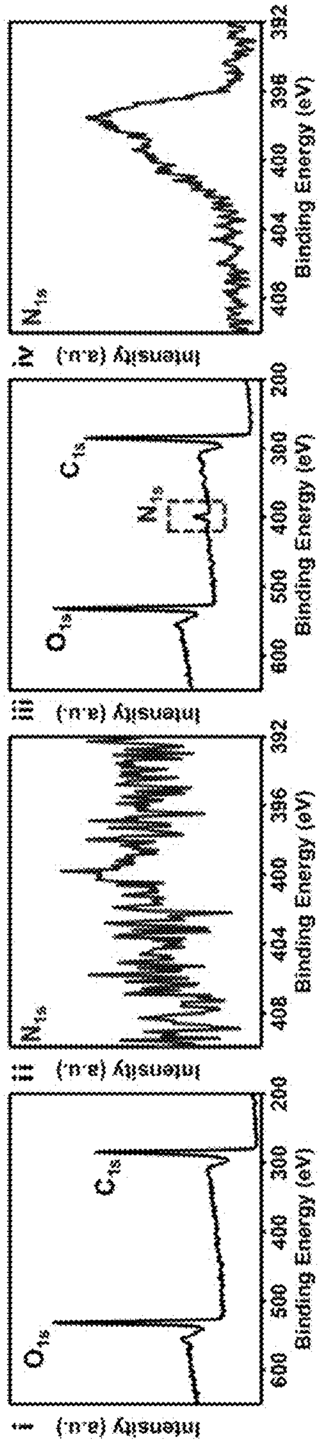
FIG. 11B: XPS (i) survey spectra, (ii) $N_{1s}$ spectra of H-AMNP; (iii) Survey spectra, (iv) $N_{1s}$ spectra of H-AMNP-$NMe_2$.
Figure 11C:
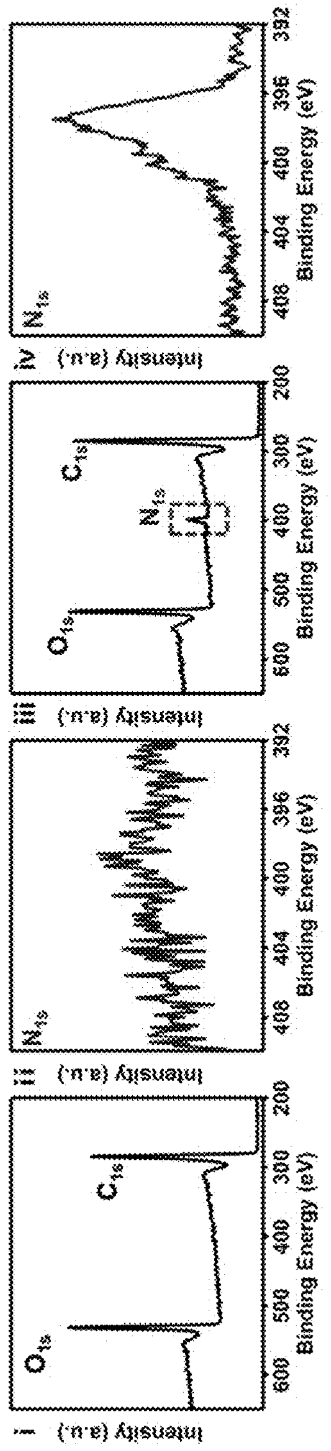
FIG. 11C: XPS (i) survey spectra, (ii) $N_{1s}$ spectra of L-AMNP; (iii) Survey spectra, (iv) $N_{1s}$ spectra of L-AMNP-$NMe_2$.
Figure 12A:
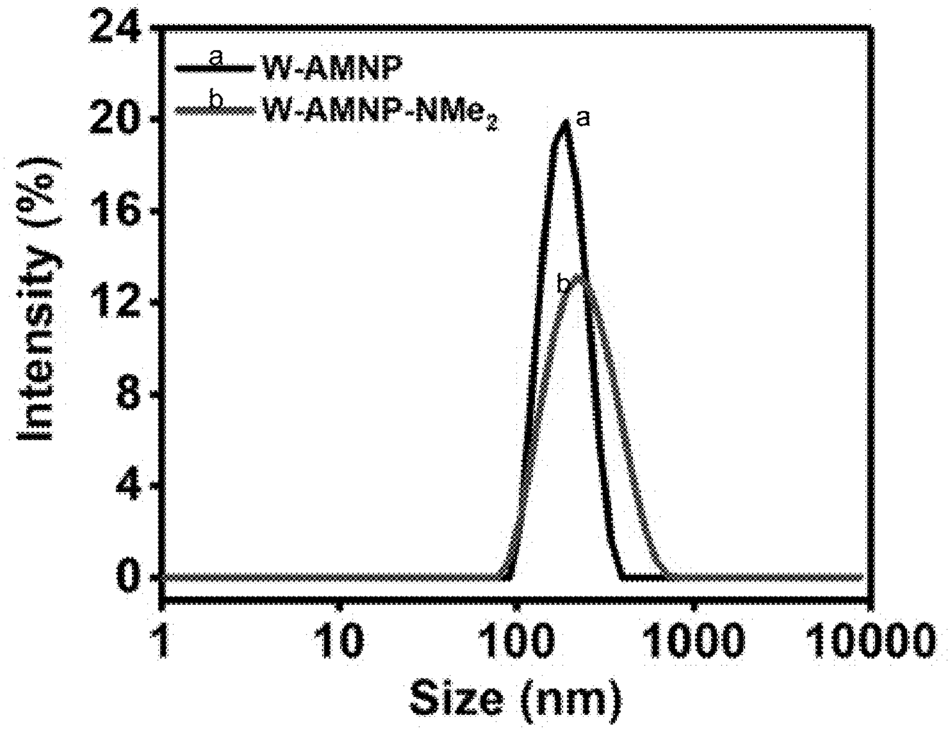
FIGS. 12A-12D: Hydrodynamic diameter of (FIG. 12A) W-AMNP (179.4 nm, PDI=0.054) and W-AMNP-$NMe_2$ (213.4 nm, PDI=0.133)
Figure 12B:
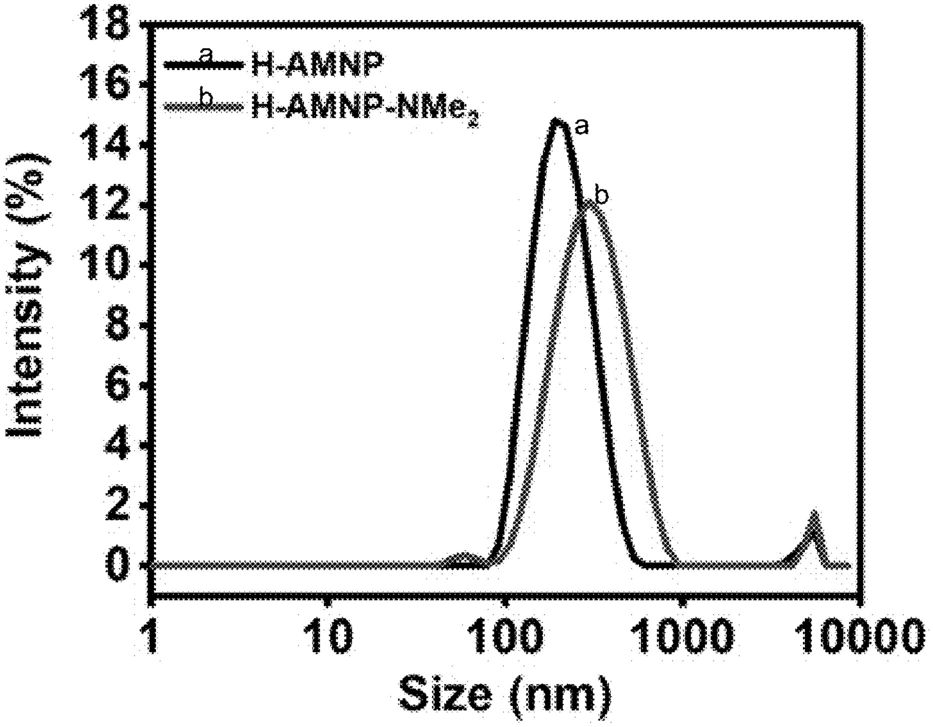
Figure 12C:
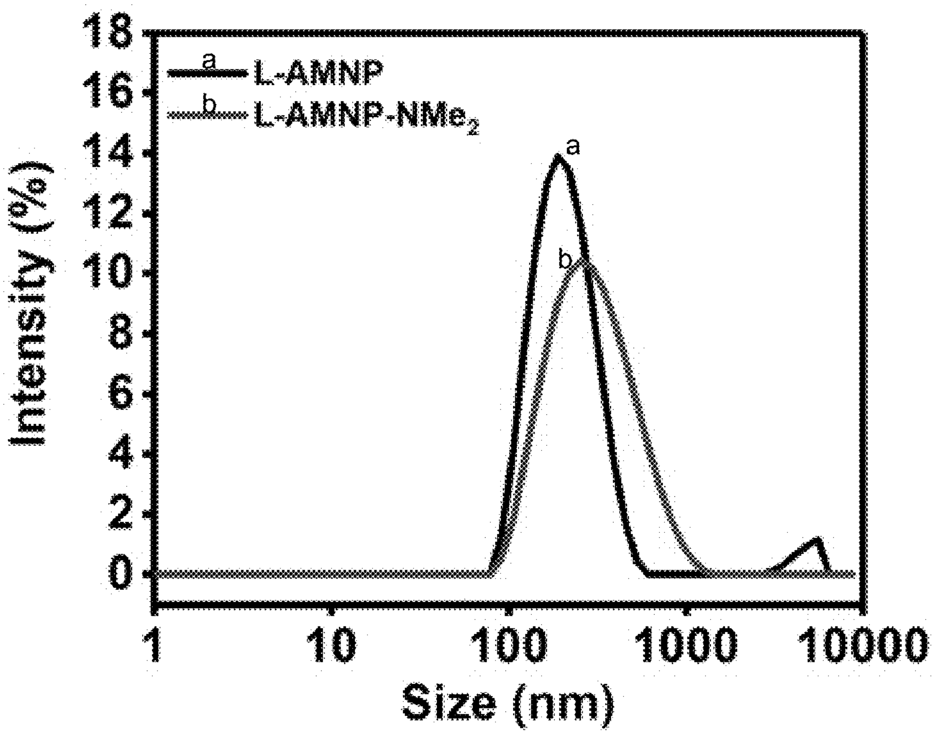
Figure 12D:
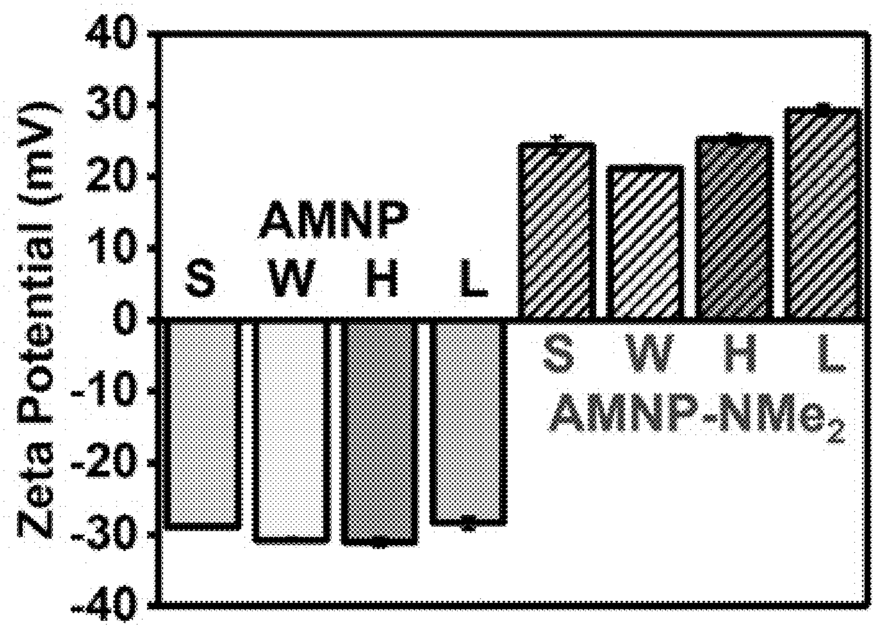

Scanning TEM (STEM) energy dispersive X-ray (EDX) spectroscopy (STEM-EDX) was conducted to develop elemental maps for S-AMNP-NMez which revealed a uniformly distributed nitrogen signal, similar to C and O (FIG. 2D). This is consistent with the fact that these synthetic allomelanins have been found to exhibit intrinsic microporosity, with BET areas ranging from 600 to 800 $m^2/g$.[28] Therefore, DMEN can diffuse into the micropores to functionalize the interior. To look for any changes in porosity caused by the modification, $N_2$ gas physisorption measurements were performed at 77K. Nitrogen isotherms revealed Brunauer-Emmett-Teller (BET) areas of 565 $m^2/g$ for S-AMNP, and 70 $m^2/g$ for S-AMNP-$NMe_2$ (FIGS. 9A-9B). DFT calculations showed a major pore around 6.8 Å for S-AMNP, while no corresponding pore was observed for S-AMNP-$NMe_2$ along with a significant decrease in the pore volume, which is consistent with the micropores being occupied by DMEN. To further confirm the existence of nitrogen inside the particle, S-AMNP-NMez was ultramicrotomed to 50 nm sections, and imaged via STEM-EDX, revealing a similar uniform distribution of nitrogen (FIG. 10). Combining the distribution of nitrogen in STEM-EDX mapping with the decrease of porosity, the evidence suggests that modifications occurred both on the surface and to some extent, the inside of AMNPs. Finally, this PSM strategy was applied to AMNPs with different morphologies (FIG. 1B). XPS characterization again confirmed the presence of covalently bound DMEN to W-AMNP, H-AMNP, and L-AMNP (FIGS. 11A-11C). In addition, zeta potentials of all types of AMNP revealed a switch from negative to positive values (FIGS. 12A-12D).

Synthesis and Characterization of Hydrophobic Allomelanin Nanoparticles: Like other melanin-based materials, AMNP has excellent colloidal dispersity in aqueous solution due to the hydrophilic hydroxyl groups on the surface, while the dispersity in nonpolar organic solvents is very poor. Therefore, after proving the feasibility of the PSM strategy, we turned to the goal of modifying melanin to generate hydrophobic analogues using both hexylamine ($C_6$—$NH_2$) and octadecylamine ($C_{18}$—$NH_2$) (FIGS. 3A-3E).

Figure 3C:
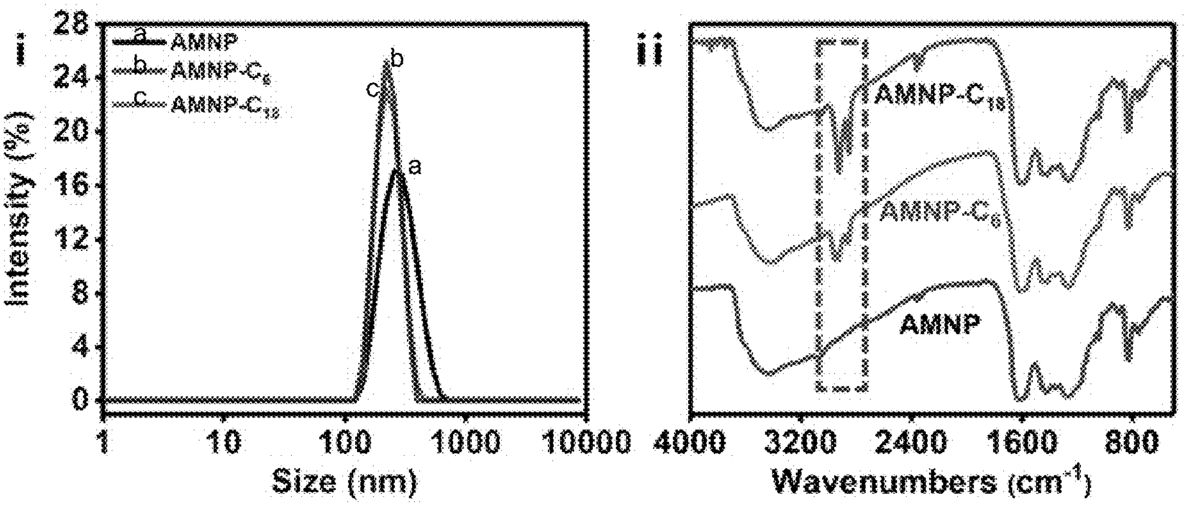
Figure 13:
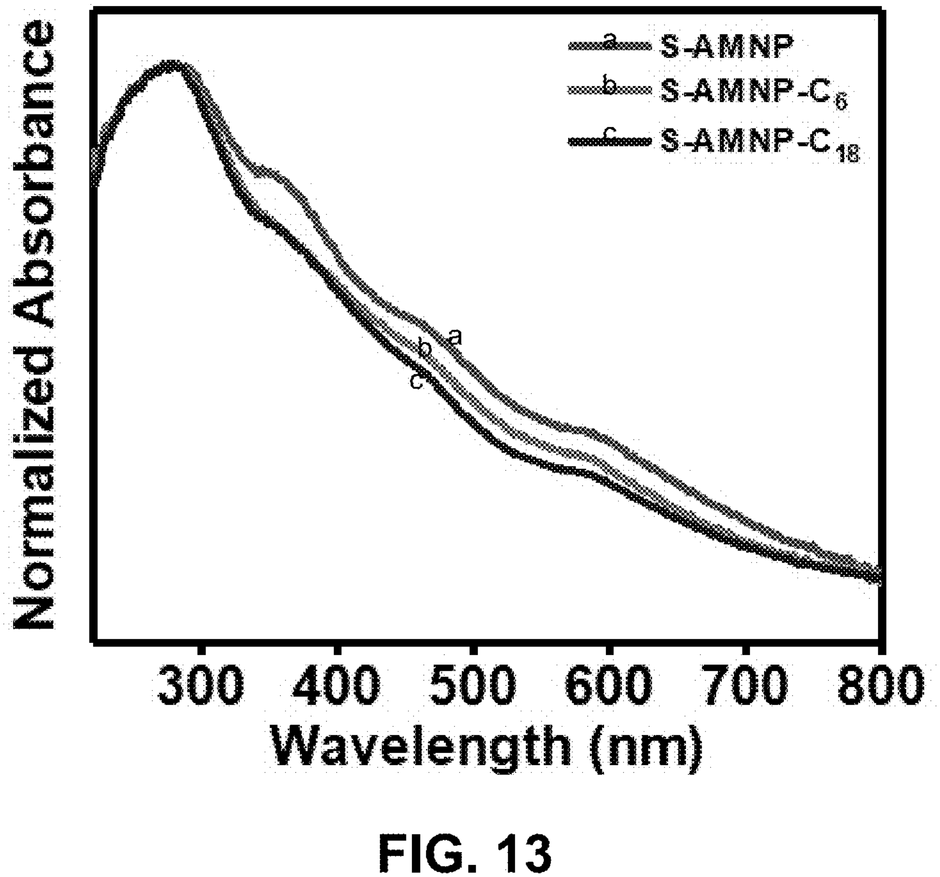
FIG. 13: UV-Vis of S-AMNP, S-AMNP-$C_6$, and S-AMNP-$C_{18}$ in EtOH.
Figure 14A:
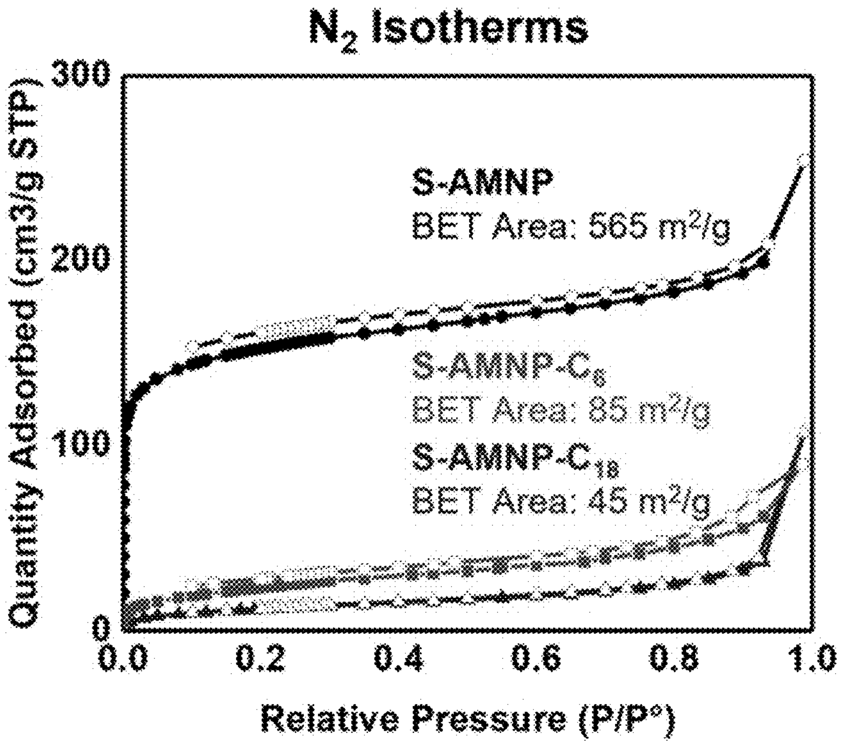
FIG. 14A: Nitrogen isotherms at 77 K and (FIG. 14B) pore size distributions of S-AMNP, S-AMNP-$C_6$, and S-AMNP-$C_{18}$.
Figure 14B:
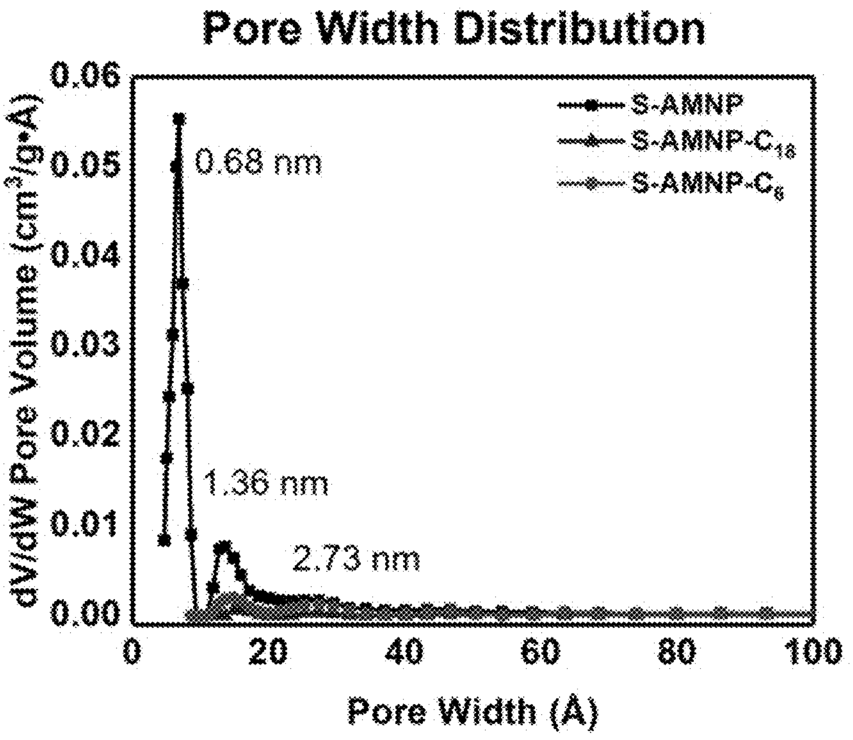

Briefly, AMNP was mixed with the amine-functionalized alkanes for 24 hours in ethanol (EtOH) followed by centrifugation and washing with EtOH. The resulting particles were obtained and denoted as S-AMNP-$C_6$ and S-AMNP-$C_{18}$, respectively (FIG. 3A). XPS characterization of S-AMNP-$C_6$ and S-AMNP-$C_{18}$ showed significant nitrogen signals confirming successful conjugation (FIG. 3B). DLS indicated hydrodynamic diameters of 278 nm for S-AMNP, 222 nm for S-AMNP-$C_6$, and 225 nm for S-AMNP-$C_{18}$ in ethanol (FIG. 3C i). UV-vis absorbance spectra showed similar features before and after modification (FIG. 13). New characteristic peaks at 2955 $cm^{-1}$, 2929 $cm^{-1}$, 2868 $cm^{-1}$, and 2858 $cm^{-1}$ were observed in the Fourier transform infrared (FTIR) spectrum of S-AMNP-$C_6$, corresponding to symmetric and asymmetric stretching vibrations of aliphatic hydrocarbon groups from $C_6$—$NH_2$ (FIG. 3C ii). Similar peaks at 2925 $cm^{-1}$ and 2852 $cm^{-1}$ were observed in the FTIR spectrum of S-AMNP-$C_{18}$ (FIG. 3C ii). Nitrogen isotherms revealed a decrease of BET surface areas from 565 $m^2/g$ for S-AMNP, to 85 $m^2/g$ for S-AMNP-$C_6$ and 45 $m^2/g$ for S-AMNP-$C_{18}$ (FIGS. 14A-14B). STEM-EDX mapping of S-AMNP-$C_{18}$ revealed a uniform distribution of nitrogen on the spherical particles (FIG. 15).

Figure 3D:
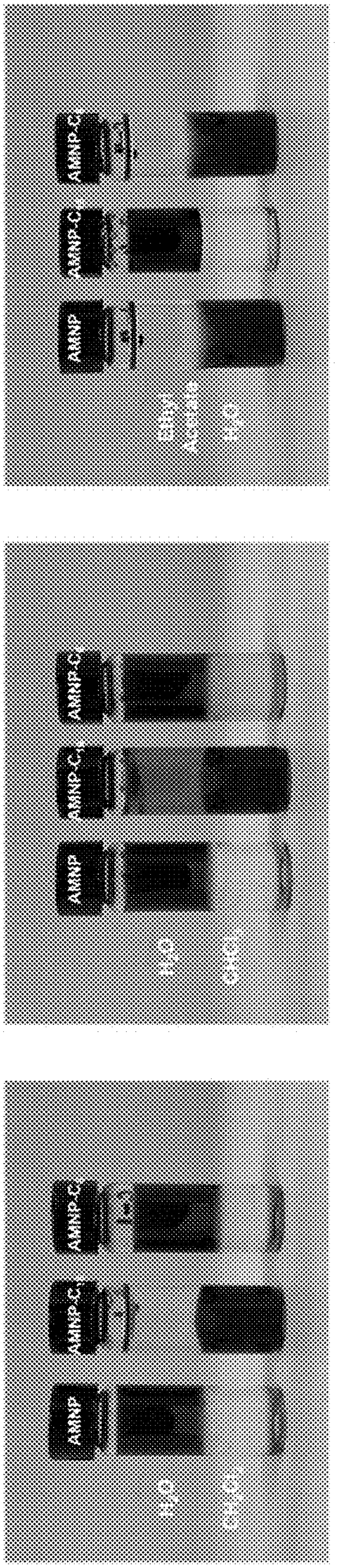
Figure 3E:
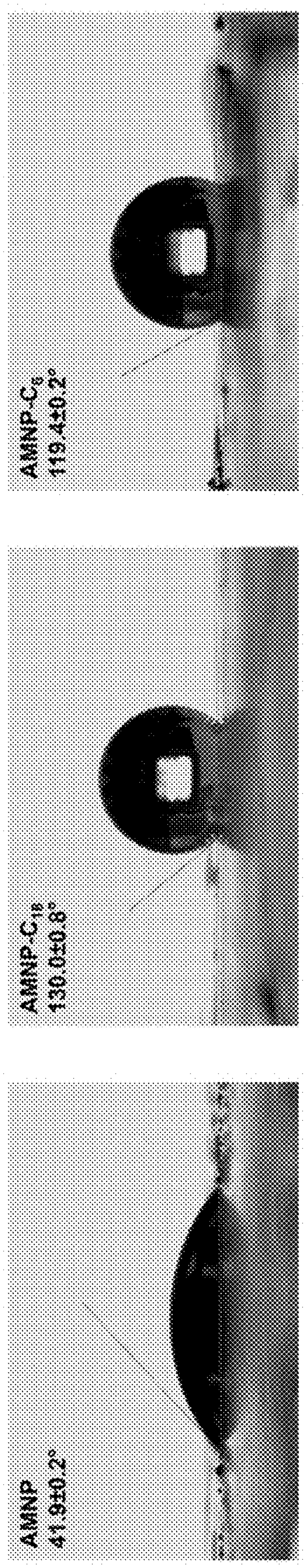
Figure 16:
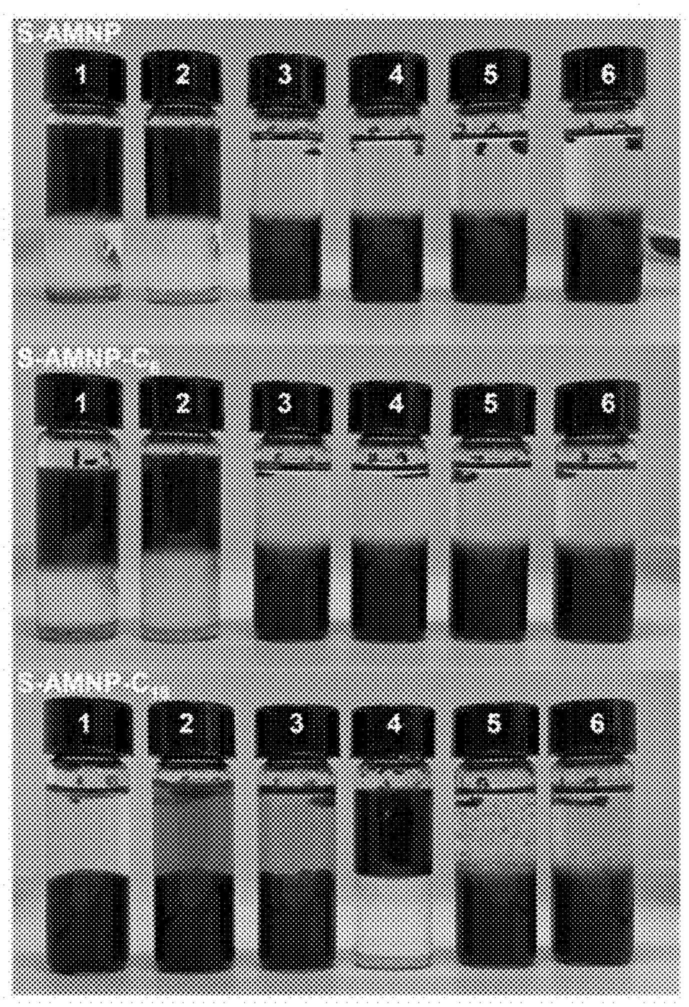
FIG. 16: Distribution of S-AMNP, S-AMNP-$C_6$, and S-AMNP-$C_{18}$ in water and different solvents ($CH_2Cl_2$, $CHCl_3$, toluene, ethyl acetate, hexane, and cyclohexane).
Figure 17:
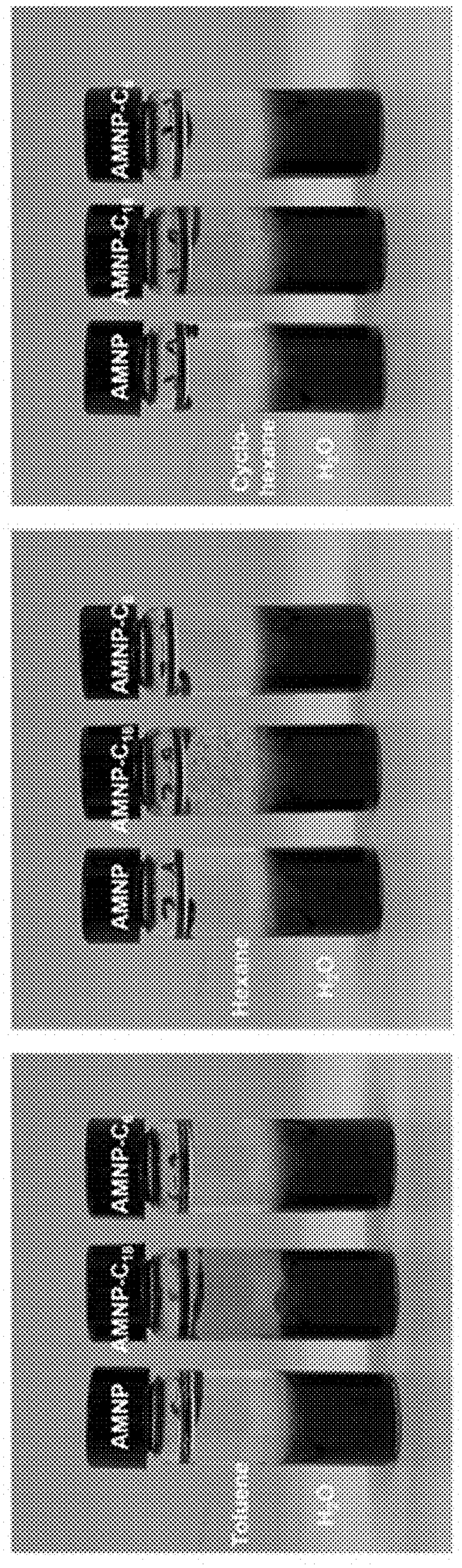
FIG. 17: Distribution of S-AMNP, S-AMNP-$C_6$, and S-AMNP-$C_{18}$ in water and toluene, hexane, and cyclohexane.
Figure 18A:
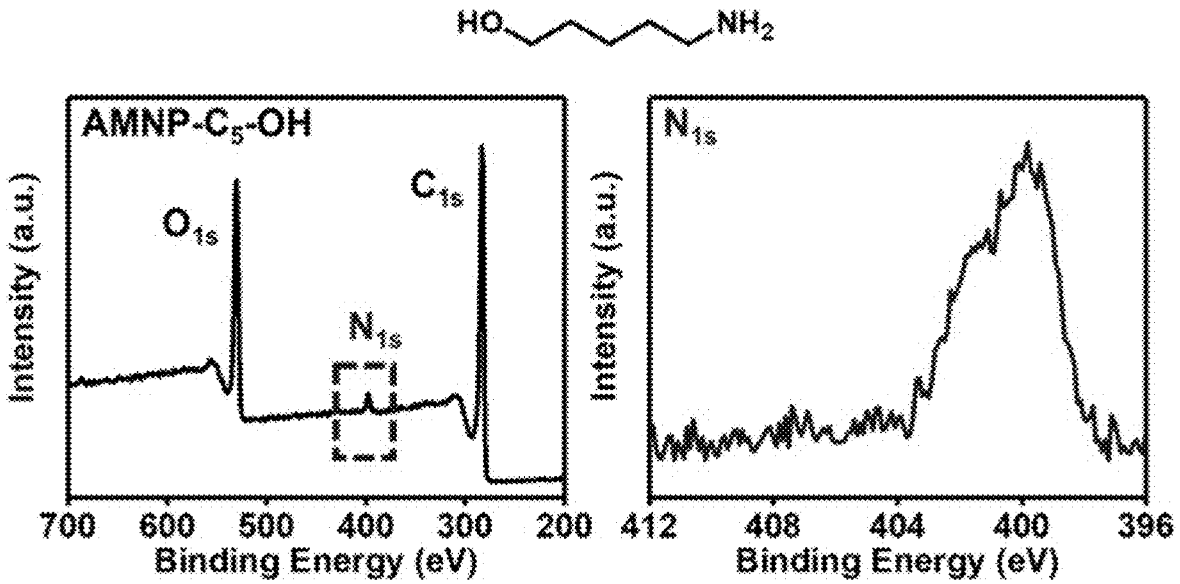
FIGS. 18A-18E: XPS of modified S-AMNP.
Figure 18B:
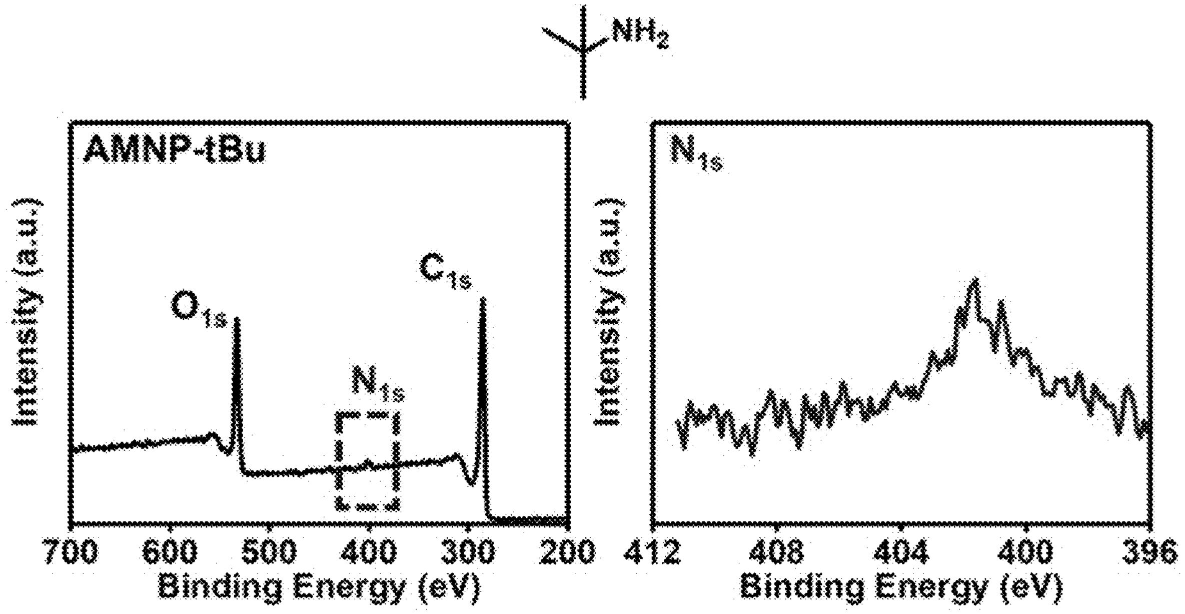
Figure 18C:
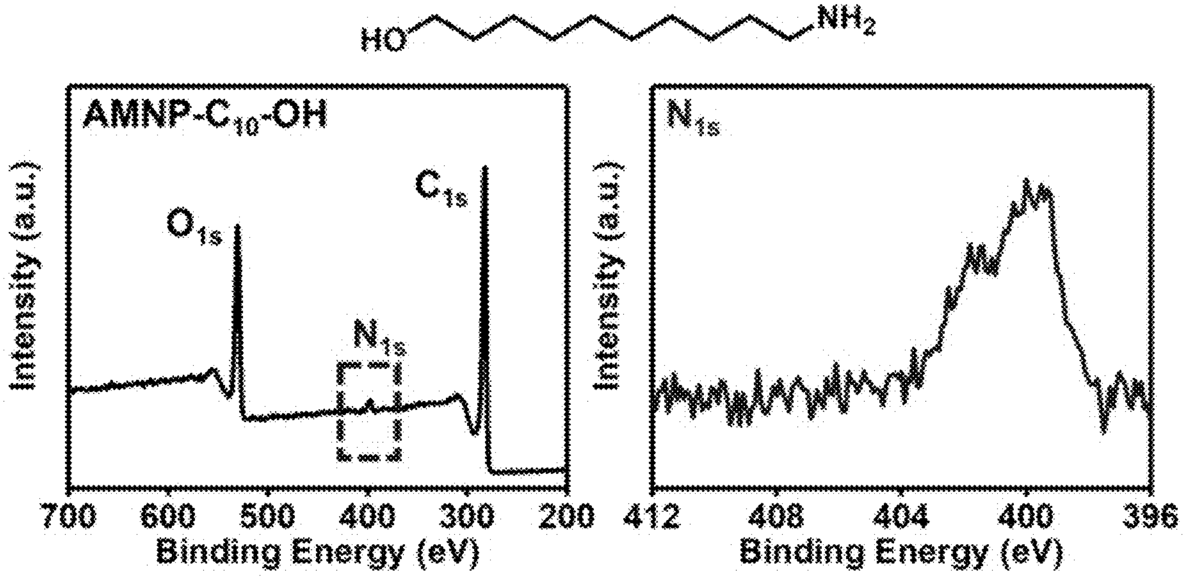
Figure 18D:
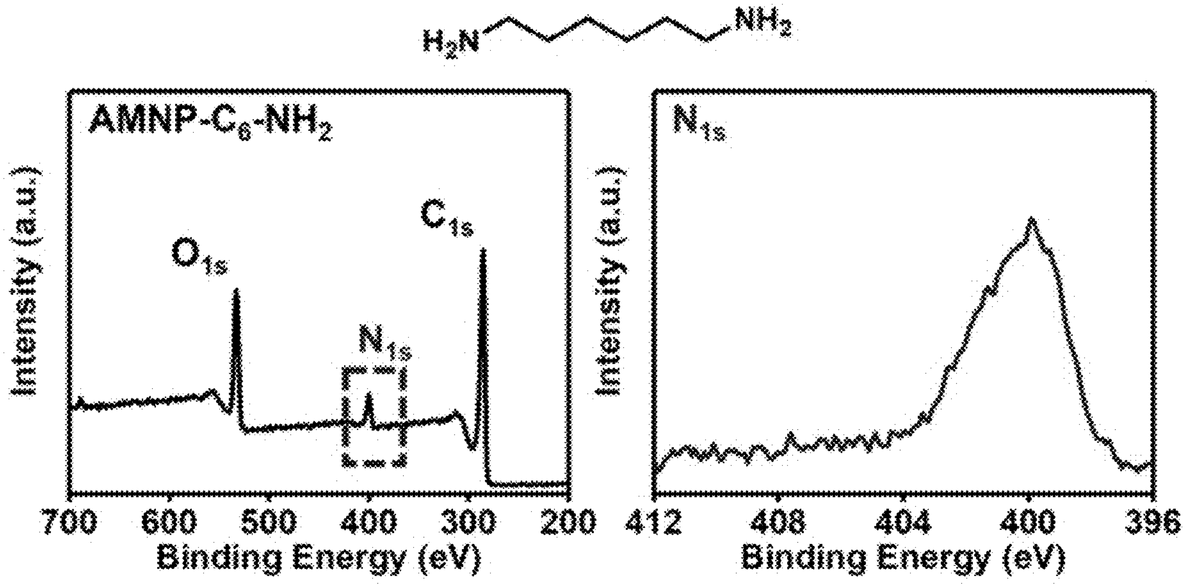
Figure 18E:
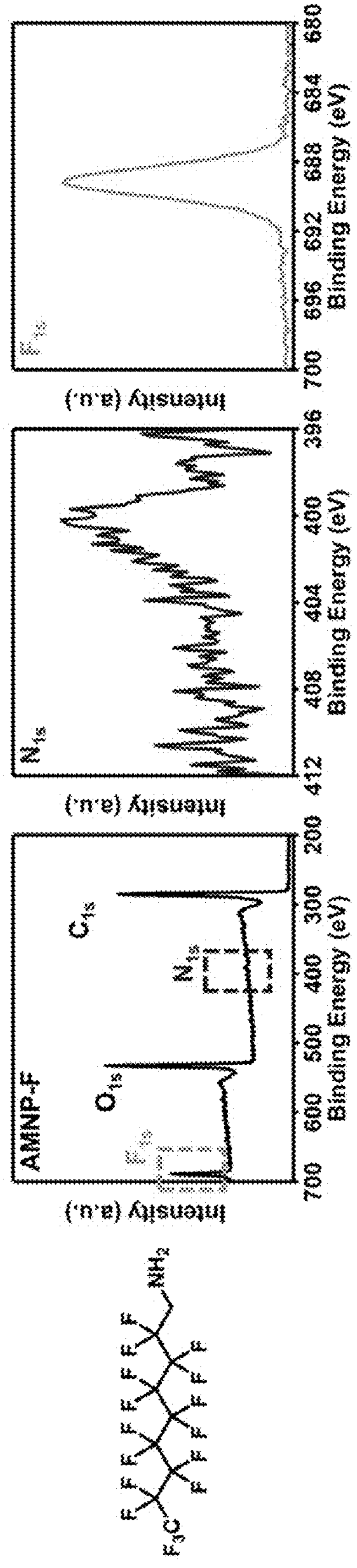
Figure 29A:
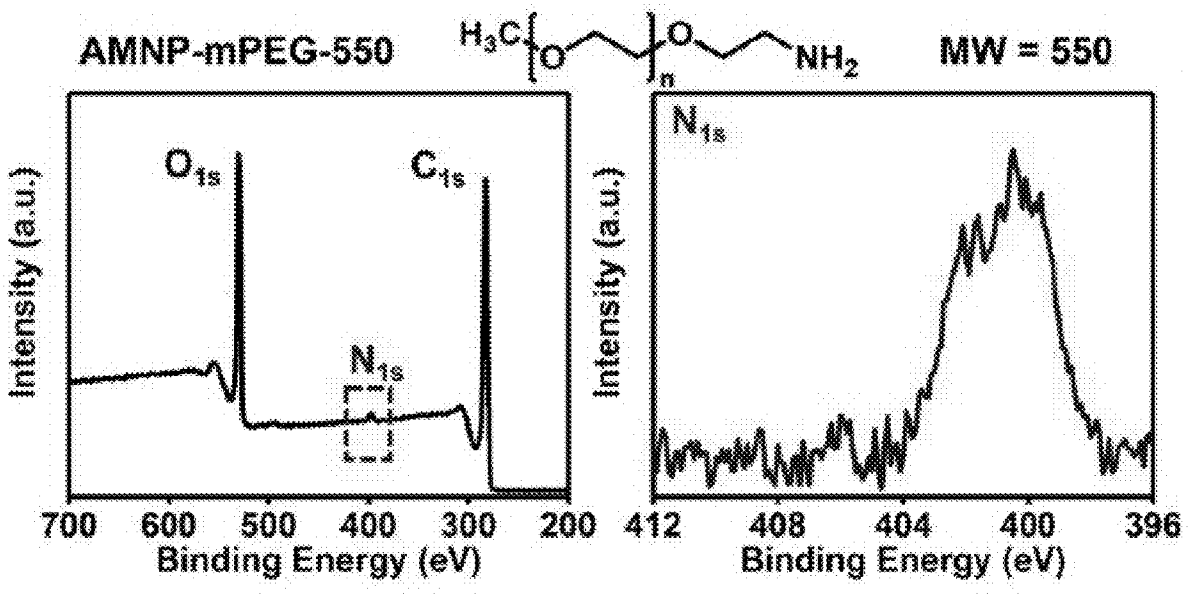
FIGS. 29A-29B: XPS of modified S-AMNP. (A) Survey and $N_{1s}$ spectra of AMNP-mPEG-550 modified by mPEG-$NH_2$ (MW 550); (B) Survey and $N_{1s}$ spectra of AMNP-mPEG-2000 modified by mPEG-$NH_2$ (MW 2000).
Figure 29B:
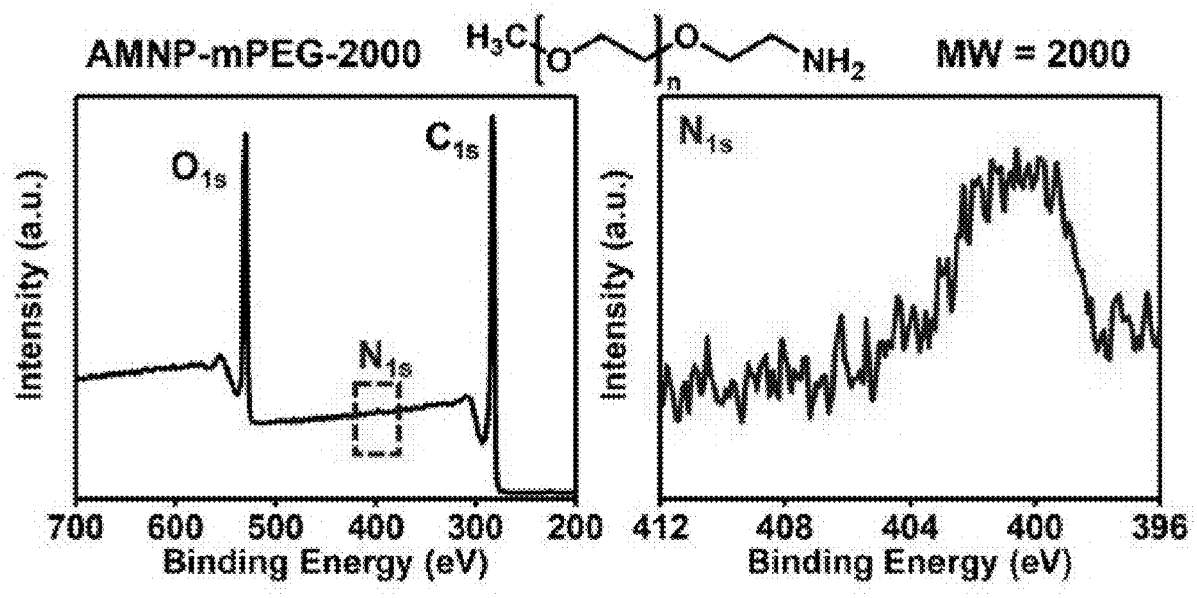
Figures 30, 31:
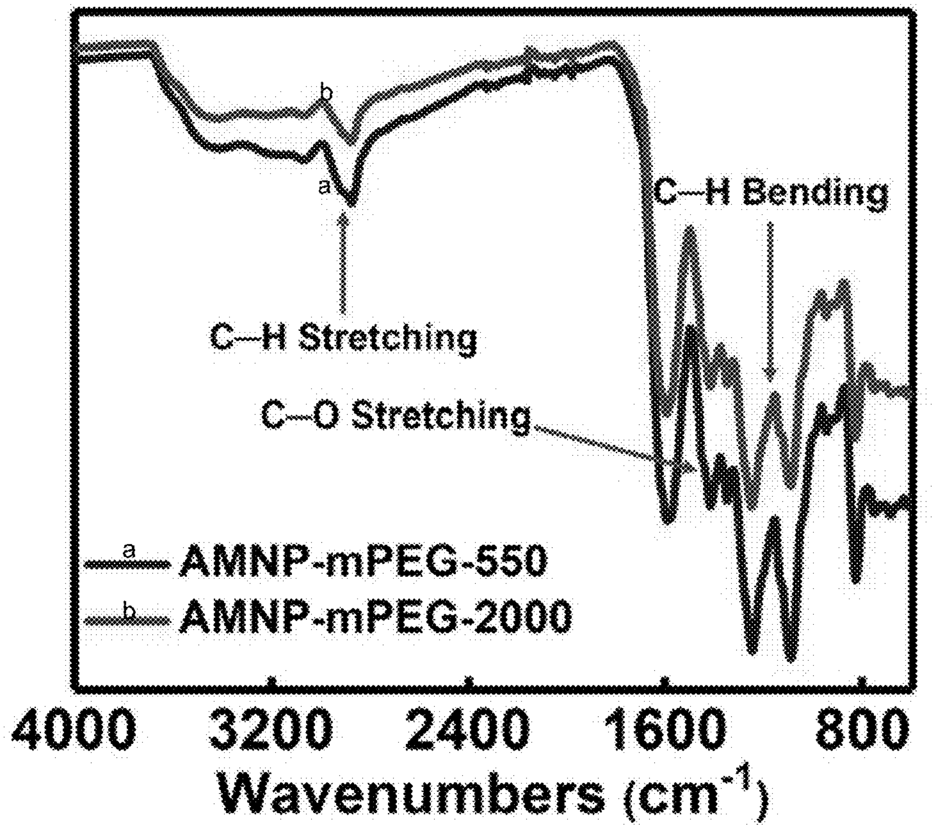
FIG. 30: FTIR spectra of S-AMNP-mPEG-550 and S-AMNP-mPEG-2000.
FIG. 31: Table showing thickness of AMNP-$C_{18}$ thin films obtained from SEM.

To further examine the outcome of the chemical modification, the dispersion of S-AMNP, S-AMNP-$C_6$, and S-AMNP-$C_{18}$ in water and different organic solvents (dichloromethane ($CH_2Cl_2$), chloroform ($CHCl_3$), toluene, ethyl acetate, hexane, and cyclohexane) was investigated (FIG. 16). Qualitatively, S-AMNP-$C_6$ was found in the aqueous phase in all cases. S-AMNP-$C_{18}$ was dispersed in the organic phase ($CH_2Cl_2$, $CHCl_3$, and ethyl acetate) or remained in the aqueous phase (toluene, hexane, and cyclohexane) (FIG. 3D, FIG. 17). To quantitatively measure the hydrophobicity, AMNPs were dispersed in THF (10 mg/mL) and then drop cast to fabricate films on a glass slide for water contact angle measurements. As expected, the film having S-AMNP-$C_{18}$ possessed the highest water contact angle (130.0±0.8°) (FIG. 3E). S-AMNP-$C_6$ also demonstrated high hydrophobicity (119.4±0.2°) compared to that of S-AMNP (41.9±0.2°) (FIG. 3E). Further, we note the PSM is generalizable to other primary amines. Modification with 5-amino-1-pentanol, t-butylamine, 10-amino-1-decanol, 1,6-hexanediamine, and 2,2,3,3,4,4,5,5,6,6,7,7,8,8,9,9,9-heptadecafluorononylamine were confirmed using XPS (FIGS. 18A-18E). Besides small molecules, polymers with amine-functionalized end group were also studied in PSM. Polyethylene glycol amines (mPEG-$NH_2$) with different molecular weights (MW 550, MW 2000) were utilized to functionalize AMNP. Modification was confirmed using XPS by detecting nitrogen signals (FIGS. 29A-29B), and FTIR by observing characteristic peaks corresponding to PEG (2872 $cm^{-1}$ for C—H stretching, 1416 $cm^{-1}$, 1348 $cm^{-1}$ for C—O stretching, and 1252 $cm^{-1}$, 1085 $cm^{-1}$ for C—H bending) (FIG. 30).

Air/Water Interfacial Self-Assembly of Hydrophobic Allomelanin Nanoparticles: As a natural pigment with a high refractive index and broadband absorption, natural and synthetic melanins of diverse morphologies have been an attractive material in the production of structural colors.[33] While numerous strategies including dip-coating,[34] spray coating,[35] inkjet printing,[36] and reverse emulsion self-assembly have been applied to generate structural colors using melanin materials,[37,38] achieving a large area of well-ordered structural color remains a challenge. Air/water interfacial self-assembly has been elucidated as a versatile approach for the fast and controlled self-assembly of a variety of micro- and nanoscale materials, such as silica nanoparticles, gold nanoparticles, and polymeric micro/nanospheres, to form layered and two-dimensional arrays.[39-42] We reasoned that hydrophobic allomelanin nanoparticles would be amenable to this approach to achieve large-area homogenous thin films with closed-packed arrangements and controlled multilayers, and as such we investigated the process and the morphological dependence on color and packing (FIGS. 4A-4G).

Figure 4A:
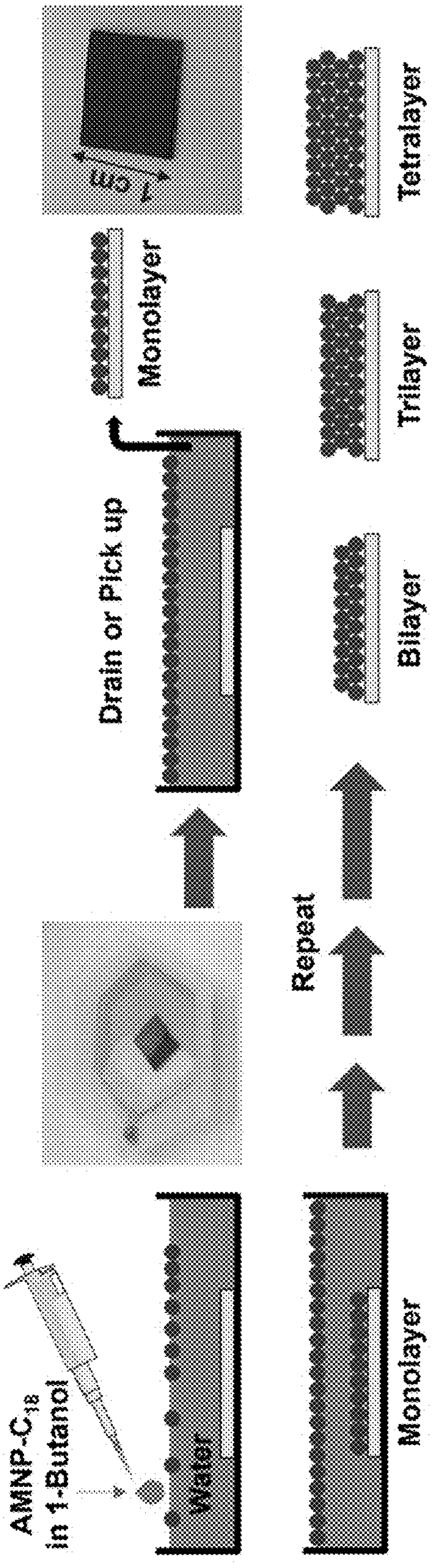
FIGS. 4A-4G: Air/water interfacial self-assembly of hydrophobic allomelanins.
Figure 4B:
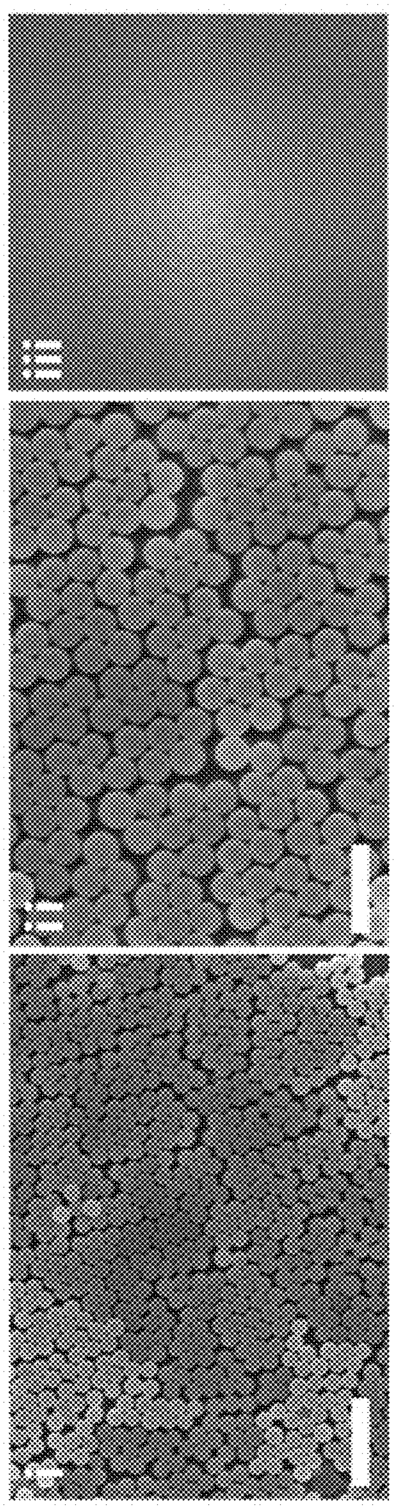
Figure 4C:
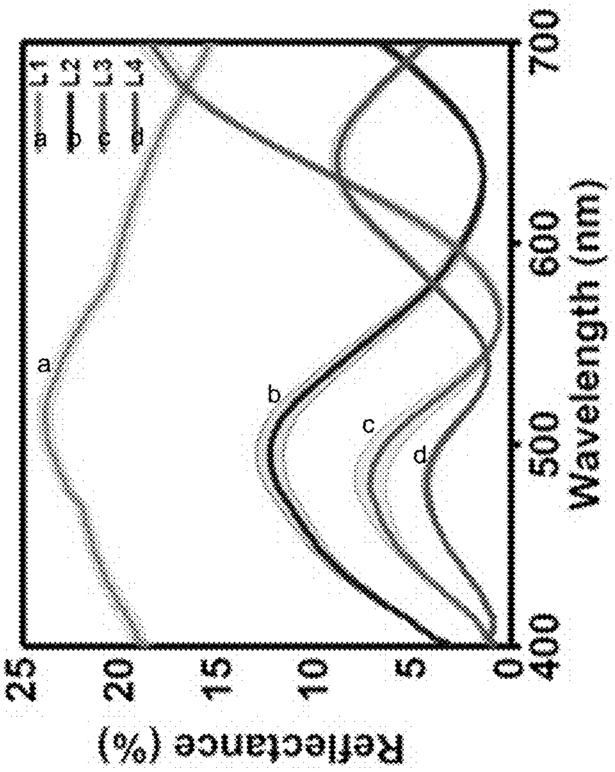
Figure 4D:
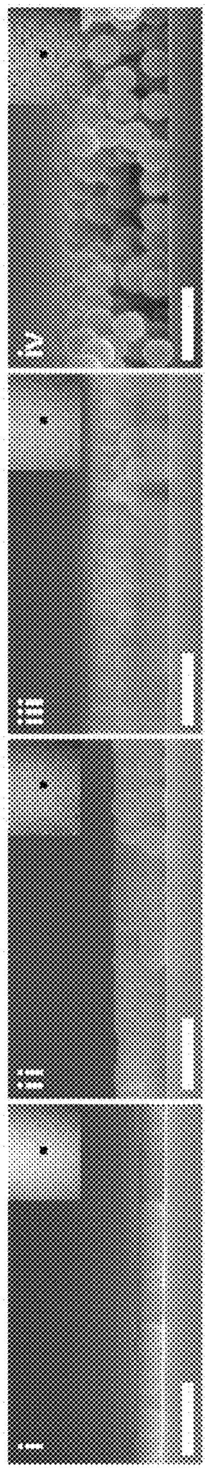
Figure 4E:
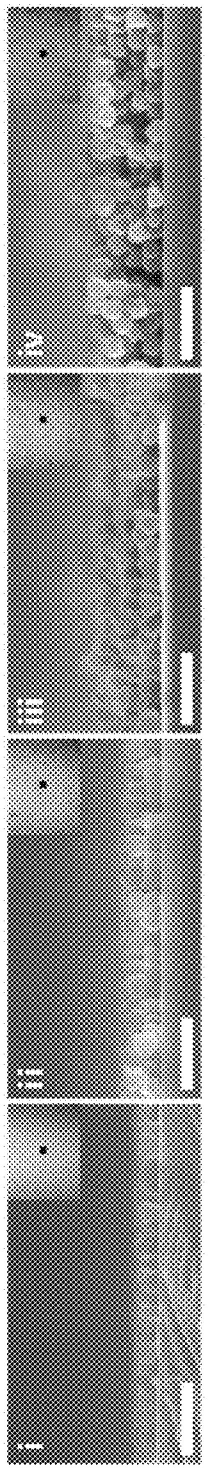
Figure 4F:
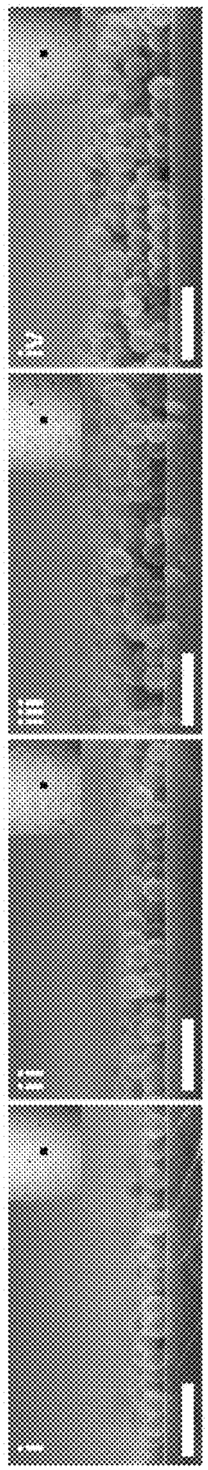
Figure 4G:
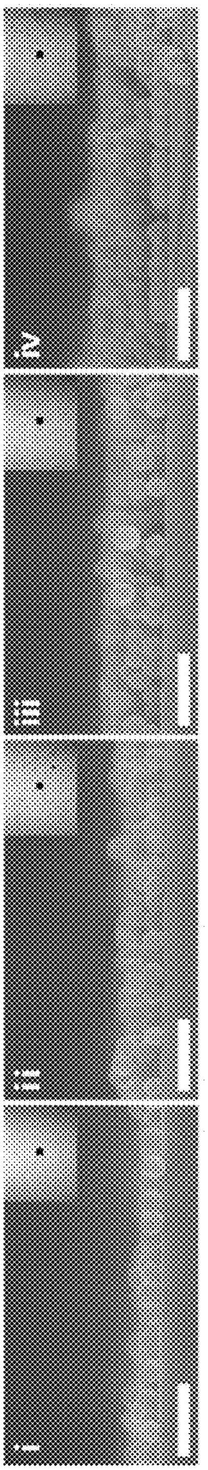
Figure 5:
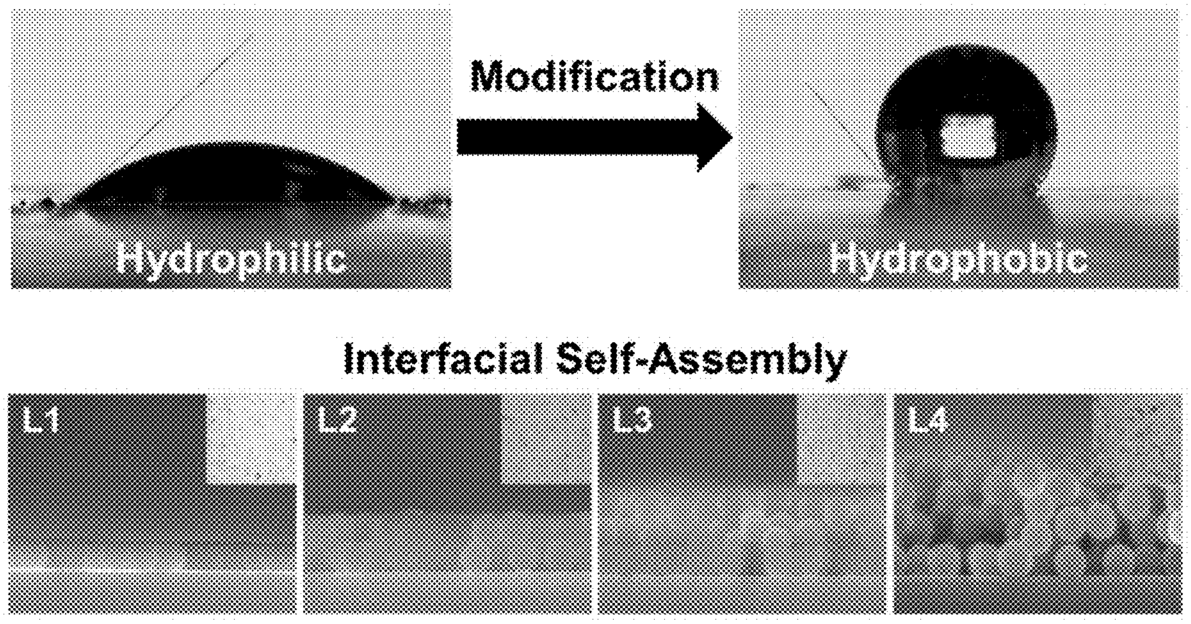
FIG. 5: Top portion shows that functionalization (or, "modification"), according to embodiments herein, changes hydrophilic artificial melanin nanoparticles to hydrophobic artificial melanin nanoparticles, as evidenced by an increase in contact angle from less than 90° to greater than 90°. The bottom portion of FIG. 5 shows self-assembly of monolayers of the functionalized artificial melanin nanoparticles with L1-L4 representing 1, 2, 3, or 4 layers of nanoparticles, respectively.
Figure 19A:
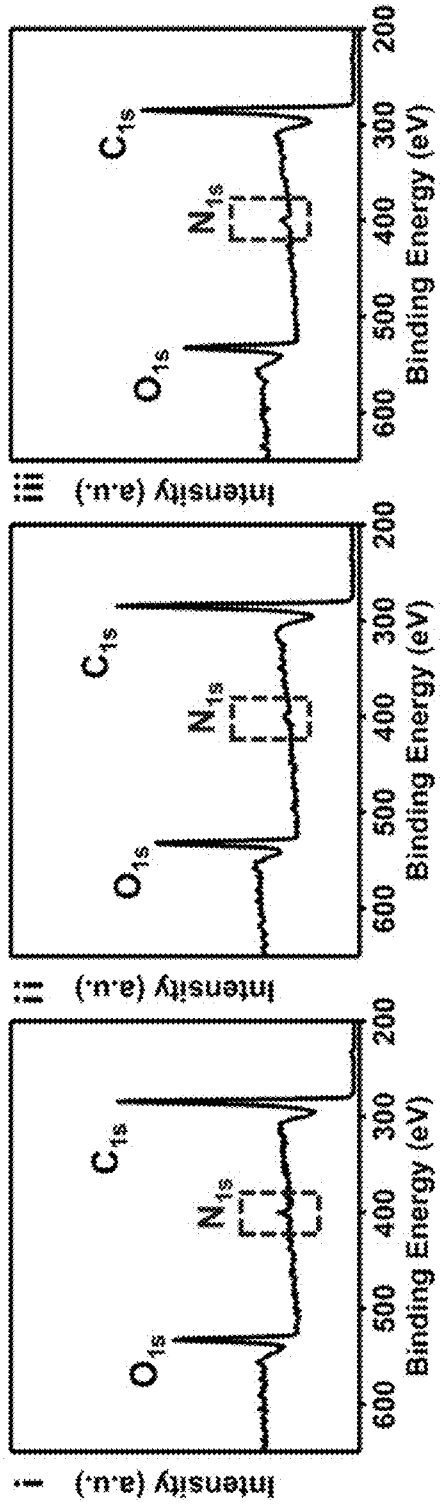
FIG. 19A: XPS survey spectra of (i) W-AMNP-$C_{18}$, (ii) H-AMNP-$C_{18}$, and (iii) L-AMNP-$C_{18}$.
Figure 19B:
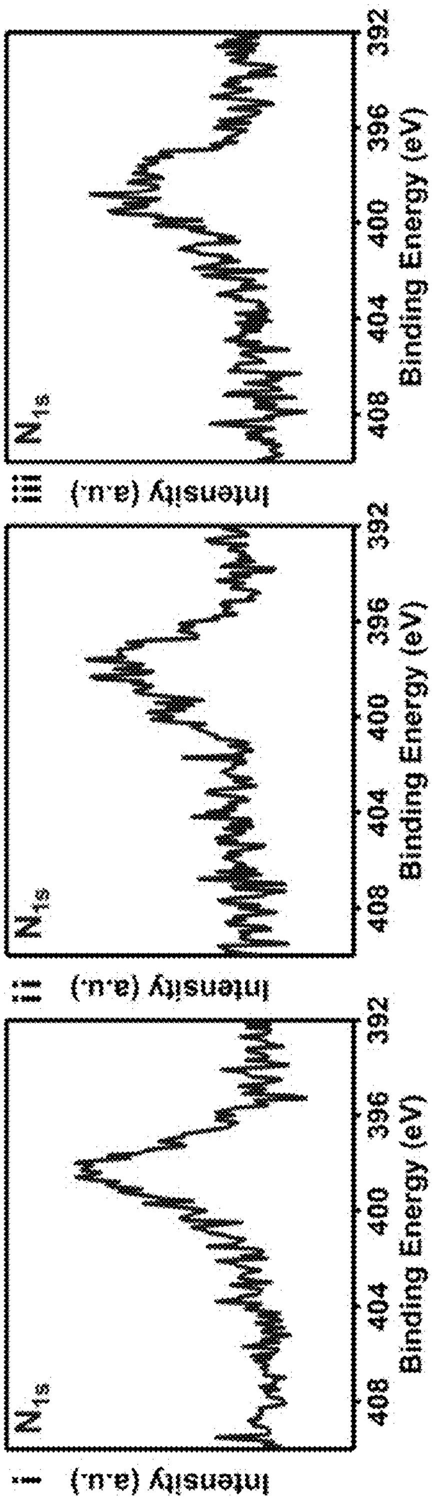
FIG. 19B: XPS $N_{1s}$ spectra of (i) W-AMNP-$C_{18}$, (ii) H-AMNP-$C_{18}$, and (iii) L-AMNP-$C_{18}$.
Figure 20A:
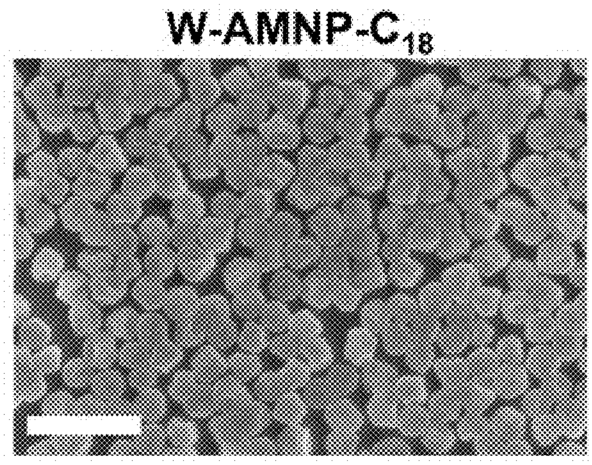
FIGS. 20A-20C: Top-view SEM images of (FIG. 20A) W-AMNP-$C_{18}$ monolayer, (FIG. 20B) H-AMNP-$C_{18}$ monolayer, (FIG. 20C) L-AMNP-$C_{18}$ monolayer, scale bars 500 nm.
Figure 20B:
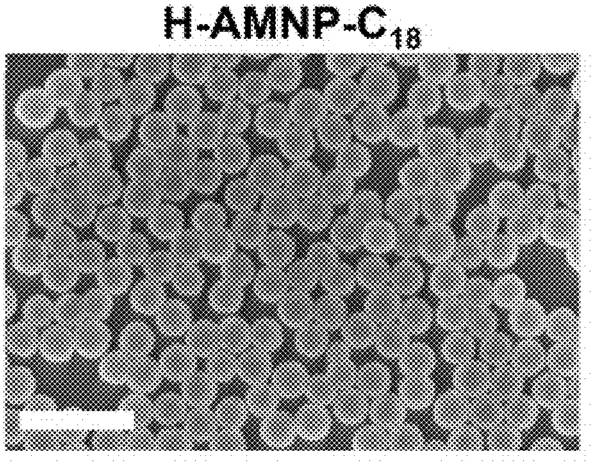
Figure 20C:
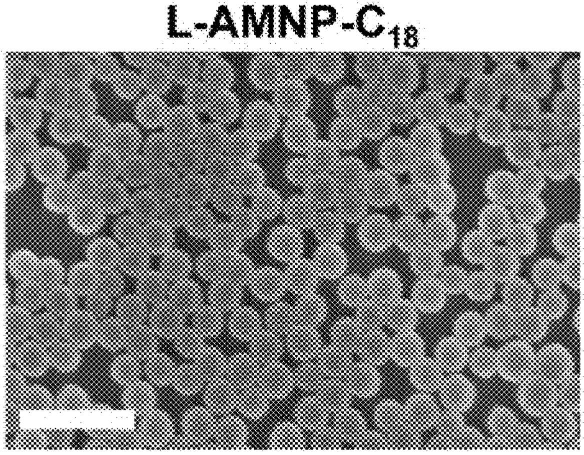
Figure 21:
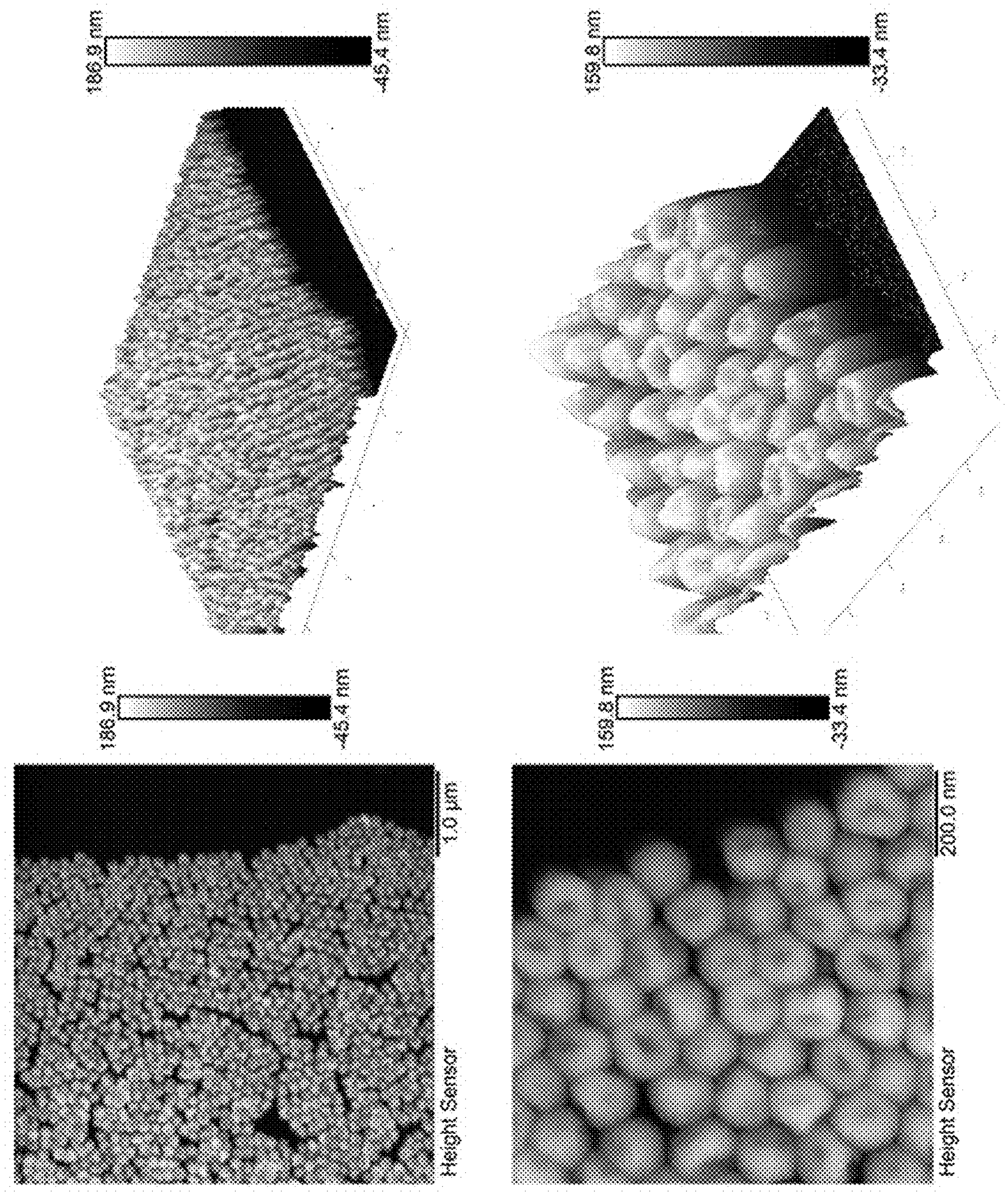
FIG. 21: AFM images of W-AMNP-$C_{18}$ monolayer, showing the contour of the nanoparticles.
Figure 22A:
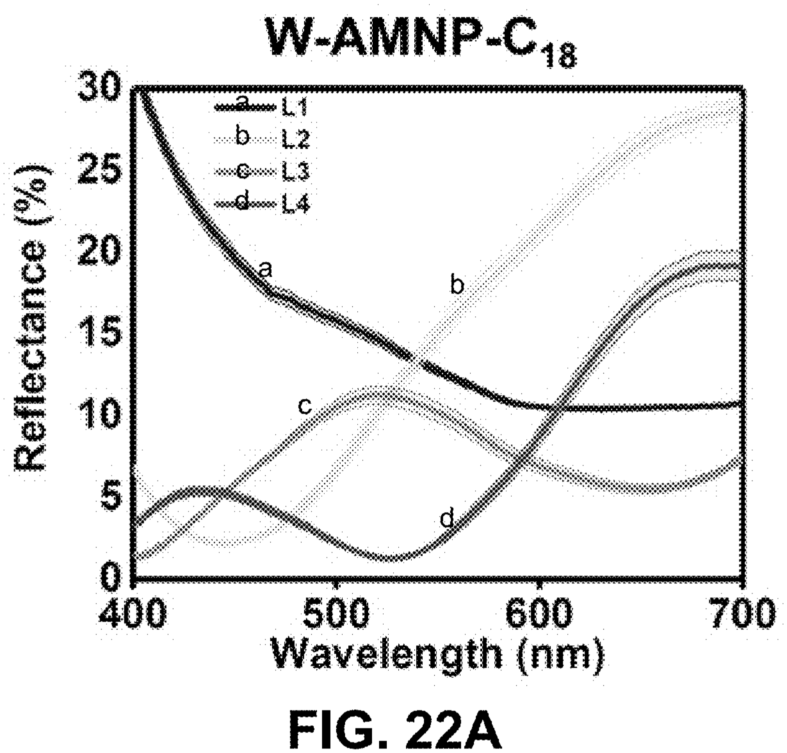
FIGS. 22A-22C: Reflectance spectra of monolayer (L1), bilayer (L2), trilayer (L3), and tetralayer (L4) films formed by (FIG. 22A) W-AMNP-$C_{18}$, (FIG. 22B) H-AMNP-$C_{18}$, (FIG. 22C) L-AMNP-$C_{18}$. The experimental reflectance curves are averaged over 5 locations on the film and the shaded region represents error bars as standard deviation.
Figure 22B:
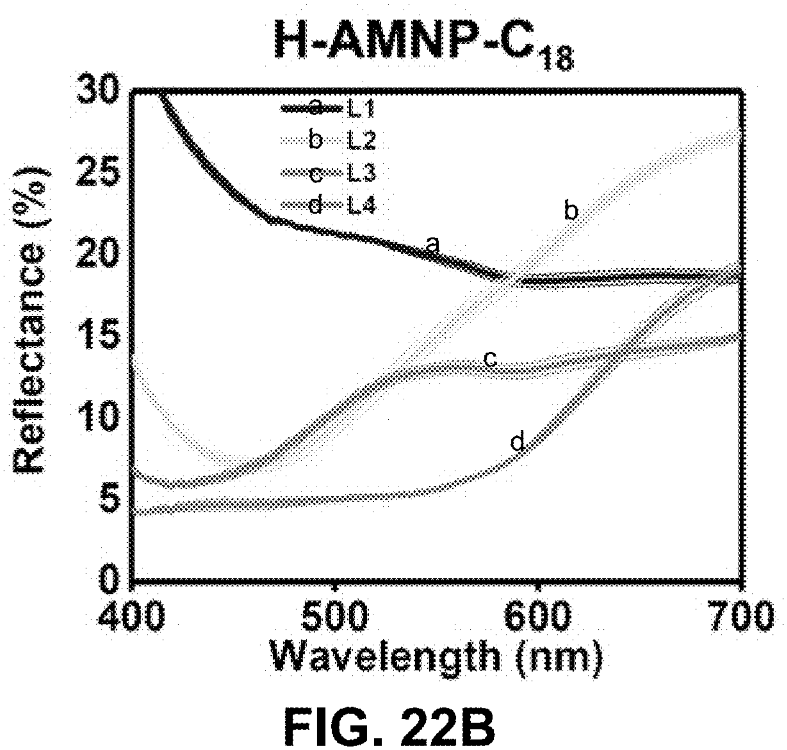
Figure 22C:
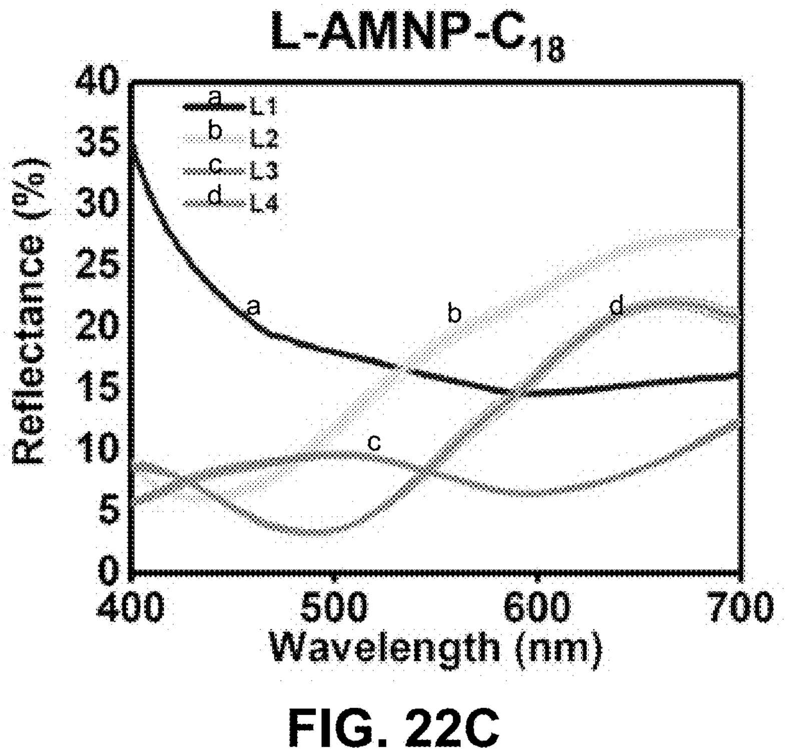

Allomelanin nanoparticles with different architectures (S-AMNP, W-AMNP, H-AMNP, and L-AMNP) were synthesized and further modified with $C_{18}$—$NH_2$. Modification was confirmed using XPS (FIGS. 19A-19B). Before adding the colloidal suspension, a transfer substrate (silicon wafer) was placed at the bottom of the container filled with Milli-Q water. AMNP-$C_{18}$ was ultrasonically dispersed in 1-butanol at a concentration of 2.0 mg/mL. This colloidal suspension was slowly added onto the water surface using a pipette. Continuous addition of AMNP-$C_{18}$ led to the formation of a uniform and close-packed AMNP-$C_{18}$ monolayer. Once the water surface was fully occupied, the monolayer could be transferred to the substrate by either draining the water or lifting the substrate. A typical photograph of the monolayer of W-AMNP-$C_{18}$ on a silicon wafer (1 cm×1 cm) displayed a homogenous blue color to the naked-eye (FIG. 4A). Scanning electron microscopy (SEM) images of the top view of the monolayer films showed quasi-hexagonal close-packed AMNP-$C_{18}$ confirmed by the corresponding two-dimensional fast Fourier transform (FFT) (FIG. 4B, FIGS. 20A-20C). All of the nanoparticles, including the irregular, walnut-shaped AMNP-$C_{18}$ assumed the quasi-hexagonal close packing formation (SEM images, FIG. 20A and atomic force microscope images, FIG. 21).

Figure 32:
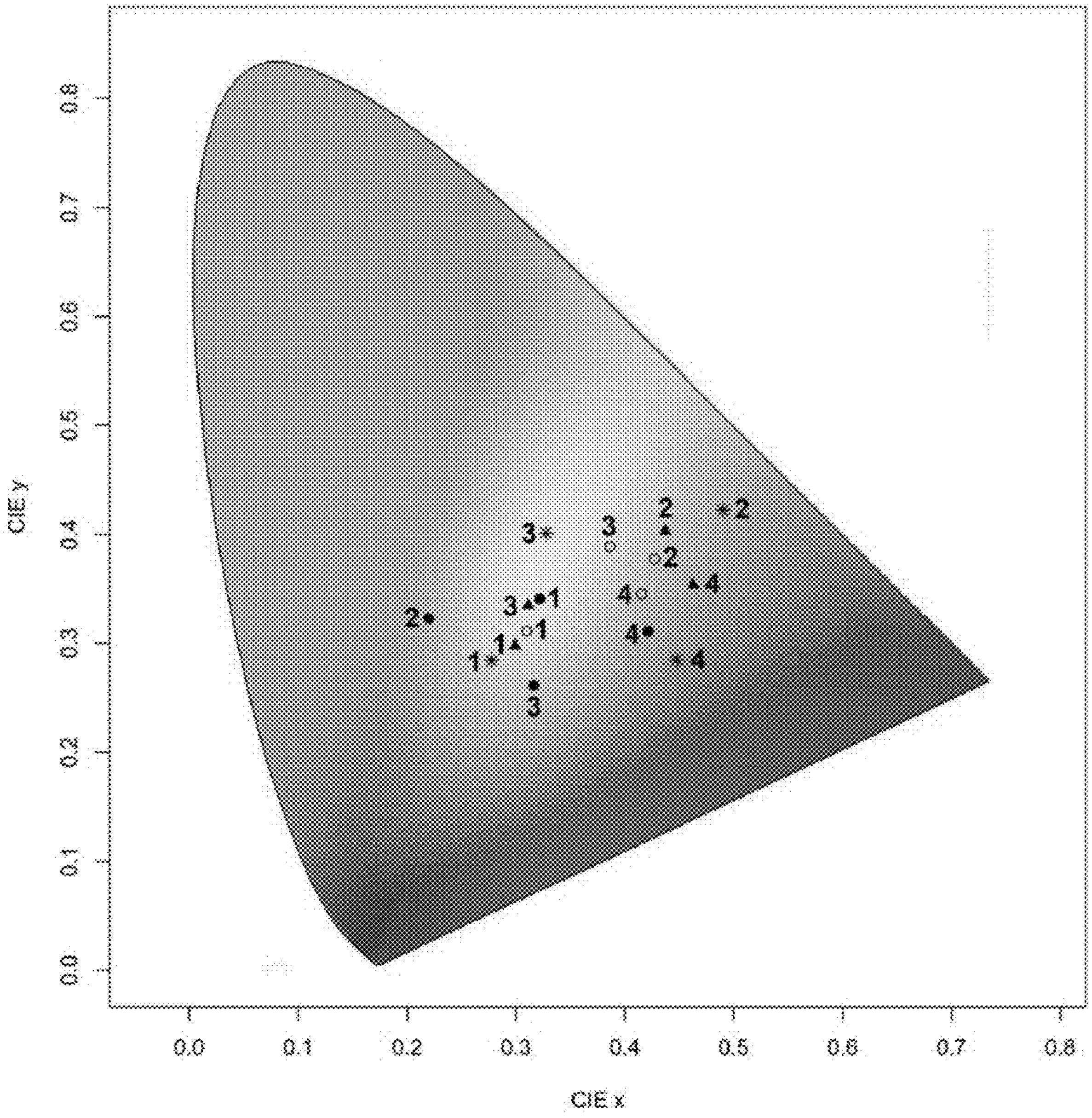
FIG. 32: Reflectance spectra visualized in a CIE 1931 chromaticity diagram for human color vision for different melanin architecture and layer number (filled circles: S-AMNP-$C_{18}$, asterisk: W-AMNP-$C_{18}$, hollow circles: H-AMNP-$C_{18}$, filled triangles: L-AMNP-$C_{18}$).

The fact that the particles reliably localized at the interface allowed for the fabrication of multilayered films via layer-by-layer self-assembly. Multilayer films with a desired number of layers could be achieved by repeating the transfer procedure multiple times (FIG. 4A). Monolayer (L1), bilayer (L2), trilayer (L3), and tetralayer (L4) films of hydrophobic allomelanin nanoparticles with different morphologies (solid, walnut, hollow, and lacey) were successfully obtained. Cross-sectional SEM images confirmed the features of L1, L2, L3, and L4, respectively for all four types of AMNP-$C_{18}$ (FIGS. 4D-4G), which shows homogenous assembly from one layer to four layers over a large area. The thickness of each film was summarized (FIG. 31). The uniform structural colors generated by the thin films were captured using optical microscopy (FIGS. 4D-4G), as well as from the corresponding reflectance spectra (FIG. 4C, FIGS. 22A-22C) and visualized in a CIE1931 chromaticity diagram based on human color vision (FIG. 32). These results demonstrated a fast and precise method for the fabrication large, two-dimensional arrays of melanin nanoparticles with well-defined layering.

Conclusion for Example 2A: We have developed an effective strategy to functionalize synthetic allomelanin nanoparticles. The surface properties can be tuned using amines with desired functional groups. Specifically, the targeted hydrophobic allomelanins were successfully prepared by covalently incorporating long carbon chains. This hydrophobic feature was exemplified via the controlled air/water interfacial self-assembly of allomelanin nanoparticles with different shapes, to produce large area, uniform structural colors with precise arrangements and defined particle layers. We envision this PSM method will be valuable for obtaining melanin-based materials with more diverse functionalities than are possible with either the natural product itself, or its unfunctionalized synthetic analogues.

Exemplary Experimental Aspects for Example 2A

Synthesis of Solid AMNP (S-AMNP): S-AMNP were synthesized in much the same manner as AMNP-1 in previous work.[27] Briefly, 1,8-DHN (150 mg) was dissolved in 7.5 mL acetonitrile in a round bottom flask. To this solution, 142.5 mL Milli-Q water was added, and the mixture was stirred for 5 minutes before quickly injecting 1 mL of 1 N $NaIO_4$ solution in water. The reaction quickly turned yellow and then grey after injection of the oxidant. The reaction was stirred for 20 hours and then purified by centrifugation at 11,500 rpm for 10 minutes, with three cycles of washing by redispersion in Milli-Q water. After the final wash, the particles were re-suspended in 12 mL of Milli-Q water in a 50 mL Falcon tube, and stored at room temperature, capped, and under ambient conditions.

General Procedure for Natural Oxidation (Aging) of AMNP: After obtaining fresh S-AMNP and W-AMNP, the particles suspended in Milli-Q water in a 50 mL Falcon tube, were stored at room temperature, capped, and kept under ambient conditions over 30 days for further natural oxidation and crosslinking. H-AMNP and L-AMNP were synthesized from a purified batch of fresh S-AMNP. After a certain amount of processing time to obtain purified H-AMNP (9 days) and L-AMNP (10 days), these particles, suspended in Milli-Q water in a 50 mL Falcon tube, were stored at room temperature, capped, and kept under ambient conditions over another 21 days and 20 days, respectively, for further natural oxidation and crosslinking.

General Procedure for Post-Synthetic Modification: Briefly, AMNP (5 mg) was dispersed in water in glass vial. To this solution, amine (3.0 equiv. compared to DHN unit) dissolved in water was added, and the final concentration for AMNP is 1.0 mg/mL. The mixture was stirred for 24 hours, and then purified by centrifugation at 11,500 rpm for 10 minutes, with three cycles of washing by redispersion in Milli-Q water. For those amines with poor solubility in water, EtOH was selected as the dispersant for AMNP and amine to replace water.

General Procedure for Air/Water Interfacial Self-Assembly: Briefly, AMNP-$C_{18}$ was dispersed in 1-butanol at the concentration of 2.0 mg/mL, and then sonicated for 15 mins.

A clean container (e.g., a hexagonal plastic cup, a petri dish, a well plate, or a beaker) filled with Mili-Q water was used in the entire self-assembly process. AMNP-$C_{18}$ in 1-butanol was slowly added onto the water surface using a pipette. Continuous addition of AMNP-$C_{18}$ led to the formation of a uniform and close-packed AMNP-$C_{18}$ monolayer. Silicon wafer substrate was placed at the bottom of the container prior to the addition. Once the water surface was fully occupied, the monolayer could be transferred to the substrate through either draining or pick-up. Multilayer films could be achieved by repeating the transfer procedure for different times. For instance, a bilayer film could be obtained by using a monolayer covered substrate to pick up another floated monolayer on at the air/water interface.

Static Water Contact Angle Measurement: The films were fabricated using 10 mg/mL THF suspensions of AMNP nanoparticles. The THF suspensions of AMNPs were dropped onto slides (1 cm×1 cm) slowly until the slides full of the THF suspensions. After THE volatilized from the slides completely, the drop-casted AMNP films were obtained. Water contact angle measurements were collected on a VCA Optima XE.

Microspectrophotometry+Chromaticity Diagram: We measured specular reflectance of multilayered allomelanin materials, deposited on a silicon wafer, using a CRAIC AX10 microspectrophotometer (CRAIC Technologies, Inc.) with a 10× objective and a 75-W Xenon short arc lamp (Ushio UXL-75XE) for the white light source. For our reflectance standards we used a silver mirror and turned the lamp off as a dark standard. We report reflectance values as an average of 45 measurements. Images were taken using the PixeLINK™ 1.3 Megapixel FireWire Camera using the PixeLINK Capture software on standard settings. Average reflectance spectra for melanin particles with different morphology and layer number were visualized in a CIE 1931 color space for human color vision using the pavo package in R.[45,46] As this package assumes a range for reflectance spectra from 300 to 700 nm and our measurements only range from 400 to 700 nm, the 300 to 400 nm part of the spectrum is automatically interpolated by the package. This has no impact on the calculation of the color space coordinates as human sensitivity in the UV is absent. The R script can be found at Example 2B.

References Corresponding to Example 2A (1) D'Alba, L.; Shawkey, M. D. Melanosomes: Biogenesis, Properties, and Evolution of an Ancient Organelle. *Physiol. Rev.* 2019, 99, 1-19.

(2) Hu, Z.; Sun, H.; Thompson, M. P.; Xiao, M.; Allen, M. C.; Zhou, X.; Ni, Q. Z.; Wang, Z.; Li, W.; Burkart, M. D.; Deheyn, D. D.; Dhinojwala, A.; Shawkey, M. D.; Gianneschi, N. C. Structurally Colored Inks from Synthetic Melanin-Based Crosslinked Supraparticles. *ACS Materials Lett.* 2020, 3, 50-55.

(3) Cao, W.; McCallum, N. C.; Ni, Q. Z.; Li, W.; Boyce, H.; Mao, H.; Zhou, X.; Sun, H.; Thompson, M. P.; Battistella, C.; Wasielewski, M. R.; Dhinojwala, A.; Shawkey, M. D.; Burkart, M. D.; Wang, Z.; Gianneschi, N. C. Selenomelanin: An Abiotic Selenium Analogue of Pheomelanin. *J. Am. Chem. Soc.* 2020, 142, 12802-12810.

(4) Mavridi-Printezi, A.; Menichetti, A.; Guernelli, M.; Montalti, M. The Photophysics and Photochemistry of Melanin-Like Nanomaterials Depend on Morphology and Structure. *Chem. Eur. J.* 2021, 27, 16309-16319.

(5) Yang, P.; Gu, Z.; Zhu, F.; Li, Y. Structural and Functional Tailoring of Melanin-Like Polydopamine Radical Scavengers. *CCS Chemistry* 2020, 2, 128-138.

(6) Zou, Y.; Chen, X.; Yang, P.; Liang, G.; Yang, Y.; Gu, Z.; Li, Y. Regulating the absorption spectrum of polydopamine. *Sci. Adv.* 2020, 6, eabb4696.

(7) Yang, P.; Zhu, F.; Zhang, Z.; Cheng, Y.; Wang, Z.; Li, Y. Stimuli-responsive polydopamine-based smart materials. *Chem. Soc. Rev.* 2021, 50, 8319-8343.

(8) Rogalla, S.; D'Alba, L.; Verdoodt, A.; Shawkey, M. D. Hot wings: thermal impacts of wing coloration on surface temperature during bird flight. *J. R. Soc. Interface* 2019, 16, 20190032.

(9) Rogalla, S.; Nicolai, M. P. J.; Porchetta, S.; Glabeke, G.; Battistella, C.; D'Alba, L.; Gianneschi, N. C.; van Beeck, J.; Shawkey, M. D. The evolution of darker wings in seabirds in relation to temperature-dependent flight efficiency. *J. R. Soc. Interface* 2021, 18, 20210236.

(10) Wang, Z.; Zou, Y.; Li, Y.; Cheng, Y. Metal-Containing Polydopamine Nanomaterials: Catalysis, Energy, and Theranostics. *Small* 2020, e1907042.

(11) Cao, W.; Zhou, X.; McCallum, N. C.; Hu, Z.; Ni, Q. Z.; Kapoor, U.; Heil, C. M.; Cay, K. S.; Zand, T.; Mantanona, A. J.; Jayaraman, A.; Dhinojwala, A.; Deheyn, D. D.; Shawkey, M. D.; Burkart, M. D.; Rinehart, J. D.; Gianneschi, N. C. Unraveling the Structure and Function of Melanin through Synthesis. *J. Am. Chem. Soc.* 2021, 143, 2622-2637.

(12) d'Ischia, M.; Napolitano, A.; Pezzella, A.; Meredith, P.; Buehler, M. Melanin Biopolymers: Tailoring Chemical Complexity for Materials Design. *Angew. Chem. Int. Ed.* 2020, 59, 2-12.

(13) Shen, W.; Wang, R.; Fan, Q.; Gao, X.; Wang, H.; Shen, Y.; Li, Y.; Cheng, Y. Natural Polyphenol Inspired Polycatechols for Efficient siRNA Delivery. *CCS Chemistry* 2020, 2, 146-157.

(14) Liu, H.; Yang, Y.; Liu, Y.; Pan, J.; Wang, J.; Man, F.; Zhang, W.; Liu, G. Melanin-Like Nanomaterials for Advanced Biomedical Applications: A Versatile Platform with Extraordinary Promise. *Adv. Sci.* 2020, 7, 1903129.

(15) Yang, P.; Zhang, S.; Chen, X.; Liu, X.; Wang, Z.; Li, Y. Recent developments in polydopamine fluorescent nanomaterials. *Mater. Horiz.* 2020, 7, 746-761.

(16) Battistella, C.; McCallum, N. C.; Gnanasekaran, K.; Zhou, X.; Caponetti, V.; Montalti, M.; Gianneschi, N. C. Mimicking Natural Human Hair Pigmentation with Synthetic Melanin. *ACS Cent. Sci.* 2020, 6, 1179-1188.

(17) Lee, H.; Dellatore, S. M.; Miller, W. M.; Messersmith, P. B. Mussel-Inspired Surface Chemistry for Multifunctional Coatings. *Science* 2007, 318, 426-430.

(18) Siwicka, Z. E.; Son, F. A.; Battistella, C.; Moore, M. H.; Korpanty, J.; McCallum, N. C.; Wang, Z.; Johnson, B. J.; Farha, O. K.; Gianneschi, N. C. Synthetic Porous Melanin. *J. Am. Chem. Soc.* 2021, 143, 3094-3103.

(19) Xie, Y.; Krug, K. A.; Cay, K. S.; Kalaj, M.; McCallum, N. C.; Siwicka, Z. E.; Wang, Z.; Gianneschi, N. C.; Burkart, M. D.; Rinehart, J. D. Peroxidase-Like Reactivity at Iron-Chelation Sites in a Mesoporous Synthetic Melanin. *CCS Chemistry* 2021, 3, 1483-1490.

(20) Eisenman, H. C.; Casadevall, A. Synthesis and assembly of fungal melanin. *Appl. Microbiol. Biotechnol.* 2012, 93, 931-940.

(21) Manini, P.; Lino, V.; Franchi, P.; Gentile, G.; Sibillano, T.; Giannini, C.; Picardi, E.; Napolitano, A.;

Valgimigli, L.; Chiappe, C.; d'Ischia, M. A Robust Fungal Allomelanin Mimic: An Antioxidant and Potent TT-Electron Donor with Free-Radical Properties that can be Tuned by Ionic Liquids. *ChemPlusChem* 2019, 84, 1-8.

(22) Cecchini, M. M.; Reale, S.; Manini, P.; d'Ischia, M.; De Angelis, F. Modeling Fungal Melanin Buildup: Biomimetic Polymerization of 1,8-Dihydroxynaphthalene Mapped by Mass Spectrometry. *Chem. Eur. J.* 2017, 23, 8092-8098.

(23) Manini, P.; Bietti, M.; Galeotti, M.; Salamone, M.; Lanzalunga, O.; Cecchini, M. M.; Reale, S.; Crescenzi, O.; Napolitano, A.; De Angelis, F.; Barone, V.; d'Ischia, M. Characterization and Fate of Hydrogen-Bonded Free-Radical Intermediates and Their Coupling Products from the Hydrogen Atom Transfer Agent 1,8-Naphthalenediol. *ACS Omega* 2018, 3, 3918-3927.

(24) Manini, P.; Lino, V.; D'Errico, G.; Reale, S.; Napolitano, A.; De Angelis, F.; d'Ischia, M. "Blackness" is an index of redox complexity in melanin polymers. *Polym. Chem.* 2020, 11, 5005-5010.

(25) Manini, P.; Lucci, V.; Lino, V.; Sartini, S.; Rossella, F.; Falco, G.; Chiappe, C.; d'Ischia, M. Synthetic mycomelanin thin films as emergent bio-inspired interfaces controlling the fate of embryonic stem cells. *J. Mater. Chem. B* 2020, 8, 4412-4418.

(26) Robertson, K. L.; Mostaghim, A.; Cuomo, C. A.; Soto, C. M.; Lebedev, N.; Bailey, R. F.; Wang, Z. Adaptation of the Black Yeast Wangiella dermatitidis to Ionizing Radiation: Molecular and Cellular Mechanisms. *PLoS ONE* 2012, 7, e48674.

(27) Zhou, X.; McCallum, N. C.; Hu, Z.; Cao, W.; Gnanasekaran, K.; Feng, Y.; Stoddart, J. F.; Wang, Z.; Gianneschi, N. C. Artificial Allomelanin Nanoparticles. *ACS Nano* 2019, 13, 10980-10990.

(28) McCallum, N. C.; Son, F. A.; Clemons, T. D.; Weigand, S. J.; Gnanasekaran, K.; Battistella, C.; Barnes, B. E.; Abeyratne-Perera, H.; Siwicka, Z. E.; Forman, C. J.; Zhou, X.; Moore, M. H.; Savin, D. A.; Stupp, S. I.; Wang, Z.; Vora, G. J.; Johnson, B. J.; Farha, O. K.; Gianneschi, N. C. Allomelanin: A Biopolymer of Intrinsic Microporosity. *J. Am. Chem. Soc.* 2021, 143, 4005-4016.

(29) Zhou, X.; Gong, X.; Cao, W.; Forman, C. J.; Oktawiec, J.; D'Alba, L.; Sun, H.; Thompson, M. P.; Hu, Z.; Kapoor, U.; McCallum, N. C.; Malliakas, C. D.; Farha, O. K.; Jayaraman, A.; Shawkey, M. D.; Gianneschi, N. C. Anisotropic Synthetic Allomelanin Materials via Solid-State Polymerization of Self-Assembled 1,8-Dihydroxynaphthalene Dimers. Angew. *Chem. Int. Ed.* 2021, 60, 17464-17471.

(30) Jia, Z.; Wen, M.; Cheng, Y.; Zheng, Y. Strategic Advances in Spatiotemporal Control of Bioinspired Phenolic Chemistries in Materials Science. *Adv. Funct. Mater.* 2021, 31, 2008821.

(31) Yang, J.; Cohen Stuart, M. A.; Kamperman, M. Jack of all trades: versatile catechol crosslinking mechanisms. *Chem. Soc. Rev.* 2014, 43, 8271-8298.

(32) Wu, D.; Zhou, J.; Creyer, M. N.; Yim, W.; Chen, Z.; Messersmith, P. B.; Jokerst, J. V. Phenolic-enabled nanotechnology: versatile particle engineering for biomedicine. *Chem. Soc. Rev.* 2021, 50, 4432-4483.

(33) Xiao, M.; Shawkey, M. D.; Dhinojwala, A. Bioinspired Melanin-Based Optically Active Materials. *Advanced Optical Materials* 2020, 8.

(34) Xiao, M.; Li, Y.; Allen, M. C.; Deheyn, D. D.; Yue, X.; Zhao, J.; Gianneschi, N. C.; Shawkey, M. D.; Dhinojwala, A. Bio-Inspired Structural Colors Produced via Self-Assembly of Synthetic Melanin Nanoparticles. *ACS Nano* 2015, 9, 5454-5460.

(35) Hong, S. H.; Hong, S.; Ryou, M. H.; Choi, J. W.; Kang, S. M.; Lee, H. Sprayable Ultrafast Polydopamine Surface Modifications. *Adv. Mater. Interfaces* 2016, 3.

(36) Hu, Z.; Bradshaw, N. P.; Vanthournout, B.; Forman, C.; Gnanasekaran, K.; Thompson, M. P.; Smeets, P.; Dhinojwala, A.; Shawkey, M. D.; Hersam, M. C.; Gianneschi, N. C. Non-Iridescent Structural Color Control via Inkjet Printing of Self-Assembled Synthetic Melanin Nanoparticles. *Chem. Mater.* 2021, 33, 6433-6442.

(37) Xiao, M.; Hu, Z.; Wang, Z.; Li, Y.; Tormo, A. D.; Le Thomas, N.; Wang, B.; Gianneschi, N. C.; Shawkey, M. D.; Dhinojwala, A. Bioinspired Bright Noniridescent Photonic Melanin Supraballs. *Sci. Adv.* 2017, 3, e1701151.

(38) Xiao, M.; Hu, Z. Y.; Gartner, T. E.; Yang, X. Z.; Li, W. Y.; Jayaraman, A.; Gianneschi, N. C.; Shawkey, M. D.; Dhinojwala, A. Experimental and theoretical evidence for molecular forces driving surface segregation in photonic colloidal assemblies. *Sci. Adv.* 2019, 5, eaax1254.

(39) Dai, Z.; Dai, H.; Zhou, Y.; Liu, D.; Duan, G.; Cai, W.; Li, Y. Monodispersed Nb2O5 Microspheres: Facile Synthesis, Air/Water Interfacial Self-Assembly, Nb2O5-Based Composite Films, and Their Selective NO2 Sensing. *Adv. Mater. Interfaces* 2015, 2, 1500167.

(40) Liu, D.; Li, C.; Zhou, F.; Zhang, T.; Liu, G.; Cai, W.; Li, Y. Capillary Gradient-Induced Self-Assembly of Periodic Au Spherical Nanoparticle Arrays on an Ultralarge Scale via a Bisolvent System at Air/Water Interface. *Adv. Mater. Interfaces* 2017, 4, 1600976.

(41) Li, X.; Chen, L.; Weng, D.; Chen, C.; Li, Z.; Wang, J. Tension gradient-driven rapid self-assembly method of large-area colloidal crystal film and its application in multifunctional structural color displays. *Chem. Eng. J.* 2022, 427, 130658.

(42) Vogel, N.; de Viguerie, L.; Jonas, U.; Weiss, C. K.; Landfester, K. Wafer-Scale Fabrication of Ordered Binary Colloidal Monolayers with Adjustable Stoichiometries. *Adv. Funct. Mater.* 2011, 21, 3064-3073.

As well as:

Mavridi-Printezi, A.; Guernelli, M.; Menichetti, A.; Montalti, M. Bio-Applications of Multifunctional Melanin Nanoparticles: From Nanomedicine to Nanocosmetics. *Nanomaterials* 2020, 10.

Carmignani, A.; Battaglini, M.; Sinibaldi, E.; Marino, A.; Vighetto, V.; Cauda, V.; Ciofani, G. In Vitro and Ex Vivo Investigation of the Effects of Polydopamine Nanoparticle Size on Their Antioxidant and Photothermal Properties: Implications for Biomedical Applications. *ACS Appl. Nano Mater.* 2022, 5, 1702-1713.

Maia, R.; Gruson, H.; Endler, J. A.; White, T. E. pavo 2: New tools for the spectral and spatial analysis of colour in r. *Methods in Ecology and Evolution* 2019, 10, 1097-1107.

Example 2B: Supporting Information-Hydrophobic Melanin Via Post-Synthetic Modification for Controlled Self-Assembly

Non-Limiting Material and Method Aspects

Optionally, all chemicals used are reagent grade and are used as supplied unless otherwise noted. Sodium periodate ($NaIO_4$) (99.8%), sodium hydroxide (NaOH) (extra pure), HPLC-grade acetonitrile ($CH_3CN$) (≥99.99%), methanol (99.8%), methylene chloride (DCM) (99.5%), N,N-dimethylformamide (DMF) (≥99.8%), 1-butanol (HPLC grade), ethyl acetate (EtOAc) (≥99.5%), hexane (98.5%), isopropanol (≥99.5%), tetrahydrofuran Optima™ (THF) (99.9%), toluene (99.5%), HPLC-grade chloroform, tert-butylamine (98%), 1,6-hexanediamine (99.5+%), and SnakeSkin™ dialysis tubing (3.5 K MWCO, 22 mm*35 feet dry diameter, 34 mm dry flat width, 3.7 mL/cm) were purchased from Thermo Fisher Scientific. Hexylamine (99%), octadecylamine (97%), 5-amino-1-pentanol (≥92.0%), hydrochloric acid (HCl) (37%), and 2,2,3,3,4,4,5,5,6,6,7,7,8,8,9,9,9-heptadecafluorononylamine (>90%) were purchased from Sigma-Aldrich. 1,8-Dihydroxynaphthalene (1,8-DHN) (95+%) was purchased from Matrix Scientific. N,N-dimethylethylenediamine (DMEN) (99%), was purchased from Acros Organics. Cyclohexane (99+%), and 10-amino-1-decanol (98.0+%) were purchased from TCI America. 6-Amino-1-hexanol (98%) was purchased from Combi-blocks. mPEG-$NH_2$ (MW 550) and mPEG-$NH_2$ (MW 2000) were purchased from Laysan Bio, Inc. Ultrapure Milli-Q water was purified using a Branstead GenPure xCAD Plus system from ThermoFisher Scientific and used in all experiments. All grids for transmission electron microscopy (TEM) and scanning electron microscopy (SEM) were purchased from Electron Microscopy Sciences (EMS) unless otherwise noted. Lacey carbon, 300 mesh, copper grids, and Ultra-flat 6-inch silicon wafers were purchased from Ted Pella.

Non-Limiting Method Aspects

Fourier Transform Infrared Spectrometry (FTIR): FTIR spectra were obtained on a Nexus 870 spectrometer (Thermo Nicolet).

X-ray Photoelectron Spectroscopy (XPS): XPS samples were drop-casted onto a silicon substrate, and spectra were collected on a Thermo Scientific ESCALAB 250Xi.

Dynamic Light Scattering (DLS) and Zeta Potential: Hydrodynamic diameters and Zeta potentials were measured on a Zetasizer. AMNP and AMNP-$NMe_2$ samples were measured in ultrapure Milli-Q water, and AMNP-$C_{18}$ samples were measured in EtOH. pH-dependence study was conducted in Milli-Q water, using NaOH and HCl to adjust the pH value.

Transmission Electron Microscopy (TEM): Dry state TEM of nanoparticles was conducted on a Hitachi HD2300 at an accelerating voltage of 200 kV.

Scanning Electron Microscopy (SEM): Samples were coated with 8 nm osmium before imaging. The side views were obtained by cutting the films using a diamond knife. SEM images were acquired on a Hitachi SU8030.

Atomic Force Microscope (AFM): AFM Images were acquired in tapping mode in air on a Bruker Fastscan with Fastscan A tips.

Ultraviolet-Visible Spectroscopy (UV-Vis): UV-Vis spectra were recorded using a NanoDrop 2000c UV-Vis spectrophotometer.

Scanning Transmission Electron Microscopy (STEM): STEM images and energy-dispersive X-ray spectroscopy (EDX) mapping images were acquired on a JEOL 200 ARM at an accelerating voltage of 200 kV.

Embedding of S-AMNP-$NMe_2$ in Resin for STEM-EDX Imaging: S-AMNP-NMez were pelletized in an Eppendorf tube. Dehydration occurred with a graded series of ethanol and acetone prior to infiltration with EMBed812 epoxy resin and the resin polymerized at 60° C. for 48 hours prior to ultramicrotomy using a Leica EM UC7 Ultramicrotome to obtain ultra-thin sections (50 nm). Micrographs were obtained on a JEOL 200 ARM at an accelerating voltage of 200 kV.

CHNS Elemental Analysis: CHNS elemental combustion analyses of AMNP and modified AMNP samples were performed on Elementar Vario EL Cube. Sulfanilamide was used as the standard sample. Measurment for each sample was repeated for three times. Carbon, hydrogen, nitrogen, and sulfur were quantitatively determined in percent composition.

Nitrogen Sorption Measurements: AMNP or AMNP-$NMe_2$, stored in Milli-Q water, were centrifuged at 11,500 rpm for 12 minutes, and the water was removed and replaced with EtOH. This process was repeated twice more with addition of fresh EtOH each time to ensure effective removal of water. AMNP-$C_{18}$ stored in EtOH were directly used. Samples were activated using a tousimis SAMDRI-PVT-3D Advanced Manual Critical Point Dryer. Using the supercritical dryer, particles were added to the sample chamber, cooled to 0-10° C., and pressurized to 800 psi. EtOH was exchanged with liquid $CO_2$ over a 10-hour period, purging the system for five minutes every two hours. After the fifth purge, the temperature was raised to 40° C. and the system was pressurized to 1200-1400 psi to obtain supercritical $CO_2$. Pressure was released slowly overnight at a rate of 0.5 cc/min. Samples were immediately transferred onto a Micromeritics ASAP 2420 and were placed under vacuum for two hours at 25° C. prior to sorption measurements. Nitrogen physisorption measurements were collected using a Micromeritics ASAP 2420 instrument at 77 K. Pore-size distributions were obtained using DFT calculations with a carbon slit geometry and an $N_2$ DFT model.

R-Script:

```
require (pavo)
data <-read.csv ("pathway to input file", head=TRUE, sep=",", dec=".", fileEncoding="UTF-8-BOM")
melanin <-as.rspec (data, whichwl=1, inter=TRUE, lim=c (300, 700))
#Estimate quantum catches, using the cie10-degree viewer matching function
vis.melanin <-vismodel(melanin, visual="cie10", illum="D65", vonkries=TRUE, relative=FALSE)
#Model floral spectra in the CIEXYZ space
melanin.ciexyz<-colspace (vis.melanin, space="ciexyz") #visualize in a ciexyz chromaticity diagram
plot (melanin.ciexyz, pch=c (1, 1,1, 1,19, 19,19, 19,8, 8,8, 8,17, 17,17, 17))
```

Non-limiting experimental and method aspects:

Synthesis of Walnut AMNP (W-AMNP): W-AMNP were synthesized in much the same manner as AMNP-1 (walnut) in previous work.[1] Briefly, 1,8-DHN (150 mg) was dissolved in 7.5 mL acetonitrile in a round bottom flask. To this solution, 142.5 mL Milli-Q water was added, and the mixture was stirred for 5 minutes before quickly injecting 2 mL of 1 N $NaIO_4$ solution in water. The reaction quickly turned yellow and then grey after injection of the oxidant. The reaction was stirred for 20 hours and then purified by centrifugation at 11,500 rpm for 10 minutes, with three cycles of washing by redispersion in Milli-Q water. After the final wash, the particles were re-suspended in 12 mL of Milli-Q water in a 50 mL Falcon tube, and stored at room temperature, capped, and under ambient conditions.

Synthesis of Hollow AMNP (H-AMNP): H-AMNP were synthesized in much the same manner described in previous work.[2] H-AMNP were synthesized from a fresh batch of purified S-AMNP. S-AMNP were stored in Milli-Q water, under ambient conditions, in a capped, plastic tube for 24 hours after synthesis. At this 24-hour mark, they were pelletized by centrifugation at 11,500 rpm for 12 minutes. The water was removed and replaced with MeOH to a final concentration of 0.5 mg/mL. The pellet was vortexed until full mixing was achieved (approximately 30 seconds), and the solution/suspension was then placed onto a horizontal shaker at 90 rpm for 6 days. This mixture was then dialyzed into Milli-Q water using 10 k molecular weight cutoff snakeskin dialysis tubing (Thermo Scientific), with the water changed 3 times over 2 days. If necessary, the particles were then re-concentrated to the desired amount by centrifuging at 11,500 rpm for 12 minutes and removing excess water.

Synthesis of Lacey AMNP (L-AMNP): L-AMNP were synthesized in much the same manner described in previous work.[2] L-AMNP were synthesized from a fresh batch of purified S-AMNP. S-AMNP were stored in Milli-Q water, under ambient conditions, in a capped, plastic tube for 48 hours after synthesis. At this 48-hour mark, they were pelletized by centrifugation at 11,500 rpm for 12 minutes. The water was removed and replaced with MeOH to a final concentration of 0.5 mg/mL. The pellet was vortexed until full mixing was achieved (approximately 30 seconds), and the solution/suspension was then placed onto a horizontal shaker at 90 rpm for 6 days. This mixture was then dialyzed into Milli-Q water using 10 k molecular weight cutoff snakeskin dialysis tubing, with the water changed 3 times over 2 days. If necessary, the particles were then re-concentrated to the desired amount by centrifuging at 11,500 rpm for 12 minutes and removing excess water.

References Corresponding to Example 2B (1) Zhou, X.; McCallum, N. C.; Hu, Z.; Cao, W.; Gnanasekaran, K.; Feng, Y.; Stoddart, J. F.; Wang, Z.; Gianneschi, N. C. Artificial Allomelanin Nanoparticles. *ACS Nano* 2019, 13, 10980-10990.

(2) McCallum, N. C.; Son, F. A.; Clemons, T. D.; Weigand, S. J.; Gnanasekaran, K.; Battistella, C.; Barnes, B. E.; Abeyratne-Perera, H.; Siwicka, Z. E.; Forman, C. J.; Zhou, X.; Moore, M. H.; Savin, D. A.; Stupp, S. I.; Wang, Z.; Vora, G. J.; Johnson, B. J.; Farha, O. K.; Gianneschi, N. C. Allomelanin: A Biopolymer of Intrinsic Microporosity. *J. Am. Chem. Soc.* 2021, 143, 4005-4016.

Example 3: Additional Aspects, Including Polydopamine Particles

Melanin is a natural pigment that is found across all kingdoms of life. In humans, it is found in skin and hair, serving a primary role in UV radiation protection by absorption of incident radiation and by radical scavenging activity. Synthetic melanins successfully recapitulate these properties, obtained via oxidative polymerization of inexpensive monomers, bypassing issues of yield and purity that arise from natural extraction. The two synthetic mimics covered here are polydopamine, which is a mimic for mammalian eumelanin, and allomelanin, a nitrogen-free melanin often found in plants and fungi. The resulting synthetic melanin materials are hydrophilic, which limits the application of these materials beyond aqueous systems. Described herein is a simple post-synthetic modification strategy to change the hydrophobicity of the particles via reaction with a primary alkyl amine. The resulting particles exhibit preserved spherical morphology and good long-term stability in organic solvents, and expand applications into self-assembly and additional biological applications.

Synthetic melanin particles are obtained from the oxidative polymerization of 1,8-dihydroxynapthalene for allomelanin (AMNP) and dopamine for polydopamine (PDA) respectively. Once the particles are harvested, they are dispersed in ethanol at 1 mg/mL and reacted with the primary alkyl amine in a 1:3 molar ratio of synthetic melanin: primary alkyl amine overnight under constant stirring. The resulting hydrophobic particles (AMNP-$C_{18}$ and PDA-$C_{18}$) are washed in ethanol and their morphology is confirmed by Transmission Electron Microscopy (TEM) (FIGS. 23A-23B).

Analysis of the particles reveals an increase in particle diameter post-modification and maintains a negative zeta potential post-modification, indicating good colloidal stability in ethanol (Table 3). The Fourier Transform Infrared (FTIR) spectra of all particles pre and post modification were measured as a KBr pellet (FIGS. 24A-24B). When compared to original particles, the spectrum for synthetically modified synthetic melanin particles contains two additional peaks at 2920 $cm^{-1}$ and 2850 $cm^{-1}$. These correspond to alkane C—H bond stretch, indicating attachment of the alkylamine to the surface of the particle.

TABLE 3

Particle Diameter and Zetapotential of Synthetic Melanin Particles

| Sample | Diameter (nm) | Zeta Potential (mV) |
|---|---|---|
| AMNP | 220.3 | −28.9 |
| AMNP-C18 | 224.7 | −12.8 |
| PDA | 332 | −24.4 |
| PDA-C18 | 400 | −44.3 |

To confirm hydrophobicity, contact angles of the particles was obtained. Films of synthetic melanin were prepared drop-casting solutions on silica chips. The water contact angle was then obtained. The pristine particles have a hydrophilic water contact angle of 41.9±0.2° and 46.35±0.06° for AMNP and PDA respectively. Upon surface functionalization, the water contact angle increases to 130.0±0.8° and 135±4° for AMNP-$C_{18}$ and PDA-$C_{18}$ respectively (Table 4).

TABLE 4

Water Contact Angles of Synthetic Melanin Films

| Sample | Angle (°) |
|---|---|
| AMNP | 41.9 ± 0.2 |
| *AMNP-$C_{18}$ | 130.0 ± 0.8 |
| PDA | 46.35 ± 0.06 |
| *PDA-$C_{18}$ | 135 ± 4 |

Chemical modification of the surface can impact scavenging activity of synthetic melanins, so was assayed in vitro by the 2,2-diphenyl-1-picrylhydrazyl (DPPH) assay. DPPH is a shelf-stable radical that is purple in solution and turns yellow as the radical is quenched, which is monitored at 516 nm. At 50 µg of AMNP, 60% of the radical is scavenged, while at the same amount of AMNP-C18, 40% of the free radical is scavenged (FIG. 25A). Similarly, at 50 µg of PDA, 60% of the radical is scavenged, while at the same amount of PDA-C18, 50% of the free radical is scavenged (FIG. 25B). While this is a decrease compared to pristine particles, radical scavenging activity is still maintained.

Solubility of the hydrophobic particles was qualitatively assayed in commercially available vehicles: Vaseline, Aquaphor, squalene, and squalane. Vaseline and Aquaphor are petrolatum jelly-based ointments and have been used in the clinic for skin applications in the case of wound healing. These vehicles were selected for their clinical and biological relevance. Solubility of the synthetic melanin particles were assayed in these compounds by vigorously mixing. Both hydrophobic particles, AMNP-C18 and PDA-C18, exhibit better qualitatively solubility in the various excipients compared to pristine particle by observation of fewer particulates in the suspension and even distribution of the hydrophobic particles by color (FIG. 26). Pristine particle solubility in Aquaphor can be attributed to the addition of hydrophilic glycerin in the petroleum jelly, making Aquaphor overall less hydrophobic compared to the other vehicles. In petroleum jelly, AMNP and PDA do not incorporate into the ointment, as seen by the dark particulates surrounded by clear ointment. In the case of squalene and squalane, PDA-C18 is found to better incorporate per the more uniform brown color of the solution and fewer particulates, while squalane and squalene have PDA particles settled on the bottom of the glass substrate (FIGS. 27A-27B).

Examples 4-7

Sulfur mustard (SM) was used as a chemical warfare agent during World War I and many times thereafter[1], including in Iraq in 1988 (OPCW.org) and in present day conflicts. By the 1940s, the alkylating properties of mustard compounds found utility in clinical medicine. Nitrogen mustard (NM), the first prototypic "chemotherapy" was introduced as a treatment for patients with lymphoma. Today, NM and derivative chemotherapeutic agents are in use, providing insight into dose-dependent toxic effects that parallel the original chemical warfare agent.[2]

Rationale for Injury Mechanism:

SM and NM are bifunctional alkylating agents known to react rapidly with a variety of small molecules and macromolecules.[3] Mustard cross-links and induces DNA strand breaks leading to eventual cell death.[4] The short half-life (mins) of mustard on contact with the human skin surface at body temperature creates an implausible intervention window to neutralize SM directly in a mass casualty scenario. The current CDC guidelines (www.cdc.gov/chemicalemergencies) are removal of vesicant-contaminated clothing and washing of exposed surfaces with water and soap. In 2019, Silverlon™ received FDA 510 (k) clearance as a device for the treatment of SM skin wounds (accessdata.fda.gov). The silver-plated nylon dressing has long used by clinicians for general wounds remains a supportive treatment. Mustard-induced skin responses include swelling, blisters, eschars (hemorrhagic crust), delayed wound healing, scarring, and fibrosis. Absorption through the skin can trigger immune activation resulting in delayed multi-system illness.[5] To-date, no countermeasure drug has been cleared.

Detriments of oxidative stress in the skin from mustard exposure:

Oxidative stress is one of the main mechanisms underlying impaired healing in skin injury and in chronic wounds.[6,7] While low levels of reactive oxygen species (ROS) serve essential antimicrobial and signaling roles in wound healing,[8-11] excessive production of free radical species overwhelms the oxidant-antioxidant homeostatic balance and leads to molecular dysfunction, cellular damage, and pathologic inflammation. SM and NM exposure leads to DNA damage and oxidative stress.[12-14] The epidermis itself attempts to upregulate endogenous antioxidant and stress proteins.[15] This makes the redox system a good target for a countermeasure strategy.[16,17] Indeed, topical application of compounds with antioxidant properties such as curcumin-loaded poly (lactic acid) nanofibers[18], chitosan-loaded eugenol,[19] and citrate-based hydrogels[20] have been explored for benefits in skin wound repair. However, weaknesses with topical compound biocompatibility and inefficient delivery continue to pose significant challenges for therapeutic use.

Mustard-Induced Skin Damage Attracts Immune Cells that Amplify Tissue Injury:

Toxicity of mustard is dose and duration dependent, causing severe epithelial and deep tissue injury characterized by acute inflammation, swelling, and blistering.[21-23] Cell damage induces apoptosis and necrosis of keratinocytes, disruption of skin attachment to the basement membrane, induction of proteolytic enzymes, mast cell degranulation, vascular leakage, and inducible nitric oxide synthase (iNOS) induction.[15,24-29] SM-damaged skin releases pro-inflammatory cytokines and chemokines for neutrophils, monocyte/macrophages (Mo/Mf), and T cells.[30] Hours after exposure, the skin is densely infiltrated with myeloperoxidase releasing neutrophils that further injures surrounding tissue.[31-33] In the sequence of events, proinflammatory Mo/Mf arrive and persists for days producing a toxic inflammatory milieu and with degradative enzymes such as MMP-9.[34-39] Targeting specific cytokines with biologics (i.e. antibodies) has revolutionized the treatment of chronic inflammatory diseases (skin, joints, GI, lungs), but such an approach would be inefficient for mustard injury due to different acuity, kinetics, and dramatically elevated levels of inflammation.

Combatting skin iNOS and activated macrophages can ameliorate the toxic effects of mustard:

Nitric oxide (NO) reaction with superoxide anion leads to production of peroxynitrite, a strong oxidant and activator of inflammation that mediates destruction of surrounding tissue.[40-42] Targeting mustard-induced iNOS and activity of NO showed promised in vitro.[38,43,44] While promising in vitro, topical iNOS inhibitors failed to be protective in vivo in part due to surface biology of the skin.[45]

Figure 33:
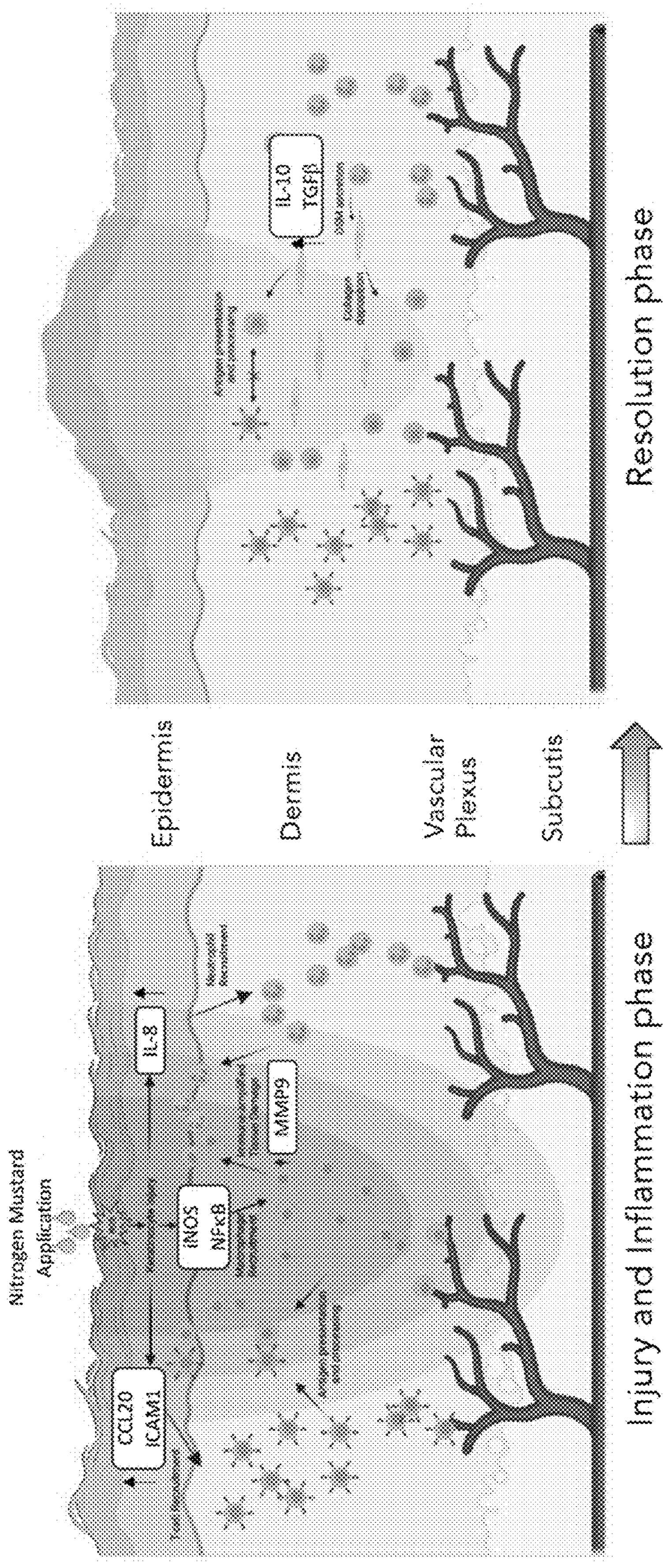
FIG. 33: Schematic of cellular and molecular markers following NM exposure (injury phase). The landscape is changed in the resolution phase.

Instead, aspects herein target the cellular source of iNOS by depleting activated skin Mo/Mf using liposomal clodronate resulting in protection against NM mediated skin wounds and death ($LD_{90}$ model).[46] In complementary studies, we also showed that vitamin D3, known to modulate NF-kB in Mo/Mf, downregulated TNFa and iNOS expression.[47-49] This intervention halted wound expansion and prevented death from NM and SM exposure by 100% and 40%, respectively.[46,50] In our recent work (*J Clin Invest Insight,* 2023), we translated these observations into human studies in a double-blinded placebo-controlled RCT.[51] High dose oral vitamin D3 mitigated several skin inflammatory proteins and injury markers produced by damaged keratinocytes and Mo/Mf in subjects experimentally exposed to NM (n=28). RNAseq and Olink proteomics analysis identified several markers (FIG. 33) that offer translational insight and inform the framework we employed to map responses in the endpoints in the human skin explants (Example 5), mouse model (Example 6), and porcine model (Example 7).

In some aspects, materials and formulations herein for therapy of skin mustard exposure include: the ability to stabilize and halt blister formation, have immunomodulatory function to enable rapid resolution of inflammation, and limiting extent of scarring.

In aspects herein, a treatment approach is based on the nanoscale Synthetic Melanin Particle (SMP). In aspects, It is contemplated that melanin in the form of SMPs can be mimicked synthetically and applied topically following skin injury, where it would be effective in healing after chemical exposure. Melanin's protective role as pigment in the hair and skin,[52,53] is intrinsically linked to its photoprotective properties.[53-55] In addition to being upregulated in response to UV light (tanning), studies show increases in melanin skin pigmentation in response to chemicals in air pollutants.[56] Indeed, aspects and examples demonstrate that topical SMPs improve skin wounds in vivo in mice[58] and ex vivo in human skin explants. Excitingly, the outcomes of topical application of SMP include inhibition of blister formation, rescue of superoxide dismutase (SOD), downregulation of MMP9, and recruitment of reparative immune cells to the skin.

Example 4: Identification of Useful SMPs

More than 200 types of SMPs are synthesized and characterized, both as natural mimetics from across organisms and as engineered materials for a range of applications from structural color to thermal insulators, to biocatalysts, toxin absorbers and beyond. In aspects, various types or variations of SMPs are useful as therapeutic SMPs and in SMP formulations in aspects herein to reduce morbidity from toxic NM/SM skin exposure, for example. In various aspects and examples, results are benchmarked against the PDA SMP.

In aspects, particular exemplary SMP types are characterized and analyzed with respect to desired activity in the skin as interventions after NM exposure. 59-64 For example, FIGS. 34A-34E show exemplary SMP types and aspects of modifications described herein. In aspects and certain examples, starting particles are polydopamine (PDA) and a lipophilic PDA-C18, an 18-carbon chain derivative of PDA made according to aspects herein (FIG. 34A).[65] PDA is shown to remain in the stratum corneum (FIG. 35) (human explants, in vivo murine and porcine models) following administration (1 mg/$cm^2$) in aqueous buffers and gels. PDA-C18 is prepared as a lipophilic version of PDA for better spreading in the hydrophobic stratum corneum and formulation in hydrophobic vehicles. Both SMPs (PDA and PDA-C18) show efficacy.

Figure 34A:
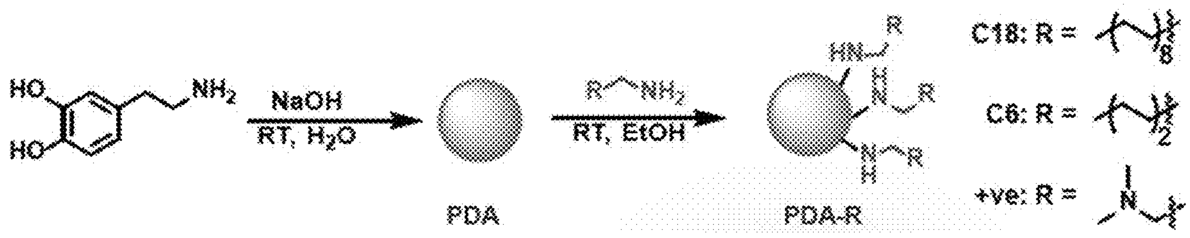
FIGS. 34A-34E: Synthesis of 10 candidate interventions (SMPs).
Figure 34B:
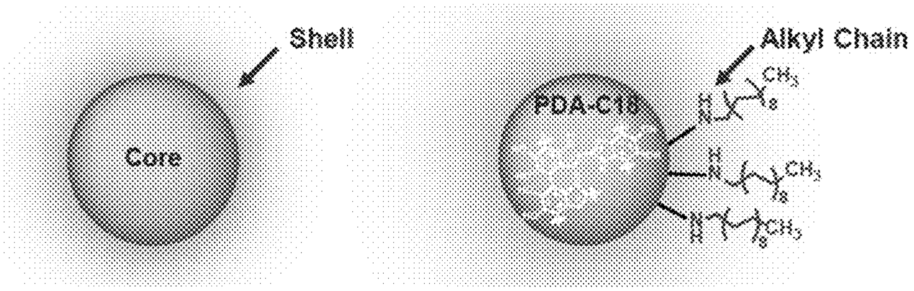
Figure 34C:
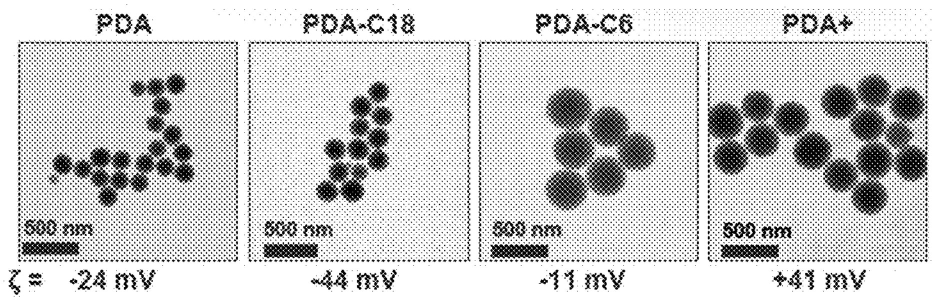
Figure 34D:
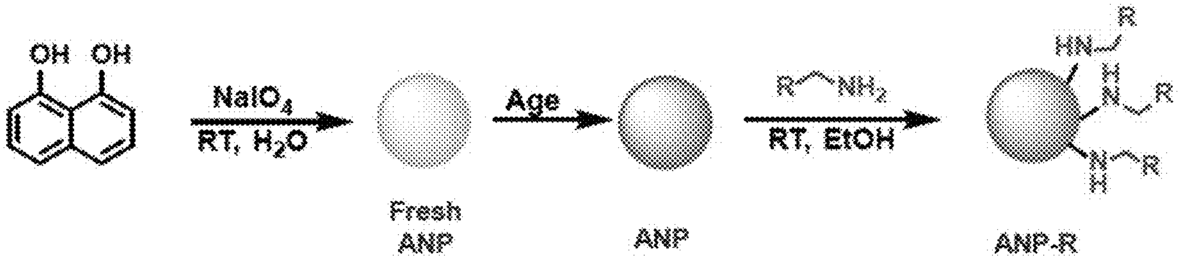
Figure 34E:
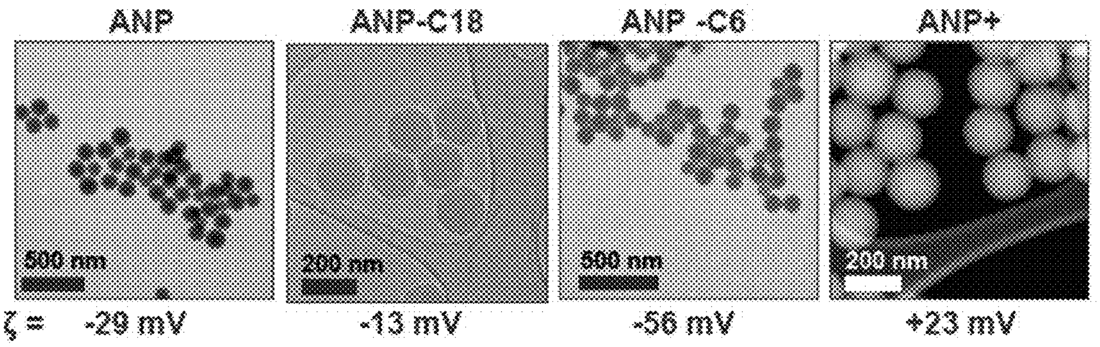
Figure 35:
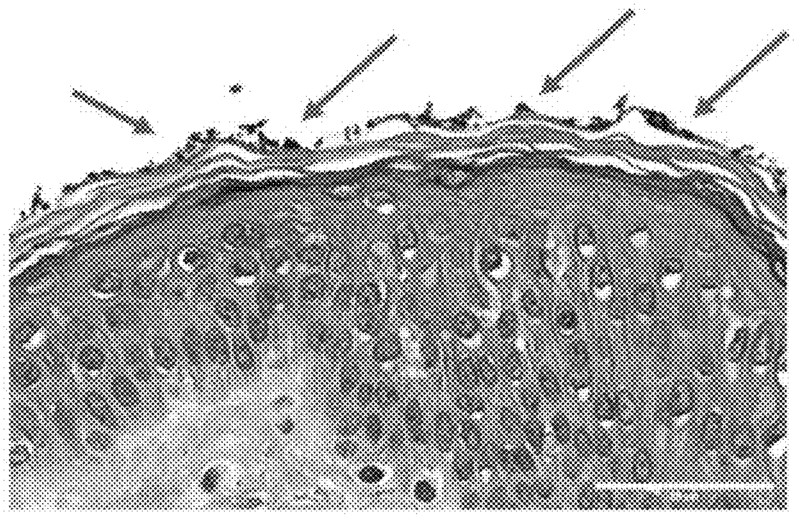
FIG. 35: Healthy human skin cross section, with PDA applied. The PDA can be seen within and on the stratum corneum (arrows).

From this starting point, a collection of SMPs is prepared that modify and vary core and shell chemistry to adapt to the inherent properties of skin (FIG. 34B). For example, PDA-C6 (n-hexylamine-modified PDA) to access intermediate hydrophobicity, enabling both aqueous- and lipophilic phase solubility (FIG. 34C). For example, PDA+ prepared for better adhering to the negatively charged stratum corneum. Keratinocyte stem cell niche resides in the follicles, so it is contemplated that local reduction in inflammation within the follicles may lead to better therapeutic outcomes.

Also contemplated are artificial melanin particles based on the nitrogen-free analogue of fungal allomelanins, developed by instant Inventors, such as based on 1,8-dihydroxynaphthalene precursors (DHN)[67], which exhibit superior radical scavenging capacity due to their higher radical content and high intrinsic surface areas approaching 800 $m^2/g$ (polymers of intrinsic microporosity (PIMs)) (FIG. 34D).[68] It is contemplated that high porosity and radical scavenging capability manifests in better efficacy following topical application. In particular, in aspects and examples, ANP-C18, ANP-C6, and ANP+ SMPs are described.

Example 5

NM- and SM-activated immune response drives many of the pathologic features of mustard exposure. In particular, accumulation of pro-inflammatory $iNOS^+$ macrophages plays a critical role in mediating local damage and systemic toxicity.[46,50,69,70] The interval between the initial molecular contact of mustard with the skin and the subsequent immune activation is a feasible window for countermeasure intervention, allowing implementation of practical strategies in the event of mass emergency in pre-hospital triage and in hospitals. The multi-functional properties and ease of application of topical SMP has the potential to reduce morbidity from mustard exposure (blisters, pain, necrosis, and scarring) above the current standard-of-care, which remains highly supportive care.

It is contemplated that to protect the skin from the damaging effects of vesicants, a therapeutic intervention needs to 1) counter oxidative stress, 2) limit excessive production of MMPs and basement membrane degradation, and/or (preferably, and) 3) dampen tissue destruction by recruited inflammatory cells.

In aspects, selection criteria contemplated, for example for therapeutic formulations, include effective skin blister mitigation. In aspects, selection criteria contemplated, for example for therapeutic formulations, include enhanced skin recovery based on wound reduction, time to eschar (scab) detachment, and dermal scar reduction, reflecting the functions of anti-inflammatory IL-10, reparative monocytes and macrophages, and TGFb, respectively. In aspects, the effectiveness of materials and formulations herein is tested using human skin explants and in vivo mouse studies of skin injury, for example.

Optimizing SMP surface hydrophobicity, charge, particle shape, and size to yield lead candidates that inhibits subepidermal blistering and necrotic keratinocytes in human skin ex vivo:

For example, primary screening of compounds using human skin explants is the $1^{st}$ Go/No-Go decision. Skin explants permit direct assessment of epidermal damage and blister formation without the contribution of the circulatory system to delineate innate factors released by damaged keratinocytes, fibroblasts, and endothelial cells that serve as chemotactic signals for immune cells.

Figure 36:
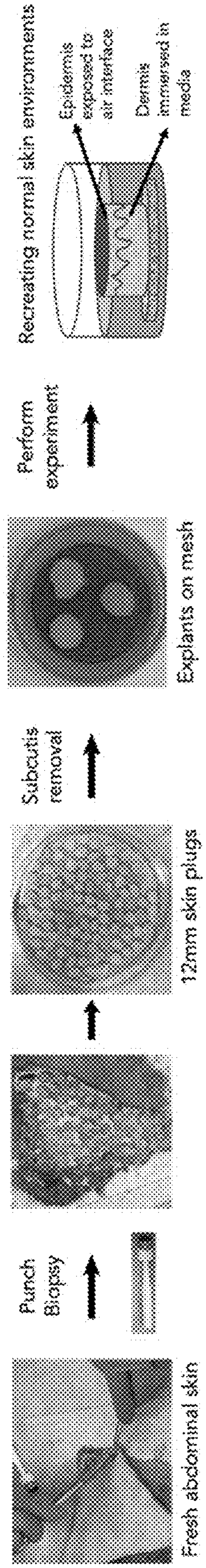
FIG. 36: Workflow setup of human skin explants for nitrogen mustard exposure and SMP treatment.

SMPs are prepared by methods disclosed herein and in references cited and incorporated by reference herein (FIGS. 34A-34E).[59] For example, a skin flap (15 cm×20 cm) can generate 50-75 full thickness 12 mm skin plugs (FIG. 36). Explant are rested for 24 h cultured at the air-liquid interface to mimic in vivo conditions where cultures maintain populations of epidermal keratinocytes, dermal fibroblasts, melanocytes, and skin-resident immune cells for up to 1 week. Skin explants respond to external stimuli, e.g., NM mustard, UV, allowing query of keratinocyte and epidermis-specific contributions. In aspects, explants are exposed to to 0.5% topical NM (1.5% DMSO/PBS) above the liquid-air interface. Two hours (2 hrs) from the initial NM application, SMPs are applied to the skin. 48 hrs later, the skin is evaluated for histology and biomarkers. All skin experiments performed in duplicates.

Figure 37A:
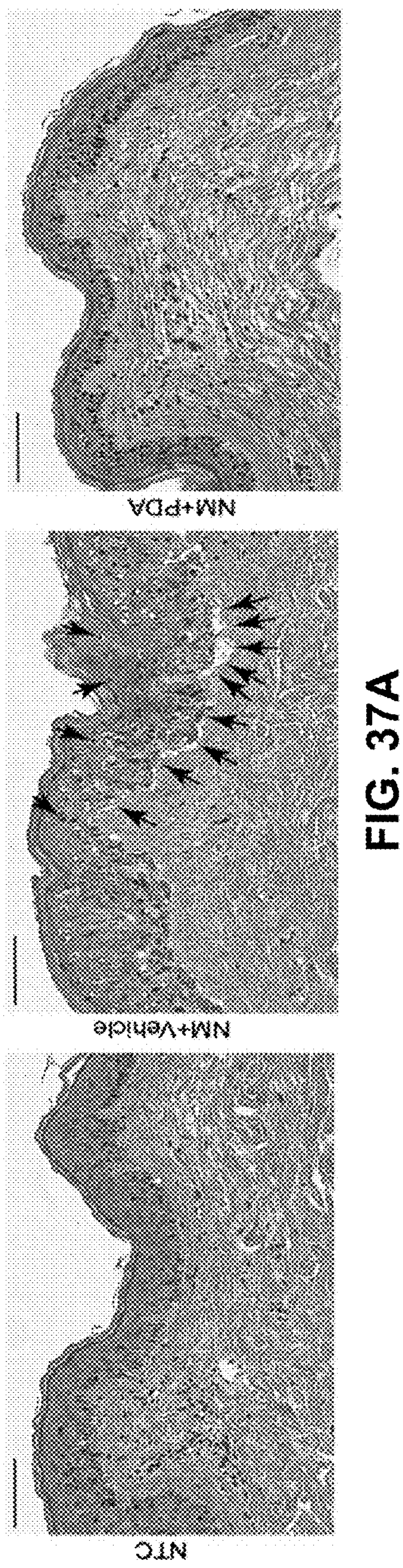
Figure 37B:
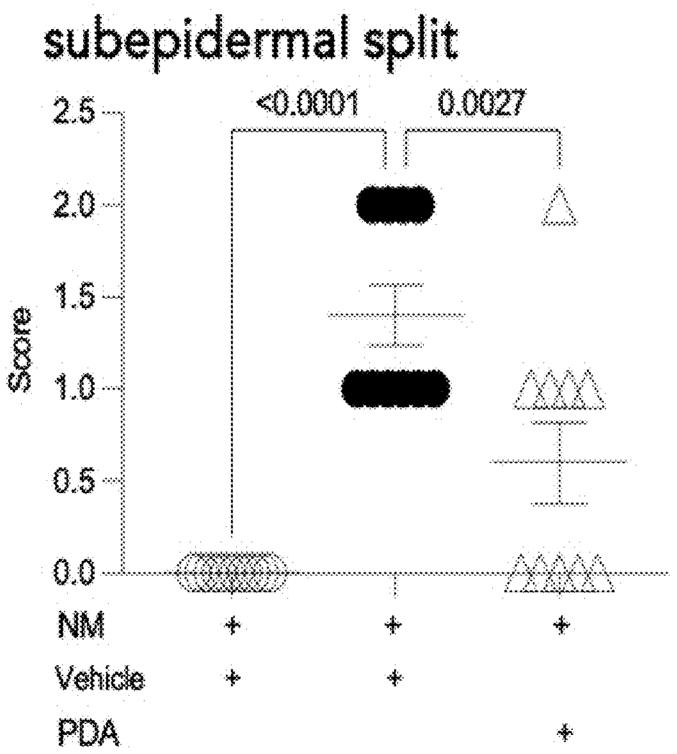
Figure 37C:
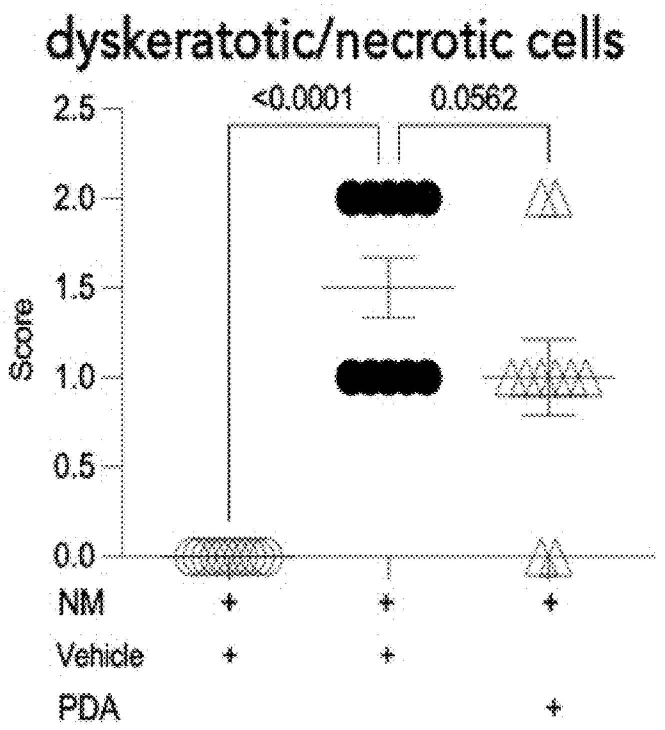
Figure 38C:
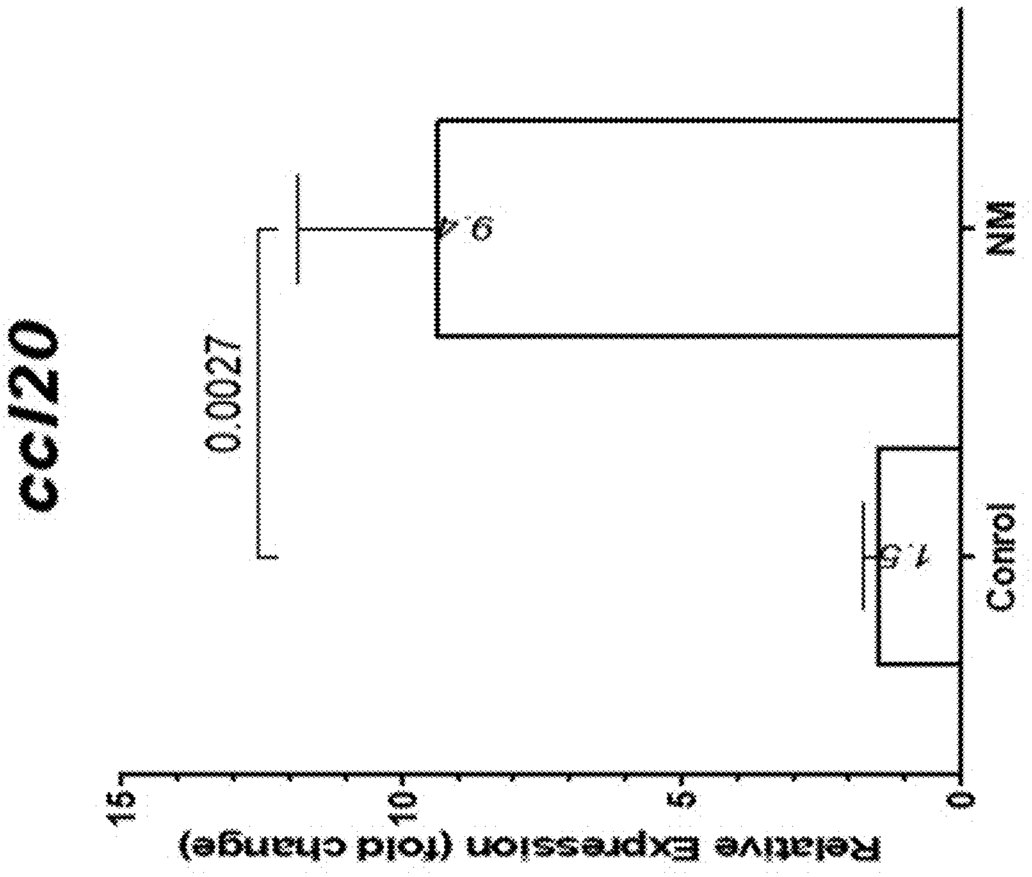
Figure 38D:
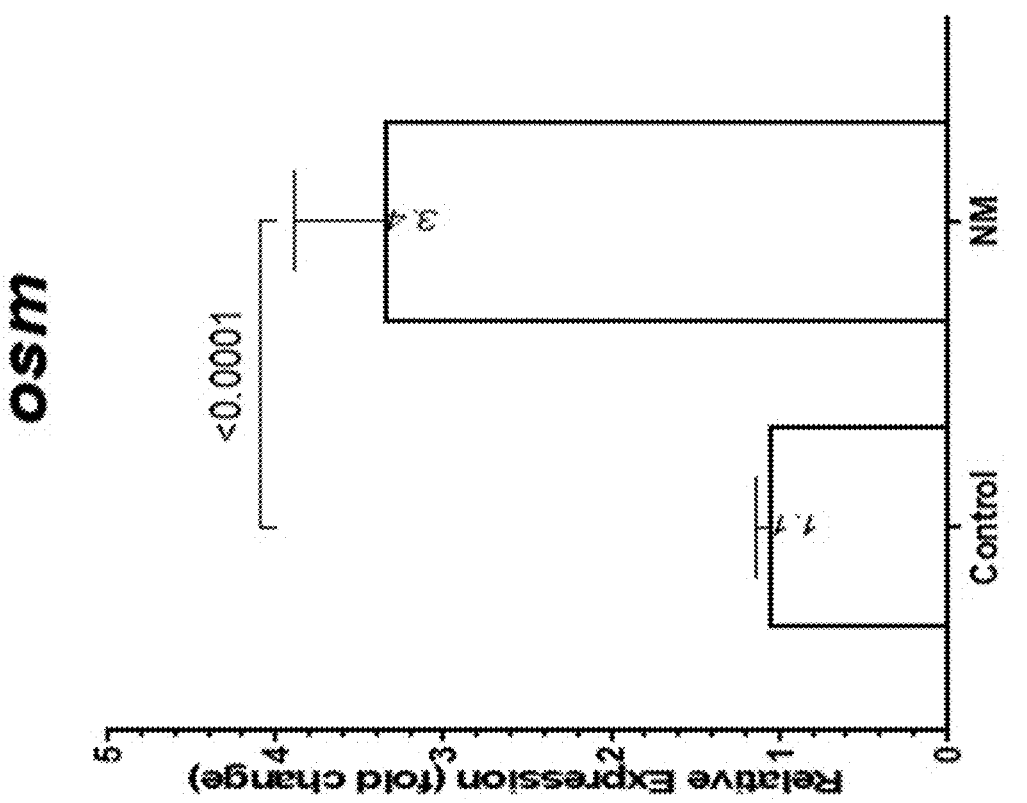
Figure 39:
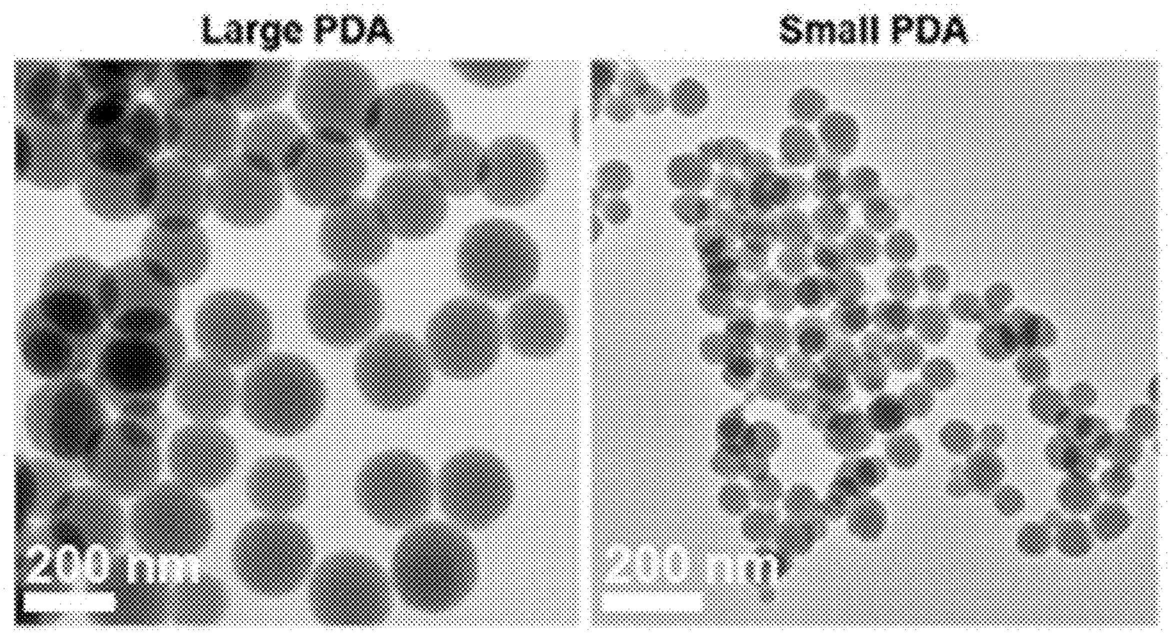
FIG. 39: Small 40 nm PDA particles.

Chemical-induced damage, such as Nitrogen Mustad (NM) exposure on human skin explants:

In the natural course following chemical exposure such as NM exposure, histological evidence demonstrates presence of dyskeratotic/necrotic keratinocytes ultimately leading to epidermal split from the dermis. At 48 h all tissue explants have at least ≥grade 1 severe blister formation (50% grade 1, 50% grade 2). Topical PDA intervention significantly inhibits blister formation from 10 subjects (50% grade 0, p=0.0027) at 48 h (FIGS. 37A-37B). Pair-wise analysis of each subject w/and w/o PDA intervention shows an average D=−0.8 (p=0.01), a reduction in blister severity (avg D of blister scores). Levels of necrotic keratinocytes inhibited by PDA (20% grade 0, p=0.0562, FIG. 37C) with D=−0.6 reduction pairwise comparison. In some aspects, these values serve as the benchmarks to screen candidate SMPs.

In some aspects, selection of artificial melanin materials and formulations for therapeutic applications includes: observation of significant reduction in subepidermal split; pair-wise analysis of each subject with and without topical artificial melanin material or formulation intervention following chemical (e.g., NM) exposure, for example D of subepidermal blister score where the threshold is optionally an average D≥−0.5; pair-wise analysis of each subject with and without topical artificial melanin material or formulation intervention following chemical (e.g., NM) exposure, for example D of dyskeratosis/necrosis score where the threshold is optionally D≥−0.5; and inhibition of skin NM biomarkers. Optionally, inhibition of IL-8, ICAM1, CCL20/OSM is determined. Optionally, four biomarkers (IL-8, ICAM1, ccl20, and oncostatin-m) are measured or observed. The biomarkers are optionally confirmed and quantified using Raybiotech (quantitative membrane-based protein assessment) and RT-PCR in the skin explants (FIGS. 38A-38D).

Some samples have a mean (S.D.) epidermal skin blister of score of 1.4 (0.49) with NM exposure and a score of 0.6 (0.66) after exposure to NM and PDA. In some aspects, to achieve 80% power at an a=0.05, a total of 7 or more specimens must be analyzed. Using more stringent parameters, a power of 95% and an a=0.01 can be achieved with a sample size of 14 (calculated using a paired-samples t-test power calculation in SPSS, version 29). The statistical analysis optionally involves employing Analysis of Variance (ANOVA) followed by a post-hoc Tukey test to compare the impact of the SMP intervention against NM+vehicle. ANOVA is applied to examine variance in outcomes across multiple particles, specifically assessing whether there were significant differences among subepidermal split, subepidermal blister score, dyskeratosis/necrosis score and selected biomarker scores. Post-hoc Tukey test is subsequently conducted to perform pairwise comparisons between the each of intervention group and NM+vehicle, aiming to identify specific interventions that exhibit statistically significant differences compared with vehicle. Adjusted p values <0.05 will be considered statistically significant.

Additional aspects are contemplated, such as varying SMP size (e.g., diameter). For example, small particles, such as a 40 nm, can provide increased surface area per gram of material applied to the skin.

Example 6: Artificial Melanin Materials and Formulations for In Vivo Re-Epithelialization and Scar Reduction Cutaneous exposure to SM remains a principal route of penetration to inflict pathology[73]. Cutaneous exposure to SM results in erythema and burning[21,74], while higher doses are associated with full thickness necrosis, skin vesication and disruption of the dermal-epidermal junction[75].

Figure 40A:
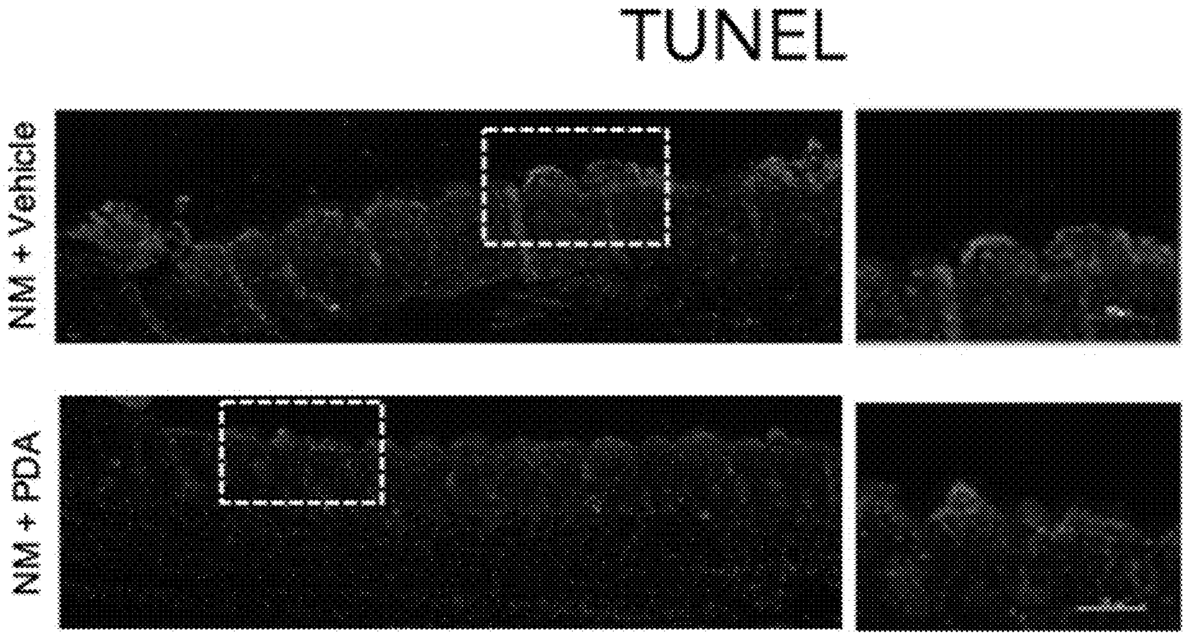
FIGS. 40A-40D: PDA intervention in NM exposed mice significantly down regulated (FIG. 40A) apoptosis quantified by TUNEL (FIG. 40B) expression of MMP9 (FIG. 40C) phosphorylated ERK1/2. PDA intervention increased early wound healing angiogenesis marker CD31 (FIG. 40D).
Figure 40B:
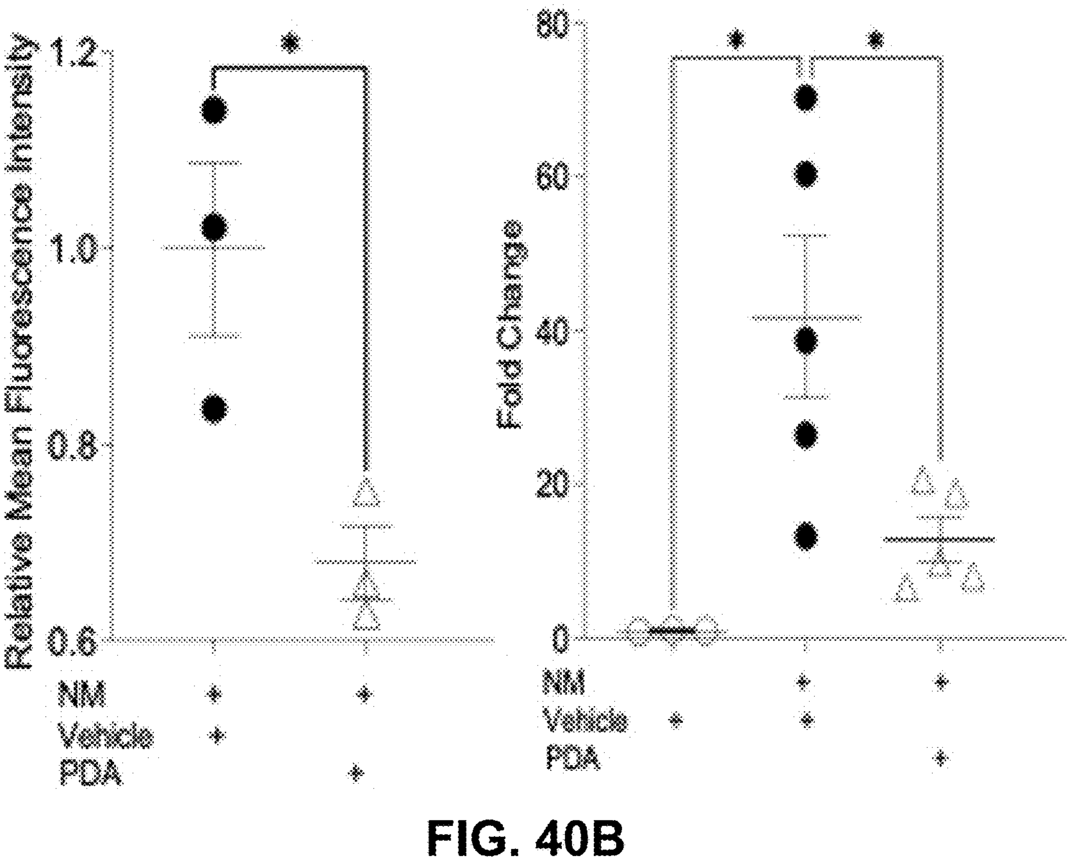
Figure 40C:
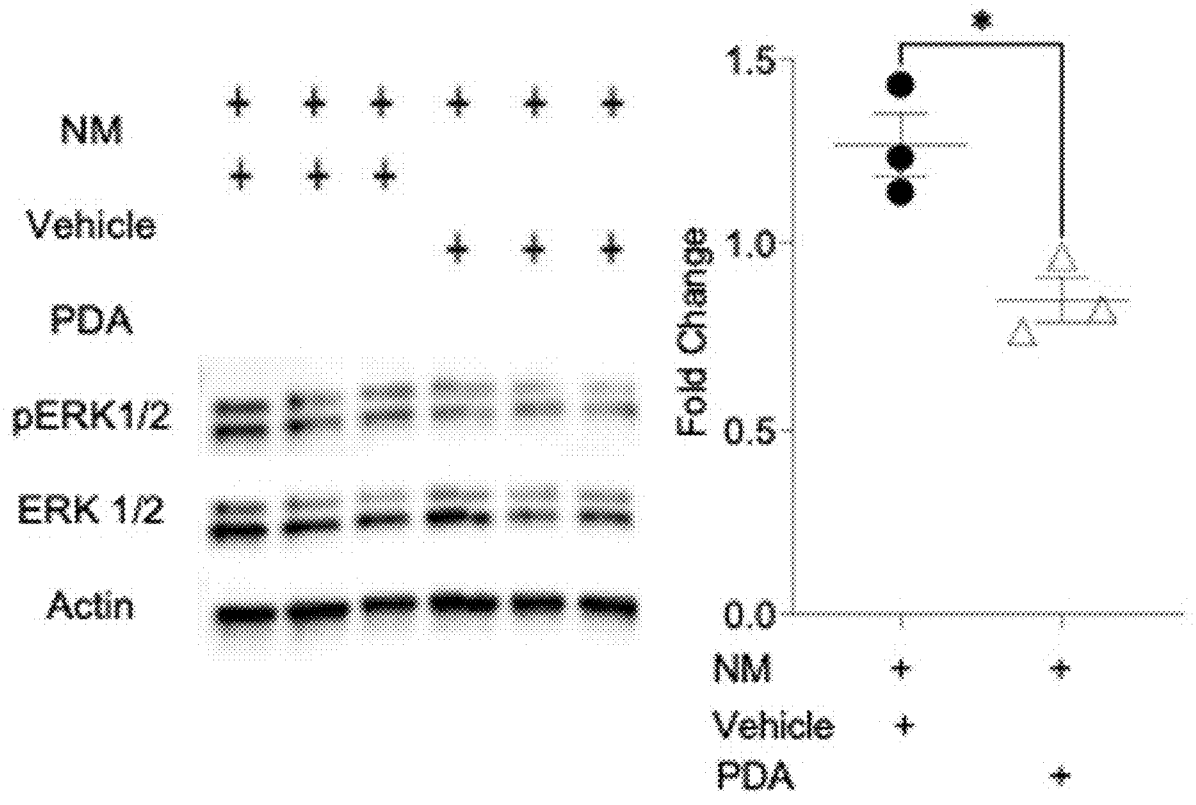
Figure 40D:
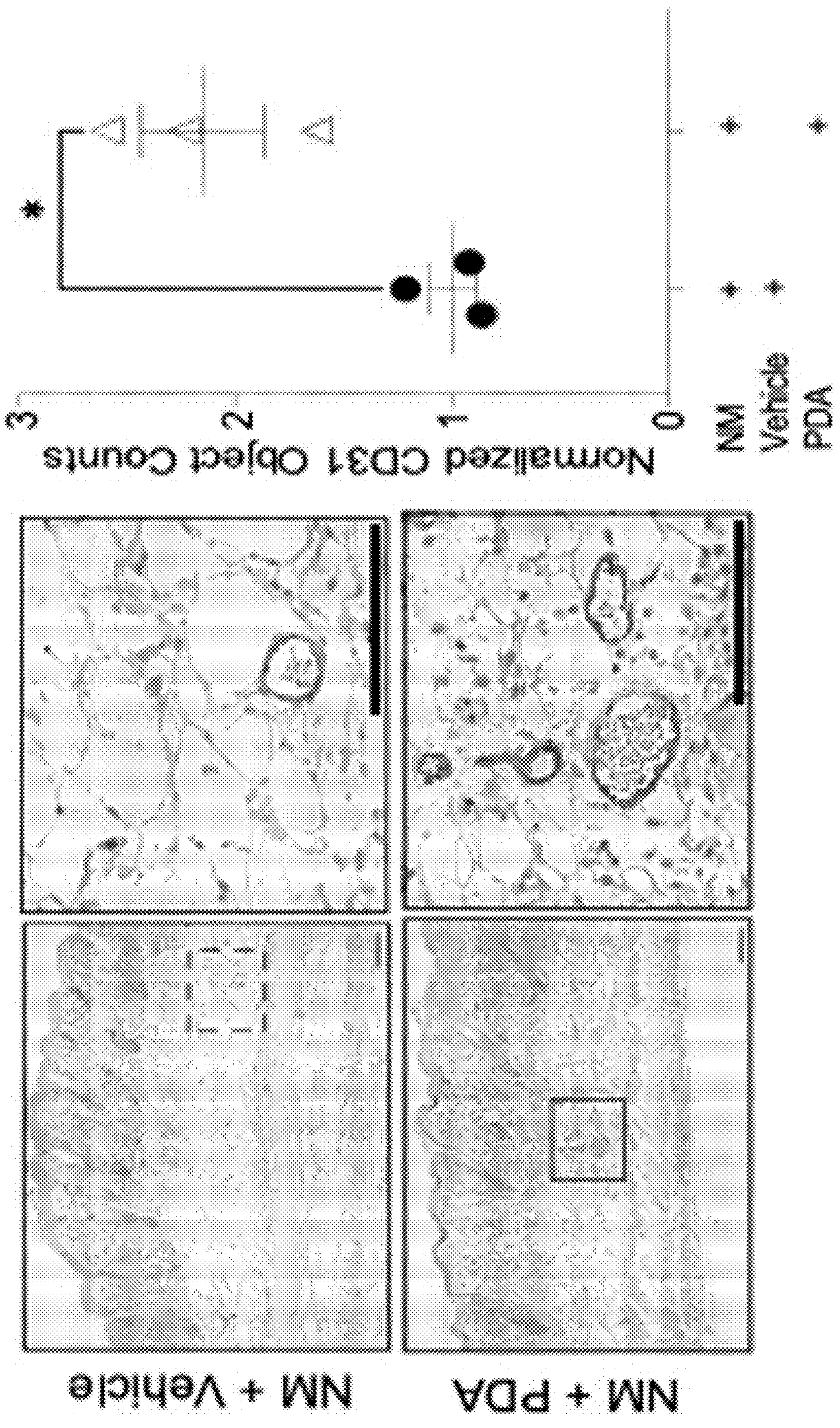
Figure 41A:
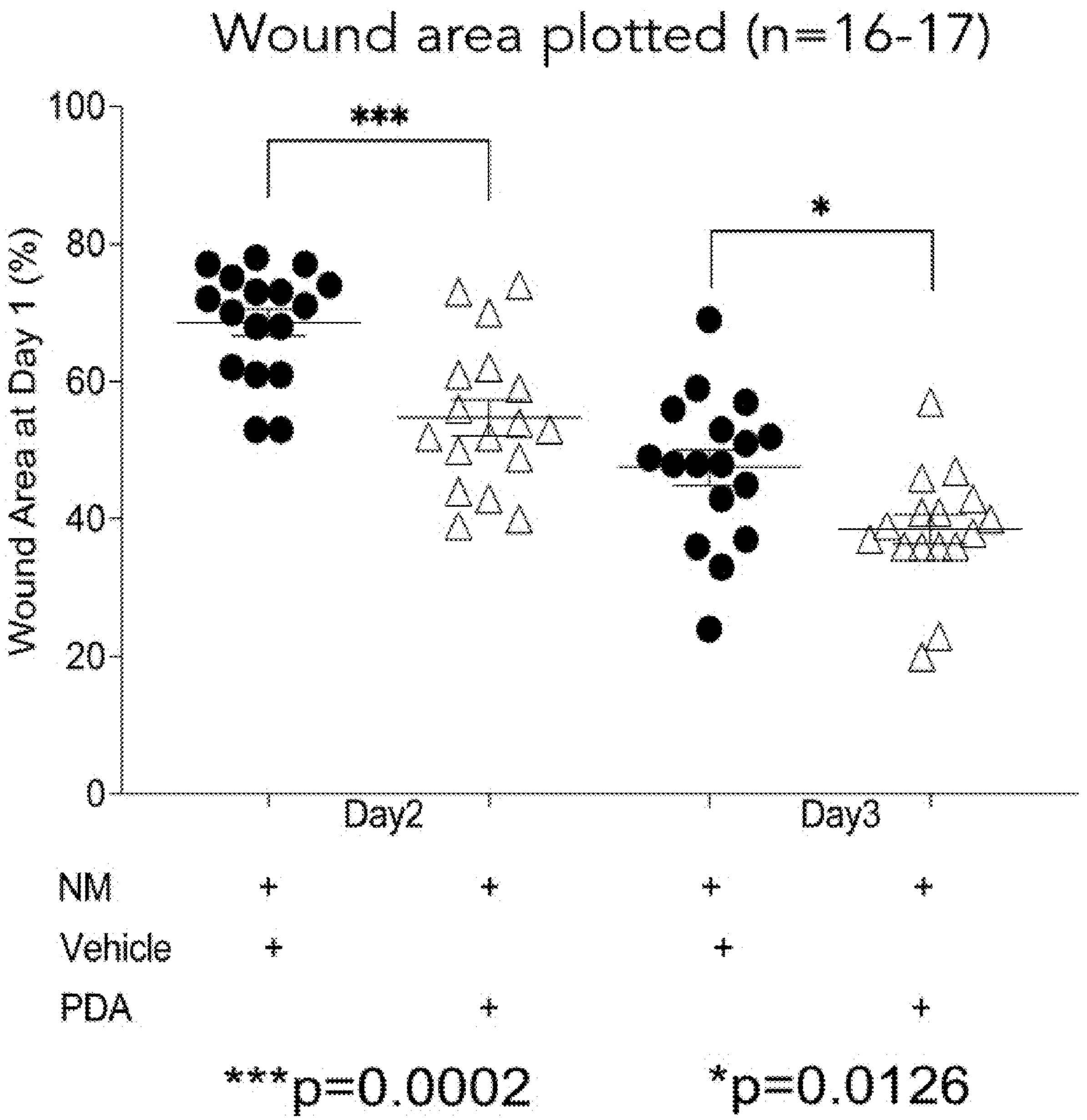
FIGS. 41A-41D: Skin wounds following NM exposure.
Figure 41B:
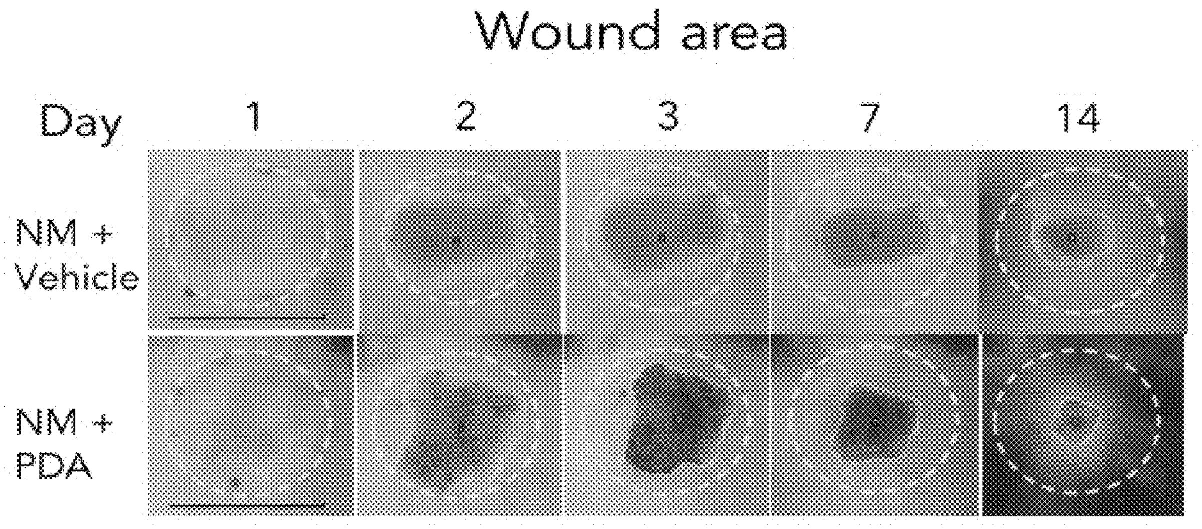
Figure 41C:
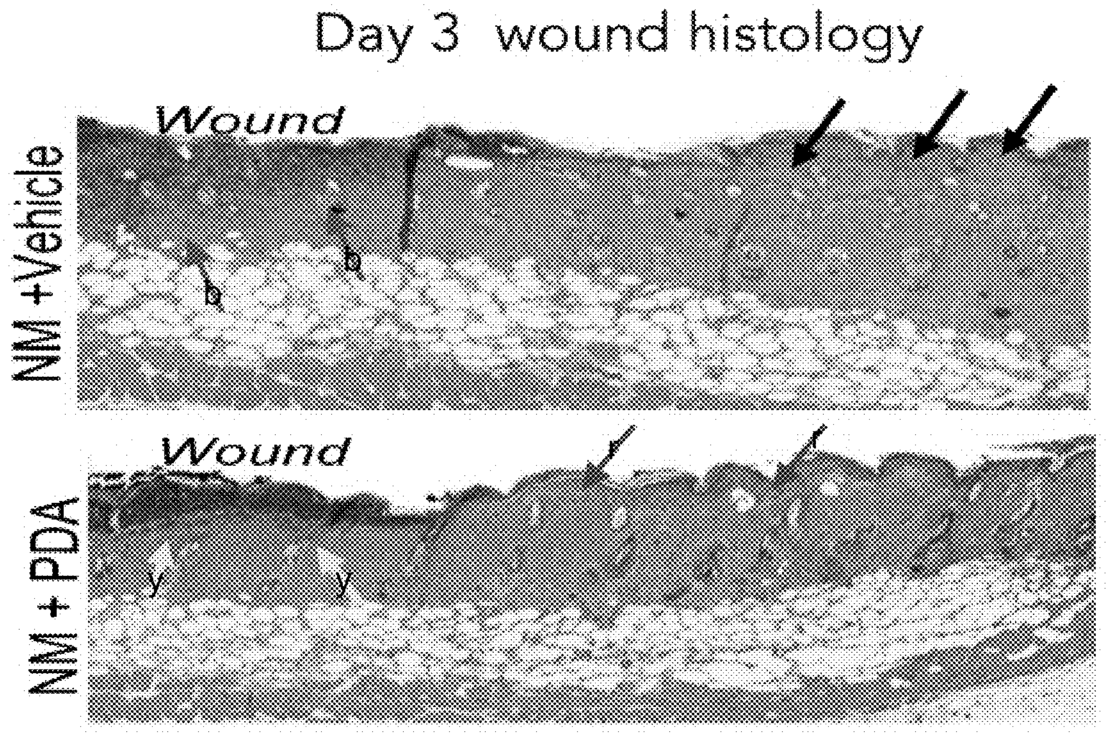
Figure 41D:
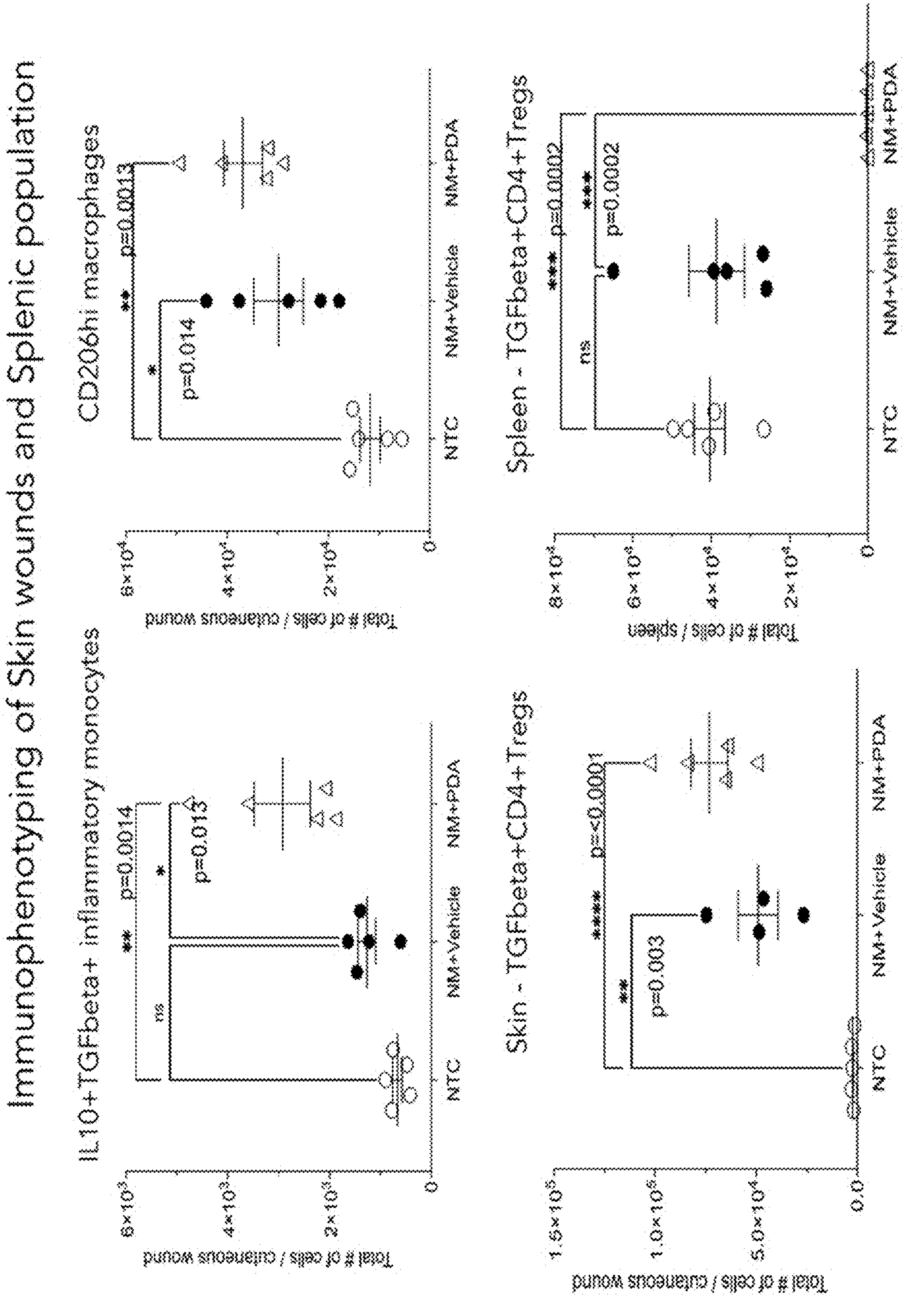

NM Exposure in Mouse Model:

TaqMan mouse immune arrays performed on skin harvested from C57bl/6 mice exposed to topical NM are used to generate data which identifies upregulation of several genes differentiating NM from NM+topical PDA intervention (1 mg/$cm^2$ in PBS). Analysis using the PANTHER Classification System identifies apoptosis signaling and inflammation mediated by chemokine and cytokine signaling as the major pathways affected by PDA intervention. Quantification of TUNEL staining on skin sections confirms decreased apoptosis with PDA intervention, by MFI (p<0.029, n=3) (FIG. 40A). It is confirmed that NM exposure induces phosphorylation of extracellular signal-regulated kinase ½ (ERK1/2) pro-inflammatory signaling (p=0.016, n=3) and upregulation of mmp9 (p=0.034, n=5) [33,77-79] and downregulated by PDA at 24 h and 72 h, respectively (FIGS. 40B-40C). PDA also has a >2-fold increase in early wound healing angiogenesis (CD31 marker, p=0.019, n=3) (FIG. 40D). Topical PDA intervention significantly decreases wound area size on days 2 and 3 (p=0.0002 and p=0.0126, respectively) resulting in rapid wound healing by day 14 (FIGS. 41A-41B). H&E reveals injury limited to the epidermis (yellow or "y" arrows) and normalized adjacent epidermis with PDA intervention (red or "r" arrows). In contrast NM has full-thickness necrosis extending through the deep dermis (blue or "b" arrows) with adjacent reactive hyperplasia (black arrows) (FIG. 41C). A 25-color full immunophenotyping of cells is performed in the wound and spleen of animals exposed to NM and with PDA intervention. Shown here is an exciting finding in which PDA orchestrates recruitment of reparative and anti-inflammatory immune cells in the wound area on day 3 ($CD206^{hi}$ "M2" Mf, IL $10^+$ $TGFb^+CD206^{hi}$ Mf, and Tregs $TGFb^+CD4^+CD25^+FoxP3^+$) with a concomitant egress of those populations from the spleen (FIG. 41D). No changes were seen in B cells, neutrophils, CD8 T cells, NK cells, dendritic cells.

Figure 42A:
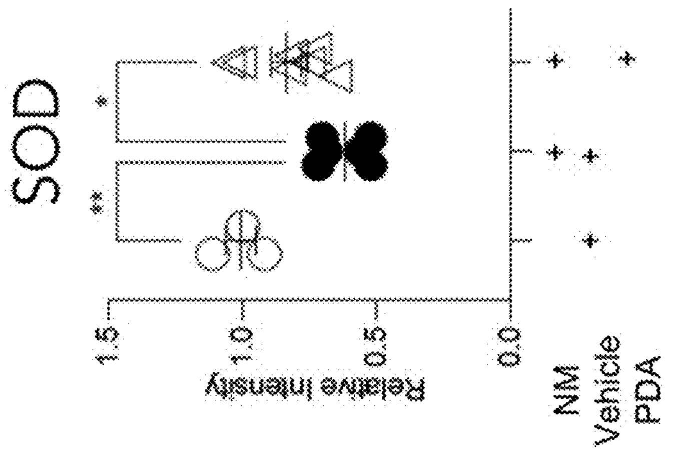
FIG. 42A: SOD activity following NM exposure is decreased (**p<0.01) and rescued with PDA (*p<0.05) (n=3-7).
Figure 42B:
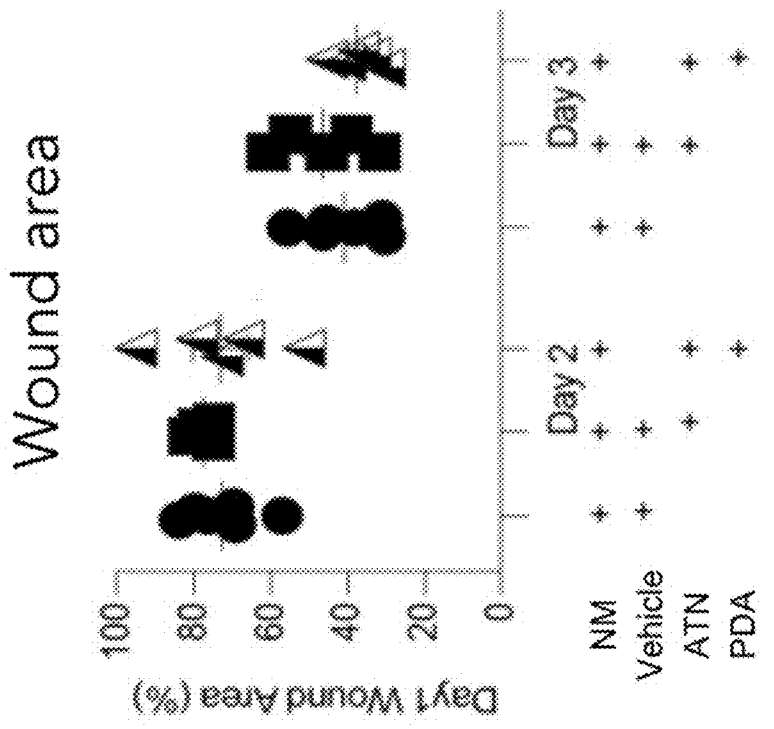
FIGS. 42B-42C: SOD inhibitor ATN-224 abolished previously observed positive effects of PDA on wound healing and apoptosis.
Figure 42C:
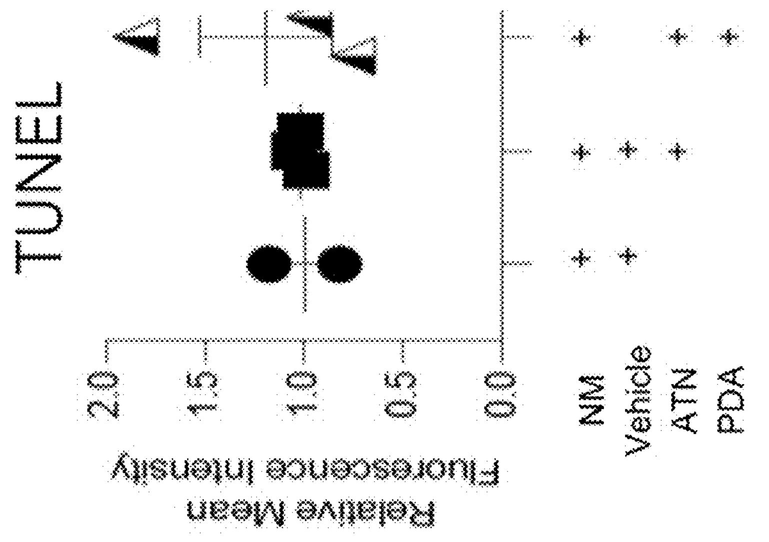

NM exposure leads to DNA damage and ROS.[14] Antioxidant enzymes (AOX) play a major protective role against the deleterious effects of ROS, and superoxide dismutase (SOD) is among the most important of these enzymes[80,81]. NM exposure results in suppression of SOD activity compared to control at 24 h (FIG. 42A). PDA intervention however rescued SOD activity. This is not observed with catalase and thioredoxin reductase, other AOX enzymes important in the skin (data not shown). To confirm the dependence on SOD activity, mice are pretreated with ATN-224, a small molecule copper-chelator inhibitor of SOD1. ATN abolishes the positive effects of PDA on wound healing and apoptosis (FIGS. 42B-42C).

Figure 43A:
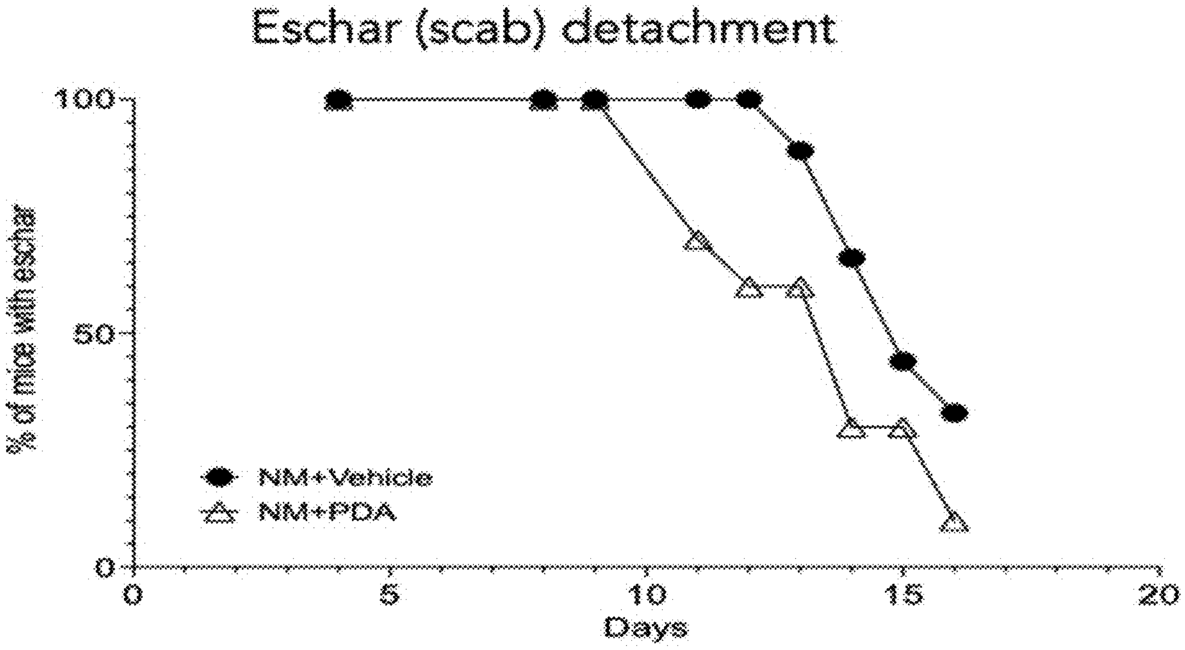
FIGS. 43A-43D: Re-epithelialization and epidermal recovery.
Figure 43B:
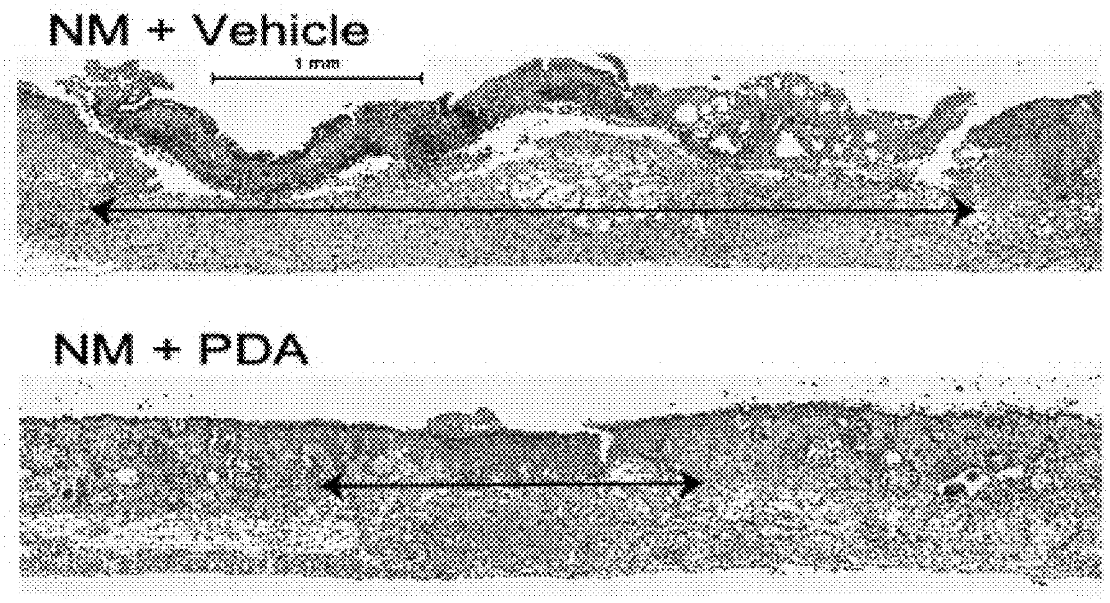
Figure 43C:
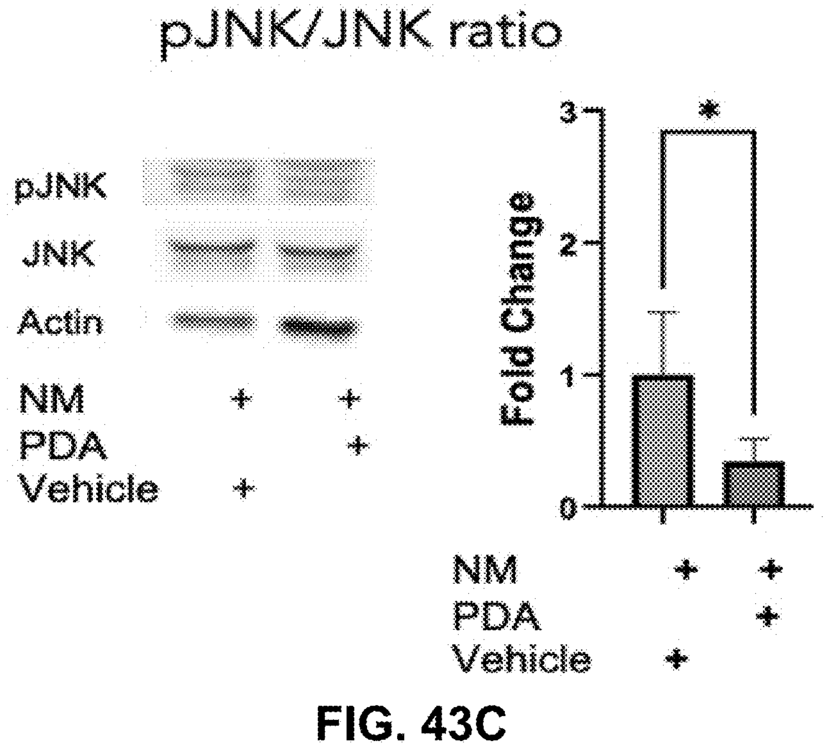
Figure 43D:
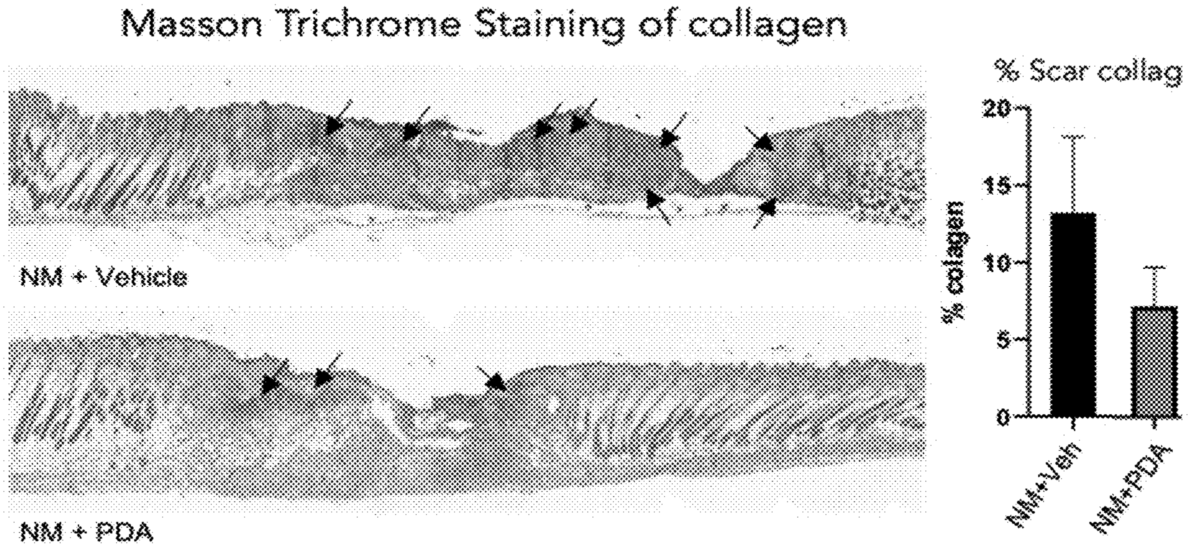

Following the experiments through day 16, it is observed that topical PDA intervention promoted re-epithelialization characterized by rapid rate of eschar detachment, with 40% difference at day 12 (FIG. 43A). This is seen histologically as recovered epidermis with evidence of new hair follicles in contrast to retain necrotic eschar in the NM group (FIG. 43B). This corroborates gross images of pigmented hair growth closing around the wound in FIG. 41B on day 14. Lastly, levels of phosphorylated JUN are assayed, the major component of transcription factor AP-1, shown to be a critical driver of tissue scarring.[82] JUN was recently shown up-regulate fibrotic signaling pathways in reticular fibroblasts the integral membrane protein CD36 on fibroblast.[83] It is observed that p-JUN which is significantly downregulated in day 16 mouse skin treated NM with topical PDA intervention compared to NM exposed mice (FIG. 43C). These results prompt confirmation of whether the skin has increased in new condensed collagen. Using Masson's trichome staining, a routine clinical pathology connective tissue stain, an increase in 50% reduction in dense collagen/total dermis area is observed.

In aspects, one model uses 6-8 week old C57BL/6 mice that are shaved and depilated on the dorsal back and then rested for 3 days to minimize skin irritation before exposure.[46,84] Mice are exposed to 40 μl on the dorsal back (12 mm template) of a freshly prepared solution of 0.5% NM in 1.5% DMSO-PBS solution. Daily non-invasive skin edema thickness (bi-fold skin digital calipers) measurements are taken for 5 days, when formed eschars preclude malleability. Daily photographs of wounds are obtained and measured by ImageJ™. Skin is harvested on day 3 for immunophenotyping and assessment of inflammatory factors by RT-PCR, proteomics, and multi-color FACs. Day 3 and 21 skin are used for histology, Masson's trichome collagen stain, Verhoeff stain for elastin/scar, and confocal microscopy.

In aspects, characterization of artificial melanin nanoparticles and formulations thereof include: observing a significant reduction in wound area on day 2 or day 3; observing eschar detachment in ≥40% of animals at day 12; dermal scar area assessment via Masson-Trichome stain of ≥40% reduction at day 21; observation of significant reduction in mmp9 expression from wound areas on day 3; and therapeutic intervention for 6 hours* for assessment of reduction in mmp9 expression on day 3. In aspects, burst of innate immune cell infiltration by neutrophils is prevalent at 6 hours, an important cellular source of MMP9.

Topical PDA demonstrates infiltration by reparative CD206+macrophages, IL-10/TGFβ monocytes, and TGFβ Tregs in the skin early in the healing process in mice in vivo. These immune cells function to resolve inflammation and limit the extent of tissue damage in the skin. In data, this is reflected by concomitant reduction of the corresponding immune cell populations from the spleen, an immune reservoir and surrogate for circulating immune cells in mice.

In aspects, based on 40% of the scabs to detach off the skin at day 12 with NM+vehicle retaining 100% of the scabs, power is based on the primary outcome of proportion of animals that develop the NM-induced response. A sample size of 15 in each group (total n=30 in two groups) may achieve 80% power to detect a 40% difference in developing scabs between the NM+PDA vs. NM+vehicle groups. Sample size of 23 in each group (total n=46 in two groups) may achieve 95% power to detect the 40% difference. In aspects a two-sample proportion test is employed to assess the percentage of animals with scab detachment or not at the identified optimal endpoint, which is day 12 according to some analysis.

In some aspects, experiments are designed with positive and negative controls. In some aspects, measurements are made individually by at least two individuals who are blinded to the SMP treatment group. In some aspects, experiments are done in batches of 6 mice (3 female/3 male) testing 6 compounds simultaneously with positive and negative controls to minimize environmental variations (48 mice per experiment). In some aspects, 5 independent experiments are performed for a target of 30 animals per group.

In some aspects, the model contemplates the skin increases in thickness by 250-300% (bi-fold thickness) at 24 h and 48 h ($p<0.0001$) with focal eschar formation appearance.

In some aspects, observations and data supporting skin healing include abrogation of early oxidative damage resulting in a limited wound by radial and vertical dimensions. In some aspects, observations and data supporting skin healing include minimizing blistering and dampening immune-mediated activation in the skin contributes to limited wound depth. In some aspects, observations and data supporting skin healing include recruitment of reparative Mo/Mf, and Tregs promotes resolution of inflamed tissue and prepares the matrix for new collagen formation and crosslinking. In some aspects, observations and data supporting skin healing include a new foundation for keratinocytes to migrate over and re-epithelialize with regeneration of appendageal hair structures. In some aspects, a principal method by which the skin heals in a model is by regeneration and migration.

Example 7: Determine Reduction of Skin Inflammation Confers Protection from Partial Thickness Skin Damage from NM and SM in Porcine Models A porcine model is generally accepted as a standard animal model with resemblance to human skin in structure, thickness, lipid content, blood supply, appendageal structures, collagen, and reactions to external perturbagens and wound healing.[90-93] Furthermore, the immune cells including Mo/Mf, and dendritic cells in pig skin are highly comparable to humans.[94] Interventions/applications of artificial melanin materials and formulations thereof are tested in post-exposure porcine studies against NM and SM. Aquaphor® is selected in some aspects as a vehicle for in vivo dose-ranging due to being a safe commonly used OTC 41% petrolatum-based ointment used clinically for dry skin.

Figure 44A:
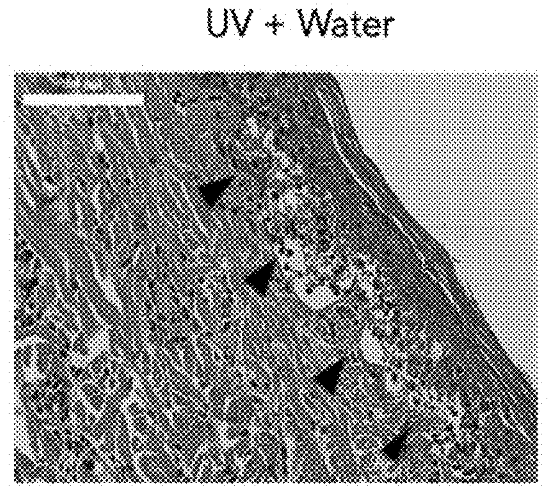
FIGS. 44A-44G: Pilot study of blisters induced by UV in vivo in porcine model. (black arrows point at area of interest). H&E of (FIG. 44A) UV shows full sub-epidermal blisters.
Figure 44B:
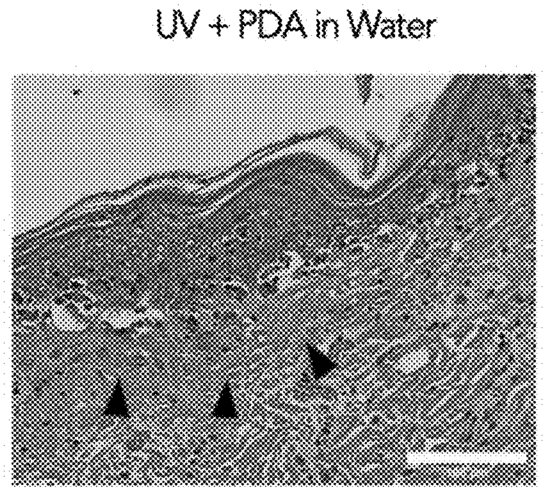
Figure 44C:
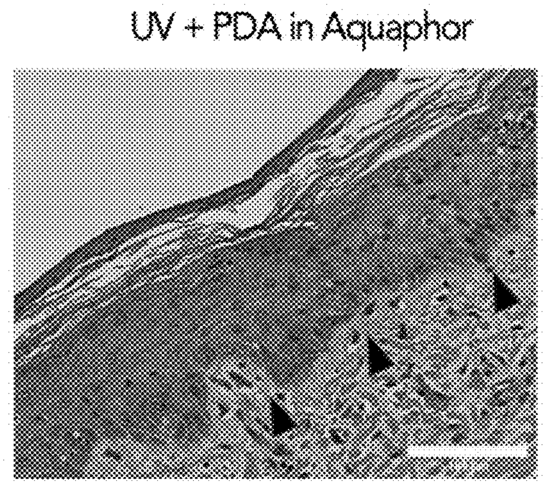
Figure 44D:
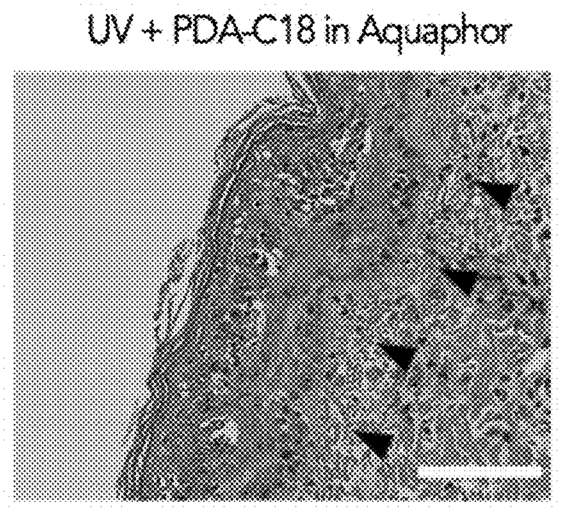
Figure 44E:
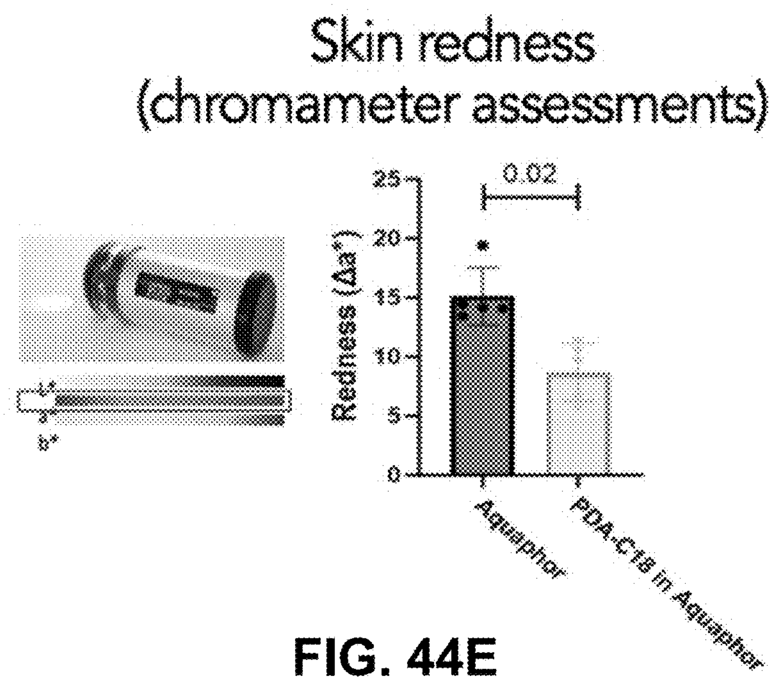

Preliminary Data in a Skin Blister Porcine Model:

For example, Yorkshire/Landrace hybrid pigs (Premier BioSource, IN) are exposed to a severe sunburn (100 $mj/cm^2$) to induce blisters followed by intervention with topical PDAs 2 hours later. Histology reveals a full thickness epidermal split after irradiation (FIG. 44A). PDA in water mitigates partial thickness with preservation of the lower half of the epidermis (FIG. 44B), while PDA in Aquaphor® offered more protection of the epidermis with only focal superficial damage with fully intact attachment of the epidermis to the basement membrane (FIG. 44C). PDA-C18 also partially mitigates histologic damage following a severe sunburn (FIGS. 44D-44E) and significantly reduce skin redness in vivo. This is assessed using a chromameter, a device used in human clinical studies. These studies are enabled by the solubilities of modified SMPs (FIG. 44F) which permitted testing in a variety of commercially available vehicles such as ceramide containing Cerave® cream (FIG. 44G).

Figures 45, 46:
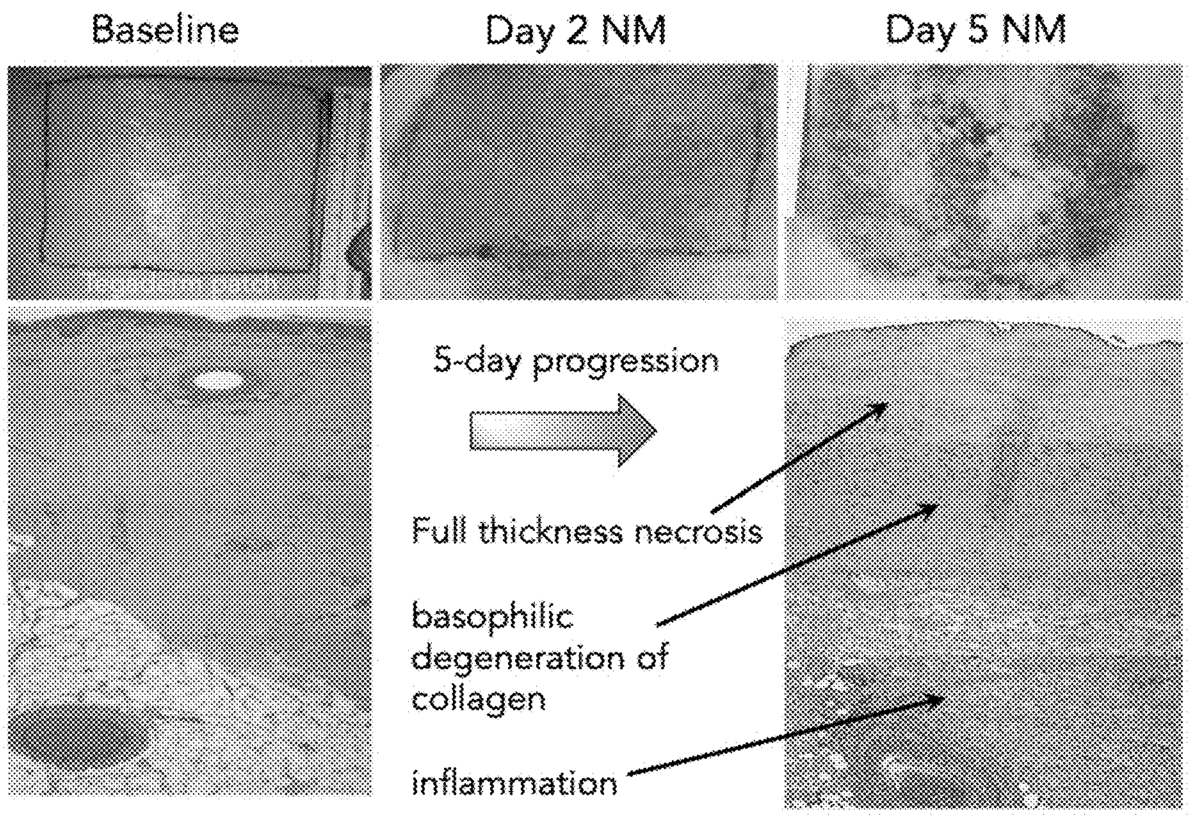
FIG. 45: Nitrogen mustard porcine model. Skin progression of redness and eschar formation. H&E contrasts normal baseline skin and NM-induced full thickness necrosis.
FIG. 46: Test randomization schedule for testing SMPs in porcine model. #indicates animal. Randomization is based 6 tests spots per animal.
Figure 47:
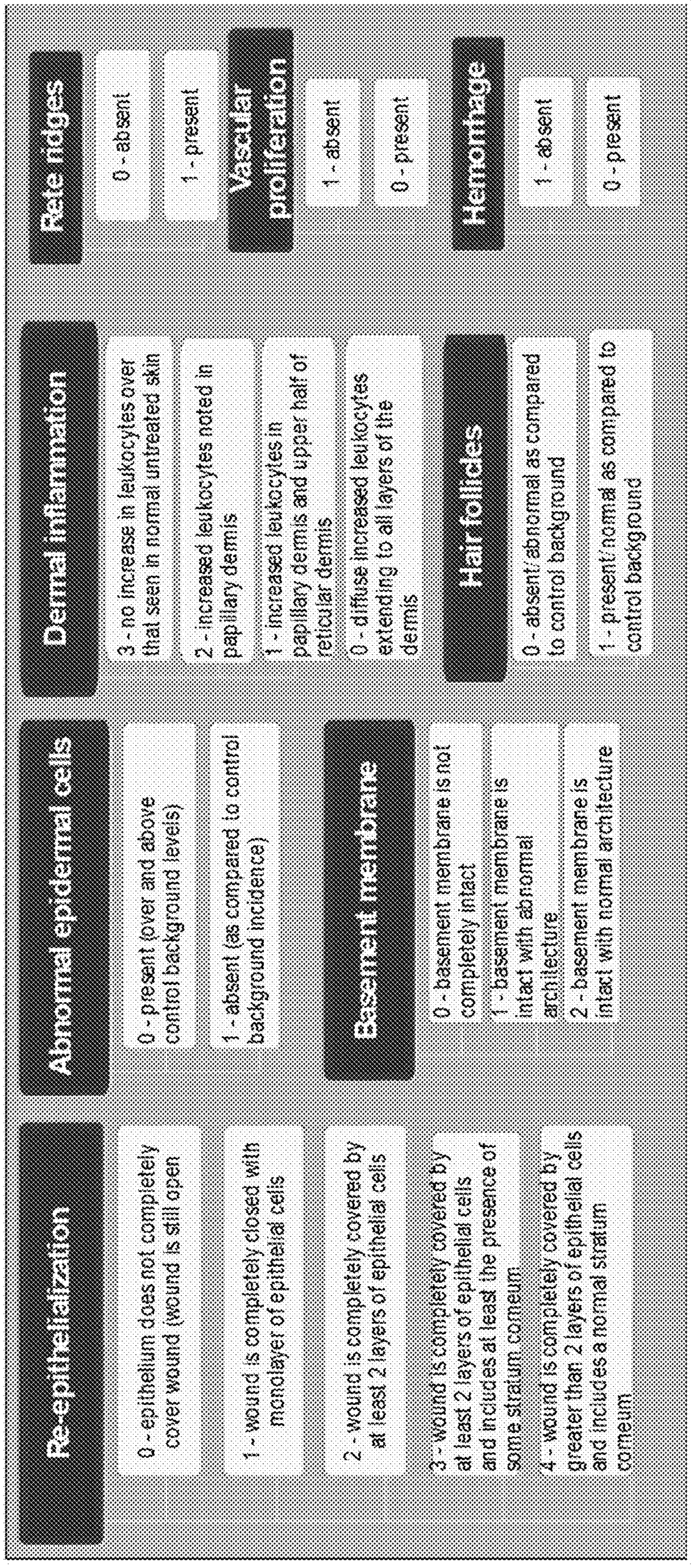
FIG. 47: 15-point histopathology scoring instrument adapted from Barillo et al, 2020. Criteria employed for FDA-approval of Silverlon.
Figure 48A:
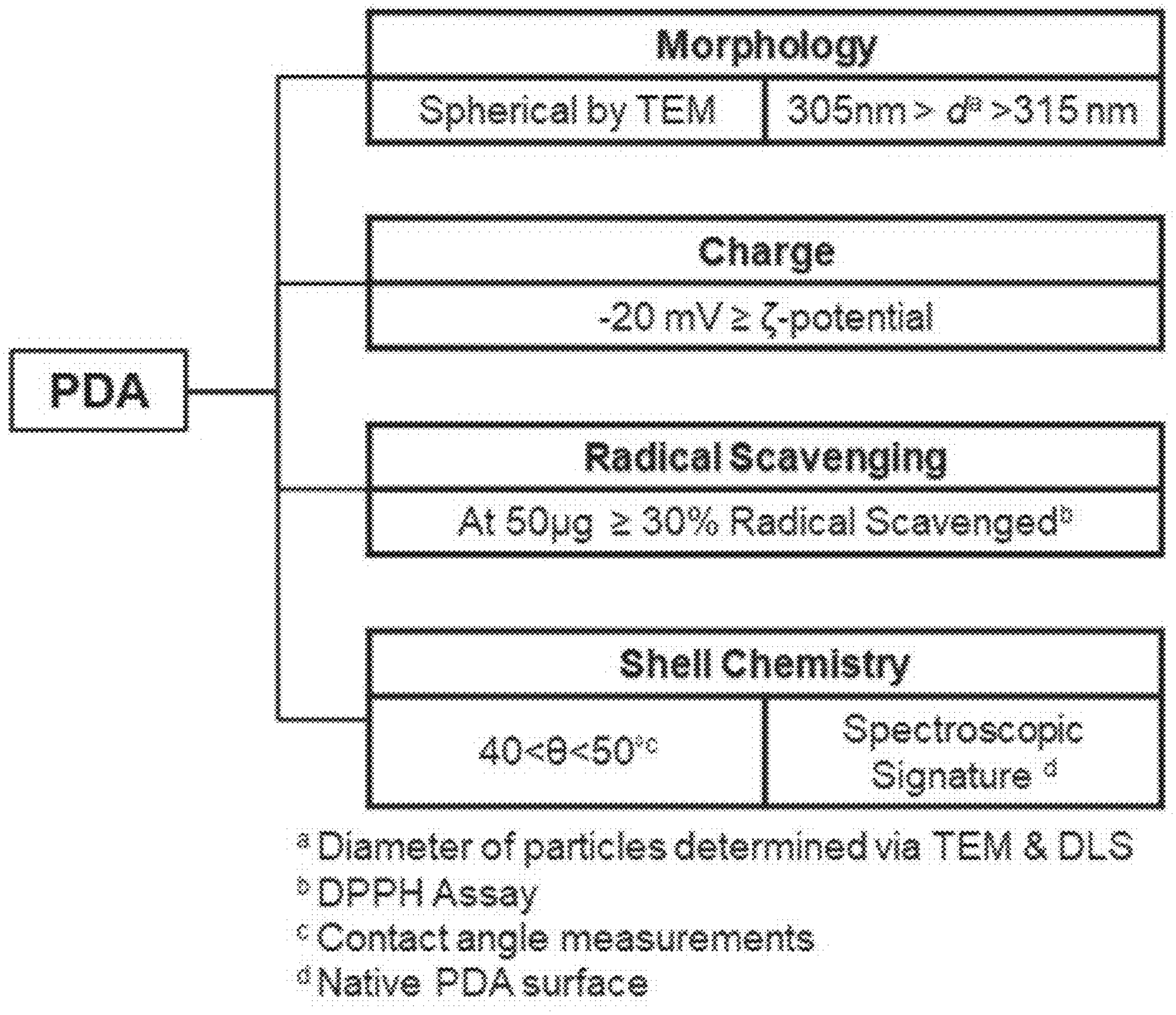
FIGS. 48A-48B: Specifications for (FIG. 49A) PDA and (FIG. 49B) PDA-C18.
Figure 48B:
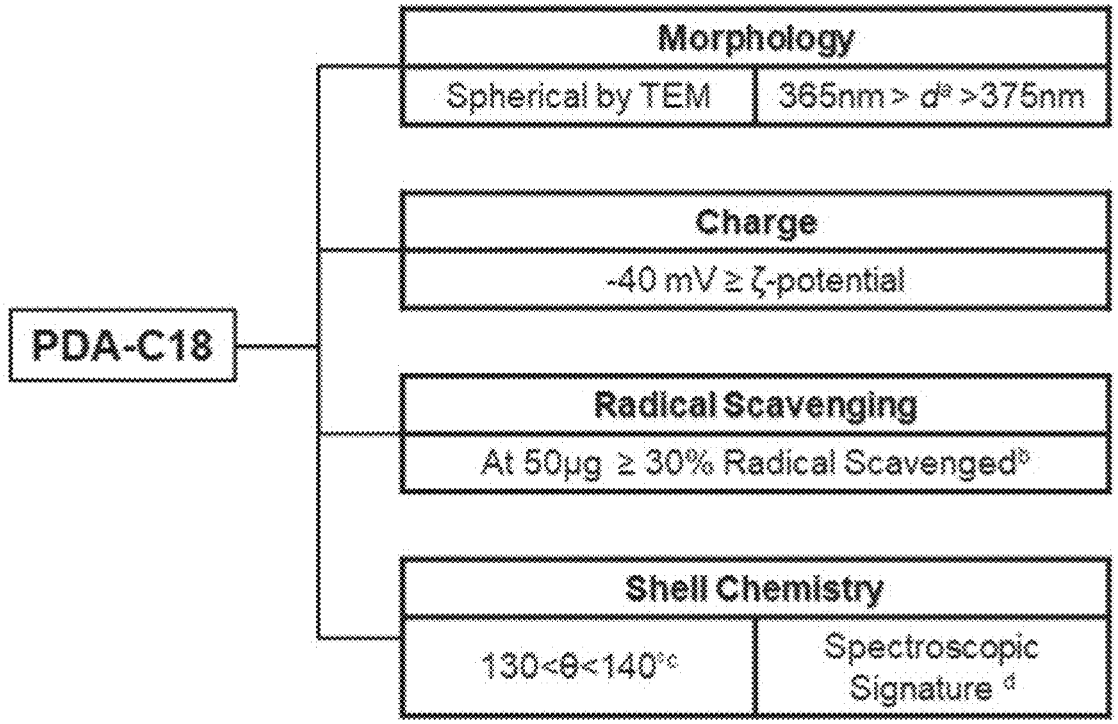

NM Porcine Model:

For example, experiments established a 2% NM model in Yorkshire pigs (FIG. 45). Rapid development of skin erythema is seen at 6 hours, peaking between 2-3 days. Day 5 shows desquamation and development of hemorrhagic eschars. H&E reveals full thickness necrosis, severe dermal necrosis with basophilic degradation of collagen with inflammation.

1. Fitzgerald G J. Chemical warfare and medical response during World War I. *Am J Public Health.* 2008; 98 (4): 611-625.PMC2376985
2. DeVita V T, Jr., Chu E. A history of cancer chemotherapy. *Cancer Res.* 2008; 68 (21): 8643-8653
3. Kehe K, Balszuweit F, Steinritz D, Thiermann H. Molecular toxicology of sulfur mustard-induced cutaneous inflammation and blistering. *Toxicology.* 2009; 263 (1): 12-19

4. Mattes W B, Hartley J A, Kohn K W. DNA sequence selectivity of guanine-$N_7$ alkylation by nitrogen mustards. *Nucleic Acids Res.* 1986; 14 (7): 2971-2987.PMC339715
5. Darchini-Maragheh E, Balali-Mood M. Delayed Complications and Long-term Management of Sulfur Mustard Poisoning: Recent Advances by Iranian Researchers (Part I of II). *Iran J Med Sci.* 2018; 43 (2): 103-124.PMC5936843
6. Li J, Chen J, Kirsner R. Pathophysiology of Acute Wound Healing. *Clin Dermatol.* 2007; 25 (1): 9-18
7. Sies H. Oxidative Stress: A Concept in Redox Biology and Medicine. *Redox Biol.* 2015; 4:180-183.PMC4309861
8. Cho M, Hunt T K, Hussain M Z. Hydrogen Peroxide Stimulates Macrophage Vascular Endothelial Growth Factor Release. *Am J Physiol Heart Circ Physiol.* 2001; 280: H2357-H2363
9. Roy S, Khanna S, Nallu K, Hunt T K, Sen C K. Dermal Wound Healing Is Subject to Redox Control. *Mol Ther.* 2006; 13 (1): 211-220
10. Loo A E, Ho R, Halliwell B. Mechanism of Hydrogen Peroxide-Induced Keratinocyte Migration in a Scratch-Wound Model. *Free Radic Biol Med.* 2011; 51 (4): 884-892
11. Shi M M, Godleski J J, Paulauskis J D. Regulation of Macrophage Inflammatory Protein-1a mRNA by Oxidative Stress. *J Biol Chem.* 1996; 271 (10): 5878-5883
12. Laskin J D, Black A T, Jan Y H, et al. Oxidants and antioxidants in sulfur mustard-induced injury. *Ann N Y Acad Sci.* 2010; 1203:92-100.PMC4023473
13. Naghii M R. Sulfur mustard intoxication, oxidative stress, and antioxidants. *Mil Med.* 2002; 167 (7): 573-575
14. Kumar D, Tewari-Singh N, Agarwal C, et al. Nitrogen mustard exposure of murine skin induces DNA damage, oxidative stress and activation of MAPK/Akt-AP1 pathway leading to induction of inflammatory and proteolytic mediators. *Toxicol Lett.* 2015; 235 (3): 161-171.PMC4430414
15. Wahler G, Heck D E, Heindel N D, Laskin D L, Laskin J D, Joseph L B. Antioxidant/stress response in mouse epidermis following exposure to nitrogen mustard. *Exp Mol Pathol.* 2020; 114:104410.PMC7237310
16. Comino-Sanz I M, López-Franco M D, Castro B, Pancorbo-Hidalgo P L. The Role of Antioxidants on Wound Healing: A Review of the Current Evidence. *J Clin Med.* 2021; 10 (16): 3558
17. Deng Z, Shi F, Zhou Z, et al. M1 Macrophage Mediated Increased Reactive Oxygen Species (ROS) Influence Wound Healing via the MAPK Signaling in vitro and in vivo. *Toxicol Appl Pharmacol.* 2019; 366:83-95
18. Nguyen T T T, Ghosh C, Hwang S-G, Tran L D, Park J S. Characteristics of Curcumin-Loaded Poly (Lactic Acid) Nanofibers for Wound Healing. *J Mater Sci.* 2013; 48 (20): 7125-7133
19. Jung B—O, Chung S-J, Lee S B. Preparation and Characterization of Eugenol-Grafted Chitosan Hydrogels and their Antioxidant Activities. *J App Polym Sci.* 2006; 99 (6): 3500-3506
20. Xiao J, Chen S, Yi J, Zhang H F, Ameer G A. A Cooperative Copper Metal-Organic Framework-Hydrogel System Improves Wound Healing in Diabetes. *Adv Funct Mater.* 2017; 27 (1): 1604872
21. Requena L, Requena C, Sanchez M, et al. Chemical warfare. Cutaneous lesions from mustard gas. *J Am Acad Dermatol.* 1988; 19 (3): 529-536
22. Sharma M, Pant S C, Pant J C, Vijayaraghavan R. Nitrogen and sulphur mustard induced histopathological observations in mouse visceral organs. *J Environ Biol.* 2010; 31 (6): 891-905
23. Sharma M, Vijayaraghavan R, Agrawal O P. Comparative toxic effect of nitrogen mustards (HN-1, HN-2, and HN-3) and sulfur mustard on hematological and biochemical variables and their protection by DRDE-07 and its analogues. *Int J Toxicol.* 2010; 29 (4): 391-401
24. Casillas R P, Kiser R C, Truxall J A, et al. Therapeutic approaches to dermatotoxicity by sulfur mustard. I. Modulaton of sulfur mustard-induced cutaneous injury in the mouse ear vesicant model. *J Appl Toxicol.* 2000; 20 Suppl 1: S145-151
25. Jain A K, Tewari-Singh N, Gu M, Inturi S, White C W, Agarwal R. Sulfur mustard analog, 2-chloroethyl ethyl sulfide-induced skin injury involves DNA damage and induction of inflammatory mediators, in part via oxidative stress, in SKH-1 hairless mouse skin. *Toxicol Lett.* 2011; 205 (3): 293-301.PMC3207490
26. Joseph L B, Composto G M, Perez R M, et al. Sulfur mustard induced mast cell degranulation in mouse skin is inhibited by a novel anti-inflammatory and anticholinergic bifunctional prodrug. *Toxicol Lett.* 2018; 293: 77-81.PMC5938161
27. Joseph L B, Gerecke D R, Heck D E, et al. Structural changes in the skin of hairless mice following exposure to sulfur mustard correlate with inflammation and DNA damage. *Exp Mol Pathol.* 2011; 91 (2): 515-527.PMC3630073
28. Kan R K, Pleva C M, Hamilton T A, Anderson D R, Petrali J P. Sulfur mustard-induced apoptosis in hairless guinea pig skin. *Toxicol Pathol.* 2003; 31 (2): 185-190
29. Paromov V, Suntres Z, Smith M, Stone W L. Sulfur mustard toxicity following dermal exposure: role of oxidative stress, and antioxidant therapy. *J Burns Wounds.* 2007; 7: e7.PMC2064967
30. Chang Y C, Soriano M, Hahn R A, et al. Expression of cytokines and chemokines in mouse skin treated with sulfur mustard. *Toxicol Appl Pharmacol.* 2018; 355:52-59.PMC6438172
31. Lindsay C D, Rice P. Assessment of the biochemical effects of percutaneous exposure of sulphur mustard in an in vitro human skin system. *Hum Exp Toxicol.* 1996; 15 (3): 237-244
32. Shakarjian M P, Heck D E, Gray J P, et al. Mechanisms mediating the vesicant actions of sulfur mustard after cutaneous exposure. *Toxicol Sci.* 2010; 114 (1): 5-19.PMC2819970
33. Jain A K, Tewari-Singh N, Inturi S, Orlicky D J, White C W, Agarwal R. Myeloperoxidase deficiency attenuates nitrogen mustard-induced skin injuries. *Toxicology.* 2014; 320:25-33.PMC4019690
34. Au L, Meisch J P, Das L M, et al. Suppression of Hyperactive Immune Responses Protects Against Nitrogen Mustard Injury. *J Invest Dermatol.* 2015
35. Laskin D L, Sunil V R, Gardner C R, Laskin J D. Macrophages and tissue injury: agents of defense or destruction? *Annu Rev Pharmacol Toxicol.* 2011; 51:267-288
36. Sunil V R, Shen J, Patel-Vayas K, Gow A J, Laskin J D, Laskin D L. Role of reactive nitrogen species generated via inducible nitric oxide synthase in vesicant-induced lung injury, inflammation and altered lung functioning. *Toxicol Appl Pharmacol.* 2012; 261 (1): 22-30
37. Joseph L B, Composto G M, Heck D E. Tissue injury and repair following cutaneous exposure of mice to sulfur mustard. *Ann N Y Acad Sci.* 2016; 1378 (1): 118-123.PMC5063676
38. Nyska A, Lomnitski L, Maronpot R, et al. Effects of iodine on inducible nitric oxide synthase and cyclooxygenase-2 expression in sulfur mustard-induced skin. *Arch Toxicol.* 2001; 74 (12): 768-774
39. Vallet V, Poyot T, Clery-Barraud C, et al. Acute and long-term transcriptional responses in sulfur mustard-exposed SKH-1 hairless mouse skin. *Cutan Ocul Toxicol.* 2012; 31 (1): 38-47
40. Radi R. Oxygen radicals, nitric oxide, and peroxynitrite: Redox pathways in molecular medicine. *Proc Natl Acad Sci USA.* 2018; 115 (23): 5839-5848.PMC6003358
41. Guzik T J, Korbut R, Adamek-Guzik T. Nitric oxide and superoxide in inflammation and immune regulation. *J Physiol Pharmacol.* 2003; 54 (4): 469-487
42. Tripathi P, Tripathi P, Kashyap L, Singh V. The role of nitric oxide in inflammatory reactions. *FEMS Immunol Med Microbiol.* 2007; 51 (3): 443-452
43. Steinritz D, Elischer A, Balszuweit F, et al. Sulphur mustard induces time- and concentration-dependent regulation of NO-synthesizing enzymes. *Toxicol Lett.* 2009; 188 (3): 263-269
44. Yaren H, Mollaoglu H, Kurt B, et al. Lung toxicity of nitrogen mustard may be mediated by nitric oxide and peroxynitrite in rats. *Res Vet Sci.* 2007; 83 (1): 116-122
45. Sawyer T W, Risk D. Effects of selected arginine analogues on sulphur mustard toxicity in human and hairless guinea pig skin keratinocytes. *Toxicol Appl Pharmacol.* 2000; 163 (1): 75-85
46. Au L, Meisch J P, Das L M, et al. Suppression of Hyperactive Immune Responses Protects against Nitrogen Mustard Injury. *J Invest Dermatol.* 2015; 135 (12): 2971-2981.PMC4648631
47. Chen Y, Kong J, Sun T, et al. 1,25-Dihydroxyvitamin D (3) suppresses inflammation-induced expression of plasminogen activator inhibitor-1 by blocking nuclear factor-kappaB activation. *Arch Biochem Biophys.* 2011; 507 (2): 241-247.PMC3049452
48. Cohen-Lahav M, Shany S, Tobvin D, Chaimovitz C, Douvdevani A. Vitamin D decreases NFkappaB activity by increasing IkappaBalpha levels. *Nephrol Dial Transplant.* 2006; 21 (4): 889-897
49. Lagishetty V, Liu N Q, Hewison M. Vitamin D metabolism and innate immunity. *Mol Cell Endocrinol.* 2011; 347 (1-2): 97-105.PMC3200473
50. Das L M, Binko A M, Traylor Z P, et al. Early indicators of survival following exposure to mustard gas: Protective role of 25 (OH) D. *Toxicol Lett.* 2016; 248:9-15.PMC5588853
51. Ernst M K, Evans S T, Techner J M, et al. Vitamin D3 and deconvoluting a rash. *JCI Insight.* 2023; 8 (2).PMC9977299
52. Lin J Y, Fisher D E. Melanocyte Biology and Skin Pigmentation. *Nature.* 2007; 445 (7130): 843-850
53. Brenner M, Hearing V J. The Protective Role of Melanin Against UV Damage in Human Skin. *Photochem Photobiol.* 2008; 84 (3): 539-549
54. Simon J D, Peels D N. The Red and the Black. *Acc Chem Res.* 2010; 43 (11): 1452-1460
55. Huang Y, Li Y, Hu Z, et al. Mimicking Melanosomes: Polydopamine Nanoparticles as Artificial Microparasols. *ACS Cent Sci.* 2017; 3 (6): 564-569.PMC5492417
56. Grether-Beck S, Felsner I, Brenden H, et al. Air Pollution-Induced Tanning of Human Skin. *Br J Dermatol.* 2021; 185 (5): 1026-1034
57. Siwicka Z E, Son F A, Battistella C, et al. Synthetic Porous Melanin. *JACS.* 2021; 143 (8): 3094-3103
58. Neil J E, Brown M B, Williams A C. Human Skin Explant Model for the Investigation of Topical Therapeutics. *Sci Rep* 2020; 10 (1)
59. Cao W, Zhou X, McCallum N C, et al. Unraveling the Structure and Function of Melanin through Synthesis. *J Am Chem Soc.* 2021; 143 (7): 2622-2637
60. Hu Z, Sun H, Thompson M P, et al. Structurally Colored Inks from Synthetic Melanin-Based Crosslinked Supraparticles. *ACS Materials Letters.* 2021; 3 (1): 50-55
61. Cao W, McCallum N C, Ni Q Z, et al. Selenomelanin: An Abiotic Selenium Analogue of Pheomelanin. *J Am Chem Soc.* 2020; 142 (29): 12802-12810
62. Cao W, Mao H, McCallum N C, et al. Biomimetic pheomelanin to unravel the electronic, molecular and supramolecular structure of the natural product. *Chem Sci.* 2023; 14 (15): 4183-4192.PMC10094096
63. Zhou X, Gong X, Cao W, et al. Anisotropic Synthetic Allomelanin Materials via Solid-State Polymerization of Self-Assembled 1,8-Dihydroxynaphthalene Dimers. *Angew Chem Int Ed Engl.* 2021; 60 (32): 17464-17471
64. Cao W, Mantanona A J, Mao H, et al. Radical-Enriched Artificial Melanin. *Chemistry of Materials.* 2020; 32 (13): 5759-5767
65. Zhou X, Su S, Vanthournout B, et al. Hydrophobic Melanin via Post-Synthetic Modification for Controlled Self-Assembly. *ACS Nano.* 2022; 16 (11): 19087-19095
66. Friedman N, Dagan A, Elia J, Merims S, Benny O. Physical properties of gold nanoparticles affect skin penetration via hair follicles. *Nanomedicine.* 2021; 36:102414
67. Zhou X, McCallum N C, Hu Z, et al. Artificial Allomelanin Nanoparticles. *ACS Nano.* 2019; 13 (10): 10980-10990
68. McCallum N C, Son F A, Clemons T D, et al. Allomelanin: A Biopolymer of Intrinsic Microporosity. *J Am Chem Soc.* 2021; 143 (10): 4005-4016
69. Biyashev D, Onay U V, Dalal P, et al. A novel treatment for skin repair using a combination of spironolactone and vitamin D3. *Ann N Y Acad Sci.* 2020
70. Das L M, Binko A M, Traylor Z P, Duesler L, Lu K Q. Defining the timing of 25 (OH) D rescue following nitrogen mustard exposure. *Cutan Ocul Toxicol.* 2018; 37 (2): 127-132.PMC6025804
71. Guo Y, Cao X, Lan X, Zhao C, Xue X, Song Y. Solution-Based Doping of Manganese into Colloidal ZnO Nanorods. *The Journal of Physical Chemistry C.* 2008; 112 (24): 8832-8838
72. Liu H-y, Feng Z-b, Wang J, Diao J-y, Su D-s. Synthesis of hollow carbon nanostructures using a ZnO template method. *New Carbon Materials.* 2016; 31 (1): 87-91
73. Langenberg J P, van der Schans G P, Spruit H E, et al. Toxicokinetics of sulfur mustard and its DNA-adducts in the hairless guinea pig. *Drug Chem Toxicol.* 1998; 21 Suppl 1:131-147
74. Borak J, Sidell F R. Agents of chemical warfare: sulfur mustard. *Ann Emerg Med.* 1992; 21 (3): 303-308

75. Holstege C P, Kirk M, Sidell F R. Chemical warfare. Nerve agent poisoning. *Crit Care Clin.* 1997; 13 (4): 923-942
76. Thomas P D, Campbell M J, Kejariwal A, et al. PANTHER: A Library of Protein Families and Subfamilies Indexed by Function. *Genome Res.* 2003; 13 (9): 2129-2141
77. Kumar D, Tewari-Singh N, Agarwal C, et al. Nitrogen Mustard Exposure of Murine Skin Induces DNA Damage, Oxidative Stress and Activation of MAPK/Akt-AP1 Pathway Leading to Induction of Inflammatory and Proteolytic Mediators. *Toxicol Lett.* 2015; 235 (3): 161-171
78. Shakarjian M P, Bhatt P, Gordon M K, et al. Preferential Expression of Matrix Metalloproteinase-9 in Mouse Skin After Sulfur Mustard Exposure. *J Appl Toxicol.* 2006; 26 (3): 239-246
79. Ries C, Popp T, Egea V, Kehe K, Jochum M. Matrix metalloproteinase-9 expression and release from skin fibroblasts interacting with keratinocytes: Upregulation in response to sulphur mustard. *Toxicology.* 2009; 263 (1): 26-31
80. Wang Y, Branicky R, Noë A, Hekimi S. Superoxide Dismutases: Dual Roles in Controlling ROS Damage and Regulating ROS Signaling. *J Cell Biol.* 2018; 217 (6): 1915-1928
81. Laskin J D, Black A T, Jan Y-H, et al. Oxidants and Antioxidants in Sulfur Mustard-Induced Injury. *Ann N Y Acad Sci.* 2010; 1203 (1): 92-100
82. Cui L, Chen S Y, Lerbs T, et al. Activation of JUN in fibroblasts promotes pro-fibrotic programme and modulates protective immunity. *Nat Commun.* 2020; 11 (1): 2795.PMC7270081
83. Griffin M F, Borrelli M R, Garcia J T, et al. JUN promotes hypertrophic skin scarring via CD36 in preclinical in vitro and in vivo models. *Sci Transl Med.* 2021; 13 (609): eabb3312.PMC8988368
84. Biyashev D, Onay U V, Dalal P, et al. A novel treatment for skin repair using a combination of spironolactone and vitamin D3. *Ann N Y Acad Sci.* 2020; 1480 (1): 170-182.PMC7754145
85. Das C, Olmsted P D. The physics of stratum corneum lipid membranes. *Philos Trans A Math Phys Eng Sci.* 2016; 374 (2072).PMC4920276
86. Suzuki M, Ohno Y, Kihara A. Whole picture of human stratum corneum ceramides, including the chain-length diversity of long-chain bases. *J Lipid Res.* 2022; 63 (7): 100235.PMC9240646
87. Yilmaz E, Borchert H H. Effect of lipid-containing, positively charged nanoemulsions on skin hydration, elasticity and erythema—an in vivo study. *Int J Pharm.* 2006; 307 (2): 232-238
88. Baspinar Y, Borchert H H. Penetration and release studies of positively and negatively charged nanoemulsions—is there a benefit of the positive charge? *Int J Pharm.* 2012; 430 (1-2): 247-252
89. Banerjee R. Overcoming the stratum corneum barrier: a nano approach. *Drug Delivery and Translational Research.* 2013; 3 (3): 205-208
90. Summerfield A, Meurens F, Ricklin M E. The immunology of the porcine skin and its value as a model for human skin. *Molecular Immunology.* 2015; 66 (1): 14-21
91. Ansell D M, Holden K A, Hardman M J. Animal models of wound repair: Are they cutting it? *Experimental Dermatology.* 2012; 21 (8): 581-585
92. Abdullahi A, Amini-Nik S, Jeschke M G. Animal models in burn research. *Cellular and Molecular Life Sciences.* 2014; 71 (17): 3241-3255
93. Montagna W, Yun J S. The Skin of the Domestic Pig. *J Invest Dermatol.* 1964; 42:11-21
94. Ezquerra A, Revilla C, Alvarez B, Pérez C, Alonso F, Domínguez J. Porcine myelomonocytic markers and cell populations. *Developmental & Comparative Immunology.* 2009; 33 (3): 284-298
95. Barillo D J, Croutch C R, Barillo A R, Reid F, Singer A. Safety evaluation of silver-ion dressings in a porcine model of deep dermal wounds: A GLP study. *Toxicol Lett.* 2020; 319:111-118
96. Kim S K, Karadeniz F. Biological importance and applications of squalene and squalane. *Adv Food Nutr Res.* 2012; 65:223-233
97. Sanchez-Quesada C, Lopez-Biedma A, Toledo E, Gaforio J J. Squalene Stimulates a Key Innate Immune Cell to Foster Wound Healing and Tissue Repair. *Evid Based Complement Alternat Med.* 2018; 2018: 9473094.PMC6186384.

Example 8

Figure 44F:
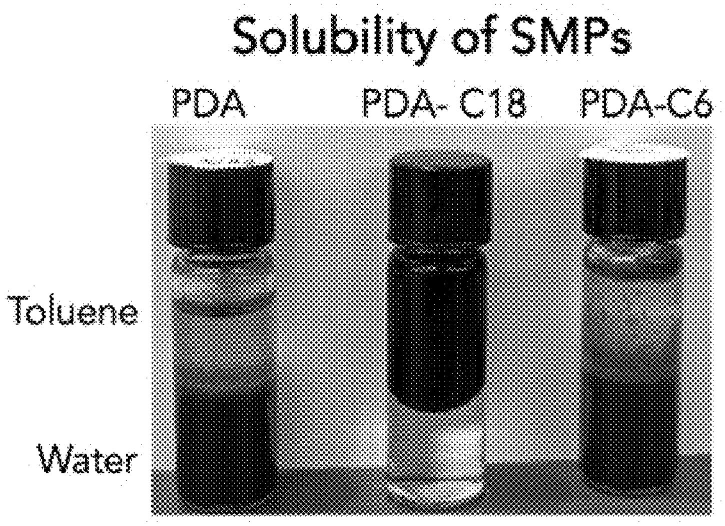
Figure 44G:
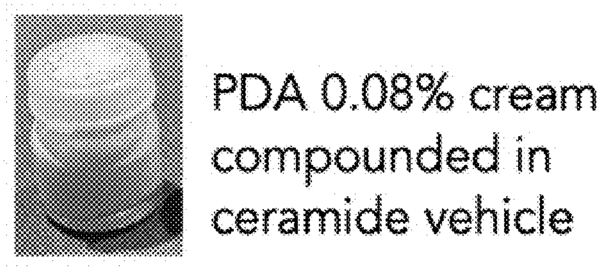

With reference to FIG. 44F, surface modifications of PDA to form PDA-C18 and PDA-C6 changes solubility. The surface modifications results in changes in hydrophobicity (PDA-C18) and intermediate hydrophobicity/hydrophilicity (PDA-C6). Shown here are PDA forms separated in fractions of water and an organic solvent (i.e. toluene).

Example 9

With reference to FIGS. 44A and 44D, Yorkshire/Landrace hybrid pigs are exposed to a severe blistering sunburn (100 mj/$cm^2$) followed by intervention with topical PDA-C18 two hours later. Histology on day 3 reveals full thickness necrosis and epidermal separation after UV irradiation (arrows point to blisters) (FIG. 44A). Intervention with PDA-C18 (FIG. 44D) treatment demonstrated an intact epidermis w/o blisters at the basement membrane (black arrows).

Example 10

With reference to FIG. 44E, Yorkshire/Landrace hybrid pigs are exposed to a severe blistering sunburn (100 mj/$cm^2$) followed by intervention with topical PDA-C18 two hours later. Skin redness is measured using a chromameter which measures skin redness, a clinical and reliable indicator of skin reaction and inflammation, a device used in human clinical studies. Intervention with PDA-C18 after severe UV exposure resulted in chromameter readings that showed PDA-C18 significantly reduced skin redness (n=5, P=0.02, day 3). Thus, PDA-C18 rescues the skin in vivo porcine of skin burns (UV model).

Example 11

Swine have greater similarity to human skin and immunology and are therefore chosen to validate findings in the murine model. Ten 3-month-old Yorkshire/Landrace hybrid (5 per condition), from 20-25 kg were housed in pairs under controlled temperature (25° C.) and light conditions (12 h light, 12 h dark). Animals were fed twice daily. Before the experiment, animals were acclimated to the facility for 4 days.

Samples were prepared with either MilliQ water or Aquaphor handled aseptically. 2% w/w PDA, and 2% w/w PDA-C18 were prepared by removing the solvent the particles were suspended in, followed by mixing with Aquaphor. The sunscreen (La Roche Posay Melt-in Milk SPF 60) was also handled aseptically and the 0.08% PDA-C18 in sunscreen ointment was prepared the same way as the Aquaphor ointments.

Animals were sedated with Tiletamine/Zolazepam (Telazol) (2-8 mg/kg) and anesthesia with isoflurane (5%) was maintained with constant monitoring over the course of the experiment. The template, a UV Daavlin patch with 2×2 cm windows, is placed over one side of the back of the animal (If orienting oneself facing the animal) along the back, exposing specific area for irradiation, and the rest of the animal is covered. Areas for irradiation were spaced 2 cm apart. Using a DSM-III Chromameter, chromameter measurements of both the treatment and control areas are taken.

In the post-UV exposure condition, animals are positioned under the UV-B lamp (Panasol II, National Biological) while under anesthesia, ensuring animal comfort and template placement fidelity. The UV-B lamp is turned on and the animal is irradiated with 100 mJ/cm$^2$ of light for approximately 6 minutes. The UV dosage is monitored and quantified using a detector. The lamp is removed, and the animal is left under anesthesia for 1 hour. Pre-weighed aliquots of 200 mg of experimental ointments and creams were applied in 2×2 cm squares on the UV-irradiated and non-UV irradiated sides of the animal using a spatula, and then covered with Tegaderm. Once recovered from anesthesia, animals were returned to separated housing, with opportunities for snout-to-snout contact.

In the prophylactic condition, pre-weighed aliquots of 200 mg of experimental ointments and creams were applied in 2×2 cm squares on the sedated animal within the Daavlin template with a spatula. The ointments sat on the skin for 30 minutes, then the skin was exposed to the UV-B lamp.

At 24 and 48 hours post exposure, ointments from the day before were gently wiped off with a damp paper towel. Chromameter measurements were obtained with the DSM-III chromameter in triplicate. Pre-weighed aliquots of 200 mg of experimental ointments and creams are applied in 2×2 cm squares on the UV-irradiated and non-UV irradiated sides of the animal using a spatula at 24 and 48 hours.

At 72 hours post-exposure, animals were sedated with Tiletamine/Zolazepam (Telazol) (2-8 mg/kg) and anesthesia with isoflurane (5%) was maintained with constant monitoring over the course of the experiment. Material from the day before, the area of skin is gently wiped off with a damp paper towel, and chromameter measurements were obtained. Animals were then euthanized, and full-thickness skin biopsies were harvested, which were then processed to be fixed in 10% neutral buffered formalin solution, flash frozen, and in O.C.T compound.

Figure 49B:
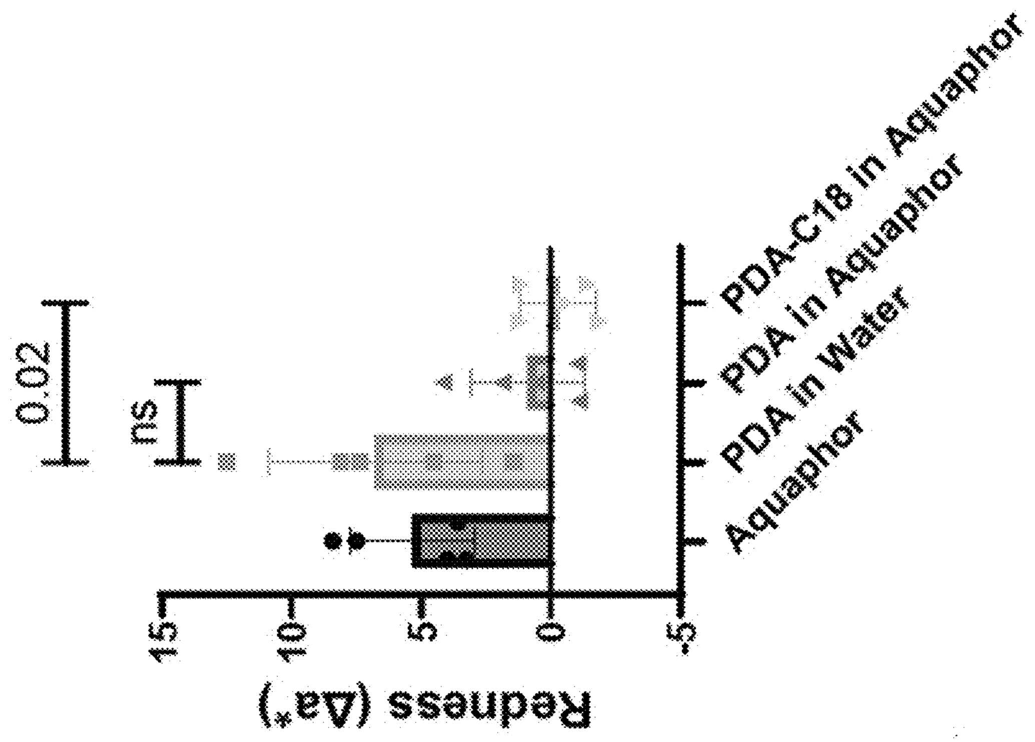
FIGS. 49A-49B: Redness of skin post-UV exposure (FIG. 49A) with application of formulation to skin as labeled, where topical application of 2% w/w PDA-$C_{18}$ in Aquaphor® yielded decreased rate of redness over the course of the experimental period and also demonstrated significance in decreased redness compared to the vehicle control. Redness of skin in the case of prophylaxis (FIG. 49B) with application of formulation to skin as labeled, where topical application of 2% w/w PDA-C18 behaves like a sunscreen and performs similarly to the control sunscreen (SPF 60) in that it was successful in preventing UV-B induced damage.
Figure 49A:
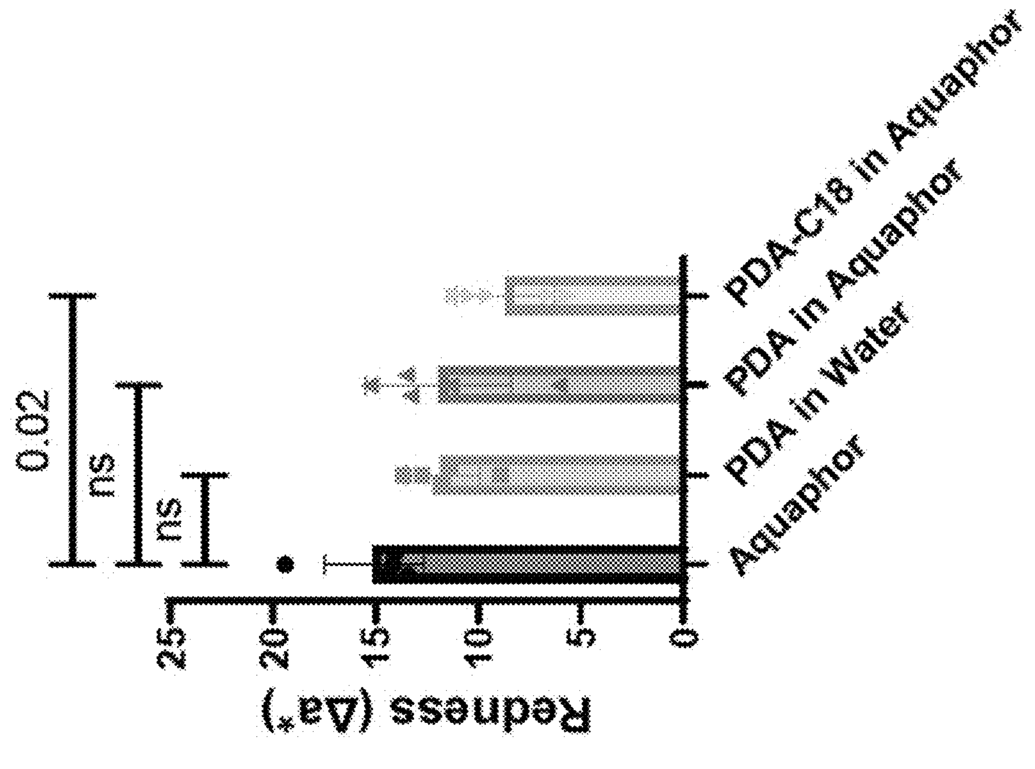
Figure 50A:
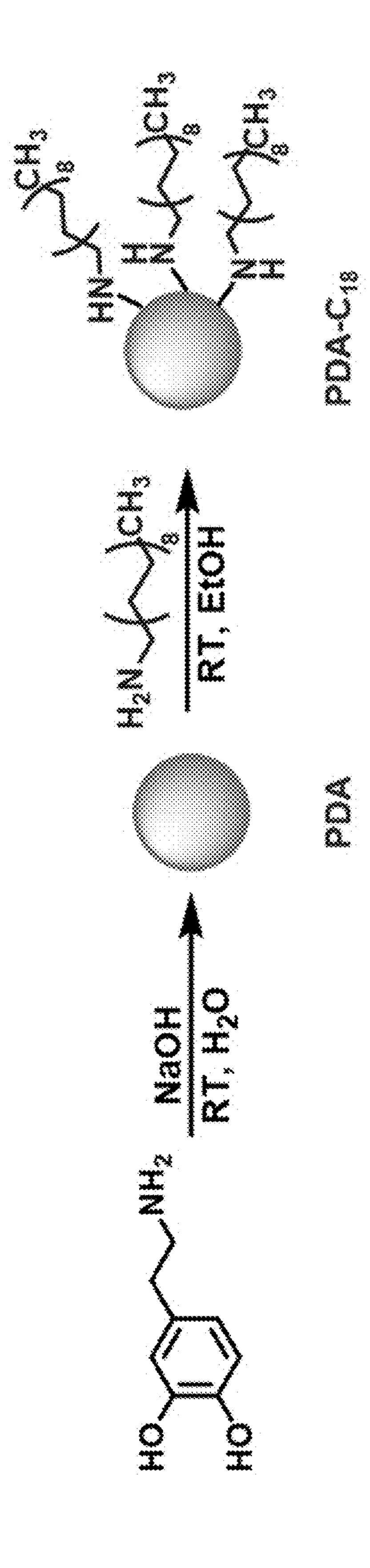
FIGS. 50A-50B: A reaction schematic for forming PDA-$C_{18}$, according to aspects herein.
Figure 50B:
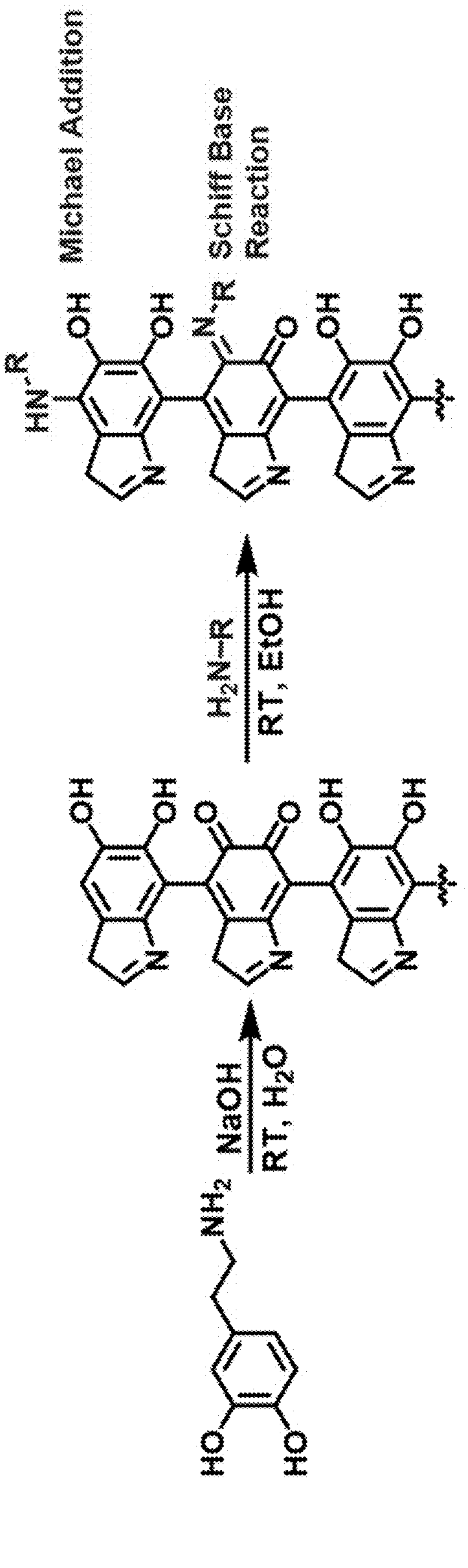
Figure 51A:
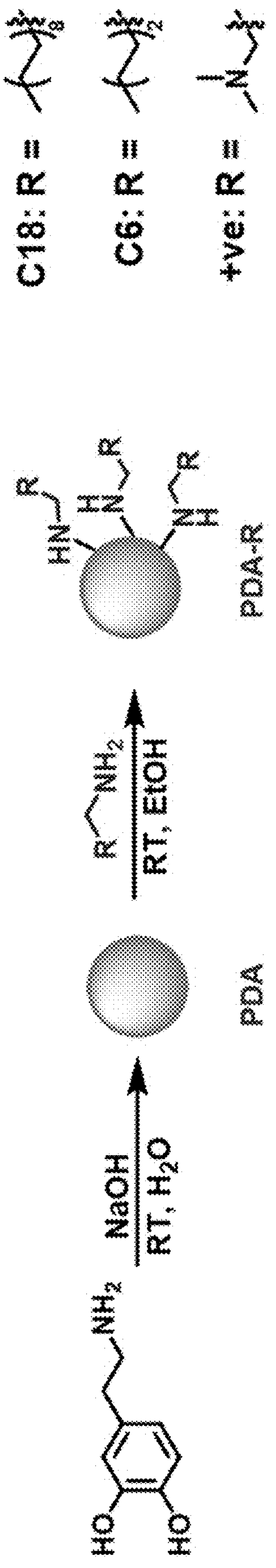
FIGS. 51A-51B: Reaction schemes for forming functionalized artificial PDA nanoparticles (FIG. 51A), according to aspects herein, and for forming functionalized artificial ANP nanoparticles (FIG. 51B), according to aspects herein. As used herein, "ANP" and "AMNP" are equivalent and interchangeable and refer to artificial allomelanin nanoparticles.
Figure 51B:
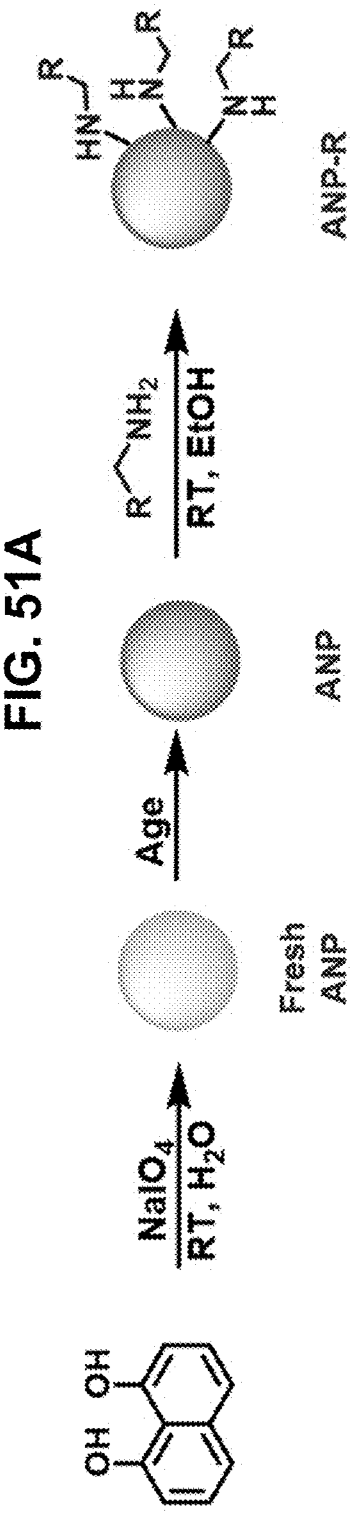
Figure 52:
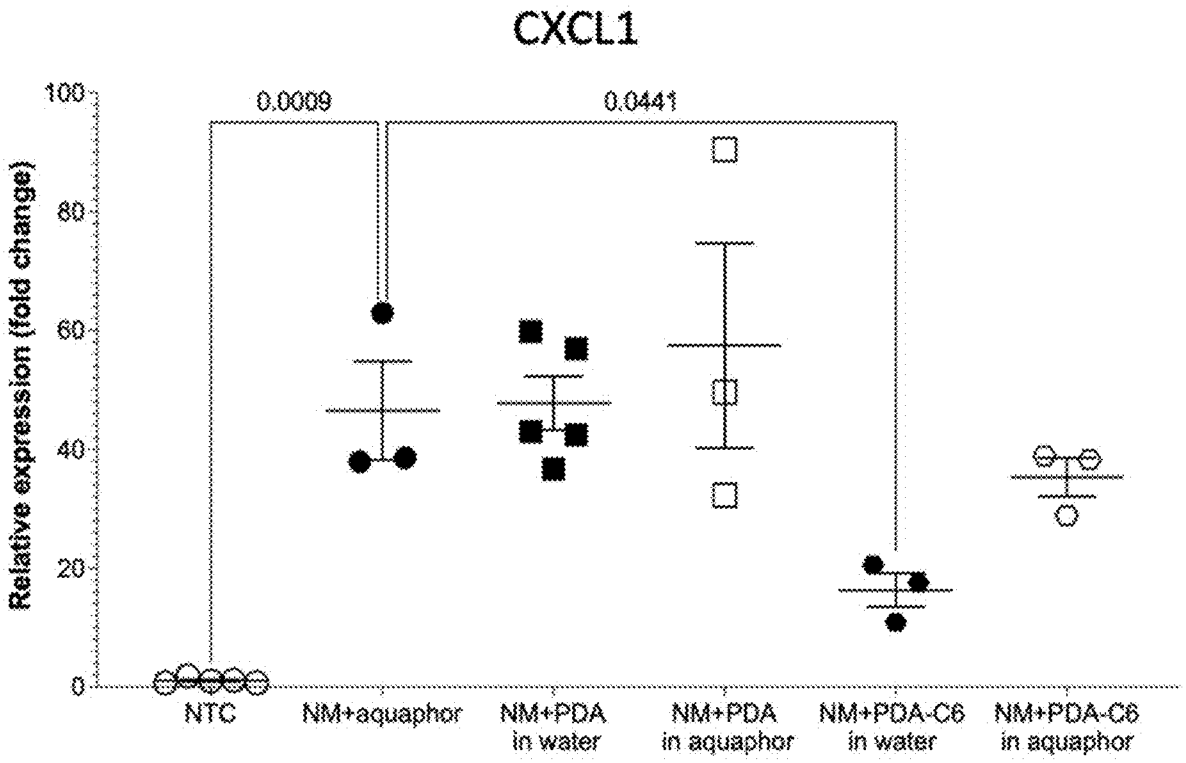
FIG. 52: In vivo in mouse skin injury/chemical burn model. PDA-C6 significantly downregulates a key factor in inflammation and tissue destruction. PDA-C6 is differentiated from PDA in its ability to downregulate CXCL1, a potent cytokine that is a chemotactic signal for recruiting neutrophils (n=3, P, 0.041). Neutrophilic activity is rapid in the skin leading to destruction of surrounding tissue. Intervention with PDA-C6 offers additional benefits in the down selection process.
Figure 53:
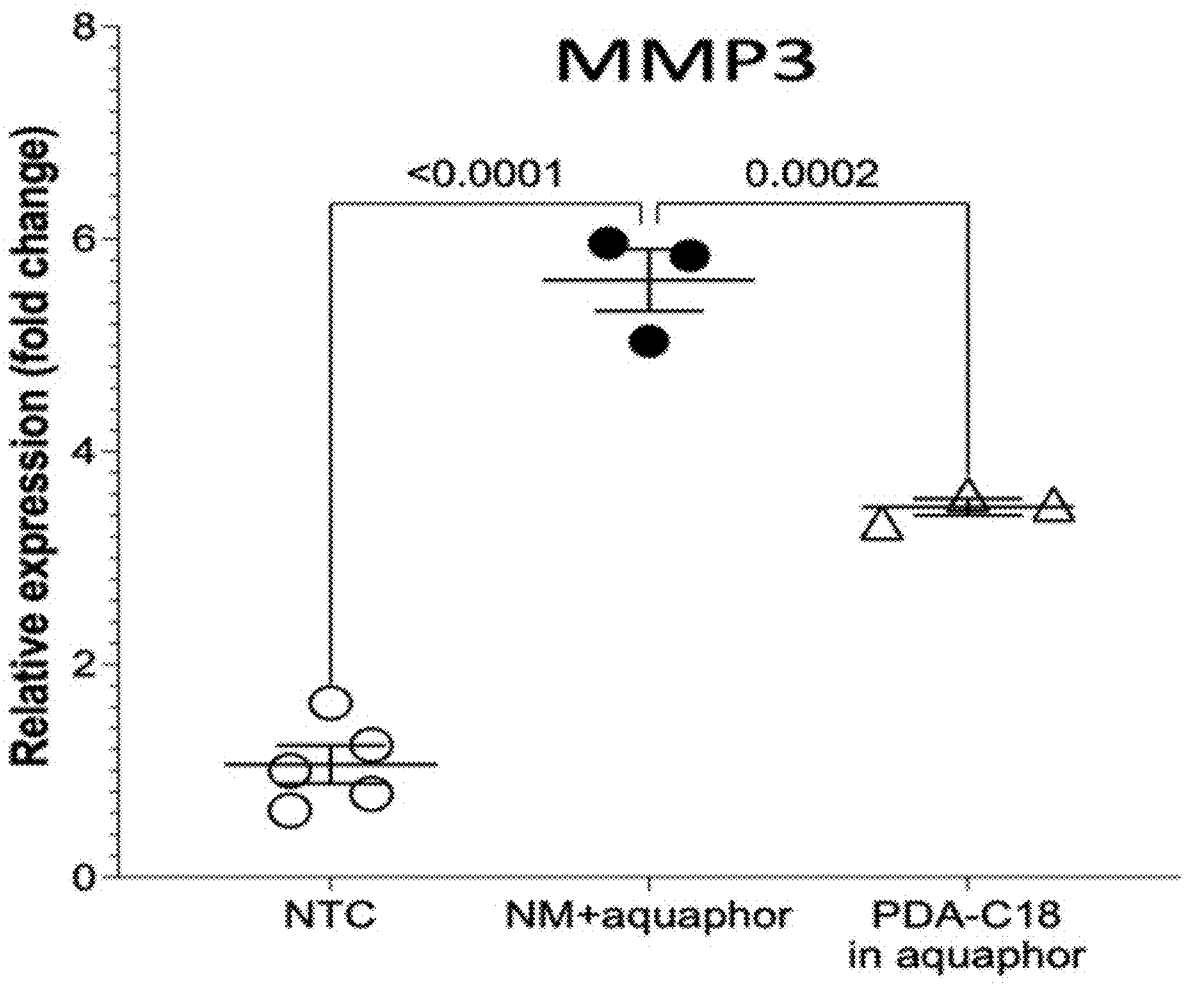
FIG. 53: In vivo in mouse skin injury/chemical burn model. PDA-C18 inhibits a key factor in collagen breakdown which is significant in tissue repair, recover, and scarring. PDA-C18 is special in its ability to suppress MMP3, a matrix metalloproteinase enzyme (n=3, P<0.0002). MMP3 plays a significant role in inflammation mediated collagen degradation of the skin. Downregulation of MMP3 is important for skin recovery, repair, and scarring.
Figure 54A:
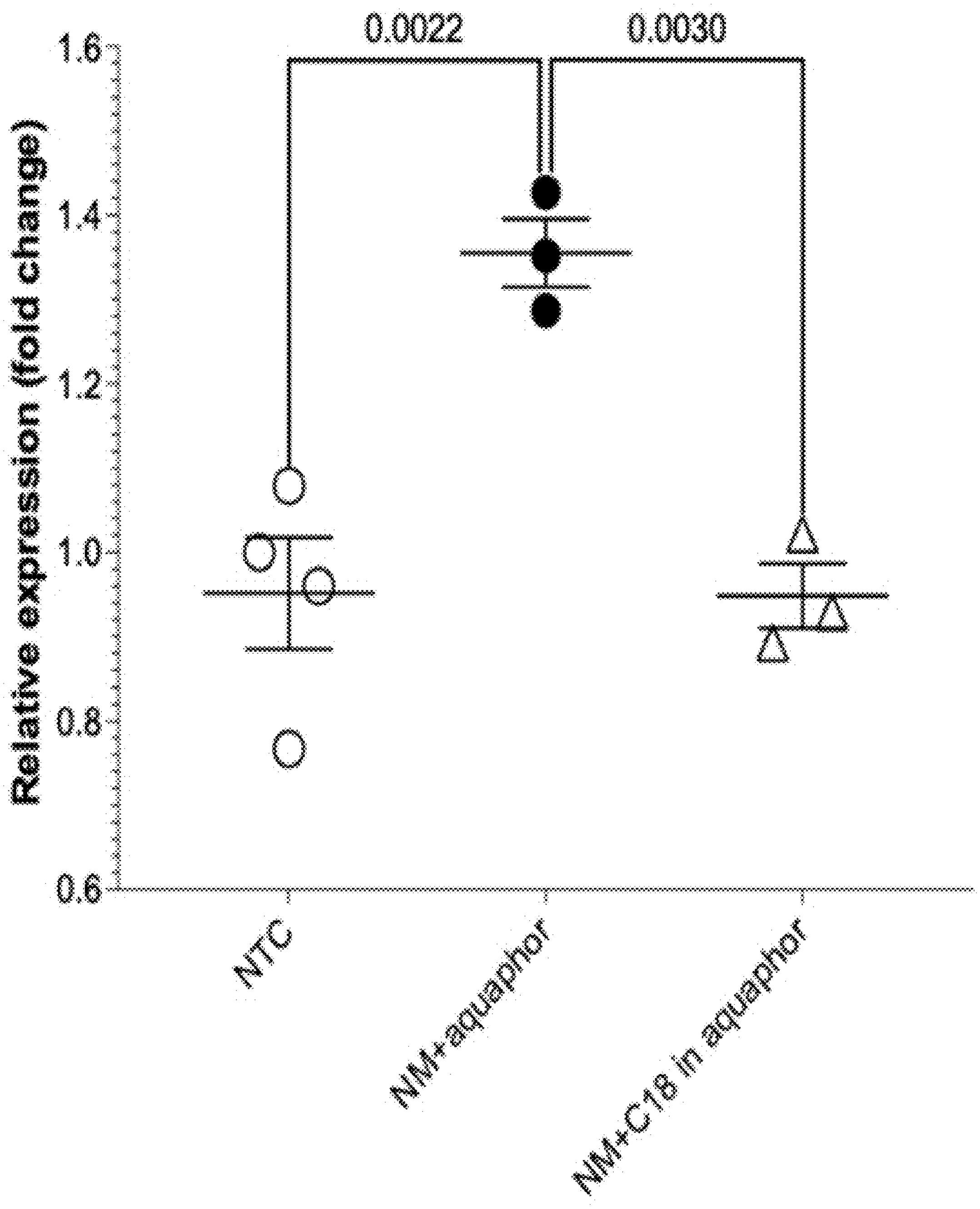
FIGS. 54A-B: In vivo in mouse skin injury/chemical burn model: PDA-C18 and PDA-C6 significantly downregulates gene involved in excess collagen and scarring. Both PDA-C18 and PDA-C6 downregulate Col3a1, the gene that encodes collagen III. Collagen III is significantly increased in hypertrophic scars and even more increased in keloids. PDA-C18 significantly decreased Col3a1 compared to control (n=3, p=0.003). PDA-C6 significantly decreased Col3a1 independent of vehicle-water (n=3, p=0.009) or Aquaphor ointment (n=3, p=0.039). The model involves exposure of animals to a severe blistering dose of nitrogen mustard as a chemical irritant which produces swelling, redness, and scab formation.
Figure 54B:
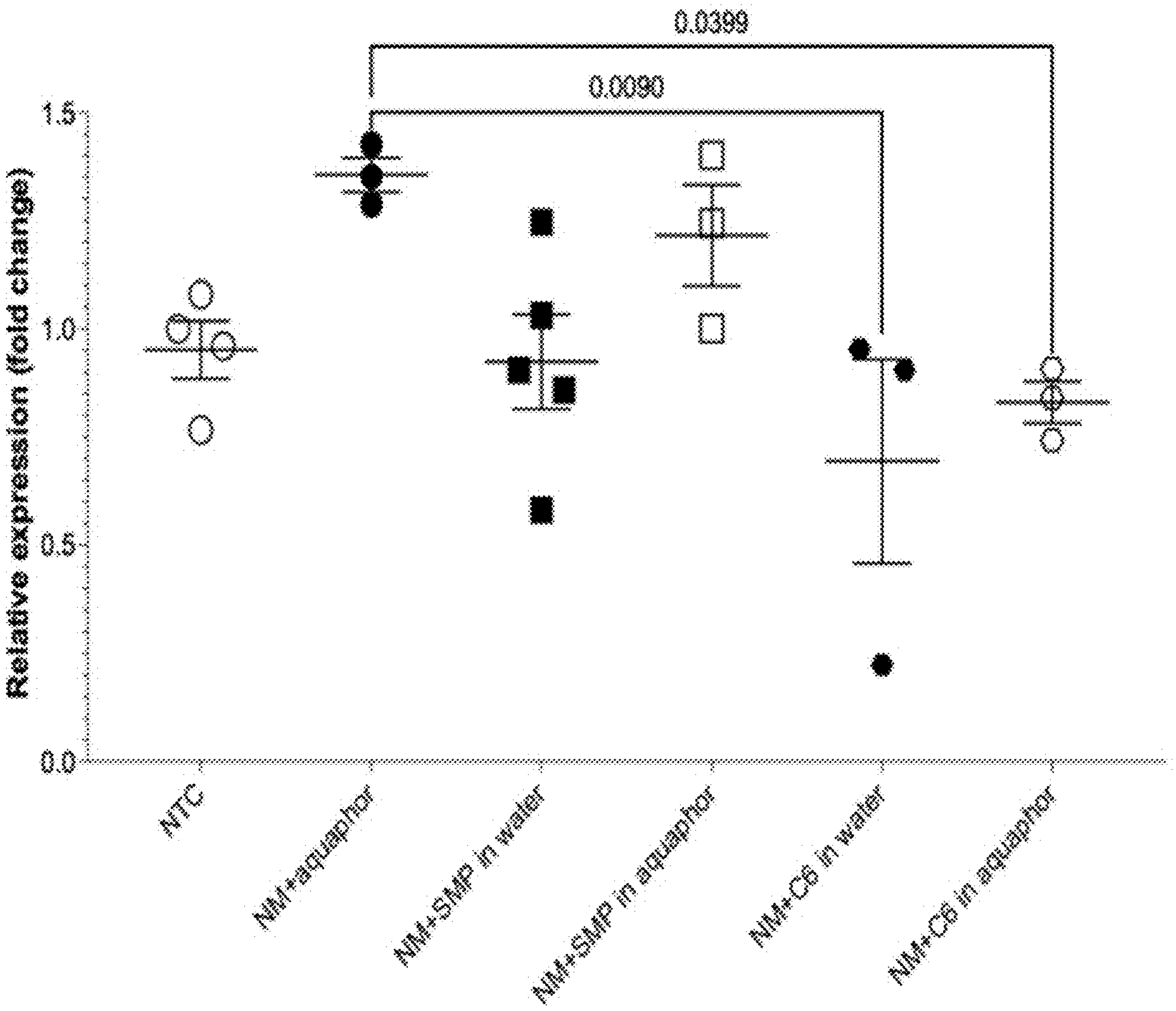
Figure 55:
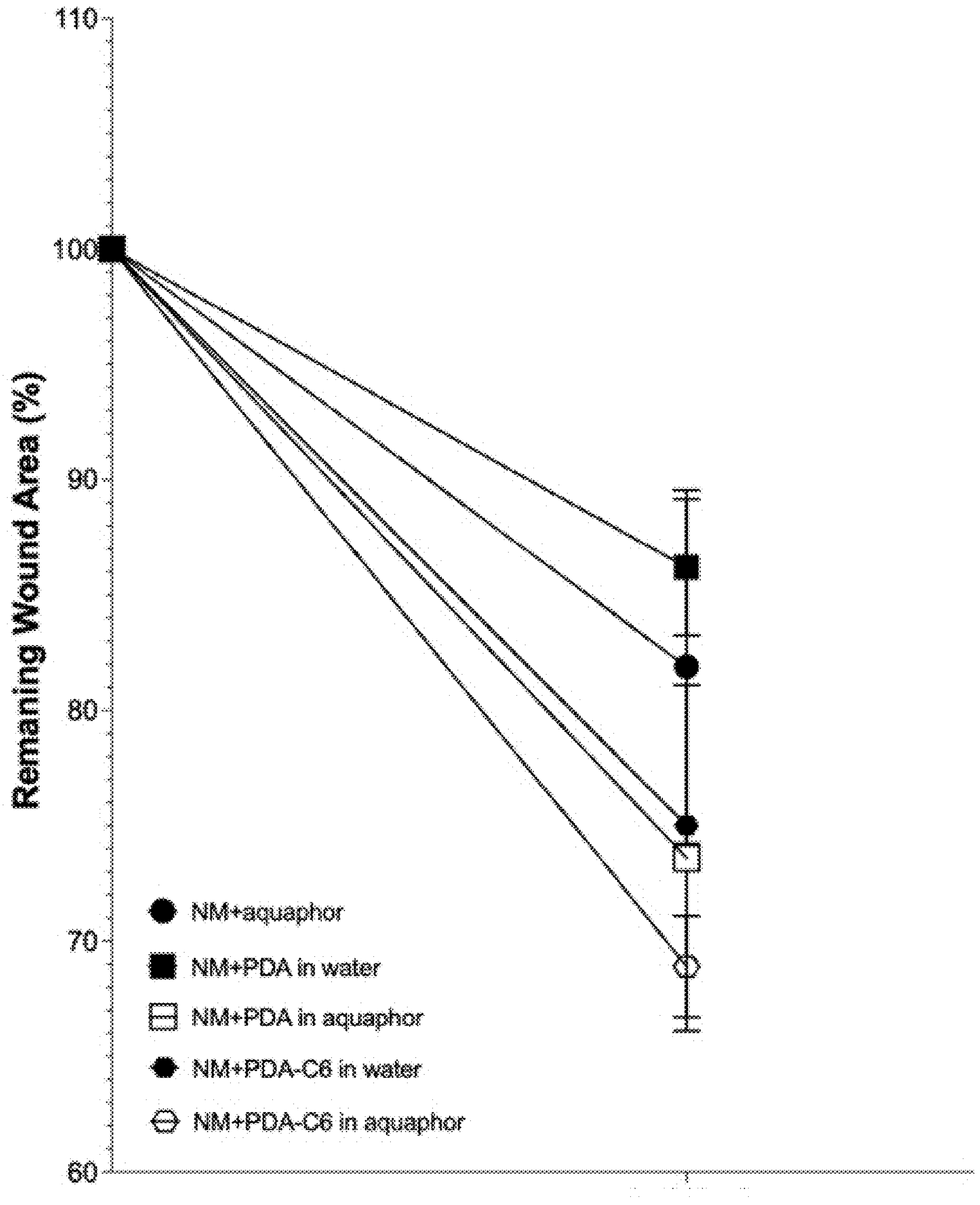
FIG. 55: In vivo in mouse skin injury/chemical burn model: PDA-C6 decreases skin wound size. PDA-C6 in water vehicle and PDA-C6 (n=3, p=0.02) in Aquaphor® ointment decreased wound sizes following a severe burn injury as measured on day 3. The model involves exposure of animals to a severe blistering dose of nitrogen mustard as a chemical irritant which produces swelling, redness, and scab formation. The model involves inducing a burn which is fully established on day 2 with a clear scab. The change from day 2 to 3 is an important early timepoint to observe wound reduction.
Figure 56:
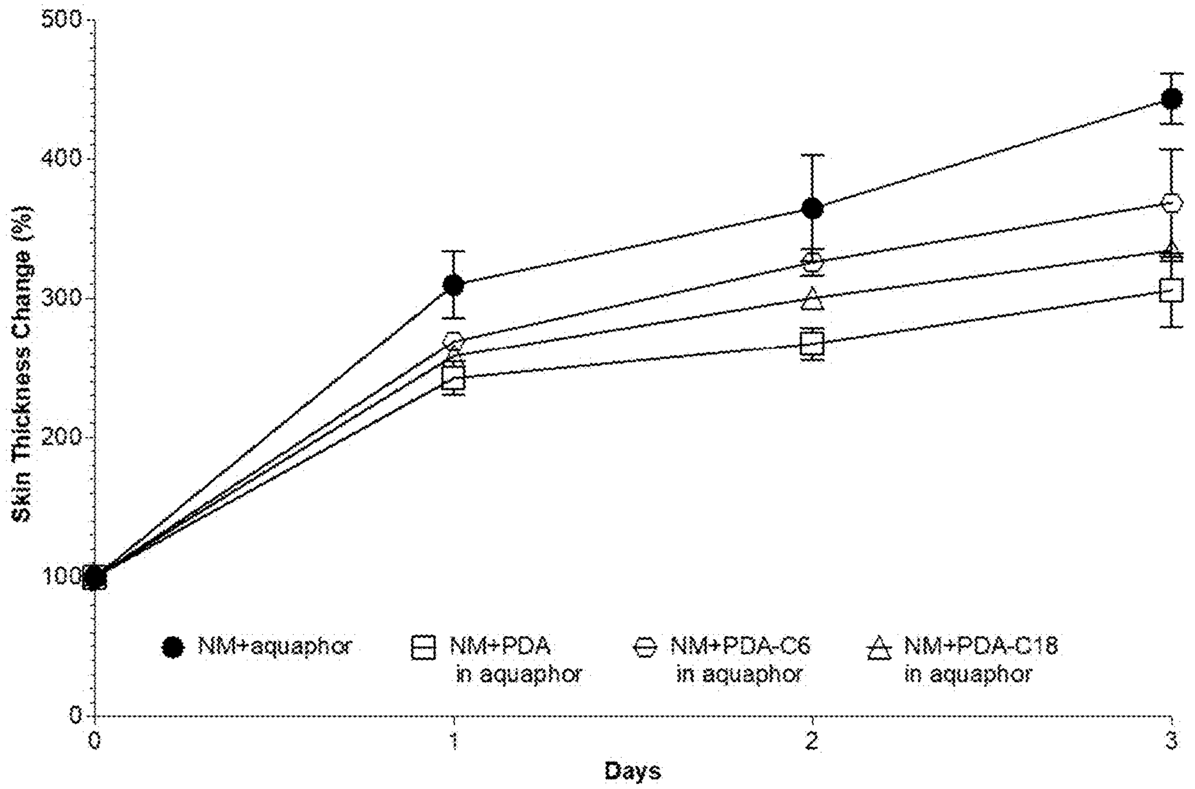
FIG. 56: In vivo in mouse skin injury/chemical burn model: PDA-C18 in Aquaphor® and PDA-C6 in Aquaphor® significantly reduces skin swelling thickness reaction. PDA-C6 and PDA-C18 significantly decreased skin thickness by day 3 following the initiation of the wound. The model involves exposure of animals to a severe blistering dose of nitrogen mustard as a chemical irritant which produces swelling, redness, and scab formation. Notes: PDA-C6 in Aquaphor® vs. control (n=3, p=0.03); PDA-C18 in Aquaphor® vs. control (n=3, p<0.01); PDA in Aquaphor® vs. control (n=3, p<0.01).
Figure 57:
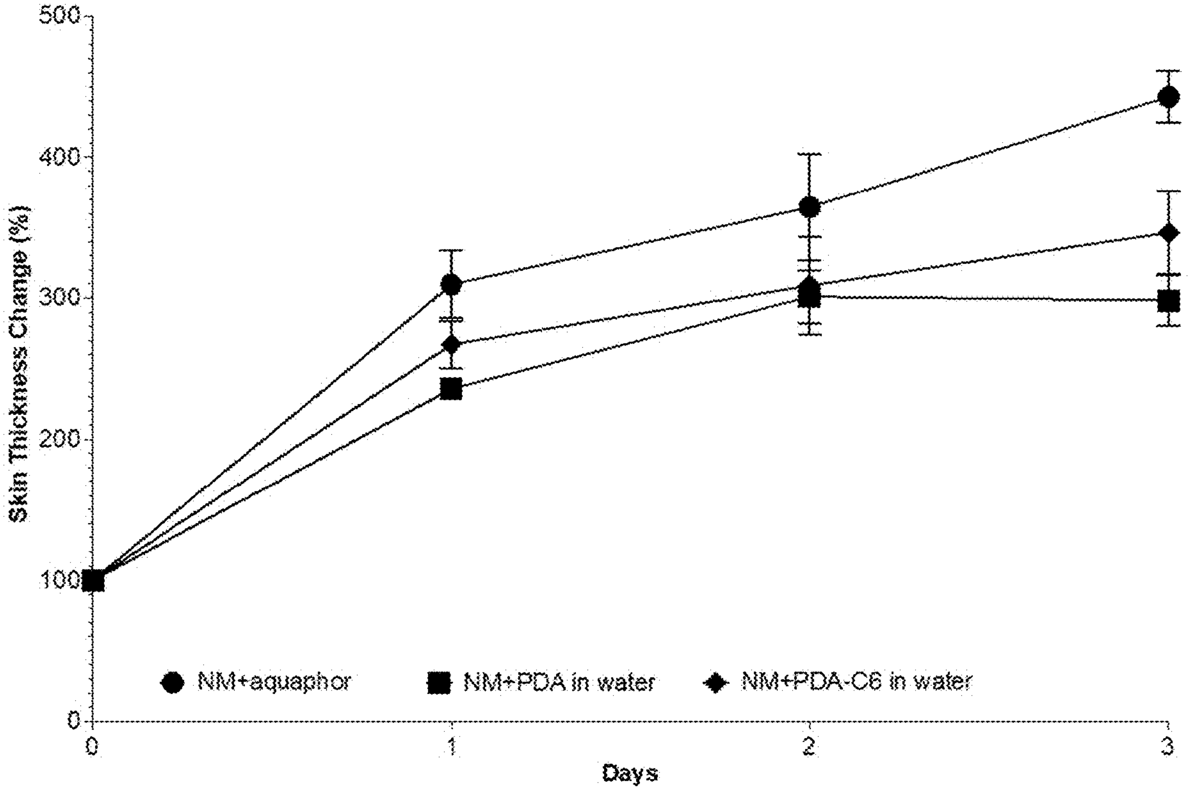
FIG. 57: In vivo in mouse skin injury/chemical burn model: PDA-C6 in water-based vehicle significantly reduces skin swelling thickness reaction. PDA-C6 in water significantly decreased skin thickness by day 3 following the initiation of the wound. The model involves exposure of animals to a severe blistering dose of nitrogen mustard as a chemical irritant which produces swelling, redness, and scab formation. Note: PDA-C6 in water vs. control (n=3, p=0.01)
Figure 58:
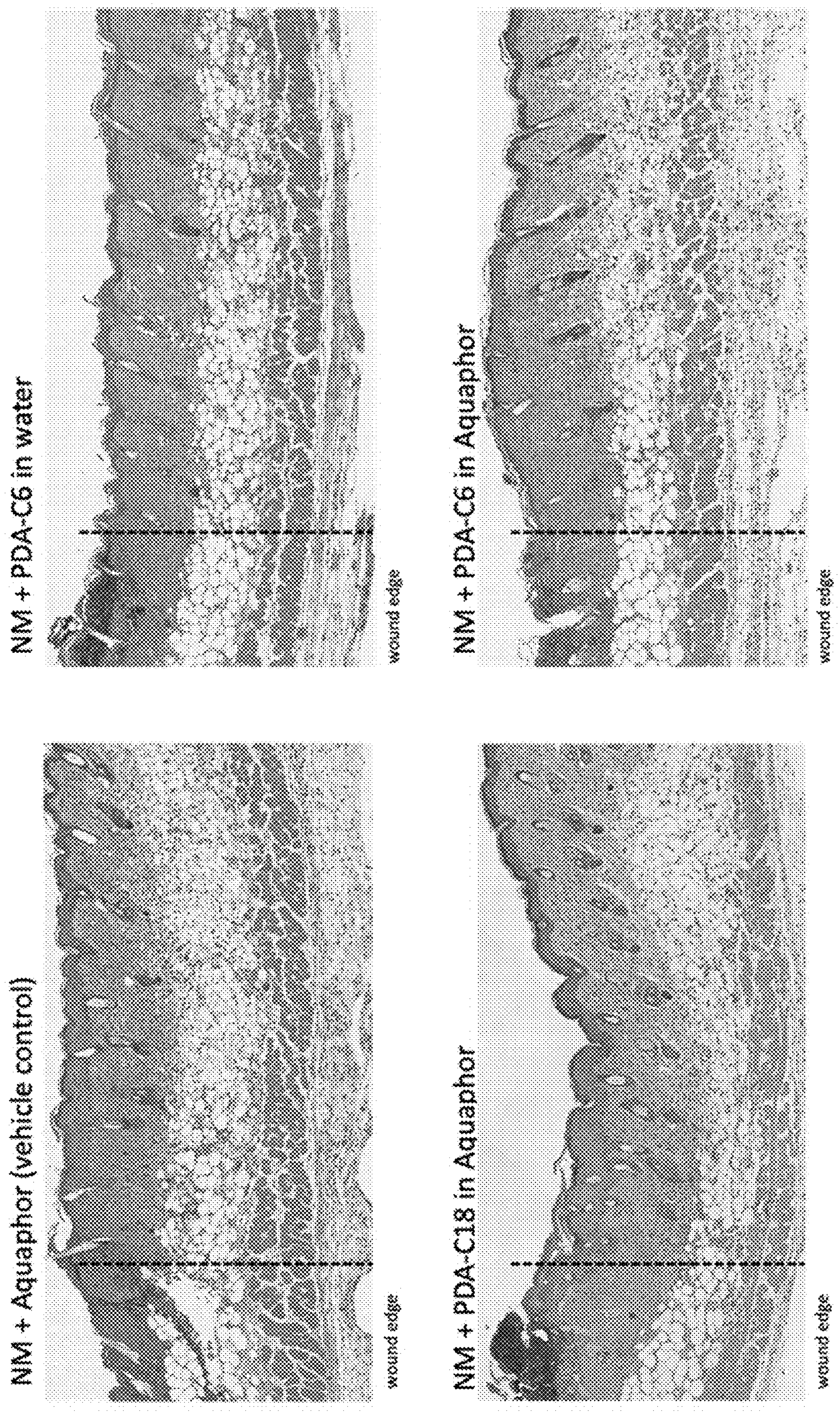
FIG. 58: In vivo in mouse skin injury/chemical burn model: PDA-C18 and PDA-C6 tissue histology shows less skin tissue swelling and degree of inflammatory cells. In this model mice are to a severe blistering dose of nitrogen mustard (NM) as a chemical irritant which produces swelling, redness, and scab formation. On day 3 animals are sacrificed and the skin is harvested. Shown here are hematoxylin & eosin stain. The histology shows that with NM exposure there is significant increase in inflammatory cells in all layers of the skin, skin swelling, reactive hyperplasia. Intervention with PDA-C6 in water, PDA-C6 in Aquaphor®, or PDA-C18 in Aquaphor® demonstrate decrease in inflammatory cell infiltrates, less reactive hyperplasia, and tissue edema. All images are full scan with orientation of wound edge on the left.
Figure 59A:
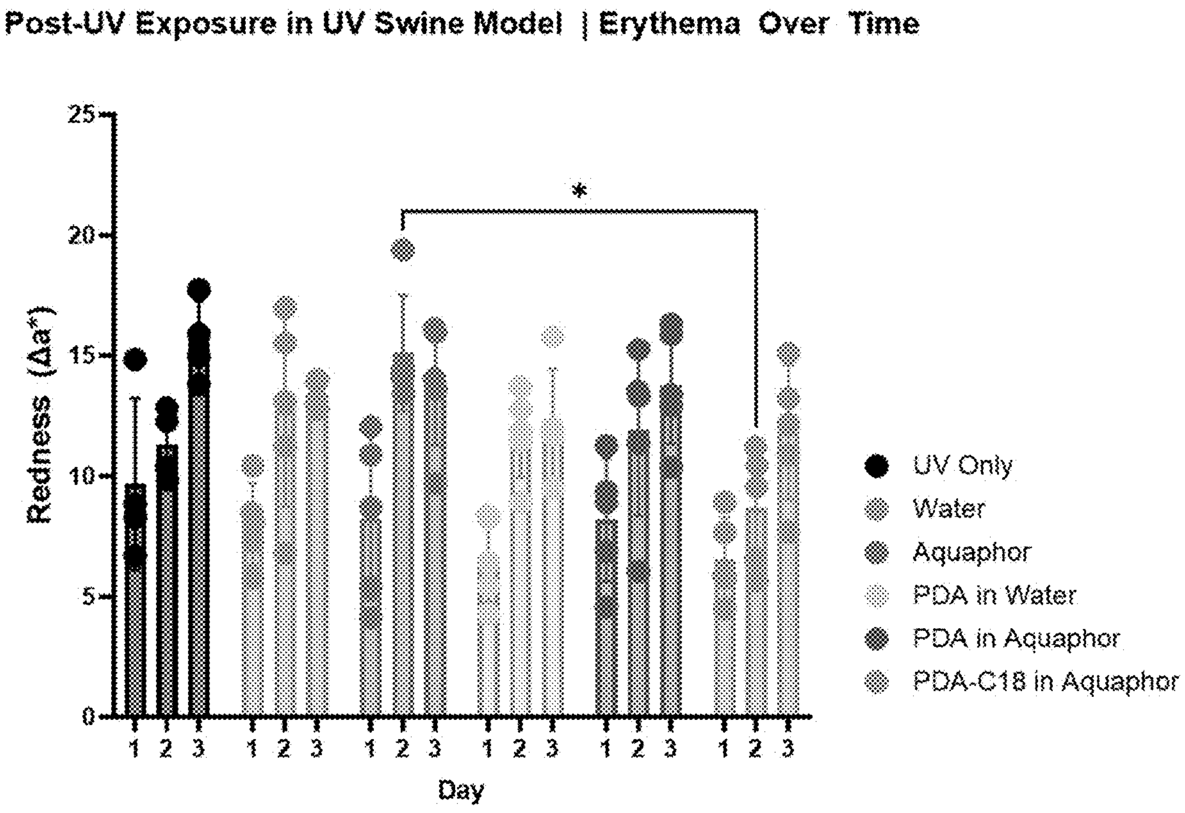
FIGS. 59A-B: Inflammation of skin directly correlates to the amount of inflammation in skin. In the Post-UV exposure condition (FIG. 59A), topical application of 2% w/w PDA-C18 in Aquaphor® yielded decreased rate of redness over the course of the experimental period and also demonstrated significance in decreased redness compared to the vehicle control. In the prophylaxis case (FIG. 59B), 2% w/w PDA-C18 behaves like a sunscreen and performs similarly to the control sunscreen (SPF 60) in that it was successful in preventing UV-B induced damage. This is corroborated through analysis of the histology samples as shown in FIGS. 60A-C, where prophylactic application of PDA-C18 results in healthy-looking skin.
Figure 59B:
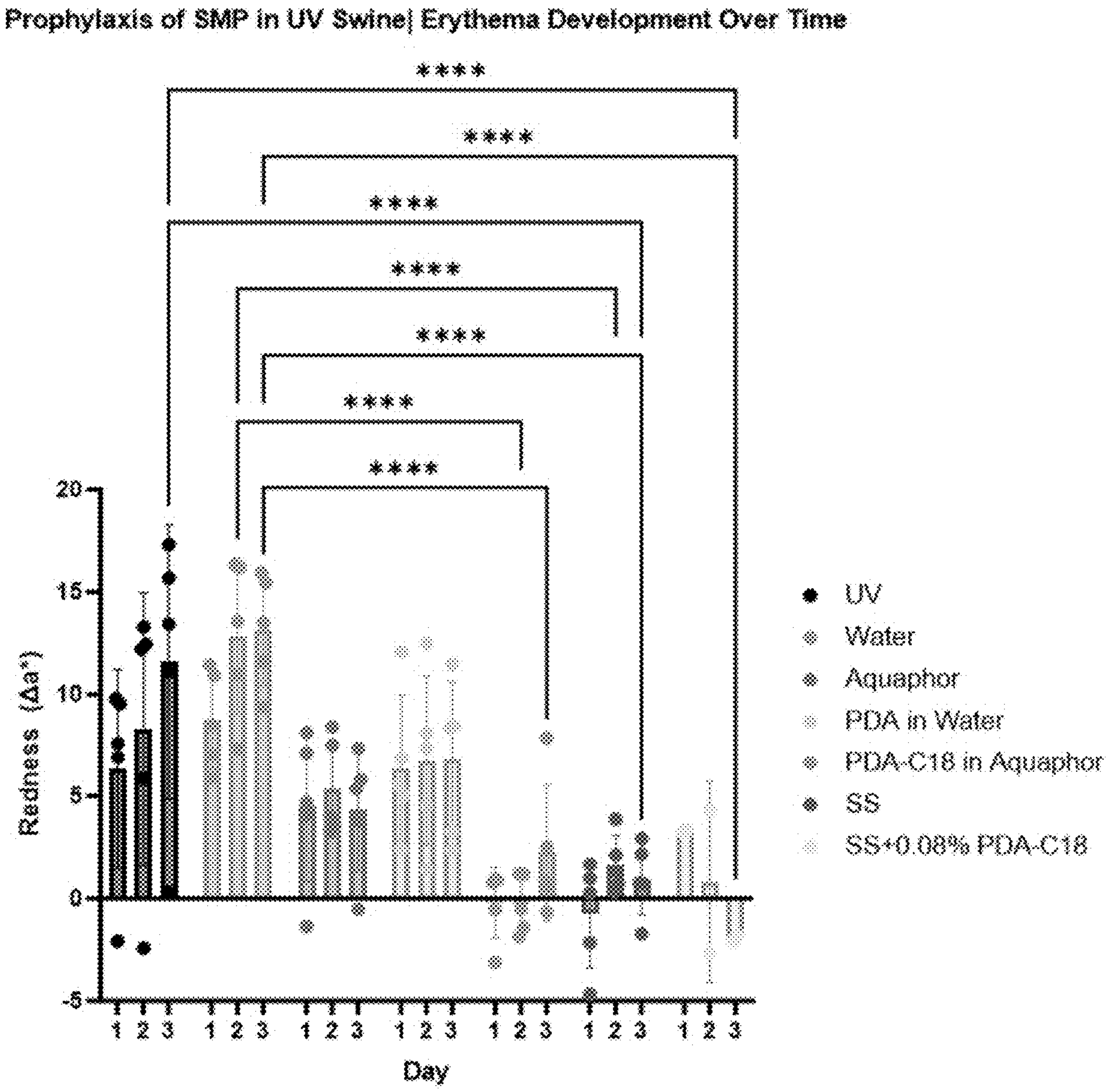
Figure 60A:
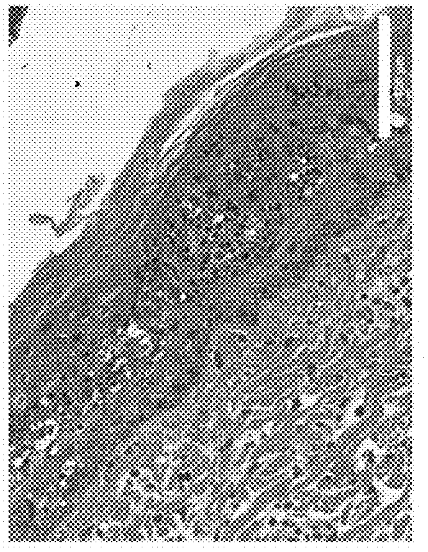
FIGS. 60A-C: Histology showing skin after UV-exposure without treatment or protection (FIG. 60A), skin with PDA-C18 in Aquaphor® (FIG. 60B), and skin with sunscreen (FIG. 60C).
Figure 60B:
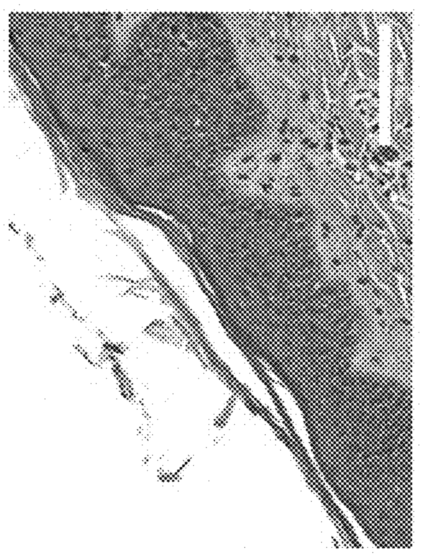
Figure 60C:

Inflammation of skin directly correlates to the amount of inflammation in skin.[1] In the Post-UV exposure condition (FIG. 59A), topical application of 2% w/w PDA-C18 in Aquaphor yielded decreased rate of redness over the course of the experimental period and also demonstrated significance in decreased redness compared to the vehicle control. In the prophylaxis case (FIG. 59B), 2% w/w PDA-C18 behaves like a sunscreen and performs similarly to the control sunscreen (SPF 60) in that it was successful in preventing UV-B induced damage. This is corroborated through analysis of the histology samples (FIGS. 60A-C), where prophylactic application of PDA-C18 results in healthy-looking skin. See also FIGS. 49A-49B.

TABLE 5

Samples Used in Prophylaxis in UV Swine Study:

| | Sample |
|---|---|
| 1 | UV |
| 2 | Water |
| 3 | Aquaphor |
| 4 | 2% w/w PDA in Water |
| 5 | 2% w/w PDA in Aquaphor |
| 6 | 2% w/w PDA-C18 in Aquaphor |
| 7 | Sunscreen (La Roche Posay Melt-in-Milk SPF 60 |
| 8 | Sunscreen + 0.08% w/w PDA-C18 |

TABLE 6

Samples Used in Post-UV Exposure in UV Swine Study:

| | Sample |
|---|---|
| 1 | UV |
| 2 | Water |
| 3 | Aquaphor |
| 4 | 2% w/w PDA in Water |
| 5 | 2% w/w PDA in Aquaphor |
| 6 | 2% w/w PDA-C18 in Aquaphor |
| 7 | Sunscreen (La Roche Posay Melt-in-Milk SPF 60 |
| 8 | Sunscreen + 0.08% w/w PDA-C18 |

Reference 1: Frew, J.; Penzi, L.; Suarez-Farinas, M.; Garcet, S.; Brunner, P. M.; Czarnowicki, T.; Kim, J.; Bottomley, C.; Finney, R.; Cueto, I.; Fuentes-Duculan, J.; Ohmatsu, H.; Lentini, T.; Yanofsky, V.; Krueger, J. G.; Guttman-Yassky, E.; Gareau, D., The erythema Q-score, an imaging biomarker for redness in skin inflammation. *Experimental Dermatology* 2021, 30 (3), 377-383.

Example 12

Porous PDA was prepared based on a reported literature method.[20] 250 mg of MS was sonicated for 1 h in ultrapure water. To 225 mL of ultrapure water and 25 mL of ethanol (9:1 H2O:EtOH by volume), 250 mg MS and 225 mg dopamine was added and stirred for 1 h at room temperature. Tris (10 mM, pH 8.5) was then added to the reaction and stirred for an additional 4 h. After the allotted time the reaction was centrifuged and washed with ultrapure water 5 times. The template was removed through a hydrofluoric acid (10 wt %) etch overnight, and then centrifuged and washed with ultrapure water 5 times.

Example 13

Solid PDA was synthesized through the oxidative polymerization of dopamine. Briefly, 900 mg of dopamine was dissolved in 300 mL of ultrapure water and 4 mL of 1 M NaOH was added to the solution at room temperature and stirred for 18 h. The solution was then centrifuged and washed with ultrapure water 5 times.

Example 14

DPPH radical scavenging activity of artificial melanin nanoparticles was determined according to a reported literature method (Ju, K.-Y.; Lee, Y.; Lee, S.; Park, S. B.; Lee, J.-K., Bioinspired Polymerization of Dopamine to Generate Melanin-Like Nanoparticles Having an Excellent Free-Radical-Scavenging Property. *Biomacromolecules* 2011, 12

(3), 625-632). 100 μL of artificial melanin nanoparticles dispersed in water was added to an 1.8 mL solution of DPPH (0.2 mM in 95% ethanol). The total amount of artificial melanin nanoparticles was varied from 5 to 200 μg. The solutions were left in the dark for 20 min. Afterwards the scavenging activity was monitored by taking the absorbance of the solutions at 516 nm. To determine the DPPH radical scavenging activity the following calculation (Eq. 1) was used.

$$I = \frac{1-(A_i - A_j)}{A_c} \times 100\% \quad \text{Eq. 1}$$

l is the DPPH radical scavenging activity, $A_i$ is the absorbance of the samples with DPPH, $A_j$ is the absorbance of the samples without DPPH, and $A_c$ is the absorbance of the DPPH without the melanin nanoparticle samples.

Example 15

Nitrogen Isotherms were collected on a Micromeritics TriStar physisorption instrument at 77 K.

Example 16

Nitrogen physisorption measurements were collected using a Micromeritics ASAP 2020 instrument at 77 K. Pore-size distributions were obtained using density functional theory (DFT) calculations with a carbon slit geometry and a $N_2$ DFT model.

Example 17

Nitrogen Mustard Skin Injury Model: In some aspects, the dorsal area of the mice was shaved and chemically depilated 48 hours before skin injury induction. Mice were anesthetized and placed on a heat pad under a chemical fume hood. 0.5% of mechloroethamine hydrochloride (nitrogen mustard, NM) (Sigma, 122564) solution in 1.5% DMSO-PBS was prepared immediately before the application. Total of 40 μl of NM solution was applied on a circular (12 mm diameter) area in two consecutive applications. After the application mice were placed in a temporary housing space under a chemical fume hood for two hours.

Example 18

UV Radiation Skin Injury Model: In some aspects, Mice were exposed to UV radiation as described previously [X]. Briefly, a 12 mm diameter circular area of back skin depilated of hair was exposed to UVB irradiation from six FS-40 fluorescent lamps filtered through Kodacel (Eastman Kodak Co., Rochester, NY). UVB emission was measured with an IL-443 phototherapy radiometer (International Light, Newburyport, MA) furnished with an IL SED 240 detector. Mice were exposed to a single UVB dose of 100 $mJ/cm^2$ to induce skin inflammation.

Example 19

Monitoring Skin Injury and Measurement of Wound Healing: In some aspects, mice were followed up non-invasively after induction of skin injury. Monitoring was performed daily, starting at the day of skin injury. Photographs of the injured area were taken, the bi-fold skin thickness of the injured area was measured using a digital calipers (Mitutoyo, PK0505CPX), and weight was measured. The area of the inflammation/wound was measured using Image J and QuPath software.

STATEMENTS REGARDING INCORPORATION BY REFERENCE AND VARIATIONS

All references throughout this application, for example patent documents including issued or granted patents or equivalents; patent application publications; and non-patent literature documents or other source material; are hereby incorporated by reference herein in their entireties, as though individually incorporated by reference, to the extent each reference is at least partially not inconsistent with the disclosure in this application (for example, a reference that is partially inconsistent is incorporated by reference except for the partially inconsistent portion of the reference).

The terms and expressions which have been employed herein are used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments, exemplary embodiments and optional features, modification and variation of the concepts herein disclosed may be resorted to by those skilled in the art, and that such modifications and variations are considered to be within the scope of this invention as defined by the appended claims. The specific embodiments provided herein are examples of useful embodiments of the present invention and it will be apparent to one skilled in the art that the present invention may be carried out using a large number of variations of the devices, device components, methods steps set forth in the present description. As will be obvious to one of skill in the art, methods and devices useful for the present methods can include a large number of optional composition and processing elements and steps.

As used herein and in the appended claims, the singular forms "a", "an", and "the" include plural reference unless the context clearly dictates otherwise. Thus, for example, reference to "a cell" includes a plurality of such cells and equivalents thereof known to those skilled in the art. As well, the terms "a" (or "an"), "one or more" and "at least one" can be used interchangeably herein. It is also to be noted that the terms "comprising", "including", and "having" can be used interchangeably. The expression "of any of claims XX—YY" (wherein XX and YY refer to claim numbers) is intended to provide a multiple dependent claim in the alternative form, and in some embodiments is interchangeable with the expression "as in any one of claims XX—YY."

When a group of substituents is disclosed herein, it is understood that all individual members of that group and all subgroups, including any isomers, enantiomers, and diastereomers of the group members, are disclosed separately. When a Markush group or other grouping is used herein, all individual members of the group and all combinations and subcombinations possible of the group are intended to be individually included in the disclosure. When a compound is described herein such that a particular isomer, enantiomer or diastereomer of the compound is not specified, for example, in a formula or in a chemical name, that description is intended to include each isomers and enantiomer of the compound described individual or in any combination. Additionally, unless otherwise specified, all isotopic variants of compounds disclosed herein are intended to be encompassed by the disclosure. For example, it will be understood that any one or more hydrogens in a molecule disclosed can be replaced with deuterium or tritium. Isotopic variants of a molecule are generally useful as standards in assays for the molecule and in chemical and biological research related to the molecule or its use. Methods for making such isotopic variants are known in the art. Specific names of compounds are intended to be exemplary, as it is known that one of ordinary skill in the art can name the same compounds differently.

Certain molecules disclosed herein may contain one or more ionizable groups [groups from which a proton can be removed (e.g., —COOH) or added (e.g., amines) or which can be quaternized (e.g., amines)]. All possible ionic forms of such molecules and salts thereof are intended to be included individually in the disclosure herein. With regard to salts of the compounds herein, one of ordinary skill in the art can select from among a wide variety of available counterions those that are appropriate for preparation of salts of this invention for a given application. In specific applications, the selection of a given anion or cation for preparation of a salt may result in increased or decreased solubility of that salt.

Every system, composition, formulation, combination of components, step, and method described or exemplified herein can be used to practice the invention, unless otherwise stated.

Whenever a range is given in the specification, for example, a temperature range, a time range, or a composition or concentration range, all intermediate ranges and subranges, as well as all individual values included in the ranges given are intended to be included in the disclosure. It will be understood that any subranges or individual values in a range or subrange that are included in the description herein can be excluded from the claims herein.

All patents and publications mentioned in the specification are indicative of the levels of skill of those skilled in the art to which the invention pertains. References cited herein are incorporated by reference herein in their entirety to indicate the state of the art as of their publication or filing date and it is intended that this information can be employed herein, if needed, to exclude specific embodiments that are in the prior art. For example, when composition of matter are claimed, it should be understood that compounds known and available in the art prior to Applicant's invention, including compounds for which an enabling disclosure is provided in the references cited herein, are not intended to be included in the composition of matter claims herein.

As used herein, "comprising" is synonymous with "including," "containing," or "characterized by," and is inclusive or open-ended and does not exclude additional, unrecited elements or method steps. As used herein, "consisting of" excludes any element, step, or ingredient not specified in the claim element. As used herein, "consisting essentially of" does not exclude materials or steps that do not materially affect the basic and novel characteristics of the claim. In each instance herein any of the terms "comprising", "consisting essentially of" and "consisting of" may be replaced with either of the other two terms. The invention illustratively described herein suitably may be practiced in the absence of any element or elements, limitation or limitations which is not specifically disclosed herein.

One of ordinary skill in the art will appreciate that starting materials, biological materials, reagents, synthetic methods, purification methods, analytical methods, assay methods, and biological methods other than those specifically exemplified can be employed in the practice of the invention without resort to undue experimentation. All art-known functional equivalents, of any such materials and methods are intended to be included in this invention. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

We claim:

1. A functionalized artificial melanin material comprising:

a surface functionalized with a modifier agent via a linker group;

wherein the modifier agent comprises the linker group and a functional group attached to the linker group;

wherein the linker group is a nucleophilic group;

functionalized artificial melanin nanoparticles, wherein each functionalized artificial melanin nanoparticle independently comprises a surface functionalized with the modifier agent via the linker group; and wherein the functionalized artificial melanin material or each of the functionalized artificial melanin nanoparticles thereof is characterized as eumelanin, pheomelanin, allomelanin, or a combination of these.

2. A functionalized artificial melanin material comprising:

a surface functionalized with a modifier agent via a linker group;

wherein the modifier agent comprises the linker group and a functional group attached to the linker group;

wherein the linker group is a nucleophilic group;

functionalized artificial melanin nanoparticles, wherein each functionalized artificial melanin nanoparticle independently comprises a surface functionalized with the modifier agent via the linker group; and wherein the functionalized artificial melanin material comprises artificial allomelanin nanoparticles.

3. The material of claim 1, wherein the linker group is an amine group, a thiol group, or any combination thereof.

4. The material of claim 1, wherein the functional group is hydrophobic or lends hydrophobicity to the functionalized artificial melanin material or to functionalized artificial melanin nanoparticles thereof.

5. The material of claim 1, wherein:

the functionalized artificial melanin material is hydrophobic;

the functionalized artificial melanin material forms a stable colloid in a non-aqueous hydrophobic solvent at a concentration of said material selected from the range of 0.5 mg/mL to 100 mg/ml;

the functionalized artificial melanin material or the functionalized artificial melanin nanoparticles thereof have a zeta potential greater than or equal to −20 mV when dispersed in water or a non-aqueous hydrophobic solvent at a concentration selected from the range of 0.5 mg/ml to 100 mg/mL.

6. The material of claim 1, wherein a dispersion or formulation having said functionalized artificial melanin material or the functionalized artificial melanin nanoparticles thereof at a concentration selected from the range of 0.5 mg/ml to 100 mg/mL is characterized by a contact angle of at least 90°.

7. The material of claim 1, wherein the modifier agent is characterized by formula FX2A or FX2B:

(FX2A)

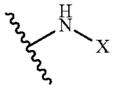

or (FX2B)

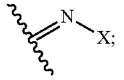

wherein X is the functional group.

8. The material of claim 1, wherein each linker group is independently attached to a phenyl group or a quinone of the artificial melanin material or of a respective artificial melanin nanoparticle.

9. The material of claim 1, wherein the modifier agent attached to the artificial melanin material or to the respective functionalized artificial melanin nanoparticle is a product of a Michael Addition or via a Schiff Base reaction.

10. The material of claim 1, wherein the linker group of the modifier agent is attached at an outer surface of the functionalized artificial melanin material or of the functionalized artificial melanin nanoparticles thereof, is attached at an inner pore surface of the functionalized artificial melanin material or of the functionalized artificial melanin nanoparticles thereof, or both.

11. The material of claim 1, wherein the functionalized artificial melanin material or at least a portion of the functionalized artificial melanin nanoparticles thereof comprise at least two different modifier agents.

12. The material of claim 1, wherein the artificial melanin material comprises at least 5% by mass of the modifier agent.

13. The material of claim 1, wherein the functional group is selected from the group consisting of a substituted or unsubstituted $C_4$-$C_{30}$ hydrocarbyl group, a substituted or unsubstituted $C_4$-$C_{30}$ alkyl group, a substituted or unsubstituted $C_4$-$C_{30}$ cycloalkyl group, a substituted or unsubstituted $C_4$-$C_{30}$ aryl group, a substituted or unsubstituted $C_4$-$C_{30}$ heteroaryl group, a substituted or unsubstituted $C_4$-$C_{30}$ acyl group, a substituted or unsubstituted $C_4$-$C_{30}$ alkoxy group, a substituted or unsubstituted $C_4$-$C_{30}$ alkenyl group, a substituted or unsubstituted $C_4$-$C_{30}$ alkynyl group, a substituted or unsubstituted $C_4$-$C_{30}$ alkylaryl group, a substituted or unsubstituted hydroxyl group, a substituted or unsubstituted carbonyl group, a substituted or unsubstituted sulfide group, a substituted or unsubstituted thiol group, a substituted or unsubstituted phosphate group, a substituted or unsubstituted azo group, a substituted or unsubstituted cyanate group, a substituted or unsubstituted primary amine group, a substituted or unsubstituted secondary amine group, a substituted or unsubstituted tertiary group, a substituted or unsubstituted imine group, a substituted or unsubstituted nitrile group, a substituted or unsubstituted pyridinyl group, a substituted or unsubstituted diamine group, a substituted or unsubstituted triamine group, a substituted or unsubstituted azide group, a substituted or unsubstituted diimine group, a substituted or unsubstituted triimine group, a substituted or unsubstituted amide group, a substituted or unsubstituted diimide group, a substituted or unsubstituted ether group, and any combination thereof.

14. The material of claim 1, wherein each modifier agent is independently selected from the group consisting of 1-hexylamine, 3,3-dimethylbutylamine, octadecylamine, 5-amino-1-pentanol, t-butylamine, 10-amino-1-decanol, 1,6-hexanediamine, and 2,2,3,3,4,4,5,5,6,6,7,7,8,8,9,9,9-heptadecafluorononylamine.

15. A functionalized artificial melanin material comprising:

a surface functionalized with a modifier agent via a linker group;

wherein the modifier agent comprises the linker group and a functional group attached to the linker group;

wherein the linker group is a nucleophilic group;

functionalized artificial melanin nanoparticles, wherein each functionalized artificial melanin nanoparticle independently comprises a surface functionalized with the modifier agent via the linker group;

wherein the functionalized artificial melanin material or each of the functionalized artificial melanin nanoparticles thereof comprises a plurality of melanin oligomers and/or polymers; and wherein each melanin oligomer and/or polymer comprises a plurality of covalently-bonded melanin base units; and wherein at least a portion of the artificial melanin material comprises melanin oligomers free of nitrogen.

16. The material of claim 1, wherein the functionalized artificial melanin material comprises artificial allomelanin nanoparticles, artificial polydopamine nanoparticles, or any combination thereof.

17. The material of claim 1, wherein the functionalized artificial melanin material or the functionalized artificial melanin nanoparticles thereof are porous and have a Brunauer-Emmett-Teller (BET) area selected from the range of 70 $m^2/g$ to 800 $m^2/g$.

18. The material of claim 1, wherein the functionalized artificial melanin material or the functionalized artificial melanin nanoparticles thereof are non-porous or have a Brunauer-Emmett-Teller (BET) area less than 20 $m^2/g$.

19. The method of claim 1, wherein the functionalized artificial melanin material comprises functionalized artificial melanin particles having a cross-sectional size on average selected from the range of 10 nm to 1000 nm, as measured by transmission electron microscopy and/or dynamic light scattering.

20. The material of claim 1, wherein the functionalized artificial melanin material is a thin film, and the thin film has an area selected from the range of 0.25 $cm^2$ to 9 $cm^2$.

21. The material of claim 20, wherein the thin film comprises one or more monolayers of the functionalized artificial melanin nanoparticles.

22. A melanin-containing formulation comprising:

one or more hydrophobic solvents; and the functionalized artificial melanin material of claim 1 dispersed in the one or more hydrophobic solvents.

23. The formulation of claim 22, wherein the one or more hydrophobic solvents comprise dichloromethane, chloroform, tetrahydrofuran, toluene, ethyl acetate, hexane, cyclohexane, squalene, squalene, a petrolatum, a petrolatum-containing solvent or solvent mixture, a petrolatum ointment, a petrolatum jelly-based ointment, or any combination thereof.

24. A method for treatment of a subject, the method comprising:

topically administering a melanin formulation to damaged skin of the subject;

wherein the melanin formulation comprises the functionalized artificial melanin material of claim 1;

wherein the melanin formulation comprises one or more hydrophobic solvents and the functionalized artificial melanin material dispersed in the one or more hydrophobic solvents; and wherein the administered functionalized artificial melanin material comprises an extracellular functionalized artificial melanin material at the damaged skin; and facilitating skin healing at the damaged skin via at least the extracellular functionalized artificial melanin material;

wherein the step of facilitating skin healing comprises at least a portion of the extracellular artificial melanin material performing a therapeutic extracellular activity.

25. The method of claim 24, wherein the therapeutic extracellular activity comprises at least a portion of the extracellular artificial melanin material directly and/or indirectly:

reducing the inflammation; and/or inhibiting apoptosis compared to when the artificial melanin material is absent.

26. The method of claim 24, wherein the step of facilitating skin healing further comprises at least a portion of the administered artificial melanin material performing a therapeutic intracellular activity, wherein the therapeutic intracellular activity comprises:

quenching intracellular free radical species; and/or adsorbing one or more intracellular inflammatory factors and/or one or more intracellular enzymatic factors.

27. A method for making the functionalized artificial melanin material of claim 1 the method comprising:

providing unfunctionalized artificial melanin nanoparticles; and exposing, for a finite time, the unfunctionalized artificial melanin nanoparticles to a precursor of the modifier agent;

wherein the step of exposing comprises:

conjugating the unfunctionalized artificial melanin nanoparticles with the precursor thereby forming functionalized artificial melanin nanoparticles having a modifier agent;

wherein the functionalized artificial melanin nanoparticles comprise a surface functionalized with the modifier agent via a linker group;

wherein the modifier agent comprises the linker group and a functional group attached to the linker group; and wherein the linker group is a nucleophilic group.

28. The material of claim 1, wherein the functionalized artificial melanin material or each of the functionalized artificial melanin nanoparticles thereof comprises a plurality of melanin oligomers and/or polymers; and wherein each melanin oligomer and/or polymer comprises a plurality of covalently-bonded melanin base units.

29. The material of claim 28, wherein said melanin base units comprise one or more substituted or unsubstituted catechol-based monomer units, substituted or unsubstituted polyol-based monomer units, substituted or unsubstituted phenol-based monomer units, substituted or unsubstituted indole-based monomer units, substituted or unsubstituted benzothiazine-based monomer units, substituted or unsubstituted benzothiazole-based monomer units, substituted or unsubstituted dopamine-based monomer units, or any combination of these.

30. The material of claim 1, wherein the functionalized artificial melanin material comprises solid or nonporous artificial allomelanin nanoparticles, walnut artificial allomelanin nanoparticles, hollow artificial allomelanin nanoparticles, lacey artificial allomelanin nanoparticles, or a combination thereof.

31. The material of claim 28, wherein at least a portion of said melanin base units each independently comprises substituted or unsubstituted naphthalene or a substituted or unsubstituted dopamine monomer.

32. The material of claim 1, wherein at least a portion of the artificial melanin material comprises melanin oligomers free of nitrogen.

33. A method for treatment of a subject, the method comprising:

topically administering a melanin formulation to damaged skin of the subject;

wherein the melanin formulation comprises the functionalized artificial melanin material of claim 2;

wherein the melanin formulation comprises one or more hydrophobic solvents and the functionalized artificial melanin material dispersed in the one or more hydrophobic solvents; and wherein the administered functionalized artificial melanin material comprises an extracellular functionalized artificial melanin material at the damaged skin; and facilitating skin healing at the damaged skin via at least the extracellular functionalized artificial melanin material;

wherein the step of facilitating skin healing comprises at least a portion of the extracellular artificial melanin material performing a therapeutic extracellular activity.

34. A method for treatment of a subject, the method comprising:

topically administering a melanin formulation to damaged skin of the subject;

wherein the melanin formulation comprises the functionalized artificial melanin material of claim 15;

wherein the melanin formulation comprises one or more hydrophobic solvents and the functionalized artificial melanin material dispersed in the one or more hydrophobic solvents; and wherein the administered functionalized artificial melanin material comprises an extracellular functionalized artificial melanin material at the damaged skin; and facilitating skin healing at the damaged skin via at least the extracellular functionalized artificial melanin material;

wherein the step of facilitating skin healing comprises at least a portion of the extracellular artificial melanin material performing a therapeutic extracellular activity.

35. A method for making the functionalized artificial melanin material of claim 2, the method comprising:

providing unfunctionalized artificial melanin nanoparticles; and exposing, for a finite time, the unfunctionalized artificial melanin nanoparticles to a precursor of the modifier agent;

wherein the step of exposing comprises:

conjugating the unfunctionalized artificial melanin nanoparticles with the precursor thereby forming functionalized artificial melanin nanoparticles having a modifier agent;

wherein the functionalized artificial melanin nanoparticles comprise a surface functionalized with the modifier agent via a linker group;

wherein the modifier agent comprises the linker group and a functional group attached to the linker group; and wherein the linker group is a nucleophilic group.

36. A method for making the functionalized artificial melanin material of claim 15, the method comprising:

providing unfunctionalized artificial melanin nanoparticles; and exposing, for a finite time, the unfunctionalized artificial melanin nanoparticles to a precursor of the modifier agent;

wherein the step of exposing comprises:

conjugating the unfunctionalized artificial melanin nanoparticles with the precursor thereby forming functionalized artificial melanin nanoparticles having a modifier agent;

wherein the functionalized artificial melanin nanoparticles comprise a surface functionalized with the modifier agent via a linker group;

wherein the modifier agent comprises the linker group and a functional group attached to the linker group; and wherein the linker group is a nucleophilic group.

* * * * *